US011261453B2

(12) United States Patent
Lindquist et al.

(10) Patent No.: US 11,261,453 B2
(45) Date of Patent: Mar. 1, 2022

(54) CELLS EXPRESSING APOLIPOPROTEIN E AND USES THEREOF

(71) Applicant: Whitehead Institute for Biomedical Research, Cambridge, MA (US)

(72) Inventors: Susan L. Lindquist, Cambridge, MA (US); Priyanka Narayan, Cambridge, MA (US)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 14/851,662

(22) Filed: Sep. 11, 2015

(65) Prior Publication Data

US 2016/0251665 A1    Sep. 1, 2016

Related U.S. Application Data

(60) Provisional application No. 62/050,045, filed on Sep. 12, 2014.

(51) Int. Cl.

| | | |
|---|---|---|
| *C12N 15/81* | (2006.01) | |
| *C07K 14/775* | (2006.01) | |
| *C07K 14/47* | (2006.01) | |
| *G01N 33/92* | (2006.01) | |
| *C12Q 1/02* | (2006.01) | |
| *G01N 33/50* | (2006.01) | |
| *G01N 33/68* | (2006.01) | |
| *A61K 38/00* | (2006.01) | |

(52) U.S. Cl.
CPC .......... *C12N 15/81* (2013.01); *C07K 14/4711* (2013.01); *C07K 14/775* (2013.01); *C12Q 1/02* (2013.01); *G01N 33/5014* (2013.01); *G01N 33/5058* (2013.01); *G01N 33/6896* (2013.01); *G01N 33/92* (2013.01); *A61K 38/00* (2013.01); *C07K 2319/02* (2013.01); *G01N 2333/775* (2013.01); *G01N 2500/10* (2013.01); *G01N 2800/2821* (2013.01); *G01N 2800/50* (2013.01); *G01N 2800/709* (2013.01)

(58) Field of Classification Search
CPC combination set(s) only.
See application file for complete search history.

(56) References Cited

U.S. PATENT DOCUMENTS

| | | | |
|---|---|---|---|
| 5,116,739 A | | 5/1992 | Teranishi et al. |
| 6,020,143 A * | | 2/2000 | St. George-Hyslop ..................... A01K 67/0275 435/7.1 |
| 7,045,290 B2 | | 5/2006 | Lindquist et al. |
| 7,452,670 B2 | | 11/2008 | Muchowski et al. |
| 7,799,535 B1 | | 9/2010 | Lindquist et al. |
| 8,192,986 B2 | | 6/2012 | Lindquist et al. |
| 8,399,241 B2 | | 3/2013 | Lindquist et al. |
| 8,440,705 B2 | | 5/2013 | Lindquist et al. |
| 8,501,465 B2 | | 8/2013 | Lindquist et al. |
| 9,018,003 B2 | | 4/2015 | Lindquist et al. |
| 2004/0214774 A1 * | | 10/2004 | Wisniewski ........... A61K 38/10 514/17.8 |
| 2005/0064548 A1 * | | 3/2005 | Lindquist ................ C07K 14/47 435/69.1 |
| 2008/0249129 A1 | | 10/2008 | Lindquist et al. |
| 2010/0273776 A1 | | 10/2010 | Lindquist et al. |
| 2011/0053857 A1 | | 3/2011 | Lindquist et al. |
| 2013/0017251 A1 * | | 1/2013 | Huang ................... C07K 16/18 424/450 |
| 2013/0022988 A1 | | 1/2013 | Matlack et al. |
| 2013/0045483 A1 | | 2/2013 | Treusch et al. |
| 2014/0179595 A1 * | | 6/2014 | Wang ................... C07K 14/775 514/4.3 |
| 2015/0361148 A1 | | 12/2015 | Haque et al. |

FOREIGN PATENT DOCUMENTS

| | | | | |
|---|---|---|---|---|
| JP | S61-96997 | 5/1986 | | |
| JP | 2004-537973 | 12/2004 | | |
| JP | 2011-142910 | 7/2011 | | |
| WO | WO 2000/050042 | 8/2000 | | |
| WO | WO-0177136 A1 * | 10/2001 | ................ | A61P 3/06 |

(Continued)

OTHER PUBLICATIONS

Holzman et al., Apolipoprotein E isoform-dependent amyloid deposition and neuritic degeneration in a mouse model of Alzheimer's disease; PNAS, vol. 97, No. 6, pp. 2892-2897, 2000).*
Cregg et al., Recombinant Protein Expression in Pichia Pastoris; Molecular Biotechnology, vol. 16, pp. 23-52, 2000 (Year: 2000).*
Baumann et al., Protein trafficking, ergosterol biosynthesis and membrane physics impact recombinant protein secretion in Pichia pastoris; Microbial Cell Factories, vol. 10, No. 93, pp. 1-15, 2011 (Year: 2011).*
Paik et al., Nucleotide sequence and structure of the human apolipoprotein E gene, 1985, PNAS, vol. 82, pp. 3445-3449 (Year: 1985).*

(Continued)

*Primary Examiner* — Antonio Galisteo Gonzalez
(74) *Attorney, Agent, or Firm* — Fish & Richardson P.C.

(57) ABSTRACT

Disclosed are yeast cells expressing a polypeptide comprising a signal sequence and a human ApoE protein. In some embodiments the polypeptide comprises ApoE2. In some embodiments the polypeptide comprises ApoE3. In some embodiments the polypeptide comprises ApoE4. Also disclosed are methods of screening yeast cells to identify compounds that prevent or suppress Apo-induced toxicity. Compounds identified by such screens can be used to treat or prevent neurodegenerative disorders such as Alzheimer's disease. Also disclosed are methods of screening yeast cells to identify genetic suppressors or enhancers of ApoE-induced toxicity. Also disclosed are genetic suppressors or enhancers of ApoE-induced toxicity identified using the methods, and human homologs thereof. Also disclosed are methods of identifying compounds that modulate expression or activity of genetic modifiers of ApoE-induced toxicity.

12 Claims, 19 Drawing Sheets
Specification includes a Sequence Listing.

(56) References Cited

FOREIGN PATENT DOCUMENTS

WO    WO 2011/088059    7/2011
WO    WO2014/145975    9/2014

OTHER PUBLICATIONS

Jordan et al.,. "Isoform-specific effect of apolipoprotein E on cell survival and beta-amyloid-induced toxicity in rat hippocampal pyramidal neuronal cultures", J. Neurosci (1998), 18(1):195-204.
International Search Report and Written Opinion for PCT Application No. PCT/US15/49674, dated Feb. 1, 2016, 26 pages.
PPICZ alpha Vector, Jun. 27, 2014, Retrieved from the Internet: URL: http://plasmid.med.harvard.edu/plasmidRepository/file/map/ppiczalpha_abc.pdf, Retrieved on Jun. 27, 2014, 1 page.
Partial Supplementary European Search Report in International Application No. EP15840274.3, dated Feb. 9, 2018, 19 pages.
Sturley et al., "Secretion and lipid association of human apolipoprotein E in *Saccharomyces cerevisiae* requires a host mutation in sterol esterification and uptake," *J Biol Chem.*, 266(25): 16273-16276, Sep. 5, 1991.
Su et al., "High yield and purification of recombinant human apolipoprotein E3 in pichia pastoris," *Protein Expr Purif.*, 68(1):7-11, Nov. 1, 2009.
Nomura et al., "High level secretion by *Saccharomyces cerevisiae* of Human Apolipoprotein E as a Fusion to Rhizomucor Rennin", Bioscience, Biotechnology and Biochemistiy, 1995, 59(3):382-387.
Nomura et al., "Secretion by *Saccharomyces cerevisiae* of Human Apolipoprotein E as a Fusion to Serum Albumin", Bioscience, Biotechnology and Biochemistiy, 1995, 59(3):532-534.

\* cited by examiner

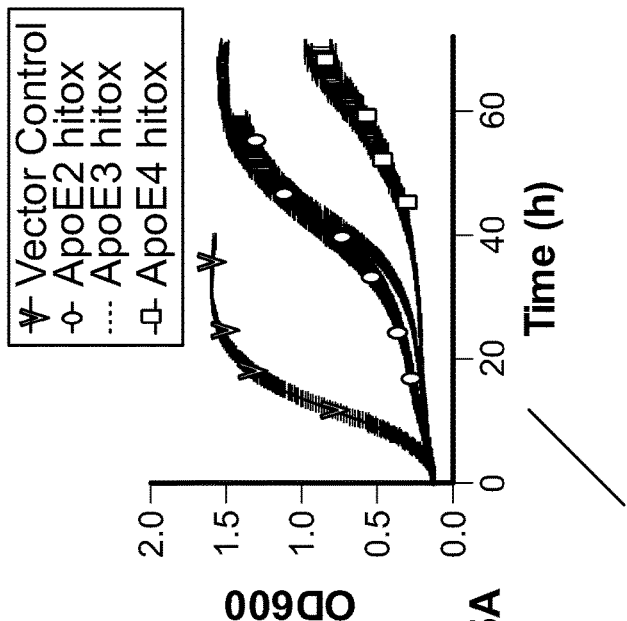
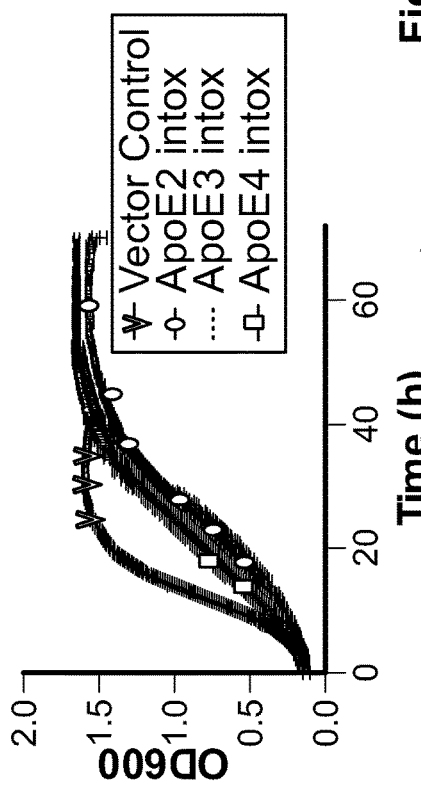
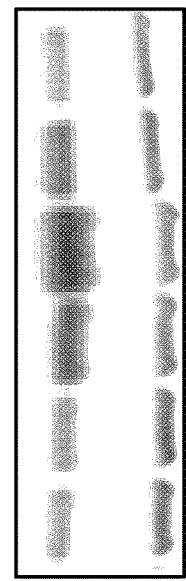
Fig. 5A
Fig. 5B

ApoE comes in three isoforms that differ at 2 AA positions

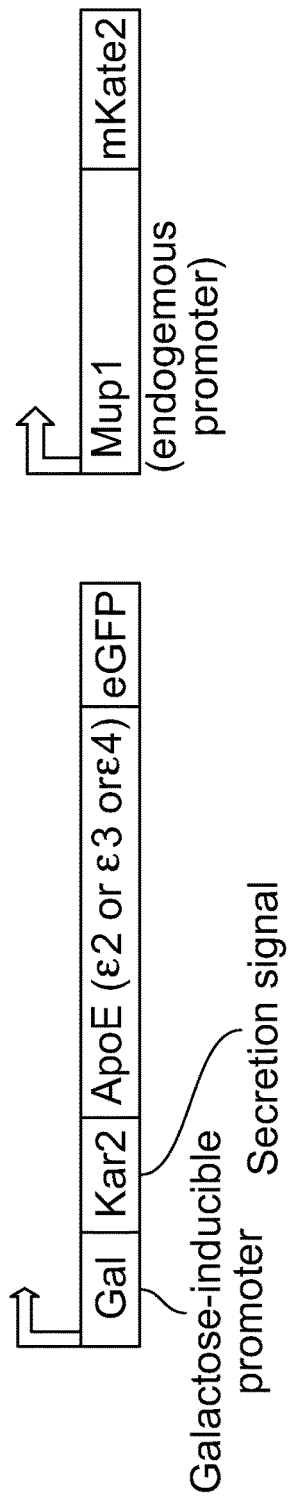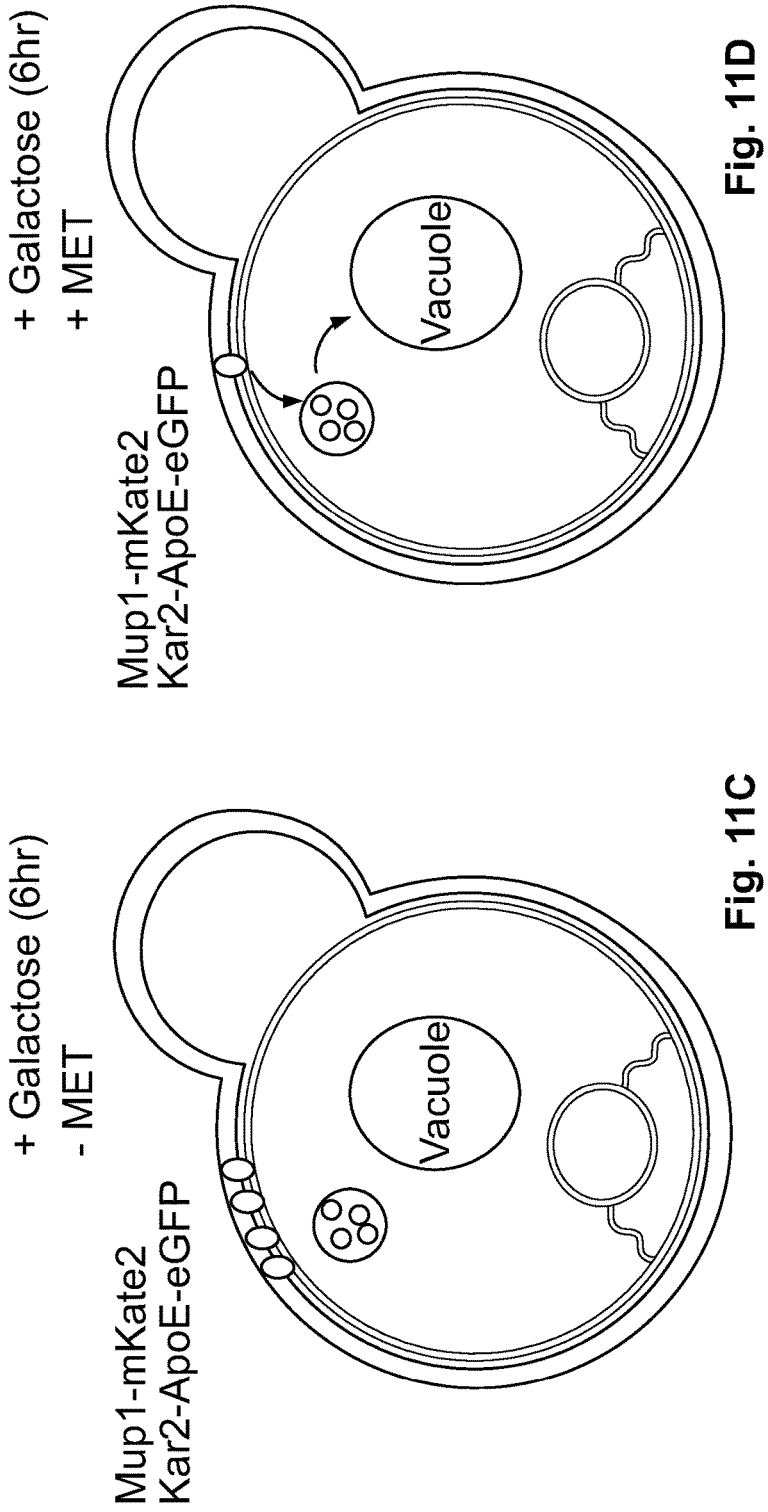

ApoE4, Aβ and α-syn disrupt endosomal trafficking in different ways
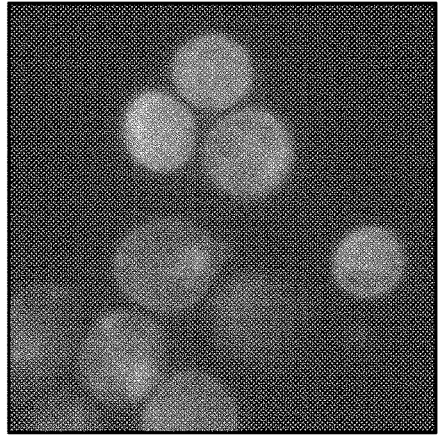
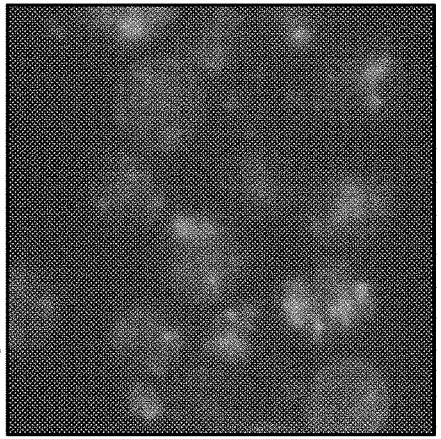
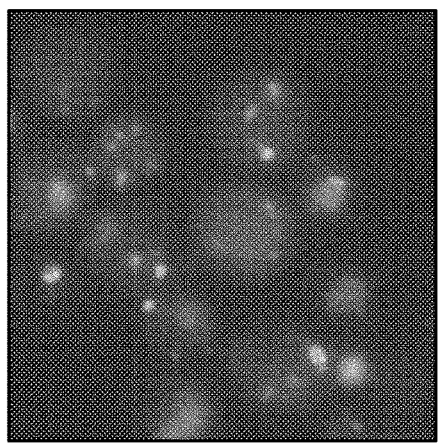
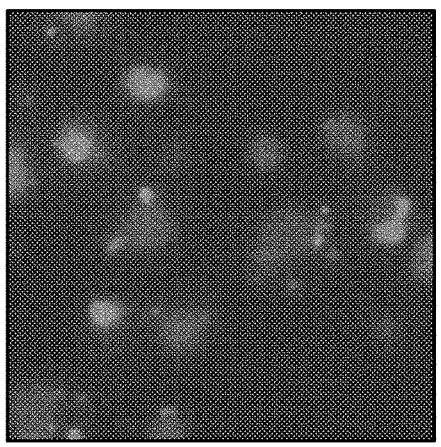
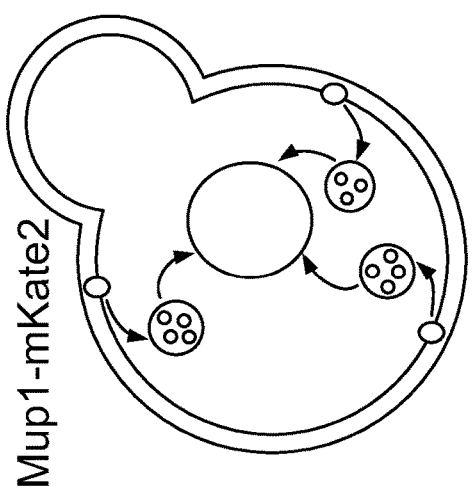
Fig. 11G
Fig. 11H

CELLS EXPRESSING APOLIPOPROTEIN E AND USES THEREOF

SEQUENCE LISTING

The instant application contains a Sequence Listing which has been submitted electronically in ASCII format and is hereby incorporated by reference in its entirety. Said ASCII copy, created on Oct. 13, 2015, is named 26495-0017001_SL.txt and is 14,498 bytes in size.

BACKGROUND

Alzheimer's disease is a neurodegenerative disorder characterized by neurofibrillary tangles and plaques containing amyloid beta peptides. Patients with Alzheimer's disease (AD) exhibit progressive dementia and personality dysfunction. Proteolytic cleavage of the amyloid precursor protein (APP) results in the generation of an amyloid beta (Aβ) peptide having a length ranging from 38 to 43 amino acids. The amyloid beta 1-42 peptide is particularly prone to self-aggregation and is strongly linked to development of Alzheimer's disease.

Human apolipoprotein E is a 299 amino acid secreted glycoprotein that plays important roles in lipid transport and metabolism. ApoE is synthesized primarily in the liver but also in a number of other organs and tissues, including the brain. In the central nervous system, ApoE is produced mainly by astrocytes and microglia and transports cholesterol to neurons via ApoE receptors. The APOE gene has three common polymorphic alleles—ε2, ε3 and ε4—which encode the ApoE isoforms known as ApoE2, ApoE3, and ApoE4, respectively. The most common isoform, ApoE3, contains cysteine and arginine at positions 112 and 158, respectively, whereas ApoE2 has cysteine at both positions and ApoE4 has arginine at both positions. Although these isoforms differ by only one or two amino acids, the differences have a number of implications. The ε4 allele of APOE is the most highly validated genetic risk factor for late onset Alzheimer's disease and is also associated with increased risk of early-onset AD and with a variety of other diseases that affect the central nervous system. The ε2 allele of APOE is associated with the lowest risk of developing AD, while the ε3 allele confers an intermediate risk of developing the disease.

SUMMARY

The invention relates at least in part to the discovery that human Apolipoprotein E (ApoE) protein is toxic when expressed in a yeast cell. The discovery of ApoE-mediated toxicity in yeast permits the carrying out of screening assays using ApoE-expressing yeast cells to identify compounds or genetic factors that modulate ApoE-induced toxicity. Compounds identified by such screens can be used for the treatment or prevention of diseases in which one or more isoforms of ApoE plays a pathological role. For example, compounds identified by such screens can be used for the treatment of diseases and disorders affecting the nervous system in which ApoE4 plays a role, e.g., neurodegenerative diseases such as Alzheimer's disease.

In some aspects, described herein is a yeast cell comprising an expression construct comprising a promoter operably linked to a nucleic acid encoding a polypeptide comprising a human ApoE protein, wherein expression of the nucleic acid and production of the polypeptide in the cell results in a decrease in growth or viability of the cell. In some embodiments, expression of the nucleic acid and production of the polypeptide renders the yeast cell non-viable. In some embodiments the human ApoE protein is a human ApoE2 protein. In some embodiments the human ApoE protein is a human ApoE3 protein. In some embodiments the human ApoE protein is a human ApoE4 protein.

In some embodiments the expression construct comprises a promoter operably linked to a nucleic acid encoding a polypeptide comprising a signal sequence and a human ApoE protein, wherein expression of the nucleic acid and production of the polypeptide in the cell results in a decrease in growth or viability of the cell. In some embodiments, expression of the nucleic acid and production of the polypeptide renders the yeast cell non-viable. A signal sequence causes a polypeptide to be targeted to the endoplasmic reticulum within a cell, whence it enters the secretory pathway. In some embodiments, the signal sequence is located at the amino terminus of the polypeptide encoded by the expression construct. In some embodiments, the signal sequence is one that directs co-translational transport of the encoded polypeptide. The signal sequence can be identical to a naturally occurring signal sequence or can be an artificial (non-naturally occurring) signal sequence. In some embodiments, the signal sequence is identical to the signal sequence of a naturally occurring yeast protein (e.g., identical to the yeast Kar2p signal sequence. In some embodiments, the signal sequence is identical to the signal sequence of a naturally occurring mammalian protein (e.g., a human protein).

In some embodiments, the polypeptide encoded by an expression construct described herein comprises or consists of a signal sequence and a human ApoE protein. In some embodiments, the polypeptide encoded by an expression construct described herein comprises or consists of a signal sequence, a linker peptide sequence, and a human ApoE protein.

In some embodiments, cleavage of the polypeptide comprising a human ApoE protein, thus removing the signal sequence, may occur before translation of the entire polypeptide is complete. This phenomenon is encompassed by the phrase "production of the polypeptide in the cell results in a decrease in growth or viability of the cell," so long as at least the human ApoE protein portion of the polypeptide is translated and results in a decrease in growth or viability of the cell.

In some embodiments, a polypeptide encoded by an expression construct described herein may contain a human ApoE protein and one or more heterologous peptide sequences. In some embodiments, a polypeptide encoded by an expression construct described herein may contain a signal sequence, a human ApoE protein, and one or more heterologous peptide sequences. A "heterologous peptide sequence" refers to any polypeptide sequence that is not an ApoE protein sequence or a signal sequence. A heterologous peptide sequence can be present at the amino terminus of the polypeptide, between the signal sequence and the human ApoE protein, at the carboxy terminus of the human ApoE protein, and/or at the carboxy terminus of the polypeptide. In some embodiments the heterologous peptide sequence comprises a "detection protein," which term refers to a protein that serves as a detectable label (e.g., a fluorescent protein, an enzyme, or an epitope tag). In some embodiments the polypeptide is a fusion protein containing a human ApoE protein and a detection protein (e.g., a fluorescent protein, an enzyme, or an epitope tag). For example, in some embodiments the polypeptide is a fusion protein containing a signal sequence, a human ApoE protein, and a detection protein.

Examples of fluorescent proteins include red fluorescent protein, green fluorescent protein, blue fluorescent protein, yellow fluorescent protein, and cyan fluorescent protein. Enzymes that may serve as detection proteins include those that are capable of acting on a substrate in a light-producing reaction or to produce a colored or otherwise detectable substance. Examples include, e.g., luciferase or beta-galactosidase.

In some embodiments the yeast cell comprises an expression construct comprising a promoter operably linked to a nucleic acid encoding a polypeptide comprising a human ApoE protein and an expression construct comprising a promoter operably linked to a nucleic acid encoding a polypeptide comprising a signal sequence and a human amyloid beta protein. In some embodiments the yeast cell comprises an expression construct comprising a promoter operably linked to a nucleic acid encoding a polypeptide comprising a signal sequence and a human ApoE protein and an expression construct comprising a promoter operably linked to a nucleic acid encoding a polypeptide comprising a signal sequence and a human amyloid beta protein. In some embodiments the yeast cell comprises an expression construct comprising a first promoter operably linked to a nucleic acid encoding a polypeptide comprising a human ApoE protein and a second promoter operably linked to a nucleic acid encoding a polypeptide comprising a signal sequence and a human amyloid beta protein. In some embodiments the ApoE protein in any of the yeast cells is ApoE2. In some embodiments the ApoE protein in any of the yeast cells is ApoE3. In some embodiments the ApoE protein in any of the yeast cells is ApoE4.

In some embodiments, a yeast cell is characterized in that expression of the nucleic acid encoding a polypeptide comprising a signal sequence and a human amyloid beta protein and production of such polypeptide in the cell would not be sufficient result in a decrease in growth or viability of the cell under conditions in which the polypeptide comprising a signal sequence and a human ApoE protein is absent or not expressed. In some embodiments, the yeast cell is characterized in that expression of the nucleic acid encoding a polypeptide comprising a signal sequence and a human amyloid beta protein and production of such polypeptide in the cell would result in a decrease in growth or viability of the cell under conditions in which the polypeptide comprising a signal sequence and a human ApoE protein is absent or not expressed.

In some embodiments a yeast cell comprising an expression construct comprising a promoter operably linked to a nucleic acid encoding a polypeptide comprising a human ApoE, e.g., encoding a polypeptide comprising a signal sequence and a human ApoE protein, does not comprise an expression construct comprising a promoter operably linked to a nucleic acid encoding a polypeptide comprising a human amyloid beta protein, e.g., a polypeptide comprising a signal sequence and a human amyloid beta protein.

In some embodiments, an expression construct described herein is integrated in the genome of the yeast cell. For example, the expression construct can be an integrative plasmid such as pRS303, pRS304, pRS305, pRS306, or a derivative thereof.

A yeast cell can have one or more (e.g., two, three, four, or more) copies (e.g., integrated copies) of an expression construct.

In some embodiments the promoter is an inducible promoter such as GAL1-10, GAL1, GALL, or GALS. In some embodiments the promoter is a constitutively active promoter such as GPD, ADH, TEF, CYC1, or MRP7. In embodiments in which the yeast cell comprises two or more expression constructs, each comprising a promoter operably linked to a nucleic acid, or comprises an expression construct comprising first and second promoters, the promoters may be the same or different.

In some embodiments, the yeast is *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida albicans, Candida utilis, Candida cacaoi, Geotrichum* sp., or *Geotrichum fermentans*.

In some embodiments, at least one gene that encodes a protein involved in drug efflux or cell permeability is disrupted in the yeast cell. For example, one or more of the genes PDR1, PDR3, PDR5, SNQ2, or ERG6 can be disrupted in the yeast cell.

Also disclosed is a method of inducing toxicity in a yeast cell by: providing a yeast cell described herein comprising a nucleic acid that encodes a polypeptide comprising an ApoE protein; and inducing a level of expression of the nucleic acid in the yeast cell that is toxic to the yeast cell. In some embodiments the polypeptide comprises a signal sequence and an ApoE protein.

Also disclosed is a method of identifying a compound that prevents or suppresses ApoE-induced toxicity by: culturing a yeast cell described herein in the presence of a candidate agent and under conditions that allow for expression of the nucleic acid encoding a polypeptide comprising an ApoE protein at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses ApoE-induced toxicity. In some embodiments the polypeptide comprises a signal sequence and an ApoE protein. In some embodiments a compound that prevents or suppresses ApoE-induced toxicity serves as a candidate therapeutic agent for an ApoE-associated disease.

Also disclosed is a method of identifying a genetic suppressor or enhancer of ApoE-induced toxicity by: providing a yeast cell described herein, wherein the yeast cell has been genetically modified to overexpress a gene; culturing the yeast cell under conditions that allow for expression of the polypeptide comprising an ApoE protein at a level that, in the absence of overexpression of the gene, is sufficient to induce toxicity in the yeast cell; measuring cell growth or viability in the presence of overexpression of the gene; and comparing cell growth or viability measured in the presence of overexpression of the gene to cell growth or viability in the absence of overexpression of the gene, wherein (i) if cell growth or viability is increased in the presence of overexpression of the gene as compared to in the absence of overexpression of the gene, then the gene is identified as a genetic suppressor of amyloid beta-induced toxicity, and (ii) if cell growth or viability is decreased in the presence of overexpression of the gene as compared to in the absence of overexpression of the gene, then the gene is identified as a genetic enhancer of ApoE-induced toxicity. In some embodiments the polypeptide comprises a signal sequence and an ApoE protein.

Also disclosed is a method of identifying a genetic suppressor or enhancer of ApoE-induced toxicity by: providing a yeast cell described herein, wherein an endogenous gene of the yeast cell has been disrupted; culturing the yeast cell under conditions that allow for expression of the polypeptide comprising an ApoE protein at a level that, in the absence of disruption of the endogenous gene, is sufficient to induce toxicity in the yeast cell; measuring cell growth or viability in the presence of disruption of the endogenous gene; and comparing cell growth or viability measured in the presence of disruption of the endogenous gene to cell growth or viability in the absence of disruption of the endogenous gene, wherein (i) if cell growth or viability is increased in the presence of disruption of the endogenous gene as compared to in the absence of disruption of the endogenous gene, then the gene is identified as a genetic enhancer of ApoE-induced toxicity, and (ii) if cell growth or viability is decreased in the presence of disruption of the endogenous gene as compared to in the absence of disruption of the endogenous gene, then the gene is identified as a genetic suppressor of ApoE-induced toxicity. In some embodiments the polypeptide comprises a signal sequence and an ApoE protein. As an alternative to use of a yeast cell that has had an endogenous gene disrupted, the method may be performed using a yeast cell wherein expression of the endogenous gene is suppressed by use of RNA interference.

In some embodiments a method of identifying a genetic suppressor or enhancer of ApoE-mediated toxicity further comprises identifying a mammalian homolog of a gene identified as a genetic suppressor of ApoE-mediated toxicity.

Also disclosed are various yeast genes identified as genetic enhancers or suppressors of ApoE-mediated toxicity according to certain of the foregoing methods, their encoded proteins, and, for some of these genes and proteins, homologs thereof found in other organisms (e.g., in mammalian species such as humans). Notably, a number of the yeast genes identified herein as genetic suppressors or enhancers of ApoE-mediated toxicity have human homologs that have been previously identified as genetic risk factors for Alzheimer's disease. The present disclosure is believed to represent the first recognition of a genetic interaction between ApoE and certain of these genetic risk factors for AD. In some embodiments, the genetic enhancer or suppressor of ApoE-mediated toxicity is listed in Table 3. In some embodiments, the genetic enhancer or suppressor of ApoE-mediated toxicity is involved in vesicle transport (e.g., ATG20, UBP3, TRS65, BRE5, MUK1, and GYPS). In some embodiments, the genetic enhancer or suppressor of ApoE-mediated toxicity is involved in endocytosis (e.g., RVS161, OSH2, RVS167, YAP1802, and OSH3). In some embodiments, the genetic enhancer or suppressor of ApoE-mediated toxicity is involved in ubiquitination/deubiquitination (e.g., APC11, UBP3, UBP7, CDC73, BRE5, and RRI2). In some embodiments, the genetic enhancer or suppressor of ApoE-mediated toxicity is involved in lipid metabolism (e.g., PER1, MDH3, GPI8, SMP3, and SUR1). In some embodiments, the genetic enhancer or suppressor of ApoE-mediated toxicity is involved in DNA repair (e.g., MGT1, PCD1, CDC73, and RAD14). In some embodiments, the genetic enhancer or suppressor of ApoE-mediated toxicity is involved in mitochondrion organization (e.g., ATG20, MHR1, MRP4, RRM3, ILM1, MST1, YTA12, POR1, and MRPL10).

In some aspects, a yeast cell that expresses a particular ApoE isoform in combination with overexpressing a yeast gene that has a human homolog that is a genetic risk factor for Alzheimer's disease, wherein overexpression of the yeast gene enhances toxicity of ApoE in the yeast cell, may serve as a model system for identifying candidate compounds for treating subjects who have or at risk of developing an ApoE-mediated disease and express the particular ApoE isoform and have the genetic risk factor for AD.

In some aspects, a yeast cell that expresses a particular ApoE isoform in combination with reduced expression of activity of a yeast gene that has a human homolog that is a genetic risk factor for Alzheimer's disease, wherein overexpression of the yeast gene suppresses toxicity of ApoE in the yeast cell, may serve as a model system for identifying candidate compounds for treating subjects who have or are at risk of developing an ApoE-mediated disease and express the particular isoform and have the genetic risk factor for AD.

Also disclosed are cells that comprise: a first expression construct comprising a first promoter operably linked to a first nucleic acid encoding a polypeptide comprising a human ApoE protein, wherein the cell: (a) further comprises a second expression construct comprising a second promoter operably linked to a second nucleic acid encoding a polypeptide encoded by a genetic suppressor or enhancer of ApoE-mediated toxicity or a human homolog thereof, or (b) has reduced or absent expression or activity of a protein encoded by a genetic suppressor or enhancer of ApoE-mediated toxicity or a human homolog thereof. In some embodiments the first nucleic acid encodes a polypeptide comprising a signal sequence and a human ApoE protein. In some embodiments the first promoter, second promoter, or both, is regulatable, e.g., inducible. In some embodiments the reduced or absent expression or activity of a protein encoded by a genetic suppressor or enhancer of ApoE-mediated toxicity or a human homolog thereof results from a mutation in the gene that encodes the protein. In some embodiments the mutation is an engineered mutation. In some embodiments the reduced or absent expression or activity is regulatable, e.g., inducible. In some embodiments the genetic suppressor or enhancer of ApoE-mediated toxicity is a yeast gene is listed in any one or more of Tables 1A, 1B, 1C, 1D, 2A, 2B, 2C, and 3. In some embodiments the genetic suppressor or enhancer of ApoE-mediated toxicity is a yeast gene listed in Table 3. In some embodiments, the genetic suppressor or enhancer of ApoE-mediated toxicity is involved in vesicle transport (e.g., ATG20, UBP3, TRS65, BRE5, MUK1, GYPS, or a mammalian (e.g., human) homolog thereof). In some embodiments, the genetic suppressor or enhancer of ApoE-mediated toxicity is involved in endocytosis (e.g., RVS161, OSH2, RVS167, YAP1802, OSH3 or a mammalian (e.g., human) homolog thereof). In some embodiments, the genetic suppressor or enhancer of ApoE-mediated toxicity is involved in ubiquitination/deubiquitination (e.g., APC11, UBP3, UBP7, CDC73, BRE5, RRI2, or a mammalian (e.g., human) homolog thereof). In some embodiments, the genetic suppressor or enhancer of ApoE-mediated toxicity is involved in lipid metabolism (e.g., PER1, MDH3, GPI8, SMP3, SUR1, or a mammalian (e.g., human) homolog thereof). In some embodiments, the genetic suppressor or enhancer of ApoE-mediated toxicity is involved in DNA repair (e.g., MGT1, PCD1, CDC73, RAD14, or a mammalian (e.g., human) homolog thereof). In some embodiments, the genetic suppressor or enhancer of ApoE-mediated toxicity is involved in mitochondrion organization (e.g., ATG20, MHR1, MRP4, RRM3, ILM1, MST1, YTA12, POR1, MRPL10, or a mammalian (e.g., human) homolog thereof).

In some embodiments the human homolog is a gene listed in any one or more of Tables 1C, 1D, 2A, 2B, and 2C. In some embodiments, the human homolog is a homolog of a yeast gene listed in Table 3. In some embodiments the human ApoE protein is a human ApoE2 protein and the genetic suppressor or enhancer is a genetic suppressor or enhancer of ApoE2-mediated toxicity, e.g., any of the genetic suppressors or enhancers of ApoE2-mediated toxicity listed in any or more of Tables 1A, 1B, 1C, 1D, 2A, and 3. In some embodiments the human ApoE protein is a human ApoE3 protein and the genetic suppressor or enhancer is a genetic suppressor or enhancer of ApoE3-mediated toxicity, e.g., any of the suppressors or enhancers of ApoE3-mediated toxicity listed in any one or more of Tables 1A, 1B, 1C, 1D, 2B, and 3. In some embodiments the human ApoE protein is a human ApoE4 protein and the genetic suppressor or enhancer is a suppressor or enhancer of ApoE4-mediated toxicity, e.g., any of the genetic suppressors enhancers of ApoE4-mediated toxicity listed in any one or more of Tables 1A, 1B, 1C, 1D, 2C, and 3. In some embodiments the cells are yeast cells. In some embodiments the cells are mammalian cells, e.g., human cells.

Also disclosed herein is a method that comprises generating or providing an expression construct comprising a promoter operably linked to a nucleic acid that encodes a mammalian homolog of a protein encoded by a yeast gene that is a genetic enhancer or suppressor of ApoE-mediated toxicity, wherein the promoter is capable of directing expression in mammalian cells, e.g., human cells. In some embodiments the mammalian homolog is a human homolog. In some embodiments the promoter is regulatable, e.g., inducible. In some embodiments expression or activity of the protein is inducible. In some embodiments the method comprises introducing the expression construct into a mammalian cell, e.g., a human cell. In some embodiments the method further comprises inducing expression or activity of the mammalian homolog in the mammalian cell. Also disclosed are mammalian cells, e.g., human cells, produced according to the methods. In some embodiments the yeast gene that is a genetic suppressor or enhancer of ApoE-mediated toxicity is listed in any one or more of Tables 1A, 1B, 1C, 1D, 2A, 2B, 2C, and 3. In some embodiments, the yeast gene that is a genetic suppressor or enhancer of ApoE-mediated toxicity is listed in Table 3. In some embodiments the mammalian homolog is a human gene listed in any one or more of Tables 1C, 1D, 2A, 2B, and 2C, or a homolog thereof found in a non-human mammal. In some embodiments the mammalian homolog is a mammalian (e.g., human) gene that is a homolog of a yeast gene listed in Table 3. In some embodiments, the genetic suppressor or enhancer of ApoE-mediated toxicity is involved in vesicle transport (e.g., ATG20, UBP3, TRS65, BRE5, MUK1, GYPS, or a mammalian (e.g., human) homolog thereof). In some embodiments, the genetic suppressor or enhancer of ApoE-mediated toxicity is involved in endocytosis (e.g., RVS161, OSH2, RVS167, YAP1802, OSH3 or a mammalian (e.g., human) homolog thereof). In some embodiments, the genetic suppressor or enhancer of ApoE-mediated toxicity is involved in ubiquitination/deubiquitination (e.g., APC11, UBP3, UBP7, CDC73, BRE5, RRI2, or a mammalian (e.g., human) homolog thereof). In some embodiments, the genetic suppressor or enhancer of ApoE-mediated toxicity is involved in lipid metabolism (e.g., PER1, MDH3, GPI8, SMP3, SUR1, or a mammalian (e.g., human) homolog thereof). In some embodiments, the genetic suppressor or enhancer of ApoE-mediated toxicity is involved in DNA repair (e.g., MGT1, PCD1, CDC73, RAD14, or a mammalian (e.g., human) homolog thereof). In some embodiments, the genetic suppressor or enhancer of ApoE-mediated toxicity is involved in mitochondrion organization (e.g., ATG20, MHR1, MRP4, RRM3, ILM1, MST1, YTA12, POR1, MRPL10, or a mammalian (e.g., human) homolog thereof).

Also disclosed herein is a method that comprises engineering a mammalian cell to have reduced or absent expression or activity of a mammalian homolog, e.g., a human homolog, of a protein encoded by a yeast gene that is a genetic enhancer or suppressor of ApoE-mediated toxicity. In some embodiments the mammalian cell is engineered by introducing a mutation into an endogenous gene encoding the mammalian homolog of a protein encoded by a yeast gene that is a genetic enhancer or suppressor of ApoE-mediated toxicity. Also disclosed are mammalian cells produced according to the methods. In some embodiments the mammalian cells are human cells. In some embodiments the yeast gene that is a genetic suppressor or enhancer of ApoE-mediated toxicity is listed in any one or more of Tables 1A, 1B, 1C, 1D, 2A, 2B, 2C, and 3. In some embodiments the mammalian homolog is a human gene listed in any one or more of Tables 1C, 1D, 2A, 2B, and 2C, or a homolog thereof found in a non-human mammal. In some embodiments, the mammalian homolog is a mammalian (e.g., human) gene that is a homolog of a yeast gene listed in Table 3. In some embodiments, the mammalian homolog is a human gene that is a homolog of a yeast gene that is involved in vesicle transport (e.g., ATG20, UBP3, TRS65, BRE5, MUK1, and GYPS) or a homolog thereof found in a non-human mammal. In some embodiments, the mammalian homolog is a human gene that is a homolog of a yeast gene that is involved in endocytosis (e.g., RVS161, OSH2, RVS167, and YAP1802) or a homolog thereof found in a non-human mammal. In some embodiments, the mammalian homolog is a human gene that is a homolog of a yeast gene that is involved in ubiquitination/deubiquitination (e.g., APC11, UBP3, UBP7, CDC73, BRE5, and RRI2) or a homolog thereof found in a non-human mammal. In some embodiments, the mammalian homolog is a human gene that is a homolog of a yeast gene that is involved in lipid metabolism (e.g., PER1, MDH3, GPI8, SMP3, and SUR1) or a homolog thereof found in a non-human mammal. In some embodiments, the mammalian homolog is a human gene that is a homolog of a yeast gene that is involved in DNA repair (e.g., MGT1, PCD1, CDC73, and RAD14) or a homolog thereof found in a non-human mammal. In some embodiments, the mammalian homolog is a human gene that is a homolog of a yeast gene that is involved in mitochondrion organization (e.g., ATG20, MHR1, MRP4, RRM3, ILM1, MST1, YTA12, POR1, and MRPL10) or a homolog thereof found in a non-human mammal.

Also disclosed are mammalian cells that comprise an endogenous gene encoding a polypeptide comprising an ApoE protein, wherein the cells: (a) further comprise an expression construct comprising a promoter operably linked to a nucleic acid encoding a polypeptide encoded by a mammalian homolog of a genetic suppressor or enhancer of ApoE-mediated toxicity; or (b) are engineered to have reduced or absent expression or activity of a protein encoded by a mammalian homolog of a yeast gene that is a genetic suppressor or enhancer of ApoE-mediated toxicity. In some embodiments the human homolog is a gene listed in any one or more of Tables 1C, 1D, 2A, 2B, and 2C. In some embodiments, the mammalian homolog is a human gene that is a homolog of a yeast gene listed in Table 3. In some embodiments, the mammalian (e.g., human) homolog is a homolog of a yeast gene that is involved in vesicle transport (e.g., ATG20, UBP3, TRS65, BRE5, MUK1, and GYPS). In some embodiments, the mammalian (e.g., human) homolog is a homolog of a yeast gene that is involved in endocytosis (e.g., RVS161, OSH2, RVS167, and YAP1802). In some embodiments, the mammalian (e.g., human) homolog is a homolog of a yeast gene that is involved in ubiquitination/deubiquitination (e.g., APC11, UBP3, UBP7, CDC73, BRE5, and RRI2). In some embodiments, the mammalian (e.g., human) homolog is a homolog of a yeast gene that is involved in lipid metabolism (e.g., PER1, MDH3, GPI8, SMP3, and SUR1). In some embodiments, the mammalian (e.g., human) homolog is a homolog of a yeast gene that is involved in DNA repair (e.g., MGT1, PCD1, CDC73, and RAD14). In some embodiments, the mammalian (e.g., human) homolog is a homolog of a yeast gene that is involved in mitochondrion organization (e.g., ATG20, MHR1, MRP4, RRM3, ILM1, MST1, YTA12, POR1, and MRPL10). In some embodiments the human ApoE protein is a human ApoE2 protein and the yeast gene that is a genetic suppressor or enhancer of ApoE-mediated toxicity is a genetic suppressor or enhancer of ApoE2-mediated toxicity. In some embodiments the human ApoE protein is a human ApoE3 protein and the genetic suppressor or enhancer is a genetic suppressor or enhancer of ApoE3-mediated toxicity. In some embodiments the human ApoE protein is a human ApoE4 protein and the genetic suppressor or enhancer is a genetic suppressor or enhancer of ApoE4-mediated toxicity.

In some embodiments of any aspect described herein pertaining to mammalian cells, the mammalian cells are human cells. In some embodiments the mammalian cells, e.g., human cells, are pluripotent stem cells or cells generated from pluripotent stem cells. In some embodiments the pluripotent stem cells are induced pluripotent stem (iPS) cells or embryonic stem (ES) cells. In some embodiments the mammalian cells are neural stem cells, neural progenitor cells, glial progenitor cells, neurons, or glial cells. In some embodiments the neural stem cells, neural progenitor cells, glial progenitor cells, neurons, or glial cells are generated in vitro from pluripotent stem cells (iPS cells or ES cells) or by transdifferentiation from a somatic cell of a different cell type. In some embodiments the cells, e.g., iPS cells, neural stem cells, neural progenitor cells, glial progenitor cells, neurons, or glial cells, are derived from a subject who suffers from an ApoE-mediated disease.

In some embodiments of any aspect described herein pertaining to human cells the APOE genotype of the cells may be ε2/ε2, ε2/ε3, ε2/ε4, ε3/ε3, ε3/ε4, or ε4/ε4. In some embodiments the cells are homozygous for APOE genes that encode ApoE2, ApoE3, or ApoE4 (i.e., their genotype is ε2/ε2, ε3/ε3, or ε4/ε4). In some embodiments the cells comprise at least one ε2 allele (i.e., their genotype is ε2/ε2, ε2/ε3, or ε2/ε4). In some embodiments the cells are heterozygous for ε2 (i.e., their genotype is ε2/ε3 or ε2/ε4). In some embodiments the cells are homozygous for ε2 (i.e., their genotype is ε2/ε2). In some embodiments the cells comprise at least one ε3 allele (i.e., their genotype is ε2/ε3, ε3/ε3, or ε3/ε4). In some embodiments the cells are heterozygous for ε3 (i.e., their genotype is ε2/ε3 or ε3/ε4). In some embodiments the cells are homozygous for ε3 (i.e., their genotype is ε3/ε3). In some embodiments the cells comprise at least one ε4 allele (i.e., their genotype is ε2/ε4, ε3/ε4, or ε4/ε4). In some embodiments the cells are heterozygous for ε4 (i.e., their genotype is ε2/ε4 or ε3/ε4). In some embodiments the cells are homozygous for ε4 (i.e., their genotype is ε4/ε4). Likewise, in any aspect pertaining to human subjects, the subjects may have any of the aforementioned APOE genotypes in various embodiments.

In some embodiments of any aspect described herein pertaining to cells, the cells may express an amyloid beta protein. In some embodiments the cells may naturally express an amyloid beta protein. In some embodiments the cells may naturally express a mutant amyloid beta protein. In some embodiments the cells are engineered to express an amyloid beta protein. In some embodiments the cells are mammalian cells engineered to overexpress an amyloid beta protein relative to non-engineered mammalian cells of the same type. In some embodiments the cells are mammalian cells are engineered to express a mutant amyloid beta protein. In any aspect pertaining to subjects, the subjects may express an amyloid beta protein. In some embodiments the subjects may naturally express an amyloid beta protein. In some embodiments the subjects are non-human animals genetically engineered to express an amyloid beta protein.

Further disclosed are screening assays and methods of treatment relating to genetic enhancers and suppressors of ApoE-mediated toxicity and/or mammalian homologs thereof. In some embodiments, the screening assays are to identify candidate compounds that prevent or suppress ApoE-mediated toxicity, and the assays make use of cells that both express ApoE and that have increased or decreased expression or activity of a protein encoded by a genetic suppressor or enhancer of ApoE-mediated toxicity or a mammalian homolog thereof. For example, disclosed is a method of identifying a candidate compound that prevents or suppresses ApoE-mediated toxicity, the method comprising: culturing a cell that comprises: a first expression construct comprising a first promoter operably linked to a first nucleic acid encoding a polypeptide comprising a human ApoE protein, wherein the cell: (a) further comprises a second expression construct comprising a second promoter operably linked to a second nucleic acid encoding a polypeptide encoded by a genetic suppressor or enhancer of ApoE-mediated toxicity or a human homolog thereof or (b) has reduced or absent expression or activity of a protein encoded by a genetic suppressor or enhancer of ApoE-mediated toxicity or a human homolog thereof in the presence of a candidate agent and under conditions that allow for expression of the polypeptide comprising an ApoE protein at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses ApoE-mediated toxicity.

Also disclosed herein is a method of identifying a candidate compound for treating or reducing the risk of an ApoE-associated disease, the method comprising: culturing the aforementioned cell in the presence of a candidate agent and under conditions that allow for expression of the polypeptide comprising an ApoE protein at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a candidate compound for treating or reducing the risk of an ApoE-associated disease.

Also disclosed is a method of identifying a candidate compound that prevents or suppresses ApoE-mediated toxicity, the method comprising: culturing a mammalian cell that comprises a gene encoding a polypeptide comprising an ApoE protein, wherein the cell: (a) further comprises an expression construct comprising a promoter operably linked to a nucleic acid encoding a polypeptide encoded by a mammalian homolog of a genetic suppressor or enhancer of ApoE-mediated toxicity or (b) is engineered to have or inducibly have reduced or absent expression or activity of a protein encoded by a mammalian homolog of a genetic suppressor or enhancer of ApoE-mediated toxicity in the presence of a candidate agent and under conditions that allow for expression of the polypeptide comprising an ApoE protein at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses ApoE-mediated toxicity.

Also disclosed herein is a method of identifying a candidate compound for treating or reducing the risk of an ApoE-associated disease, the method comprising: culturing the aforementioned mammalian cell in the presence of a candidate agent and under conditions that allow for expression of the polypeptide comprising an ApoE protein at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a candidate compound for treating or reducing the risk of an ApoE-associated disease.

In some embodiments of any of the methods of identifying a candidate compound that modulates, e.g., prevents or suppresses, ApoE-mediated toxicity, a compound identified using a cell that expresses a polypeptide comprising particular ApoE isoform (ApoE2, ApoE3, or ApoE4 protein) may be further tested to determine whether or not the compound's effects are specific to that particular isoform. In some embodiments the method comprises determining that the effects are specific to a particular isoform. In some embodiments the method comprises determining that the compound modulates toxicity, e.g., prevents or suppresses toxicity, mediated by two or all three of the ApoE isoforms. In some embodiments a compound that prevents or suppresses toxicity mediated by a particular isoform may be useful for treating a subject who has or is at risk of an ApoE-mediated disease, wherein the subject expresses the particular isoform. In some embodiments a compound that prevents or suppresses toxicity mediated by any of two or more isoforms may be useful for treating a subject who has or is at risk of an ApoE-mediated disease, wherein the subject expresses at least one of the two or more isoforms.

In some aspects, engineered yeast cells described herein may serve as models for human cells and human subjects that express particular ApoE isoform(s) in combination with having mutations or genetic variations in particular genes that are genetic risk factors for ApoE-mediated diseases. Such models may be useful for drug discovery and for identification of additional genetic factors that modify disease risk and may themselves serve as targets for drug discovery.

In some embodiments of any of the methods of identifying a candidate compound that prevents or suppresses ApoE-mediated toxicity, a compound identified using a cell that expresses a polypeptide comprising an ApoE protein and that has increased or decreased expression or activity of a protein encoded by a genetic suppressor or enhancer of ApoE-mediated toxicity or a human homolog thereof may be used to treat a subject who has or is at risk of an ApoE-mediated disease, wherein the subject has a mutation or genetic variation in the gene encoding the human homolog that is associated with an increased risk of developing the disease or is associated with an earlier age of onset of disease. In some embodiments the subject expresses the same ApoE isoform as the cell that was used to identify the compound. For example, in some embodiments a candidate compound identified as one that prevents or suppresses ApoE-mediated toxicity in a yeast cell that expresses ApoE2, and that has increased or decreased expression or activity of a protein encoded by a genetic suppressor or enhancer of ApoE2-mediated toxicity or a human homolog thereof may be used to treat a subject who has or is at risk of an ApoE-mediated disease, has a mutation or genetic variation in the gene encoding the human homolog that is associated with an increased risk of developing the disease or is associated with an earlier age of onset of disease, and expresses ApoE2. In some embodiments candidate compound identified as one that prevents or suppresses ApoE-mediated toxicity in a yeast cell that expresses ApoE3, and that has increased or decreased expression or activity of a protein encoded by a genetic suppressor or enhancer of ApoE3-mediated toxicity or a human homolog thereof may be used to treat a subject who has or is at risk of an ApoE-mediated disease, has a mutation or genetic variation in the gene encoding the human homolog that is associated with an increased risk of developing the disease or is associated with an earlier age of onset of disease, and expresses ApoE3. In some embodiments candidate compound identified as one that prevents or suppresses ApoE-mediated toxicity in a yeast cell that expresses ApoE4, and that has increased or decreased expression or activity of a protein encoded by a genetic suppressor or enhancer of ApoE4-mediated toxicity or a human homolog thereof may be used to treat a subject who has or is at risk of an ApoE-mediated disease, has a mutation or genetic variation in the gene encoding the human homolog that is associated with an increased risk of developing the disease or is associated with an earlier age of onset of disease, and expresses ApoE4.

In some embodiments any of the methods of identifying compounds (e.g., candidate therapeutic agents) may further comprise identifying a molecular target with which a compound physically interacts and whose activity is inhibited or increased by the compound, identifying genes and proteins whose expression or activity or modification state is affected by the compound, or identifying a biological pathway or process that is affected by the compound or involves the molecular target of the compound. Such molecular targets, genes, proteins, biological pathways and processes, and their molecular components may be used as targets for identification of additional compounds that modulate ApoE-mediated toxicity. In some embodiments such molecular targets, genes, proteins, biological pathways and processes, and their molecular components may be used as targets for identification of additional compounds that are candidate therapeutic agents for treating or reducing the risk of an ApoE-associated disease.

Methods that may be used to identify a molecular target of a compound include, e.g., biochemical methods such as using the compound as an affinity reagent to identify proteins to which the compound binds, cross-linking (e.g., using a cross-linkable analog of the compound) and identifying protein(s) to which the compound becomes cross-linked, and genetic methods, such as identifying genes whose deletion or overexpression significantly affects the effect of the compound on the cells. Methods that may be used to identify genes and proteins whose expression or activity or modification state is affected by the compound include, e.g., expression profiling, RNA-Seq, protein microarrays, etc. In some embodiments, described herein are methods that comprise identifying a compound that modulates (e.g., inhibits) ApoE-mediated toxicity in yeast and performing any of the afore-mentioned types of assays, or other suitable assays, to identify a molecular target of the compound.

Further disclosed herein are methods of identifying a binding partner of a human ApoE protein. Any of the preceding yeast cells or mammalian (e.g., human) cells, or any yeast cell or mammalian (e.g., human) cell described herein may be used in a method of identifying a binding partner of a human ApoE protein. In some embodiments, the methods are performed under conditions in which expression of the human ApoE protein is toxic to the cell. In other embodiments, the methods may be performed under conditions in which expression of the human ApoE protein is not toxic to the cell.

Disclosed herein is a method of identifying a binding partner of a human ApoE protein, the method comprising: providing a cell described herein; expressing a nucleic acid encoding a polypeptide comprising a human ApoE protein; and identifying an endogenous polypeptide or an endogenous lipid that binds the polypeptide, thereby identifying a human ApoE protein binding partner.

Also disclosed herein is a method of identifying a binding partner of a human ApoE protein, the method comprising: providing a yeast cell comprising an expression construct comprising a promoter operably linked to a nucleic acid encoding a polypeptide comprising a human ApoE protein; culturing the yeast cell under conditions that allow for expression of the nucleic acid; and identifying an endogenous yeast polypeptide that binds the polypeptide, thereby identifying a human ApoE protein binding partner.

Also disclosed herein is a method of identifying a binding partner of a human ApoE protein, the method comprising: expressing a nucleic acid encoding a polypeptide comprising a human ApoE protein in a yeast cell under conditions that allow for expression of the nucleic acid; and identifying an endogenous lipid or an endogenous polypeptide that binds the polypeptide, wherein said identifying comprises (i) isolating a human ApoE protein complex, and (ii) identifying an endogenous lipid or an endogenous polypeptide present in the human ApoE protein complex by mass spectrometry, thereby identifying the endogenous lipid or the endogenous polypeptide as a binding partner of the human ApoE protein.

In any of the preceding methods of identifying a binding partner of a human ApoE protein, the human ApoE protein may be selected from ApoE2, ApoE3, and ApoE4. In some embodiments, the human ApoE protein is ApoE2. In some embodiments, the human ApoE protein is ApoE3. In some embodiments, the human ApoE protein is ApoE4. In some embodiments, the polypeptide comprising a human ApoE binding protein comprises a detectable marker. In some embodiments, the detectable marker is a fluorescent protein or an epitope tag. In some embodiments, the epitope tag is selected from the group consisting of tandem affinity purification tag, glutathione-S-transferase tag, V5 tag, polyhistidine tag, maltose binding protein tag, chitin binding protein tag, calmodulin tag, E-tag, SPB tag, Strep-tag, VSV-tag, Fc, haemagglutinin tag, myc-tag, and FLAG-tag.

Any of the preceding methods of identifying a binding partner of a human ApoE protein may comprise lysing the cells to produce an extract. In some embodiments, the method further comprises isolating the human ApoE protein from the extract to form a human ApoE complex. In some embodiments, isolating the human ApoE protein comprises co-immunoprecipitation, co-purification, affinity chromatography, size-exclusion chromatography, or ion exchange chromatography. In some embodiments, the method further comprises identifying an endogenous polypeptide present in the human ApoE protein complex. In some embodiments, identifying an endogenous polypeptide present in the ApoE protein complex comprises mass spectrometry or Edman degradation. In some embodiments, the method further comprises identifying an endogenous lipid present in the human ApoE protein complex. In some embodiments, identifying an endogenous lipid comprises mass spectrometry.

In any of the preceding methods of identifying a binding partner of a human ApoE protein, the binding partner may be a candidate therapeutic target for treatment of an ApoE-associated disease. In some embodiments, the ApoE-associated disease is an ApoE4-associated neurodegenerative disease. In some embodiments, the ApoE4-associated disease is Alzheimer's disease, vascular cognitive impairment, cerebral amyloid angiopathy, traumatic brain injury, or multiple sclerosis. In some embodiments, the method further comprises identifying a biological process or biological pathway that is involved in ApoE-mediated toxicity based on the identity of a binding partner identified by the steps of the method.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

(FIG. 2A) Schematic diagram of a portion of an expression construct comprising a GAL promoter operably linked to a nucleic acid encoding a polypeptide comprising a Kar2p signal sequence and a human ApoE protein fused to eGFP (also referred to herein as "Kar2ss-ApoE-eGFP"). (FIG. 2B) Photographs of yeast cells transformed with either a galactose-inducible control vector encoding a yeast Kar2p signal sequence-eGFP fusion polypeptide (top row of each photograph) (also referred to herein as "Kar2ss-eGFP") or a galactose-inducible expression plasmid encoding a Kar2ss-ApoE2-eGFP fusion polypeptide (second row of each photograph), a galactose-inducible expression plasmid encoding a Kar2ss-ApoE3-eGFP fusion polypeptide (third row of each photograph), or a galactose-inducible expression plasmid encoding a Kar2ss-ApoE4-eGFP fusion polypeptide (bottom row of each photograph). The yeast cells were spotted on galactose (left photograph) or glucose (right photograph) at increasing dilutions (lower yeast cell concentrations) from left to right and growth was assessed. The experimental and control transformants grew equally well in the absence of ApoE expression (Glucose, ApoE "OFF"), whereas ApoE expression profoundly inhibited cell growth (Galactose, ApoE "ON"). The ApoE2 strain harbored 4 copies of the construct. The ApoE3 and ApoE4 strains harbored 3-4 copies of the construct. The relative growth level is indicated above the photographs. (FIG. 2C) Graph depicting growth curves of yeast strains expressing eGFP (control), Kar2ss-ApoE2-eGFP, Kar2ss-ApoE3-eGFP, or Kar2ss-ApoE4-eGFP fusion proteins, as indicated, cultured in galactose-containing liquid medium.

(FIG. 3A) Graph of a growth curve of yeast cells containing 4 gene copies of the Kar2ss-ApoE2-eGFP, Kar2ss-ApoE3-eGFP, or Kar2ss-ApoE4-eGFP fusion protein cultured in galactose-containing liquid medium. (FIG. 3B) Western blot showing protein levels of ApoE2, ApoE3, and ApoE4 (as assessed with an anti-GFP antibody) compared to the protein levels of PGK1, which served as a loading control.

FIGS. 5A-5B. Growth and ApoE protein levels of strains harboring different numbers of copies of expression constructs encoding Kar2ss-ApoE2-eGFP, Kar2ss-ApoE3-eGFP, or Kar2ss-ApoE4-eGFP. (FIG. 5A) Graph depicting growth curves of yeast strains expressing eGFP (control), and different amounts of ApoE2, ApoE3, or ApoE4 proteins, as indicated (as Kar2ss-ApoE-eGFP fusions), cultured in galactose-containing liquid medium. (FIG. 5B) Western blot showing different levels of ApoE2, ApoE3, and ApoE4 proteins (as assessed using an anti-GFP antibody) relative to PGK in different yeast transformed with the indicated expression constructs encoding Kar2ss-ApoE-eGFP fusion proteins containing ApoE2, ApoE3, or ApoE4.

(FIG. 6A-6B) Model structures of human ApoE isoforms ApoE2, ApoE3, and ApoE4, indicating the amino acid positions that vary among isoforms (positions 112 and 158) and the differences in proximity between Arg61 (R61) that result from these differences. (FIG. 6C-6D) Model structures of human ApoE isoforms ApoE2, ApoE3, and ApoE4, depicting that the R61T mutation makes the structure of ApoE4 resemble that of ApoE3 (Figures adapted from Hatters, D M, et al., *Trends in Biochemical Sciences,* 31(8):445-454, 2006).

(FIG. 9A) Schematic diagram showing procedure for conducting suppressor screen in yeast. (FIGS. 9B-9C) Schematic diagram showing procedure for conducting suppressor screens using specific ApoE isoforms.

FIGS. 11A-11H. (FIG. 11A-11D) Schematic diagram of MUP1 assay for endocytosis. Top part of figure shows ApoE expression construct (left) and MUP1 reporter construct encoding a MUP1-mKate 2 fusion protein (right). Lower part of figure shows schematic diagram of yeast strains harboring the ApoE expression construct and MUP1 construct in the presence of galactose and the absence of methionine conditions (-MET, left) and in the presence of galactose and methionine (+MET, right). In the absence of methionine, the MUP1 fusion protein remains at the plasma membrane (left), while in the presence of methionine, MUP1 fusion protein is endocytosed (right). (FIG. 11E-11F) Upper panel shows fluorescence images of the yeast strains expressing both (i) a human ApoE protein, alpha-synuclein, or Aβ, and (ii) the MUP 1 reporter construct. Lower panel shows growth of the various strains on galactose-containing medium. (FIG. 11G-11H) ApoE4, Aβ, and α-synuclein disrupt endosomal trafficking in different ways. The indicated strains as described in FIG. 11 (FIG. 11E-11F) were induced to express ApoE4, Aβ, and α-synuclein for 8 h. As shown in the fluorescent micrographs, trafficking of MUP1 appears different in the presence of ApoE4, Aβ, or α-synuclein.

DETAILED DESCRIPTION

Figure 1:
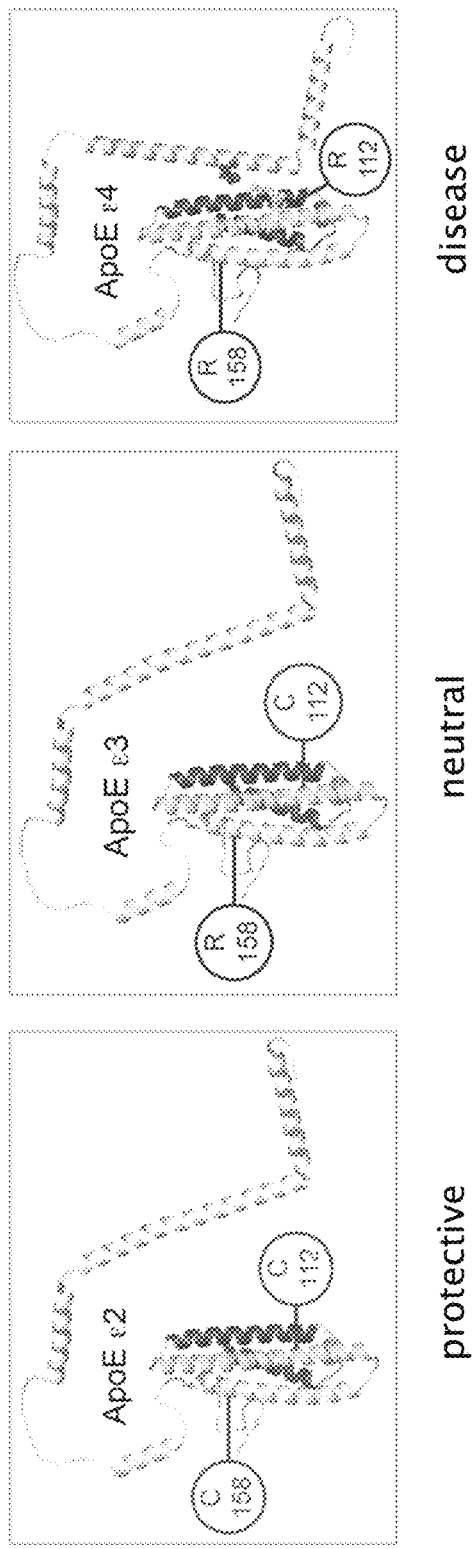
FIG. 1. Model structures of human ApoE isoforms ApoE2, ApoE3, and ApoE4, indicating the amino acid positions that vary among isoforms (positions 112 and 158) and the differences in structure that result from these differences. (Figure adapted from Hatters, D M, et al., *Trends in Biochemical Sciences*, 31(8):445-454, 2006).

In some aspects, described herein is a yeast cell engineered to produce a polypeptide comprising an ApoE protein, wherein production of the polypeptide in the cell results in a decrease in growth or viability of the cell. In some embodiments, production of the polypeptide renders the yeast cell non-viable. In some embodiments the ApoE protein is a human ApoE protein. In some embodiments the human ApoE protein is a human ApoE2 protein. In some embodiments the human ApoE protein is a human ApoE3 protein. In some embodiments the human ApoE protein is a human ApoE4 protein. In some embodiments the polypeptide comprises a signal sequence and an ApoE protein.

In some aspects, described herein is a yeast cell comprising an expression construct comprising a promoter operably linked to a nucleic acid encoding a polypeptide comprising a human ApoE protein, wherein expression of the nucleic acid and production of the polypeptide in the cell results in a decrease in growth or viability of the cell. In some embodiments, production of the polypeptide renders the yeast cell non-viable. In some embodiments the ApoE protein is a human ApoE protein. In some embodiments the human ApoE protein is a human ApoE2 protein. In some embodiments the human ApoE protein is a human ApoE3 protein. In some embodiments the human ApoE protein is a human ApoE4 protein. In some embodiments the polypeptide comprises a signal sequence and an ApoE protein.

ApoE-expressing yeast cells described herein can be used to identify compounds or genetic factors that modulate ApoE-induced toxicity, e.g., compounds that inhibit ApoE-induced toxicity. Compounds identified by such screens can be used for the treatment or prevention of ApoE-associated diseases. As used herein, an "ApoE-associated disease" is a disease characterized in that there is a statistically significant association between presence of a particular allele of the APOE gene in the genome of a subject and development of the disease, development of the disease at an age at least 3 years less on average than the average age of onset of the disease, or having a severe or rapidly progressing form of the disease. In some embodiments individuals who have at least one copy of the allele have at least a 1.05-fold, 1.1-fold, 1.2-fold, 1.3-fold, 1.4-fold, 1.5-fold, 1.75-fold, 2.0-fold, 2.5-fold, 3.0-fold, 3.5-fold, 4.0-fold, 4.5-fold, or 5-fold greater risk of developing or having the disease, as compared with the risk among individuals in the general population or as compared with the risk among individuals who do not harbor that particular allele. Individuals or groups may be age-matched.

As used herein, "ApoE-induced toxicity" and "ApoE-mediated toxicity" are used interchangeably to refer to a reduction, impairment, or other abnormality in one or more cellular functions or structures, a reduction in growth or viability, or a combination thereof, occurring as a result of or associated with expression of an ApoE protein. In the context of a yeast cell, ApoE-mediated toxicity may be manifested as a reduction in growth or viability, e.g., reduced viability or non-viability, or a reduction, impairment, or other abnormality in one or more cellular functions or structures, e.g., reduction, impairment, or other abnormality in endocytosis or vesicle trafficking. In the context of a neuron or glial cell, e.g., a mammalian neuron or glial cell, ApoE-mediated toxicity may be manifested as a reduction in growth or viability, e.g., reduced viability or non-viability, or a reduction, impairment, or other abnormality in one or more cellular functions or structures. Cellular functions include any of the biological processes and pathways performed in a cell or by a cell, either itself or together with one or more other cells, in vitro or in vivo (e.g., in the context of a tissue or organ in vivo). In some embodiments, a cellular function is endocytosis, vesicle trafficking, axonal transport, mitochondrial function (e.g., ATP production), neurite outgrowth, neurotransmission, neurogenesis, or maintaining homeostasis. ApoE-mediated toxicity in vivo may be manifested to a variety of extents and in a variety of ways ranging from cellular dysfunction to death. In some embodiments ApoE-mediated toxicity may be evidenced in a subject by development of an ApoE-mediated disease (or one or more symptoms or signs of an ApoE-mediated disease) or by an increased propensity to develop an ApoE-mediated disease in subjects who express a particular ApoE isoform. In some embodiments ApoE-mediated toxicity may be manifested at least in part as an increase in the formation, deposition, accumulation, or persistence of amyloid beta aggregates or an increase in amyloid beta-mediated toxicity as compared with a normal control. In some embodiments ApoE-mediated toxicity may be manifested as a decrease or defect in cognition, behavior, or memory, as compared with a normal control. In some embodiments, contacting mammalian cells or treating a mammalian subject with an agent as described herein alleviates one or more manifestations of ApoE-mediated toxicity.

In some embodiments an ApoE-associated disease is associated with the ε4 allele, encoding ApoE4, and may be referred to as an ApoE4-associated disease. In some embodiments an ApoE4-associated disease is a neurodegenerative disease, e.g., Alzheimer's disease (AD), dementia with Lewy bodies (DLB), mild cognitive impairment (MCI), frontotemporal dementia (FTD), cerebral amyloid angiopathy (CAA), CAA-associated intracerebral hemorrhage, vascular cognitive impairment, Parkinson's disease (PD), multiple sclerosis (MS), traumatic brain injury (TBI), or Fragile X-associated tremor/ataxia syndrome. CAA is a condition characterized by deposition of protein, mainly amyloid beta protein, in the walls of cerebral blood vessels. CAA is a frequent finding in AD patients but also occurs in the absence of evidence of AD.

In some embodiments an ApoE-associated disease is an "amyloid beta-associated disease" which term refers to any condition characterized by an abnormally high levels of production, accumulation, and/or aggregation of amyloid beta peptides, e.g., in the form of amyloid plaques, particularly in the brain. Amyloid beta-associated diseases include AD, Down's syndrome, Fragile X syndrome, CAA, CAA-associated intracerebral hemorrhage, and sporadic inclusion body myositis. It has been suggested that ApoE4 may inhibit Aβ clearance and/or is less efficient in mediating Aβ clearance compared with ApoE3 and ApoE2. Immunohistological evidence demonstrates the presence of ApoE in plaques in the brains of patients with AD along with Aβ, and Aβ deposition in plaques is more abundant in APOE ε4 carriers compared with non-carriers. In some embodiments yeast cells of the present invention may be used to identify compounds and genetic factors that modulate, e.g., inhibit, Aβ-mediated toxicity.

Yeast cells and mammalian cells described herein expressing a human ApoE protein may also be used in methods of identifying a binding partner of a human ApoE protein. The binding partner may be any binding partner within the cell and/or secreted from the cell, for example, an endogenous polypeptide or an endogenous lipid. A binding partner identified by the methods of the invention may be a candidate therapeutic target for treatment of an ApoE-associated disease. A binding partner of a human ApoE protein may also be involved in a biological pathway or a biological process involved in ApoE-mediated toxicity.

Proteins and Nucleic Acids

In some aspects, described herein are compositions and methods useful for identifying candidate compounds that inhibit ApoE-induced toxicity. In some aspects, described herein are compositions and methods useful for identifying genes (and their encoded proteins) that are suppressors or enhancers of ApoE-induced toxicity (sometimes termed "genetic suppressors" or "genetic enhancers" or collectively "genetic modifiers" or "modifiers" of ApoE-mediated toxicity). Certain of the compositions and methods described herein comprise or use a fusion polypeptide comprising a signal sequence and a human ApoE protein.

The term "human ApoE protein" includes proteins whose amino acid sequence comprises or consists of an amino acid sequence of a naturally occurring wild type ApoE protein as well as proteins whose amino acid sequence comprises or consists of an amino acid sequence of a naturally occurring mutant ApoE protein. Human APOE has NCBI Gene ID NO 348. APOE has three common alleles in humans: APOE ε2 (frequency ~8%), APOE ε3 (frequency ~80%), and APOE ε4 (frequency ~14%). Human ApoE protein is naturally synthesized as a precursor polypeptide of 317 amino acids, including an 18 amino acid signal sequence, which is cleaved to produce the mature 299 amino acid polypeptide. The sequence of human ApoE3 precursor polypeptide is found under NCBI RefSeq Acc. No. NP_000032.1. For purposes of description, the numbering of amino acids based on the mature 299 amino acid human ApoE polypeptide will be used herein.

The proteins encoded by the three common APOE alleles differ at two amino acids, located at positions 112 and 158 in the mature protein. ApoE2 has cysteine at residues 112 and 158; ApoE3 has cysteine at residue 112 and arginine at residue 158; and ApoE4 has arginine at residues 112 and 158. The sequences of the mature wild type human ApoE proteins are shown below, with the amino acids at positions 112 and 158 shown in bold and underlined.

The sequence of ApoE2 is:

(SEQ ID NO: 1)
KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVCGRLVQYRGEVQAMLGQSTEELRVRLASHLRKLRKRLLR

DADDLQKCLAVYQAGAREGAERGLSAIRERLGPLVEQGRVRAATVGSLAG

QPLQERAQAWGERLRARMEEMGSRTRDRLDEVKEQVAEVRAKLEEQAQQI

RLQAEAFQARLKSWFEPLVEDMQRQWAGLVEKVQAAVGTSAAPVPSDNH.

The sequence of ApoE3 is:

(SEQ ID NO: 2)
KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVCGRLVQYRGEVQANILGQSTEELRVRLASHLRKLRKRLL

RDADDLQKRLAVYQAGAREGAERGLSAIRERLGPLVEQGRVRAATVGSLA

GQPLQERAQAWGERLRARMEEMGSRTRDRLDEVKEQVAEVRAKLEEQAQQ

IRLQAEAFQARLKSWFEPLVEDMQRQWAGLVEKVQAAVGTSAAPVPSDNH.

The sequence of ApoE4 is:

(SEQ ID NO: 3)
KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVRGRLVQYRGEVQANILGQSTEELRVRLASHLRKLRKRLL

RDADDLQKRLAVYQAGAREGAERGLSAIRERLGPLVEQGRVRAATVGSLA

GQPLQERAQAWGERLRARMEEMGSRTRDRLDEVKEQVAEVRAKLEEQAQQ

IRLQAEAFQARLKSWFEPLVEDMQRQWAGLVEKVQAAVGTSAAPVPSDNH.

Naturally occurring ApoE mutations include ApoE4 (L28P), which confers on carriers an increased risk for late-onset AD that remains significant even after adjusting for the effect of ApoE4 itself (Kamboh, M I, et al. Neurosci Lett. 1999 Mar. 26; 263(2-3):129-32.) Other variants include E13K, R136C, G196S, Q248E, R251G, and G278W (Tindale, L C, et al., *Neurobiology of Aging*, 35, 727e1-727e3 (2014).

In some embodiments, a variant of a human ApoE protein may be used. A "variant human ApoE protein" (also referred to as a "human ApoE variant") comprises or consists of a polypeptide that differs (via substitution, deletion, and/or addition, e.g., insertion) from a naturally occurring human ApoE protein at one or more amino acids, is not known to occur in nature, and is at least 80%, 90%, 95%, 96%, 97%, 98%, 99%, or more identical to a naturally occurring human ApoE protein across a length of at least 200, 250, 260, 270, 280, 290, 295, or 299 amino acids (the full length of human ApoE). In some embodiments a variant human ApoE protein differs from a naturally occurring ApoE protein at up to 30 amino acids (e.g., differs at no more than 20 amino acids, differs at no more than 10 amino acids, differs at no more than 5 amino acids, differs at no more than 4 amino acids, differs at no more than 3 amino acids, differs at no more than 2 amino acids, or differs at 1 amino acid) and, in at least some embodiments, retains the ability to cause a decrease in growth or viability of a yeast cell when expressed in a fusion polypeptide as described herein. In some embodiments a human ApoE variant differs from a wild type or mutant ApoE at one or more specific positions, e.g., position 61 or position 255. For example, the variant may harbor an R61T alteration. In some embodiments one or more bulky and/or hydrophobic residues in the region of residues 253-289 are replaced with either smaller hydrophobic or polar/charged residues. For example, the alteration may be F257A, W264R, V269A, L279Q, and V287E. In some embodiments the alteration reduces the toxicity of the variant relative to a wild type ApoE protein. In some embodiments the alteration increases the toxicity of the variant relative to a wild type ApoE protein. In some embodiments a variant human ApoE protein comprises or consists of a fragment of a human ApoE protein ("human ApoE protein fragment"). A human ApoE protein fragment is shorter than human ApoE protein and is identical to a human ApoE protein across the full length of the fragment. In some embodiments a variant or fragment human ApoE protein has an N-terminal truncation, a C-terminal truncation, or both, relative to a full length human ApoE protein. In some embodiments a variant or fragment human ApoE protein lacks up to 1, 2, 3, 4, 5, 10, 15, 20, or 25 amino acids from the N-terminus, C-terminus, or both, of a human ApoE protein. In some embodiments a variant may alternately or additionally have one or more internal deletions of up to 1, 2, 3, 4, 5, 10, 15, 20, or 25 amino acids, up to a total of 50 amino acids. In some embodiments a variant or fragment human ApoE protein lacks at least amino acids 272 to 299 of a human ApoE protein. It should be understood that where the present disclosure refers to variant or fragment human ApoE protein, the variant or fragment may be a variant or fragment of ApoE2, ApoE3, or ApoE4. It should also be understood that where the present disclosure refers to an ApoE protein, the disclosure provides embodiments in which a variant ApoE protein or fragment of an ApoE protein is used. In some embodiments, a variant with a different level of toxicity may, for example, be used in a screen in combination with overexpression or inhibition of genes that suppressors or enhancers of ApoE-mediated toxicity.

As used herein, the term "signal sequence" or "secretion signal" refers to a peptide sequence that is present within a polypeptide and causes the polypeptide to be targeted to the endoplasmic reticulum within a cell. An exemplary signal sequence described in the working examples is the yeast Kar2p signal sequence: MFFNRLSAGKLLVPLSVVLY-ALFVVILPLQNSFHSSNVLVRG (SEQ ID NO: 4). However, a wide variety of signal sequences are known and can be used to cause endoplasmic reticulum targeting of the fusion polypeptides described herein. Signal sequences are reviewed in e.g., Wilkinson et al. (1997) J Membr Biol. 155(3):189-97, Haguenauer-Tsapis (1992) Mol Microbiol. 6(5):573-9, and Pool (2005) Mol Membr Biol. 22(1-2):3-15. In some embodiments a mammalian, e.g., human, signal sequence is used. For example, in some embodiments, a signal sequence found in a naturally occurring human ApoE precursor polypeptide may be used, e.g., MKVLWAALL-VTFLAGCQA (SEQ ID NO: 5). In some embodiments a human insulin preprotein (NCBI Gene ID 3630) secretion signal sequence may be used. Human insulin preprotein secretion signal sequence has sequence MALWMRLLPL-LALLALWGPDPAAA (SEQ ID NO: 11).

A polypeptide containing a human ApoE protein, e.g., containing a signal sequence and a human ApoE protein, may optionally comprise a second domain fused to the ApoE protein. The second domain of the fusion protein may, for example, be an immunoglobulin domain, a dimerizing domain, a targeting domain, a stabilizing domain, a purification domain, or a detection protein. Exemplary detection proteins include: a fluorescent protein such as green fluorescent protein (GFP), cyan fluorescent protein (CFP), yellow fluorescent protein (YFP), blue fluorescent protein (BFP) (including enhanced versions of GFP, CFP, YFP, or BFP, known as eGFP, eCFP, eYFP, and eBFP, respectively), Cerulean, dsRed; mKate, mTomato, mCherry, an enzyme such as β-galactosidase or alkaline phosphatase (AP). Other examples of detection proteins include an epitope such as tandem affinity purification (TAP) tag, glutathione-S-transferase (GST) tag, V5 tag, polyhistidine tag (e.g., His6 (SEQ ID NO: 12), maltose binding protein (MBP) tag, chitin binding protein (CBP) tag, calmodulin tag, E-tag, SPB tag, Strep-tag, VSV-tag, Fc, haemagglutinin (HA) tag, myc-tag, and FLAG-tag. For example, an ApoE protein can be fused to GFP at the N- or C-terminus or other parts of the ApoE protein. Such fusion proteins provide methods for rapid and easy detection and identification of the ApoE protein in the recombinant yeast cell. An ApoE protein may be fused to one, two, or more domains. For example, it may be fused to a first domain at the N-terminus and a second domain at the C-terminus. One of ordinary skill in the art will appreciate that a heterologous domain or protein may serve multiple purposes. In some embodiments there may be a linker peptide between the signal sequence and the ApoE protein, between the ApoE protein and a second domain, or both. In some embodiments a linker peptide may be between 1 and 50 amino acids long, e.g., between 5 and 25 amino acids long.

Also described herein are methods of preparing and transferring nucleic acids, e.g., plasmids, encoding a polypeptide comprising an ApoE protein into a cell so that the cell expresses the ApoE protein. The term "ApoE nucleic acid" encompasses a nucleic acid containing a sequence encoding any of the ApoE proteins described herein. Exemplary ApoE nucleic acids include those encoding human ApoE2, human ApoE3, or human ApoE4.

The term "nucleic acid" generally refers to at least one molecule or strand of DNA, RNA or a derivative or mimic thereof, containing at least one nucleobase, for example, a naturally occurring purine or pyrimidine base found in DNA or RNA. Generally, the term "nucleic acid" refers to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In some embodiments a yeast cell comprising an expression construct comprising a promoter operably linked to a nucleic acid encoding a polypeptide comprising a signal sequence and a human ApoE protein further comprises an expression construct that encodes a human amyloid beta protein. As used herein, the term "human amyloid beta protein" refers to a protein whose amino acid sequence is identical to the sequence of a naturally occurring 38-43 amino acid amyloid beta peptide that is derived via proteolytic processing of the human amyloid precursor protein (APP) and is associated with amyloid pathologies, such as Alzheimer's disease. The term "human amyloid beta protein" includes proteins whose amino acid sequence comprises or consists of an amino acid sequence of a naturally occurring wild type amyloid beta peptide as well as proteins whose amino acid sequence comprises or consists of an amino acid sequence of a naturally occurring mutant amyloid beta peptide. Wild type amyloid beta peptides include amyloid beta 1-38, amyloid beta 1-39, amyloid beta 1-40, amyloid beta 1-41, amyloid beta 1-42, and amyloid beta 1-43. Amino acids 1-43 of human amyloid beta are as follows:

(SEQ ID NO: 6)
DAEFRHDSGYEVHHQKLVFFAEDVGSNKGAIIGLMVGGVVIAT.

Amyloid beta mutations include A2T, H6R, D7N, A21G, E22G (Arctic), E22Q (Dutch), E22K (Italian), D23N (Iowa), A42T, and A42V (wherein the numbering is relative to the amyloid beta peptide of SEQ ID NO: 6). These mutations may optionally be present in any of the amyloid beta peptides 1-38, 1-39, 1-40, 1-41, 1-42, and 1-43.

In some embodiments the human amyloid beta protein is expressed as part of a fusion polypeptide comprising a signal sequence and a human amyloid beta protein. In some embodiments, the signal sequence is identical to the signal sequence of a naturally occurring yeast protein (e.g., the signal sequence is identical to the yeast Kar2p signal sequence or MATα signal sequence) and the human amyloid beta protein is wild type amyloid beta 1-42. A polypeptide containing a signal sequence and a human amyloid beta protein may optionally be fused with a second domain. The second domain of the fusion protein can optionally be an immunoglobulin domain, a dimerizing domain, a targeting domain, a stabilizing domain, a purification domain, or a detection protein, e.g., any of the second domains described above in regard to fusion proteins comprising human ApoE, and may be used for any of the same purposes, may be located at the N-terminus, C-terminus, or elsewhere in the protein, and/or may be joined to the amyloid beta protein by a linker peptide, as described above for human ApoE proteins. Exemplary nucleic acid constructs encoding a polypeptide comprising a signal sequence and a human amyloid beta protein, and their introduction into yeast cells, are described in US Patent Application Publication Nos. 20130022988 and 20130045483. Also described therein is the discovery that a fusion polypeptide containing a signal sequence and a human amyloid beta protein is toxic when expressed in a yeast cell. In certain embodiments the present invention contemplates use of any such nucleic acid construct in combination with a nucleic acid construct encoding a human ApoE protein, e.g., in a yeast cell. In certain embodiments the fusion polypeptide containing a signal sequence and a human amyloid beta protein may be expressed under control of an inducible promoter.

In some embodiments, a variant of a human amyloid beta protein can be used. For purposes of the present disclosure, a "variant human amyloid beta protein" differs (via substitution, deletion, and/or insertion) from a naturally occurring amyloid beta peptide at up to 10 amino acids (e.g., differs at no more than 5 amino acids, differs at no more than 4 amino acids, differs at no more than 3 amino acids, differs at no more than 2 amino acids, or differs at 1 amino acid) and, in at least some embodiments, has the ability to cause a decrease in growth or viability of a yeast cell when expressed in a fusion polypeptide comprising a signal sequence.

In some embodiments a yeast cell expresses a first polypeptide comprising a human ApoE protein and a first detectable domain and a second polypeptide comprising a human amyloid beta protein and a second detectable domain, wherein the first and second detectable domains are different and readily distinguishable, e.g., by color. In some embodiments the first polypeptide comprises a signal sequence fused to a human ApoE protein and a first detectable domain. In some embodiments the second polypeptide comprises a signal sequence fused to a human amyloid protein and a second detectable domain.

In some embodiments a yeast cell comprising an expression construct comprising a promoter operably linked to a nucleic acid encoding a polypeptide comprising a signal sequence and a human ApoE protein does not comprise an expression construct that encodes a human amyloid beta protein.

Exemplary nucleic acid sequences encoding polypeptides comprising ApoE are provided in the Examples. However, one of ordinary skill in the art will appreciate that due to the degeneracy of the genetic code, a given amino acid sequence may be encoded by any of a wide variety of nucleic acid sequences. Any such nucleic acid sequence may be used to encode a polypeptide of interest, e.g., a polypeptide comprising human ApoE. In some embodiments of any aspect of the present disclosure a nucleic acid sequence is codon optimized for expression in cells of a species of interest. For example, in some embodiments a polypeptide comprising human ApoE is codon optimized for expression in yeast.

Yeast Cells, Vectors

Yeast strains that can be used in the compositions and methods described herein include, but are not limited to, *Saccharomyces cerevisiae*, *Saccharomyces uvae*, *Saccharomyces kluyveri*, *Schizosaccharomyces pombe*, *Kluyveromyces lactis*, *Hansenula polymorpha*, *Pichia pastoris*, *Pichia methanolica*, *Pichia kluyveri*, *Yarrowia lipolytica*, *Candida* sp., *Candida albicans*, *Candida utilis*, *Candida cacaoi*, *Geotrichum* sp., and *Geotrichum fermentans*. Although much of the discussion herein relates to *Saccharomyces cerevisiae* this is merely for illustrative purposes. Other yeast strains can be substituted for *S. cerevisiae*.

Certain aspects of the disclosure relate to screening methods for identifying candidate therapeutic agents (e.g., pharmaceutical, chemical, or genetic agents). The methods described herein can optionally be carried out in yeast strains bearing mutations in the ERG6 gene, the PDR1 gene, the PDR3 gene, the PDR5 gene, the SNQ2 gene, and/or any other gene which affects membrane efflux pumps and/or increases permeability for drugs. In some embodiments the strain has mutations in the genes encoding PDR1 and PDR3.

A nucleic acid encoding a fusion polypeptide described herein may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2μ plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994, and successors thereof.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2µ plasmids is YEp, which contains a sequence approximately 1 kb in length (named the 2µ sequence). The 2µ sequence acts as a yeast replicon giving rise to higher plasmid copy number. For example, the copy number may be between 50 and 100 copies per cell, e.g., about 60-80 copies per cell. However, these plasmids can be unstable and may require selection for maintenance. Copy number can be increased by having on the plasmid a selection gene operatively linked to a crippled promoter.

A wide variety of plasmids can be used in the compositions and methods described herein. In some embodiments, the plasmid is an integrative plasmid (e.g., pRS303, pRS304, pRS305, pRS306, or a derivative thereof). See, e.g., Alberti et al. (2007) "A suite of Gateway cloning vectors for high-throughput genetic analysis in *Saccharomyces cerevisiae*" Yeast 24(10):913-19. In some embodiments, the plasmid is an episomal plasmid (e.g., p426GPD, p416GPD, p426TEF, p423GPD, p425GPD, p424GPD or p426GAL). In some embodiments, the plasmid is a centomeric plasmid (e.g., pRS313, pRS314, pRS315, pRS316, or a derivative thereof).

Regardless of the type of plasmid used, yeast cells are typically transformed by chemical methods (e.g., as described by Rose et al., 1990, Methods in Genetics, Cold Spring Harbor Laboratory Press, Cold Spring Harbor, N.Y., or Burke, D J, et al., Methods in Genetics: A Cold Spring Harbor Laboratory Course Manual, Cold Spring Harbor Laboratory Press, Cold Spring Harbor, N Y, 2005). The cells are typically treated with lithium acetate to achieve transformation efficiencies of approximately $10^4$ colony-forming units (transformed cells)/µg of DNA. Yeast perform homologous recombination such that the cut, selectable marker recombines with the mutated (usually a point mutation or a small deletion) host gene to restore function. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerolphosphate dehydratase or IGP dehydratase); or 5) LYS2 (α-aminoadipate-semialdehyde dehydrogenase).

The yeast vectors (plasmids) described herein may also contain promoter sequences. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one naturally associated with a nucleic acid sequence, as may be obtained by isolating the 5' non-coding sequences located upstream of the coding segment and/or exon. Such a promoter can be referred to as an "endogenous promoter." Alternatively, a promoter may be a recombinant or heterologous promoter, which refers to a promoter that is not normally associated with a nucleic acid sequence in its natural environment. Such promoters may include promoters of other genes and promoters that are not naturally occurring. The promoters employed may be constitutive or regulatable, e.g., inducible.

A variety of promoters (elements) may be employed to regulate the expression of a RNA in yeast cells. Examples of inducible yeast promoters include the galactose-inducuble promoters GAL1-10, GAL1, GALL, GALS, and the copper-inducible promoter CUP1. Examples of repressible yeast promoters include the methionine-repressible promoters Met25 and Met3. The tetO promoter may be used to achieve regulatable expression in yeast. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. It will be understood that certain genes such as ADH may be constitutive in glucose medium and may be repressed in the absence of glucose. Autonomously replicating expression vectors of yeast containing promoters inducible by glucocorticoid hormones have also been described, including the glucocorticoid responsive element (GRE). See, e.g., Mumberg, D., et al., Gene, 156: 119-122 (1995); Ronicke et al., Methods Enzymol.; 283:313-22 (1997); Funk, M., et al., Methods Enzymol.; 350:248-57 (2002), incorporated herein by reference. Yet other yeast vectors containing constitutive or inducible promoters such as alpha factor, alcohol oxidase, and PGH may be used. For reviews, see Ausubel et al., 1994.

In some embodiments, a yeast strain is used that allows for expression, e.g., inducible expression, from GAL promoters on carbon sources other than galactose. In some embodiments, the strain carries an integrated or episomal (e.g., plasmid-borne) gene encoding a fusion protein, wherein the Gal4 DNA binding domain is fused to a transcriptional activation domain and a regulatory domain. The fusion protein is characterized in that its ability to activate transcription is regulated by binding of a small molecule to the regulatory domain. For example, in some embodiments, the fusion protein does not activate transcription in the absence of the small molecule, whereas in the presence of the small molecule, the fusion protein activates transcription. Exemplary small molecules include, e.g., steroid hormones, wherein the corresponding regulatory domain comprises at least a portion of a receptor for the small molecule. For example, the small molecule may be an estrogen (e.g., estradiol), or analog thereof (e.g., tamoxifen), and the corresponding regulatory domain comprises at least a portion of the estrogen receptor (ER). Exemplary activation domains include, e.g., viral protein activation domains such as the herpes simplex virus protein VP16 activation domain. In some embodiments, the strain carries an integrated or episomal (e.g., plasmid-borne) gene encoding a Gal4-ER-VP16 fusion protein. Presence of an estrogen receptor ligand, e.g., estradiol, in the medium, allows for expression from GAL promoters on carbon sources other than galactose. See, e.g., Gao C Y and Pinkham J L et al., Biotechniques, 2000;

29(6):1226-31. One of skill in the art will appreciate that numerous ways exist to render expression of a molecule of interest, e.g., an ApoE protein, conditional, e.g., on culture media containing galactose or other carbon sources.

In some embodiments the yeast cell harbors between 1 and 20 integrated copies, e.g., 1, 2, 3, 4, 5, 6, 7, 8, 9, 10, 11, 12, 13, 14, 15, 16, 17, 18, 19, or 20 integrated copies of an nucleic acid encoding a polypeptide comprising ApoE2, ApoE3, or ApoE4. For example, in some embodiments the yeast cell harbors 4 integrated copies of a nucleic acid encoding a polypeptide comprising ApoE2. In some embodiments the yeast cell harbors 13-15 integrated copies of a nucleic acid encoding a polypeptide comprising ApoE2. In some embodiments the yeast cell harbors between 2 and 10 integrated copies, e.g., 2, 3, 4, 5, 6, 7, 8, 9, or 10 integrated copies, of a nucleic acid encoding a polypeptide comprising ApoE3. For example, in some embodiments the yeast cell harbors 3-4 integrated copies of a nucleic acid encoding a polypeptide comprising ApoE3. In some embodiments the yeast cell harbors 5-9 integrated copies of a nucleic acid encoding a polypeptide comprising ApoE3. In some embodiments the yeast cell harbors between 1 and 5 integrated copies, e.g., 1, 2, 3, 4, or 5 integrated copies, of a nucleic acid encoding a polypeptide comprising ApoE4. For example, in some embodiments the yeast cell harbors 2 integrated copies of a nucleic acid encoding a polypeptide comprising ApoE4. In some embodiments the yeast cell harbors 3-4 integrated copies of a nucleic acid encoding a polypeptide comprising ApoE4. In some embodiments multiple copies are integrated at a single locus. In some embodiments one or more copies is integrated at each of two or more loci. In some embodiments the nucleic acids encoding an ApoE isoform in a cell are operably linked to the same promoter. In some embodiments 2 or more nucleic acids encoding an ApoE isoform in a cell are operably linked to different promoters. In some embodiments 2 or more nucleic acids encoding an ApoE isoform in a cell are operably linked to a single promoter. In some embodiments 2 or more nucleic acids encoding an ApoE isoform in a cell are operably linked to individual copies of the same promoter. In some embodiments, a yeast cell may harbor one or more copies of a nucleic acid encoding a polypeptide comprising a first ApoE isoform and one or more copies of a nucleic acid encoding a polypeptide comprising a second ApoE isoform and, optionally, one or more copies of a nucleic acid encoding a polypeptide comprising the third ApoE isoform. The ApoE isoforms may be ApoE2, ApoE3, or ApoE4, in any combination. The nucleic acids are operably linked to one or more promoter(s). The strains may be used for compound screens, genetic screens, or both, such as those described herein. In some embodiments, the strains may be used in a method of identifying a human ApoE protein binding partner, such as those described herein.

In some embodiments a yeast strain contains constructs that, when expressed, cause the cell to produce or contain between 0.5-fold and 2-fold as much ApoE polypeptide as an ApoE2 intox, ApoE3 intox, or ApoE4 intox strain described in the Examples and/or Figures. In some embodiments a yeast strain contains constructs that, when expressed, cause the cell to produce or contain between 0.5-fold and 2-fold as much ApoE polypeptide as an ApoE2 hitox, ApoE3 hitox, or ApoE4 hitox strain described in the Examples and/or Figures. In some embodiments a yeast strain contains constructs that, when expressed, cause the cell to produce or contain between 0.75-fold and 1.25-fold as much ApoE polypeptide as an ApoE2 intox, ApoE3 intox, or ApoE4 intox strain described in the Examples and/or Figures. In some embodiments a yeast strain contains constructs that, when expressed, cause the cell to produce or contain between 0.75-fold and 1.25-fold as much ApoE polypeptide as an ApoE2 hitox, ApoE3 hitox, or ApoE4 hitox strain described in the Examples and/or Figures. In some embodiments a yeast strain contains constructs that, when expressed, cause the cell to produce or contain about the same amount of ApoE polypeptide as an ApoE2 intox, ApoE3 intox, or ApoE4 intox strain described in the Examples and/or Figures. In some embodiments a yeast strain contains constructs that, when expressed, cause the cell to produce or contain about the same amount of ApoE polypeptide as an ApoE2 hitox, ApoE3 hitox, or ApoE4 hitox strain described in the Examples and/or Figures. In some embodiments the amount of polypeptide may be determined by Western blot, by fluorescence, by ELISA assay, using surface plasmon resonance (e.g., BIAcore), mass spectrometry, or other suitable assays. The term "about" as used herein, generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value).

In some embodiments a yeast strain contains constructs that, when expressed, cause the cell to display about the same level of toxicity as an ApoE2 intox, ApoE3 intox, or ApoE4 intox strain described in the Examples and/or Figures. In some embodiments a yeast strain contains constructs that, when expressed, cause the cell to display about the same level of toxicity as an ApoE2 hitox, ApoE3 hitox, or ApoE4 hitox strain described in the Examples and/or Figures. In some embodiments a "lowtox" strains has fewer copies than the intox strains described in the Examples and/or Figures. For example, in some embodiments a lowtox strain has 2-3 copies of a nucleic acid encoding a polypeptide comprising ApoE2, 1-2 copies of a nucleic acid encoding a polypeptide comprising ApoE3, or 1 copy of a nucleic acid encoding a polypeptide comprising ApoE4. In some embodiments a yeast strain contains constructs that, when expressed, do not cause toxicity. In some embodiments the level of toxicity is measured in yeast cultured on solid culture medium. In some embodiments the level of toxicity is measured in yeast cultured in liquid culture medium. In some embodiments the level of toxicity of yeast cultured in liquid culture medium is measured one or more times between about 20 and about 60 hours after placing the yeast cells under conditions in which the ApoE protein is expressed. For example, in some embodiments the level of toxicity is about the same at one or more time points between 20 and 40 hours and one or more time points between 40 and 60 hours after placing the yeast cells under conditions in which the ApoE protein is expressed.

In some embodiments cell growth is measured based on optical density 600 (OD600) or cell counting. In some embodiments two strains exhibit about the same level of toxicity at a given time point after the strains are placed under conditions in which ApoE is expressed (or another toxicity-inducing condition is imposed) if their OD600 or number of cells are within ±20%, within ±10%, or within ±5% of each other.

Modulators of ApoE-Mediated Toxicity

It has been found that overexpression of certain genes results in a modulation of ApoE-mediated cellular toxicity. Compounds that modulate expression of one or more of these genes or that modulate activity of one or more of the encoded proteins can be used to modulate ApoE-mediated toxicity. Modulation of toxicity, e.g., suppression or enhancement of toxicity, can have a variety of different uses. In some aspects of the invention, compounds that modulate expression of one or more of these genes or that modulate activity of one or more of the encoded proteins can be used to inhibit ApoE-mediated toxicity, e.g., ApoE4-mediated toxicity. In some aspects of the invention, compounds that modulate expression of one or more of these genes or that modulate activity of one or more of the encoded proteins can be used to treat or prevent an ApoE-associated disease, e.g., an ApoE4-associated disease, e.g., a neurodegenerative disease such as Alzheimer's disease. In some embodiments, compounds that modulate expression of one or more of these genes or that modulate activity of one or more of the encoded proteins can be used to enhance ApoE-mediated toxicity. Enhancement of ApoE-mediated toxicity may be useful, e.g., to facilitate further screens for genes or compounds that inhibit ApoE-mediated toxicity and/or in the development of additional model systems for identifying or characterizing potential therapeutic agents for ApoE-mediated disorders.

As detailed in the accompanying Examples, a number of genes have been identified that modulate (e.g., suppress or enhance) cellular toxicity associated with expression of ApoE in yeast cells. Tables 1A, 1B, 2A, 2B, 2C, and 3 list gene names and *Saccharomyces* Genome Database (SGD) IDs of genes identified as genetic enhancers or suppressors of ApoE toxicity when overexpressed, and (in Tables 1A, 1B, and 3) non-limiting descriptive information about the proteins encoded by these genes. The genes were identified in pooled screens of yeast open reading frames carried out in yeast strains harboring expression constructs encoding polypeptides comprising either ApoE2, ApoE3, or ApoE4. Hits identified in primary screens as modulators of toxicity of at least one ApoE isoform were tested by transforming them individually into yeast strains harboring expression constructs encoding polypeptides comprising either ApoE2, ApoE3, or ApoE4. A subset of revalidated hits (see Example 7) is listed in Table 3. The sequences of mRNA and protein encoded by each gene may be obtained from various databases such as the NCBI RefSeq database, Universal Protein Resource (UniProt) database, or the SGD, among others.

A number of the yeast genes identified as modulators of ApoE-mediated toxicity in yeast cells have one or more homologous genes in humans. It is expected that the mechanisms by which ApoE induces toxicity in the yeast model system described herein is similar to the mechanisms by which ApoE, e.g., ApoE4, induces toxicity in human cells. Many of the yeast genes identified as modulating ApoE-mediated toxicity in yeast cells have homologous genes in humans. As a result, human counterparts of the identified yeast genes (and their encoded proteins) are expected to be useful targets for modulating, e.g., suppressing, ApoE-mediated toxicity in human cells. In general, a "counterpart" (used interchangeably with "homolog") of a yeast gene, e.g., a human counterpart, may be identified based on sequence similarity, structural similarity, and/or functional similarity. In some embodiments, Homologene (a system for automated detection of homologs among the annotated genes of various completely sequenced eukaryotic genomes, available on the World Wide Web at www.ncbi.nlm.nih.gov/homologene) is used. Of course other means of identifying homologs based on sequence and/or other characteristics could be used. It will be understood that homologous genes may be identified as homologous nucleic acid sequences, homologous amino acid sequences of proteins encoded by the genes, or both. Homologous structures may be identified based on predicted or experimentally determined two or three dimensional structures, e.g., determined by NMR, X-ray crystallography, molecular modeling, or other methods. In some embodiments of any aspect of the invention relating to a human gene, the human gene is a homolog of a yeast suppressor or enhancer identified herein, wherein the homology may be identified using, for example, Homologene, BioMart—Ensembl, BLAST searching, structural homology, and/or based on homologous function.

A number of the yeast genes identified in Table 1A or Table 1B have one or more human homologs. Tables 1C and 1D list human homologs of yeast genes listed in Tables 1A and 1B, respectively, and their corresponding UniProt accession numbers. Genes identified with single asterisks in Table 1A or Table 1B have one or more human homologs that are Alzheimer's disease risk factors.

Tables 2A, 2B, and 2C list official symbols (HUGO Gene Nomenclature Committee) and National Center for Biotechnology Information (NCBI) Gene ID numbers for certain of the human homologs identified herein. A number of the human genes identified herein as homologs of yeast genes that are modifiers of ApoE-mediated toxicity are known genetic risk factors for Alzheimer's disease, i.e., particular alleles of such genes or mutations in such genes are associated with AD. For example, certain alleles of some of the genes have been found to be present at a significantly higher frequency in individuals with AD than in control subjects who do not have AD and are thus considered risk alleles for AD. (See, Lambert J C, et al., Nat Genet. 2013; 45(12): 1452-8, and references therein, for description of studies that have identified genetic risk factors for AD, and other related information). Human homologs that are known Alzheimer's disease risk factors are listed in Tables 2A, 2B, and 2C. The NCBI Gene IDs of the human homolog genes are listed in Tables 2A, 2B, and 2C. In addition, AXL2 (Table 1A) and STE6 (Table 1B) are yeast modifiers that have human homologs that are AD risk factors. The human homologs are DSG2 (Gene ID1829) and ABCA7 (Gene ID 10347), respectively. Wherever aspects of the present disclosure refers to human homologs listed in any one or more of Tables 1C, 1D, 2A, 2B, and 2C, the disclosure also provides embodiments pertaining to DSG2 and ABCA7.

Table 3 lists a subset of hits that were revalidated as enhancers or suppressors in yeast cells expressing ApoE4 (see Example 7). Additional details, including human homologs of yeast genes listed in Table 3, may be found herein, for example, in Tables 1C, 1D, 2A, 2B, and 2C.

The sequences of mRNA and protein encoded by each gene may be obtained from various databases such as the NCBI RefSeq database or UniProt databases, among others.

TABLE 1A

Yeast Genes that Modulate ApoE Toxicity When Overexpressed

| Gene Name | Saccharomyces Genome Database ID | Description | Effect size on E2 (suppressor (S), enhancer(E)) | P value | Effect size on E3 (suppressor (S), enhancer (E)) | P value | Effect size on E4 (suppressor (S), enhancer(E)) | P value |
|---|---|---|---|---|---|---|---|---|
| PRS2 | YER099C | 5-phospho-ribosyl-1(alpha)-pyrophosphate synthetase, synthesizes PRPP | E 0.9 | 0.145 | 1.0 | 0.742 | S 2.7 | 0.003 |
| RVS167 | YDR388W | Actin-associated protein with roles in endocytosis and exocytosis | S 1.1 | 0.353 | S 1.5 | 0.003 | S 1.1 | 0.220 |
| PUP2* | YGR253C | Alpha 5 subunit of the 20S proteasome | E 0.7 | 0.000 | 1.0 | 0.221 | S 1.8 | 0.000 |
| FPS1 | YLL043W | Aquaglyceroporin, plasma membrane channel | S 1.1 | 0.121 | 1.0 | 1.000 | S 1.3 | 0.000 |
| RPT4 | YOR259C | ATPase of the 19S regulatory particle of the 26S proteasome | S 1.4 | 0.016 | S 1.5 | 0.017 | S 1.9 | 0.001 |
| DCP2* | YNL118C | Catalytic subunit of the Dcp1p-Dcp2p decapping enzyme complex | S 1.2 | 0.002 | S 1.1 | 0.132 | S 2.4 | 0.000 |
| MAD1 | YGL086W | Coiled-coil protein involved in spindle-assembly checkpoint | S 1.1 | 0.223 | S 1.1 | 0.018 | S 2.1 | 0.000 |
| CGI121 | YML036W | Component of the EKC/KEOPS complex | S 1.3 | 0.007 | S 1.1 | 0.071 | S 2.2 | 0.001 |
| VPS53* | YJL029C | Component of the GARP (Golgi-associated retrograde protein) complex | E 0.3 | 0.001 | E 0.5 | 0.000 | E 0.7 | 0.023 |
| CDC73 | YLR418C | Component of the Paf1p complex | E 1.0 | 0.527 | 1.0 | 0.968 | S 1.7 | 0.000 |
| KRE11 | YGR166W | Component of transport protein particle (TRAPP) complex II | S 1.3 | 0.013 | 1.0 | 0.927 | S 1.7 | 0.000 |
| SMD2 | YLR275W | Core Sm protein Sm D2 | E 0.7 | 0.043 | E 0.9 | 0.065 | S 1.8 | 0.001 |
| SIC1 | YLR079W | Cyclin-dependent kinase inhibitor (CKI) | E 0.9 | 0.082 | E 0.9 | 0.053 | S 1.3 | 0.000 |
| PCL2 | YDL127W | Cyclin, interacts with cyclin-dependent kinase Pho85p | S 1.2 | 0.154 | 1.1 | 0.022 | S 1.9 | 0.000 |
| KEL3 | YPL263C | Cytoplasmic protein of unknown function | S 1.7 | 0.034 | 1.3 | 0.001 | E 0.9 | 0.500 |
| SLA1 | YBL007C | Cytoskeletal protein binding protein | E 0.9 | 0.172 | 1.0 | 0.355 | S 1.3 | 0.008 |
| GCD2 | YGR083C | Delta subunit of the translation initiation factor eIF2B | E 0.9 | 0.421 | S 1.2 | 0.002 | E 0.9 | 0.010 |
| URA4* | YLR420W | Dihydroorotase | 1.0 | 0.923 | S 1.2 | 0.001 | S 2.1 | 0.000 |
| RRM3 | YHR031C | DNA helicase involved in rDNA replication and Ty1 transposition | S 1.2 | 0.052 | S 1.2 | 0.022 | S 2.1 | 0.000 |
| MGT1 | YDL200C | DNA repair methyltransferase (6-O-methylguanine-DNA methylase) | S 1.1 | 0.120 | S 1.2 | 0.005 | S 1.6 | 0.000 |

TABLE 1A-continued

Yeast Genes that Modulate ApoE Toxicity When Overexpressed

| Gene Name | Saccharomyces Genome Database ID | Description | Effect size on E2 (suppressor (S), enhancer(E)) | P value | Effect size on E3 (suppressor (S), enhancer (E)) | P value | Effect size on E4 (suppressor (S), enhancer(E)) | P value |
| --- | --- | --- | --- | --- | --- | --- | --- | --- |
| GPI8 | YDR331W | ER membrane glycoprotein subunit of the GPI transamidase complex | S 1.1 | 0.366 | S 1.6 | 0.039 | E 0.9 | 0.113 |
| SEC62 | YPL094C | Essential subunit of Sec63 complex | S 1.3 | 0.025 | S 1.4 | 0.013 | S 1.8 | 0.001 |
| CWC24* | YLR323C | General splicing factor | S 1.3 | 0.000 | S 1.3 | 0.000 | S 1.6 | 0.000 |
| GLK1 | YCL040W | Glucokinase | S 1.1 | 0.287 | E 0.9 | 0.008 | S 1.5 | 0.000 |
| PGI1 | YBR196C | Glycolytic enzyme phosphoglucose isomerase | E 0.9 | 0.153 | S 1.3 | 0.006 | S 1.7 | 0.003 |
| GYP5 | YPL249C | GTPase-activating protein (GAP) for yeast Rab family members | S 1.1 | 0.049 | S 1.1 | 0.168 | S 1.9 | 0.002 |
| GUD1 | YDL238C | Guanine deaminase | S 1.1 | 0.093 | E 0.9 | 0.216 | S 2.0 | 0.001 |
| VPS9* | YML097C | Guanine nucleotide exchange factor (GEF) | E 0.3 | 0.001 | E 0.5 | 0.000 | E 0.7 | 0.025 |
| HXT17 | YNR072W | Hexose transporter | S 1.3 | 0.002 | S 1.2 | 0.059 | 1.0 | 0.954 |
| STE24 | YJR117W | Highly conserved zinc metalloprotease | S 1.6 | 0.000 | 1.0 | 0.684 | E 0.9 | 0.375 |
| HMG2 | YLR450W | HMG-CoA reductase | E 0.5 | 0.003 | E 0.8 | 0.612 | S 1.3 | 0.098 |
| ERG11 | YHR007C | Lanosterol 14-alpha-demethylase | E 0.8 | 0.080 | S 1.3 | 0.262 | E 0.8 | 0.171 |
| ALG1* | YBR110W | Mannosyltransferase | S 1.3 | 0.003 | S 1.3 | 0.002 | 1.3 | 0.050 |
| OSH3 | YHR073W | Member of an oxysterol-binding protein family | 1.0 | 0.880 | S 1.7 | 0.013 | E 0.7 | 0.009 |
| OSH2 | YDL019C | Member of an oxysterol-binding protein family with seven members | E 0.8 | 0.084 | S 2.4 | 0.025 | E 0.8 | 0.044 |
| MRPL10 | YNL284C | Mitochondrial ribosomal protein of the large subunit | 1.0 | 0.383 | E 0.9 | 0.066 | S 2.2 | 0.001 |
| MRP49 | YKL167C | Mitochondrial ribosomal protein of the large subunit | 1.0 | 0.810 | S 1.2 | 0.003 | S 1.2 | 0.006 |
| ATP11 | YNL315C | Molecular chaperone | 1.0 | 0.639 | E 0.9 | 0.550 | S 1.4 | 0.000 |
| GNT1* | YOR320C | N-acetylglucosaminyl-transferase | E 0.9 | 0.206 | S 1.3 | 0.003 | S 1.8 | 0.002 |
| YLR455W | YLR455W | Nuclear protein of unknown function | 1.0 | 0.824 | E 0.5 | 0.000 | E 0.7 | 0.054 |
| PGS1 | YCL004W | Phosphatidyl-glycerolphosphate synthase | 1.0 | 0.855 | 1.0 | 0.257 | E 0.9 | 0.316 |
| SPO14 | YKR031C | Phospholipase D | E 0.7 | 0.008 | E 0.9 | 0.683 | E 0.8 | 0.032 |
| INP52 | YNL106C | Polyphosphatidylinositol phosphatase | S 1.2 | 0.035 | 1.0 | 0.510 | E 0.7 | 0.029 |
| REC102* | YLR329W | Protein involved in early stages of meiotic recombination | S 1.4 | 0.001 | E 0.9 | 0.014 | S 3.5 | 0.000 |
| MHR1 | YDR296W | Protein involved in homologous recombination in mitochondria | 1.0 | 0.020 | S 1.6 | 0.001 | S 2.0 | 0.014 |

TABLE 1A-continued

Yeast Genes that Modulate ApoE Toxicity When Overexpressed

| Gene Name | Saccharomyces Genome Database ID | Description | Effect size on E2 (suppressor (S), enhancer(E)) | P value | Effect size on E3 (suppressor (S), enhancer (E)) | P value | Effect size on E4 (suppressor (S), enhancer(E)) | P value |
|---|---|---|---|---|---|---|---|---|
| YAP1802 | YGR241C | Protein of the AP180 family, involved in clathrin cage assembly | S 1.2 | 0.054 | E 0.8 | 0.024 | S 1.9 | 0.038 |
| PER1 | YCR044C | Protein of the endoplasmic reticulum | 1.0 | 0.810 | S 1.9 | 0.020 | S 1.3 | 0.020 |
| STM1 | YLR150W | Protein required for optimal translation under nutrient stress | S 1.3 | 0.011 | S 1.3 | 0.002 | E 0.9 | 0.005 |
| SPS4 | YOR313C | Protein whose expression is induced during sporulation | E 0.8 | 0.133 | S 1.4 | 0.018 | S 2.0 | 0.000 |
| VTH2 | YJL222W | Putative membrane glycoprotein | S 2.2 | 0.015 | S 2.9 | 0.008 | S 3.0 | 0.011 |
| YDL206W | YDL206W | Putative protein of unknown function | 1.0 | 0.455 | 1.3 | 0.020 | 1.2 | 0.044 |
| YPT32* | YGL210W | Rab family GTPase involved in the exocytic pathway | E 0.3 | 0.001 | E 0.5 | 0.000 | E 0.8 | 0.028 |
| RPL34A | YER056C-A | Ribosomal 60S subunit protein L34A | S 1.1 | 0.224 | S 1.1 | 0.248 | S 1.8 | 0.002 |
| CDC42 | YLR229C | Small rho-like GTPase | S 1.3 | 0.084 | S 1.3 | 0.000 | E 0.9 | 0.201 |
| ATG20 | YDL113C | Sorting nexin family member | E 0.8 | 0.076 | S 1.6 | 0.046 | 1.8 | 0.000 |
| PRP3* | YDR473C | Splicing factor | S 1.1 | 0.011 | S 1.4 | 0.000 | 2.0 | 0.000 |
| RIM1 | YCR028C-A | ssDNA-binding protein essential for mitochondrial genome maintenance | 1.0 | 0.916 | S 1.3 | 0.020 | S 1.3 | 0.018 |
| RRI2 | YOL117W | Subunit of the COP9 signalosome (CSN) complex | E 0.8 | 0.010 | S 1.1 | 0.407 | S 1.8 | 0.000 |
| ORC3* | YLL004W | Subunit of the origin recognition complex (ORC) | E 0.8 | 0.001 | S 1.3 | 0.001 | S 1.3 | 0.004 |
| PML1* | YLR016C | Subunit of the RES complex | S 1.2 | 0.236 | S 1.4 | 0.001 | S 1.7 | 0.001 |
| TAD2 | YJL035C | Subunit of tRNA-specific adenosine-34 deaminase | E 0.9 | 0.006 | E 0.9 | 0.045 | 1.2 | 0.001 |
| UBC9 | YDL064W | SUMO-conjugating enzyme involved in the Smt3p conjugation pathway | E 0.9 | 0.419 | S 1.3 | 0.002 | E 0.9 | 0.179 |
| YDL012C | YDL012C | Tail-anchored plasma membrane protein with a conserved CYSTM module | E 0.9 | 0.094 | S 1.1 | 0.202 | S 1.5 | 0.000 |
| MBP1* | YDL056W | Transcription factor | S 1.8 | 0.003 | S 1.4 | 0.012 | S 1.6 | 0.000 |
| HAP4 | YKL109W | Transcription factor | S 1.4 | 0.002 | 1.0 | 0.627 | E 0.9 | 0.174 |
| GPI17 | YDR434W | Transmembrane protein | E 0.8 | 0.053 | 1.0 | 0.694 | E 0.8 | 0.049 |
| UBP15 | YMR304W | Ubiquitin-specific protease involved in protein deubiquitination | E 0.6 | 0.001 | E 0.8 | 0.008 | E 0.8 | 0.062 |

*Significant with p < 0.004 in at least two strains

TABLE 1B

Yeast Genes that Modulate ApoE Toxicity When Overexpressed

| Gene Name | Saccharo-myces Genome Database ID | Description | E2 revalidated OD/control | P value | E3 revalidated OD/control | P value | E4 revalidated OD/control | P value |
|---|---|---|---|---|---|---|---|---|
| DIB1 | YPR082C | 17-kDa component of the U4/U6aU5 tri-snRNP | 1.0 | 0.550 | S 1.1 | 0.237 | E 0.7 | 0.003 |
| NGL3 | YML118W | 3'-5' exonuclease specific for poly-A RNAs | E 0.8 | 0.006 | S 1.2 | 0.116 | E 0.7 | 0.002 |
| ADK1 | YDR226W | Adenylate kinase, required for purine metabolism | E 0.9 | 0.215 | E 0.9 | 0.130 | S 1.5 | 0.001 |
| ALT1 | YLR089C | Alanine transaminase (glutamic pyruvic transaminase) | 1.0 | 0.795 | S 1.3 | 0.001 | E 0.9 | 0.113 |
| PRE10 | YOR362C | Alpha 7 subunit of the 20S proteasome | E 0.2 | 0.001 | S 1.2 | 0.048 | E 0.9 | 0.108 |
| APE2* | YKL157W | Aminopeptidaseyscll | E 0.7 | 0.001 | E 0.8 | 0.015 | E 0.6 | 0.002 |
| RVS161 | YCR009C | Amphiphysin-like lipid raft protein | E 0.9 | 0.088 | S 1.1 | 0.061 | S 1.5 | 0.001 |
| LSC2 | YGR244C | Beta subunit of succinyl-CoA ligase | 0.7 | 0.001 | S 1.2 | 0.191 | E 0.9 | 0.048 |
| APL6 | YGR261C | Beta3-like subunit of the yeast AP-3 complex | E 0.9 | 0.001 | S 1.2 | 0.036 | E 0.9 | 0.584 |
| RRI1 | YDL216C | Catalytic subunit of the COP9 signalosome (CSN) complex | E 0.8 | 0.010 | S 1.3 | 0.003 | S 1.5 | 0.065 |
| CEX1 | YOR112W | Component of nuclear aminoacylation-dependent tRNA export pathway | E 0.7 | 0.001 | E 0.8 | 0.027 | E 0.9 | 0.207 |
| TRS130 | YMR218C | Component of transport protein particle (TRAPP) complex II | E 0.7 | 0.006 | E 0.7 | 0.003 | E 0.8 | 0.019 |
| RPP0 | YLR340W | Conserved ribosomal protein P0 of the ribosomal stalk | S 1.1 | 0.004 | S 1.2 | 0.007 | S 1.6 | 0.002 |
| CYS4 | YGR155W | Cystathionine beta-synthase | E 0.6 | 0.006 | E 0.9 | 0.118 | S 1.8 | 0.000 |
| CDD1 | YLR245C | Cytidine deaminase | E 0.9 | 0.179 | S 1.2 | 0.018 | S 1.3 | 0.000 |
| ADE3 | YGR204W | Cytoplasmic trifunctional enzyme C1-tetrahydrofolate synthase | 1.0 | 0.993 | S 1.1 | 0.334 | E 0.7 | 0.003 |
| FOL3 | 0.0 | Dihydrofolate synthetase, involved in folic acid biosynthesis | E 0.8 | 0.002 | S 1.4 | 0.019 | E 0.9 | 0.219 |
| DUS1 | YML080W | Dihydrouridine synthase | S 1.1 | 0.416 | 1.0 | 0.727 | S 1.7 | 0.001 |
| NTG2 | YOL043C | DNA N-glycosylase and apurinic/apyrimidinic (AP) lyase | E 0.6 | 0.000 | S 1.1 | 0.157 | E 0.8 | 0.018 |
| CTS1 | YLR286C | Endochitinase | E 0.7 | 0.012 | S 1.1 | 0.102 | E 0.6 | 0.002 |
| YNR064C | YNR064C | Epoxide hydrolase | E 0.9 | 0.422 | 1.0 | 0.496 | 1.6 | 0.001 |
| XRN1* | YGL173C | Evolutionarily-conserved 5'-3' exonuclease | E 0.5 | 0.002 | 1.0 | 0.769 | E 0.6 | 0.001 |
| STE14 | YDR410C | Farnesyl cysteine-carboxyl methyltransferase | S 1.2 | 0.068 | S 1.3 | 0.001 | S 2.3 | 0.005 |
| FBP1 | YLR377C | Fructose-1,6-bisphosphatase | 1.0 | 0.950 | 1.0 | 0.657 | S 1.6 | 0.000 |

TABLE 1B-continued

Yeast Genes that Modulate ApoE Toxicity When Overexpressed

| Gene Name | Saccharo-myces Genome Database ID | Description | E2 revalidated OD/control | P value | E3 revalidated OD/control | P value | E4 revalidated OD/control | P value |
|---|---|---|---|---|---|---|---|---|
| RPS31* | YLR167W | Fusion protein cleaved to yield ribosomal protein S31 and ubiquitin | E 0.7 | 0.000 | E 0.9 | 0.060 | E 0.6 | 0.001 |
| MUK1 | YPL070W | Guanine nucleotide exchange factor (GEF) | E 0.3 | 0.006 | E 0.5 | 0.025 | S 1.5 | 0.003 |
| NHP6A* | YPR052C | High-mobility group (HMG) protein | E 0.7 | 0.000 | E 0.9 | 0.400 | E 0.6 | 0.001 |
| AXL2 | YIL140W | Integral plasma membrane protein | E 0.9 | 0.083 | S 1.2 | 0.002 | 1.0 | 0.912 |
| SUR1 | YPL057C | Mannosylinositol phosphorylceramide (MIPC) synthase catalytic subunit | E 0.7 | 0.014 | E 0.7 | 0.015 | S 1.8 | 0.000 |
| OMA1 | YKR087C | Metalloendopeptidase of the mitochondrial inner membrane | 1.0 | 0.822 | E 0.8 | 0.011 | S 1.6 | 0.000 |
| MES1 | YGR264C | Methionyl-tRNA synthetase | E 0.8 | 0.084 | 1.0 | 0.792 | E 0.7 | 0.003 |
| PDC6 | YGR087C | Minor isoform of pyruvate decarboxylase | E 0.7 | 0.009 | E 0.8 | 0.002 | S 1.2 | 0.198 |
| ADK2 | YER170W | Mitochondrial adenylate kinase | 1.0 | 0.509 | S 1.3 | 0.007 | E 0.7 | 0.000 |
| RMD9* | YGL107C | Mitochondrial protein required for respiratory growth | E 0.8 | 0.063 | E 0.6 | 0.001 | E 0.6 | 0.002 |
| MRPL24* | YMR193W | Mitochondrial ribosomal protein of the large subunit | E 0.6 | 0.002 | E 0.8 | 0.001 | S 1.1 | 0.066 |
| MRP4 | YHL004W | Mitochondrial ribosomal protein of the small subunit | S 1.7 | 0.001 | S 1.2 | 0.035 | S 1.7 | 0.005 |
| RSM10 | YDR041W | Mitochondrial ribosomal protein of the small subunit | E 0.7 | 0.001 | 1.0 | 0.875 | S 1.1 | 0.449 |
| RSM26* | YJR101W | Mitochondrial ribosomal protein of the small subunit | E 0.5 | 0.003 | E 0.7 | 0.000 | E 0.9 | 0.120 |
| PCF11 | YDR228C | mRNA 3' end processing factor | E 0.8 | 0.032 | E 0.8 | 0.001 | E 0.8 | 0.017 |
| AIM14 | 0.0 | NADPH oxidase localized to the perinuclear ER | E 0.4 | 0.000 | E 0.8 | 0.074 | 1.0 | 0.426 |
| COQ3* | YOL096C | O-methyltransferase | 1.1 | 0.001 | E 0.5 | 0.018 | S 1.8 | 0.000 |
| CTF3* | YLR381W | Outer kinetochore protein that forms a complex with Mcm16p and Mcm22p | E 0.7 | 0.001 | E 0.8 | 0.011 | E 0.6 | 0.001 |
| RRD2 | YPL152W | Peptidyl-prolyl cis/trans-isomerase | E 0.3 | 0.001 | 1.0 | 0.413 | E 0.7 | 0.004 |
| TIP20 | YGL145W | Peripheral membrane protein required for COPI vesicle fusion to the ER | E 0.9 | 0.431 | 1.0 | 0.367 | S 1.2 | 0.001 |
| PRM2 | YIL037C | Pheromone-regulated protein | S 1.2 | 0.025 | S 1.2 | 0.069 | S 1.5 | 0.000 |
| TPS2 | YDR074W | Phosphatase subunit of the trehalose-6-P synthase/phospha-tase complex | E 0.5 | 0.004 | E 0.5 | 0.003 | E 0.7 | 0.018 |
| PTP2 | YOR208W | Phosphotyrosine-specific protein phosphatase | E 0.6 | 0.004 | E 0.6 | 0.003 | E 0.8 | 0.043 |

TABLE 1B-continued

Yeast Genes that Modulate ApoE Toxicity When Overexpressed

| Gene Name | Saccharo-myces Genome Database ID | Description | E2 revalidated OD/control | P value | E3 revalidated OD/control | P value | E4 revalidated OD/control | P value |
|---|---|---|---|---|---|---|---|---|
| STE6 | YKL209C | Plasma membrane ATP-binding cassette (ABC) transporter | E 0.8 | 0.041 | E 0.7 | 0.000 | 1.0 | 0.500 |
| ECM2 | YBR065C | Pre-mRNA splicing factor | E 0.8 | 0.003 | E 0.9 | 0.036 | E 0.7 | 0.006 |
| VRP1 | YLR337C | Proline-rich actin-associated protein | E 0.8 | 0.019 | S 1.3 | 0.000 | S 1.2 | 0.085 |
| RPS6A | YPL090C | Protein component of the small (40S) ribosomal subunit | E 0.8 | 0.001 | E 0.9 | 0.087 | E 0.9 | 0.071 |
| MAK32 | YCR019W | Protein necessary for stability of L-A dsRNA-containing particles | S 1.2 | 0.182 | S 1.2 | 0.171 | S 1.9 | 0.001 |
| SPS18* | YNL204C | Protein of unknown function, contains a putative zinc-binding domain | E 0.7 | 0.000 | S 1.1 | 0.206 | E 0.6 | 0.002 |
| TSR3 | 0.0 | Protein required for 20S pre-rRNA processing | E 0.7 | 0.012 | E 0.7 | 0.019 | S 1.4 | 0.001 |
| RMD6 | YEL072W | Protein required for sporulation | E 0.7 | 0.001 | E 0.8 | 0.257 | 1.0 | 0.899 |
| YER152C | YER152C | Protein with 2-aminoadipate transaminase activity | S 1.2 | 0.133 | E 0.8 | 0.038 | E 0.7 | 0.003 |
| RAD23* | YEL037C | Protein with ubiquitin-like N terminus | E 0.3 | 0.003 | E 0.7 | 0.002 | E 0.9 | 0.119 |
| RIX7 | YLL034C | Putative ATPase of the AAA family | E 0.6 | 0.003 | E 0.7 | 0.049 | E 0.8 | 0.031 |
| YGR250c* | YGR250C | Putative RNA binding protein | E 0.3 | 0.001 | E 0.5 | 0.000 | E 0.7 | 0.023 |
| SUT2 | YPR009W | Putative transcription factor of the Zn2Cys6 family | E 0.7 | 0.001 | E 0.8 | 0.016 | E 0.6 | 0.004 |
| GIC2 | YDR309C | Redundant rho-like GTPase Cdc42p effector | E 0.8 | 0.002 | E 0.7 | 0.036 | E 0.9 | 0.260 |
| PRP5 | YBR237W | RNA helicase in the DEAD-box family. ("DEAD" disclosed as SEQ ID NO: 13) | E 0.7 | 0.022 | E 0.6 | 0.000 | S 1.1 | 0.055 |
| RPA14 | YDR156W | RNA polymerase I subunit A14 | S 1.3 | 0.028 | E 0.9 | 0.179 | S 1.4 | 0.000 |
| RPA43 | YOR340C | RNA polymerase I subunit A43 | E 0.8 | 0.001 | E 0.8 | 0.017 | E 0.9 | 0.289 |
| RPC53 | YDL150W | RNA polymerase III subunit C53 | 1.0 | 0.752 | E 0.7 | 0.010 | E 0.6 | 0.001 |
| SAH1 | YER043C | S-adenosyl-L-homocysteine hydrolase | E 0.7 | 0.038 | E 0.7 | 0.001 | E 0.7 | 0.006 |
| SIR4 | YDR227W | SIR protein involved in assembly of silent chromatin domains | E 0.7 | 0.001 | E 0.9 | 0.501 | E 0.8 | 0.105 |
| SOR1 | YJR159W | Sorbitol dehydrogenase | E 0.8 | 0.002 | E 1.2 | 0.022 | E 0.7 | 0.015 |
| ADY4* | YLR227C | Structural component of the meiotic outer plaque | E 0.8 | 0.002 | E 0.9 | 0.236 | E 0.6 | 0.002 |
| HRP1 | YOL123W | Subunit of cleavage factor I | E 0.4 | 0.001 | 1.0 | 0.868 | E 1.1 | 0.250 |
| CAB4 | 0.0 | Subunit of the CoA-Synthesizing Protein Complex (CoA-SPC) | S 1.4 | 0.024 | S 1.3 | 0.006 | E 0.8 | 0.001 |
| HSE1 | YHL002W | Subunit of the endosomal Vps27p-Hse1p complex | S 1.2 | 0.000 | S 1.2 | 0.009 | 1.1 | 0.388 |

TABLE 1B-continued

Yeast Genes that Modulate ApoE Toxicity When Overexpressed

| Gene Name | Saccharo-myces Genome Database ID | Description | E2 revalidated OD/control | P value | E3 revalidated OD/control | P value | E4 revalidated OD/control | P value |
|---|---|---|---|---|---|---|---|---|
| GET2 | YER083C | Subunit of the GET complex | E 0.8 | 0.003 | S 1.2 | 0.005 | E 0.9 | 0.080 |
| SPT7 | YBR081C | Subunit of the SAGA transcriptional regulatory complex | E 0.7 | 0.001 | S 1.2 | 0.166 | E 0.7 | 0.008 |
| SNF11 | YDR073W | Subunit of the SWI/SNF chromatin remodeling complex | E 0.8 | 0.024 | E 0.6 | 0.000 | 1.0 | 0.441 |
| COX8 | YLR395C | Subunit VIII of cytochrome c oxidase (Complex IV) | E 0.8 | 0.002 | S 1.2 | 0.012 | E 0.9 | 0.239 |
| FLO8 | YER109C | Transcription factor | E 0.8 | 0.073 | E 0.9 | 0.023 | S 1.3 | 0.003 |
| PDR3 | YBL005W | Transcriptional activator of the pleiotropic drug resistance network | E 0.6 | 0.003 | E 0.7 | 0.009 | E 0.7 | 0.006 |
| ANB1 | YJR047C | Translation elongation factor eIF-5A | E 0.8 | 0.046 | 1.0 | 0.587 | E 0.6 | 0.001 |
| POM33 | 0.0 | Transmembrane nucleoporin | E 0.8 | 0.002 | E 0.9 | 0.314 | E 0.8 | 0.032 |
| PTC7 | YHR076W | Type 2C serine/threonine protein phosphatase (PP2C) | S 1.1 | 0.008 | S 1.2 | 0.018 | S 1.5 | 0.000 |
| AIR1* | YIL079C | Zinc knuckle protein | E 0.9 | 0.517 | E 0.8 | 0.001 | E 0.7 | 0.003 |
| YJR008W | YJR008W | #N/A | E 0.7 | 0.218 | E 0.7 | 0.000 | E 0.7 | 0.142 |

*Significant with p < 0.004 in at least two strains

TABLE 1C

Human Homologs of Yeast Genes Listed in Table 1A

| Yeast Gene Name | Yeast Systematic Name | Human Gene Name | Human Uniprot Acc. Number |
|---|---|---|---|
| ALG1 | YBR110W | ALG1 | Q9BT22 |
| ATG20 | YDL113C | SNX4 | O95219 |
| ATG20 | YDL113C | PXK | Q7Z7A4 |
| ATP11 | YNL315C | ATPAF1 | Q5TC12 |
| CDC42 | YLR229C | CDC42 | P60953 |
| CDC42 | YLR229C | RAC2 | P15153 |
| CDC42 | YLR229C | RAC1 | P63000 |
| CDC42 | YLR229C | RAC3 | P60763 |
| CDC42 | YLR229C | RHOQ | P17081 |
| CDC42 | YLR229C | RHOG | P84095 |
| CDC42 | YLR229C | RHOJ | Q9H4E5 |
| CDC42 | YLR229C | RHOU | Q7L0Q8 |
| CDC42 | YLR229C | RHOV | Q96L33 |
| CDC42 | YLR229C | RHOF | Q9HBH0 |
| CDC42 | YLR229C | RHOD | O00212 |
| CDC73 | YLR418C | CDC73 | Q6P1J9 |
| CGI121 | YML036W | TPRKB | Q9Y3C4 |
| CWC24 | YLR323C | RNF113A | O15541 |
| CWC24 | YLR323C | RNF113B | Q8IZP6 |
| DCP2 | YNL118C | DCP2 | Q8IU60 |
| ERG11 | YHR007C | CYP51A1 | Q16850 |
| FPS1 | YLL043W | AQP9 | O43315 |
| FPS1 | YLL043W | AQP3 | Q92482 |
| FPS1 | YLL043W | AQP10 | Q96PS8 |
| GCD2 | YGR083C | EIF2B4 | Q9UI10 |
| GLK1 | YCL040W | HKDC1 | Q2TB90 |
| GLK1 | YCL040W | HK2 | P52789 |
| GLK1 | YCL040W | HK3 | P52790 |
| GLK1 | YCL040W | HK1 | P19367 |
| GLK1 | YCL040W | GCK | P35557 |
| GNT1 | YOR320C | KIAA1383 | Q9P2G4 |
| GPI17 | YDR434W | PIGS | Q96S52 |
| GPI8 | YDR331W | PIGK | Q92643 |
| GUD1 | YDL238C | GDA | Q9Y2T3 |
| GYP5 | YPL249C | RABGAP1 | Q9Y3P9 |
| GYP5 | YPL249C | EVI5 | O60447 |
| GYP5 | YPL249C | RABGAP1L | Q5R372 |
| GYP5 | YPL249C | EVI5L | Q96CN4 |
| GYP5 | YPL249C | TBC1D1 | Q86TI0 |
| GYP5 | YPL249C | TBC1D4 | O60343 |
| GYP5 | YPL249C | USP6NL | Q92738 |
| HAP4 | YKL109W | ZNF654 | Q8IZM8 |
| HAP4 | YKL109W | TSKS | Q9UJT2 |
| HMG2 | YLR450W | HMGCR | P04035 |
| HXT17 | YNR072W | SLC2A2 | P11168 |
| HXT17 | YNR072W | SLC2A1 | P11166 |
| HXT17 | YNR072W | SLC2A14 | Q8TDB8 |
| HXT17 | YNR072W | SLC2A8 | Q9NY64 |
| HXT17 | YNR072W | SLC2A3 | P11169 |
| HXT17 | YNR072W | SLC2A6 | Q9UGQ3 |
| HXT17 | YNR072W | SLC2A4 | P14672 |
| HXT17 | YNR072W | SLC2A9 | Q9NRM0 |
| HXT17 | YNR072W | SLC2A11 | Q9BYW1 |
| INP52 | YNL106C | SYNJ1 | O43426 |
| INP52 | YNL106C | SYNJ2 | O15056 |
| INP52 | YNL106C | INPP5B | P32019 |
| KEL3 | YPL263C | KLHDC4 | Q8TBB5 |
| MAD1 | YGL086W | ANKRD26 | Q9UPS8 |
| MAD1 | YGL086W | CCDC144C | Q8IYA2 |
| MAD1 | YGL086W | TRIP11 | Q15643 |
| MAD1 | YGL086W | TUFT1 | Q9NNX1 |
| MAD1 | YGL086W | CALCOCO2 | Q13137 |

TABLE 1C-continued

Human Homologs of Yeast Genes Listed in Table 1A

| Yeast Gene Name | Yeast Systematic Name | Human Gene Name | Human Uniprot Acc. Number |
|---|---|---|---|
| MAD1 | YGL086W | PHLDB2 | Q86SQ0 |
| MAD1 | YGL086W | FSIP1 | Q8NA03 |
| MAD1 | YGL086W | AZI2 | Q9H6S1 |
| MAD1 | YGL086W | KRT10 | P13645 |
| MAD1 | YGL086W | CCDC42 | Q96M95 |
| MAD1 | YGL086W | KRT26 | Q7Z3Y9 |
| MAD1 | YGL086W | SCEL | O95171 |
| MAD1 | YGL086W | PIK3R3 | Q92569 |
| MAD1 | YGL086W | MIPOL1 | Q8TD10 |
| MAD1 | YGL086W | RBBP8 | Q99708 |
| MBP1 | YDL056W | ANK3 | Q12955 |
| MBP1 | YDL056W | ANK2 | Q01484 |
| MBP1 | YDL056W | ANKRD52 | Q8NB46 |
| MBP1 | YDL056W | SDCCAG3 | Q96C92 |
| MBP1 | YDL056W | ANKRD23 | Q86SG2 |
| MBP1 | YDL056W | PPFIA1 | Q13136 |
| MBP1 | YDL056W | ANKRD28 | O15084 |
| MBP1 | YDL056W | KANK4 | Q5T7N3 |
| MBP1 | YDL056W | DGKZ | Q13574 |
| MBP1 | YDL056W | ANKRD37 | Q7Z713 |
| MBP1 | YDL056W | SNCAIP | Q9Y6H5 |
| MGT1 | YDL200C | MGMT | P16455 |
| MRPL10 | YNL284C | MRPL15 | Q9P015 |
| ORC3 | YLL004W | CYP11B1 | P15538 |
| OSH2 | YDL019C | OSBP | P22059 |
| OSH2 | YDL019C | OSBP2 | Q969R2 |
| OSH2 | YDL019C | OSBPL7 | Q9BZF2 |
| OSH2 | YDL019C | OSBPL1A | Q9BXW6 |
| OSH2 | YDL019C | OSBPL6 | Q9BZF3 |
| OSH2 | YDL019C | OSBPL2 | Q9H1P3 |
| OSH2 | YDL019C | OSBPL3 | Q9H4L5 |
| OSH3 | YHR073W | OSBPL7 | Q9BZF2 |
| OSH3 | YHR073W | OSBPL6 | Q9BZF3 |
| OSH3 | YHR073W | OSBPL1A | Q9BXW6 |
| OSH3 | YHR073W | OSBPL3 | Q9H4L5 |
| OSH3 | YHR073W | OSBPL2 | Q9H1P3 |
| PCL2 | YDL127W | CCNYL2 | Q5T2Q4 |
| PCL2 | YDL127W | CCNT1 | O60563 |
| PCL2 | YDL127W | CNPPD1 | Q9BV87 |
| PER1 | YCR044C | PGAP3 | Q96FM1 |
| PGI1 | YBR196C | GPI | P06744 |
| PGS1 | YCL004W | PGS1 | Q32NB8 |
| PML1 | YLR016C | SNIP1 | Q8TAD8 |
| PML1 | YLR016C | KIAA0284 | Q9Y4F5 |
| PRP3 | YDR473C | PRPF3 | O43395 |
| PRS2 | YER099C | PRPS2 | P11908 |
| PRS2 | YER099C | PRPS1 | P60891 |
| PRS2 | YER099C | PRPS1L1 | P21108 |
| PRS2 | YER099C | PRPSAP2 | O60256 |
| PRS2 | YER099C | PRPSAP1 | Q14558 |
| PUP2 | YGR253C | PSMA5 | P28066 |
| RIM1 | YCR028C-A | SSBP1 | Q04837 |
| RPL34A | YER056C-A | RPL34 | P49207 |
| RPT4 | YOR259C | PSMC6 | P62333 |
| RRM3 | YHR031C | PIF1 | Q9H611 |
| RVS167 | YDR388W | AMPH | P49418 |
| RVS167 | YDR388W | ITSN1 | Q15811 |
| RVS167 | YDR388W | SH3D21 | A4FU49 |
| RVS167 | YDR388W | ABI2 | Q9NYB9 |
| RVS167 | YDR388W | FCHSD2 | O94868 |
| RVS167 | YDR388W | SRC | P12931 |
| RVS167 | YDR388W | GRAP2 | O75791 |
| RVS167 | YDR388W | ITSN2 | Q9NZM3 |
| RVS167 | YDR388W | GRAP | Q13588 |
| RVS167 | YDR388W | PSTPIP1 | O43586 |
| RVS167 | YDR388W | ABI1 | Q8IZP0 |
| RVS167 | YDR388W | CTTN | Q14247 |
| RVS167 | YDR388W | CD2AP | Q9Y5K6 |
| RVS167 | YDR388W | HCLS1 | P14317 |
| RVS167 | YDR388W | FCHSD1 | Q86WN1 |
| RVS167 | YDR388W | NCK2 | O43639 |
| RVS167 | YDR388W | PPP1R13L | Q8WUF5 |
| RVS167 | YDR388W | PACSIN2 | Q9UNF0 |
| RVS167 | YDR388W | NCK1 | P16333 |
| RVS167 | YDR388W | NEDD9 | Q14511 |
| SEC62 | YPL094C | SEC62 | Q99442 |
| SIC1 | YLR079W | SIPA1L3 | O60292 |
| SIC1 | YLR079W | EVL | Q9UI08 |
| SLA1 | YBL007C | FGR | P09769 |
| SLA1 | YBL007C | OSTF1 | Q92882 |
| SLA1 | YBL007C | FYN | P06241 |
| SLA1 | YBL007C | ITSN1 | Q15811 |
| SLA1 | YBL007C | GRB2 | P62993 |
| SLA1 | YBL007C | NCK1 | P16333 |
| SLA1 | YBL007C | FCHSD2 | O94868 |
| SLA1 | YBL007C | GRAP2 | O75791 |
| SLA1 | YBL007C | NCK2 | O43639 |
| SLA1 | YBL007C | EPS8L3 | Q8TE67 |
| SLA1 | YBL007C | SORBS2 | O94875 |
| SLA1 | YBL007C | SH3RF1 | Q7Z6J0 |
| SLA1 | YBL007C | YES1 | P07947 |
| SLA1 | YBL007C | PACSIN1 | Q9BY11 |
| SLA1 | YBL007C | PACSIN2 | Q9UNF0 |
| SLA1 | YBL007C | NCF1C | A8MVU1 |
| SLA1 | YBL007C | ITSN2 | Q9NZM3 |
| SLA1 | YBL007C | SORBS1 | Q9BX66 |
| SLA1 | YBL007C | SH3RF3 | Q8TEJ3 |
| SLA1 | YBL007C | NCF1B | A6NI72 |
| SMD2 | YLR275W | SNRPD2 | P62316 |
| SPO14 | YKR031C | PLD2 | O14939 |
| SPO14 | YKR031C | PLD1 | Q13393 |
| STE24 | YJR117W | ZMPSTE24 | O75844 |
| TAD2 | YJL035C | ADAT2 | Q7Z6V5 |
| UBC9 | YDL064W | UBE2I | P63279 |
| UBP15 | YMR304W | USP7 | Q93009 |
| UBP15 | YMR304W | USP47 | Q96K76 |
| VPS53 | YJL029C | VPS53 | Q5VIR6 |
| VPS9 | YML097C | RABGEF1 | Q9UJ41 |
| VPS9 | YML097C | GAPVD1 | Q14C86 |
| VPS9 | YML097C | RIN2 | Q8WYP3 |
| VTH2 | YJL222W | SORT1 | Q99523 |
| VTH2 | YJL222W | SORL1 | Q92673 |
| VTH2 | YJL222W | SORCS2 | Q96PQ0 |
| VTH2 | YJL222W | SORCS1 | Q8WY21 |
| VTH2 | YJL222W | SORCS3 | Q9UPU3 |
| YAP1802 | YGR241C | PICALM | Q13492 |
| YAP1802 | YGR241C | SNAP91 | O60641 |
| YDL012C | YDL012C | MAGEC1 | O60732 |
| YDL012C | YDL012C | NCOR1P1 | Q9H4R4 |
| YDL012C | YDL012C | CCDC86 | Q9H6F5 |
| YDL012C | YDL012C | YLPM1 | P49750 |
| YDL206W | YDL206W | SLC24A6 | Q6J4K2 |
| YDL206W | YDL206W | SLC24A2 | Q9UI40 |
| YDL206W | YDL206W | SLC24A4 | Q8NFF2 |
| YDL206W | YDL206W | SLC24A3 | Q9HC58 |
| YDL206W | YDL206W | SLC24A5 | Q71RS6 |
| YDL206W | YDL206W | SLC24A1 | O60721 |
| YDL206W | YDL206W | OR8G5 | Q8NG78 |
| YLR455W | YLR455W | GLYR1 | Q49A26 |
| YPT32 | YGL210W | RAB11B | Q15907 |
| YPT32 | YGL210W | RAB11A | P62491 |
| YPT32 | YGL210W | RAB25 | P57735 |
| YPT32 | YGL210W | RAB14 | P61106 |
| YPT32 | YGL210W | RAB13 | P51153 |
| YPT32 | YGL210W | RAB2A | P61019 |
| YPT32 | YGL210W | RAB2B | Q8WUD1 |
| YPT32 | YGL210W | RAB4B | P61018 |
| YPT32 | YGL210W | RAB4A | P20338 |
| YPT32 | YGL210W | RAB43 | Q86YS6 |
| YPT32 | YGL210W | RAB35 | Q15286 |
| YPT32 | YGL210W | RAB30 | Q15771 |
| YPT32 | YGL210W | RAB15 | P59190 |
| YPT32 | YGL210W | RAB3D | O95716 |
| YPT32 | YGL210W | RAB3B | P20337 |
| YPT32 | YGL210W | RAB19 | A4D1S5 |
| YPT32 | YGL210W | RAB3C | Q96E17 |
| YPT32 | YGL210W | RAB18 | Q9NP72 |
| YPT32 | YGL210W | RAB22A | Q9UL26 |
| YPT32 | YGL210W | RAB39B | Q96DA2 |
| ATG20 | YDL113C | SNX7 | Q9UNH6 |

TABLE 1C-continued

Human Homologs of Yeast Genes Listed in Table 1A

| Yeast Gene Name | Yeast Systematic Name | Human Gene Name | Human Uniprot Acc. Number |
|---|---|---|---|
| ATG20 | YDL113C | SNX18 | Q96RF0 |
| ATG20 | YDL113C | SNX8 | Q9Y5X2 |
| ATG20 | YDL113C | SNX2 | O60749 |
| ATG20 | YDL113C | SNX1 | Q13596 |
| ATG20 | YDL113C | SNX33 | Q8WV41 |
| ATG20 | YDL113C | SNX5 | Q9Y5X3 |
| CDC42 | YLR229C | RHOC | P08134 |
| CDC42 | YLR229C | RHOA | P61586 |
| CDC42 | YLR229C | RHOB | P62745 |
| CDC42 | YLR229C | RND3 | P61587 |
| CDC42 | YLR229C | RHOH | Q15669 |
| CDC42 | YLR229C | RND2 | P52198 |
| CDC42 | YLR229C | RND1 | Q92730 |
| CDC42 | YLR229C | RHOBTB2 | Q9BYZ6 |
| CDC42 | YLR229C | RHOBTB1 | O94844 |
| ERG11 | YHR007C | CYP26A1 | O43174 |
| ERG11 | YHR007C | CYP39A1 | Q9NYL5 |
| ERG11 | YHR007C | CYP7A1 | P22680 |
| ERG11 | YHR007C | CYP4F2 | P78329 |
| ERG11 | YHR007C | CYP4F3 | Q08477 |
| ERG11 | YHR007C | CYP26B1 | Q9NR63 |
| ERG11 | YHR007C | CYP4F22 | Q6NT55 |
| ERG11 | YHR007C | CYP4F8 | P98187 |
| ERG11 | YHR007C | CYP4F12 | Q9HCS2 |
| ERG11 | YHR007C | CYP4F11 | Q9HBI6 |
| ERG11 | YHR007C | CYP3A43 | Q9HB55 |
| ERG11 | YHR007C | CYP46A1 | Q9Y6A2 |
| ERG11 | YHR007C | CYP4Z1 | Q86W10 |
| ERG11 | YHR007C | CYP4A22 | Q5TCH4 |
| ERG11 | YHR007C | CYP4A11 | Q02928 |
| ERG11 | YHR007C | CYP4X1 | Q8N118 |
| ERG11 | YHR007C | CYP3A7 | P24462 |
| ERG11 | YHR007C | CYP27C1 | Q4G0S4 |
| ERG11 | YHR007C | CYP3A4 | P08684 |
| FPS1 | YLL043W | AQP7 | O14520 |
| FPS1 | YLL043W | AQP4 | P55087 |
| FPS1 | YLL043W | AQP6 | Q13520 |
| FPS1 | YLL043W | AQP5 | P55064 |
| FPS1 | YLL043W | AQP1 | P29972 |
| FPS1 | YLL043W | AQP2 | P41181 |
| FPS1 | YLL043W | AQP8 | O94778 |
| FPS1 | YLL043W | MIP | P30301 |
| GCD2 | YGR083C | EIF2B1 | Q14232 |
| GCD2 | YGR083C | EIF2B2 | P49770 |
| GNT1 | YOR320C | GYG2 | O15488 |
| GNT1 | YOR320C | GYG1 | P46976 |
| GPI8 | YDR331W | LGMN | Q99538 |
| GUD1 | YDL238C | AMDHD1 | Q96NU7 |
| GUD1 | YDL238C | AMDHD2 | Q9Y303 |
| GYP5 | YPL249C | TBC1D10B | Q4KMP7 |
| GYP5 | YPL249C | TBC1D10A | Q9BXI6 |
| GYP5 | YPL249C | GRTP1 | Q5TC63 |
| GYP5 | YPL249C | TBC1D14 | Q9P2M4 |
| GYP5 | YPL249C | TBC1D10C | Q8IV04 |
| GYP5 | YPL249C | SGSM3 | Q96HU1 |
| GYP5 | YPL249C | TBCK | Q8TEA7 |
| GYP5 | YPL249C | TBC1D2B | Q9UPU7 |
| GYP5 | YPL249C | TBC1D2 | Q9BYX2 |
| GYP5 | YPL249C | TBC1D3F | A6NER0 |
| GYP5 | YPL249C | TBC1D3 | Q8IZP1 |
| GYP5 | YPL249C | TBC1D3C | Q6IPX1 |
| GYP5 | YPL249C | TBC1D23 | Q9NUY8 |
| GYP5 | YPL249C | TBC1D24 | Q9ULP9 |
| HXT17 | YNR072W | SLC2A13 | Q96QE2 |
| HXT17 | YNR072W | SLC2A7 | Q6PXP3 |
| HXT17 | YNR072W | SLC2A5 | P22732 |
| HXT17 | YNR072W | SLC2A12 | Q8TD20 |
| HXT17 | YNR072W | SV2B | Q7L1I2 |
| HXT17 | YNR072W | SLC22A4 | Q9H015 |
| HXT17 | YNR072W | SV2C | Q496J9 |
| HXT17 | YNR072W | SLC22A13 | Q9Y226 |
| HXT17 | YNR072W | SLC2A10 | O95528 |
| HXT17 | YNR072W | SLC22A1 | O15245 |
| HXT17 | YNR072W | SLC22A6 | Q4U2R8 |
| INP52 | YNL106C | SACM1L | Q9NTJ5 |
| INP52 | YNL106C | INPP5F | Q9Y2H2 |
| KEL3 | YPL263C | HCFC2 | Q9Y5Z7 |
| KEL3 | YPL263C | LZTR1 | Q8N653 |
| KEL3 | YPL263C | MKLN1 | Q9UL63 |
| KEL3 | YPL263C | ATRNL1 | Q5VV63 |
| KEL3 | YPL263C | ATRN | O75882 |
| MAD1 | YGL086W | MAD1L1 | Q9Y6D9 |
| MBP1 | YDL056W | CASKIN1 | Q8WXD9 |
| MBP1 | YDL056W | ANKRD17 | O75179 |
| MBP1 | YDL056W | ANKHD1 | Q8IWZ3 |
| MBP1 | YDL056W | ANKRD30A | Q9BXX3 |
| MBP1 | YDL056W | UACA | Q9BZF9 |
| ORC3 | YLL004W | ORC3 | Q9UBD5 |
| OSH2 | YDL019C | OSBPL8 | Q9BZF1 |
| OSH2 | YDL019C | OSBPL5 | Q9H0X9 |
| OSH2 | YDL019C | OSBPL9 | Q96SU4 |
| OSH2 | YDL019C | OSBPL10 | Q9BXB5 |
| OSH2 | YDL019C | OSBPL11 | Q9BXB4 |
| OSH3 | YHR073W | OSBP2 | Q969R2 |
| OSH3 | YHR073W | OSBP | P22059 |
| OSH3 | YHR073W | OSBPL8 | Q9BZF1 |
| OSH3 | YHR073W | OSBPL5 | Q9H0X9 |
| OSH3 | YHR073W | OSBPL9 | Q96SU4 |
| OSH3 | YHR073W | OSBPL10 | Q9BXB5 |
| OSH3 | YHR073W | OSBPL11 | Q9BXB4 |
| PCL2 | YDL127W | CCNY | Q8ND76 |
| PUP2 | YGR253C | PSMA7 | O14818 |
| PUP2 | YGR253C | PSMA4 | P25789 |
| PUP2 | YGR253C | PSMA8 | Q8TAA3 |
| PUP2 | YGR253C | PSMA3 | P25788 |
| PUP2 | YGR253C | PSMA1 | P25786 |
| PUP2 | YGR253C | PSMA2 | P25787 |
| PUP2 | YGR253C | PSMA6 | P60900 |
| PUP2 | YGR253C | PSMB6 | P28072 |
| RPT4 | YOR259C | PSMC1 | P62191 |
| RPT4 | YOR259C | PSMC5 | P62195 |
| RPT4 | YOR259C | PSMC4 | P43686 |
| RPT4 | YOR259C | PSMC2 | P35998 |
| RPT4 | YOR259C | PSMC3 | P17980 |
| RPT4 | YOR259C | ATAD3B | Q5T9A4 |
| RPT4 | YOR259C | ATAD3A | Q9NVI7 |
| RRM3 | YHR031C | HELB | Q8NG08 |
| RVS167 | YDR388W | SH3GL2 | Q99962 |
| RVS167 | YDR388W | SH3GL1 | Q99961 |
| RVS167 | YDR388W | SH3GL3 | Q99963 |
| RVS167 | YDR388W | ARHGEF37 | A1IGU5 |
| RVS167 | YDR388W | DNMBP | Q6XZF7 |
| RVS167 | YDR388W | BIN3 | Q9NQY0 |
| RVS167 | YDR388W | BIN2 | Q9UBW5 |
| RVS167 | YDR388W | SH3GLB1 | Q9Y371 |
| RVS167 | YDR388W | BIN1 | O00499 |
| SLA1 | YBL007C | SH3D19 | Q5HYK7 |
| SLA1 | YBL007C | SH3KBP1 | Q96B97 |
| SLA1 | YBL007C | NCF2 | P19878 |
| SLA1 | YBL007C | SORBS3 | O60504 |
| SLA1 | YBL007C | SH3PXD2A | Q5TCZ1 |
| SLA1 | YBL007C | STAC | Q99469 |
| SLA1 | YBL007C | GRAP | Q13588 |
| SLA1 | YBL007C | CRKL | P46109 |
| SLA1 | YBL007C | CD2AP | Q9Y5K6 |
| SLA1 | YBL007C | DNMBP | Q6XZF7 |
| SLA1 | YBL007C | SH3RF2 | Q8TEC5 |
| SLA1 | YBL007C | SH3PXD2B | A1X283 |
| SMD2 | YLR275W | LSM3 | P62310 |
| SMD2 | YLR275W | LSM5 | Q9Y4Y9 |
| TAD2 | YJL035C | ADAT3 | Q96EY9 |
| UBC9 | YDL064W | UBE2A | P49459 |
| UBC9 | YDL064W | UBE2B | P63146 |
| UBC9 | YDL064W | UBE2D1 | P51668 |
| UBC9 | YDL064W | UBE2D4 | Q9Y2X8 |
| UBC9 | YDL064W | UBE2D2 | P62837 |
| UBC9 | YDL064W | UBE2D3 | P61077 |
| UBC9 | YDL064W | UBE2G2 | P60604 |
| UBC9 | YDL064W | UBE2E1 | P51965 |
| UBC9 | YDL064W | UBE2E2 | Q96LR5 |

TABLE 1C-continued

Human Homologs of Yeast Genes Listed in Table 1A

| Yeast Gene Name | Yeast Systematic Name | Human Gene Name | Human Uniprot Acc. Number |
|---|---|---|---|
| UBC9 | YDL064W | UBE2E3 | Q969T4 |
| UBC9 | YDL064W | UBE2G1 | P62253 |
| UBC9 | YDL064W | UBE2R2 | Q712K3 |
| UBC9 | YDL064W | UBE2N | P61088 |
| UBC9 | YDL064W | CDC34 | P49427 |
| UBC9 | YDL064W | UBE2S | Q16763 |
| UBC9 | YDL064W | UBE2U | Q5VVX9 |
| UBC9 | YDL064W | UBE2C | O00762 |
| UBC9 | YDL064W | UBE2T | Q9NPD8 |
| UBC9 | YDL064W | UBE2M | P61081 |
| VPS9 | YML097C | RIN3 | Q8TB24 |
| VPS9 | YML097C | RINL | Q6ZS11 |
| YPT32 | YGL210W | RAB8B | Q92930 |
| YPT32 | YGL210W | RAB1B | Q9H0U4 |
| YPT32 | YGL210W | RAB8A | P61006 |
| YPT32 | YGL210W | RAB10 | P61026 |
| YPT32 | YGL210W | RAB1A | P62820 |
| YPT32 | YGL210W | RAB5A | P20339 |
| ALG1 | YBR110W | ALG1L | Q6GMV1 |
| ERG11 | YHR007C | CYP26C1 | Q6V0L0 |
| UBP15 | YMR304W | USP40 | Q9NVE5 |
| YDL206W | YDL206W | SLC8A2 | Q9UPR5 |
| YDL206W | YDL206W | SLC8A3 | P57103 |
| YDL206W | YDL206W | SLC8A1 | P32418 |

TABLE 1D

Human Homologs of Yeast Genes Listed in Table 1B

| Yeast Gene Name | Yeast Systematic Name | Human Gene Name | Human Uniprot Acc. Number |
|---|---|---|---|
| AIR1 | YIL079C | P63145 | P63145 |
| AIR1 | YIL079C | P62683 | P62683 |
| AIR1 | YIL079C | P63126 | P63126 |
| AIR1 | YIL079C | ERVK6 | Q9Y6I0 |
| AIR1 | YIL079C | P62685 | P62685 |
| AIR1 | YIL079C | P63130 | P63130 |
| AIR1 | YIL079C | P87889 | P87889 |
| AIR1 | YIL079C | P62684 | P62684 |
| AIR1 | YIL079C | Q9YNA8 | Q9YNA8 |
| AIR1 | YIL079C | P63128 | P63128 |
| AIR1 | YIL079C | ERVK-5 | Q9HDB9 |
| AIR1 | YIL079C | TRAF6 | Q9Y4K3 |
| ANB1 | YJR047C | EIF5AL1 | Q6IS14 |
| APE2 | YKL157W | NPEPPSL1 | A6NEC2 |
| AXL2 | YIL140W | COBL | O75128 |
| CTS1 | YLR286C | SON | P18583 |
| CTS1 | YLR286C | RNF111 | Q6ZNA4 |
| FLO8 | YER109C | ANKRD36 | A6QL64 |
| FLO8 | YER109C | TNRC6A | Q8NDV7 |
| GIC2 | YDR309C | EXPH5 | Q8NEV8 |
| GIC2 | YDR309C | PWWP2A | Q96N64 |
| MUK1 | YPL070W | ARHGEF26 | Q96DR7 |
| NHP6A | YPR052C | P0C6E5 | P0C6E5 |
| NHP6A | YPR052C | HMGB1P1 | B2RPK0 |
| PTP2 | YOR208W | PTPRQ | Q9UMZ3 |
| RPC53 | YDL150W | KIAA1704 | Q8IXQ4 |
| RPP0 | YLR340W | RPLP0P6 | Q8NHW5 |
| SIR4 | YDR227W | ANKRD36 | A6QL64 |
| SIR4 | YDR227W | ALS2CR11 | Q53TS8 |
| SIR4 | YDR227W | BRCA2 | P51587 |
| SIR4 | YDR227W | LRIF1 | Q5T3J3 |
| SPT7 | YBR081C | CECR2 | Q9BXF3 |
| SPT7 | YBR081C | ANGPT2 | O15123 |
| SPT7 | YBR081C | CCDC144B | Q3MJ40 |
| SPT7 | YBR081C | SCEL | O95171 |
| SPT7 | YBR081C | FAM21B | Q5SNT6 |
| SPT7 | YBR081C | FAM21A | Q641Q2 |
| SPT7 | YBR081C | AGGF1 | Q8N302 |
| TIP20 | YGL145W | CLEC4M | Q9H2X3 |
| VRP1 | YLR337C | MUC1 | P15941 |
| VRP1 | YLR337C | MAGEE1 | Q9HCI5 |
| VRP1 | YLR337C | PRAM1 | Q96QH2 |
| VRP1 | YLR337C | CEL | P19835 |
| YGR250C | YGR250C | RBMY1C | P0DJD4 |
| YGR250C | YGR250C | RBFOX3 | A6NFN3 |
| YNR064C | YNR064C | SERHL | Q9NQF3 |
| ADE3 | YGR204W | MTHFD2L | Q9H903 |
| VRP1 | YLR337C | WIPF3 | A6NGB9 |
| TIP20 | YGL145W | LRRC45 | Q96CN5 |
| HSE1 | YHL002W | ITSN1 | Q15811 |
| SPT7 | YBR081C | PBRM1 | Q86U86 |
| SPT7 | YBR081C | BRD2 | P25440 |
| HSE1 | YHL002W | SH3D19 | Q5HYK7 |
| SPT7 | YBR081C | BAZ1A | Q9NRL2 |
| HSE1 | YHL002W | GRAP2 | O75791 |
| SPT7 | YBR081C | BAZ1B | Q9UIG0 |
| HSE1 | YHL002W | GRB2 | P62993 |
| SPT7 | YBR081C | TRIM33 | Q9UPN9 |
| SPT7 | YBR081C | BPTF | Q12830 |
| SPT7 | YBR081C | BRD7 | Q9NPI1 |
| PCF11 | YDR228C | SCAF8 | Q9UPN6 |
| SPT7 | YBR081C | BAZ2B | Q9UIF8 |
| SPT7 | YBR081C | BAZ2A | Q9UIF9 |
| SPT7 | YBR081C | BRD8 | Q9H0E9 |
| MUK1 | YPL070W | RIN3 | Q8TB24 |
| YGR250C | YGR250C | CSTF2T | Q9H0L4 |
| YGR250C | YGR250C | CSTF2 | P33240 |
| YGR250C | YGR250C | SLTM | Q9NWH9 |
| YGR250C | YGR250C | SAFB | Q15424 |
| NHP6A | YPR052C | CIC | Q96RK0 |
| YGR250C | YGR250C | SAFB2 | Q14151 |
| ADE3 | YGR204W | MTHFD2 | P13995 |
| SPS18 | YNL204C | AGFG2 | O95081 |
| YGR250C | YGR250C | RBMY1B | A6NDE4 |
| YGR250C | YGR250C | RBMY1E | A6NEQ0 |
| YGR250C | YGR250C | RBMY1D | P0C7P1 |
| YGR250C | YGR250C | RBMY1A1 | P0DJD3 |
| YGR250C | YGR250C | RBMY1F | Q15415 |
| YGR250C | YGR250C | RBM18 | Q96H35 |
| YGR250C | YGR250C | DAZL | Q92904 |
| AIR1 | YIL079C | ZCCHC3 | Q9NUD5 |
| YGR250C | YGR250C | DAZ4 | Q86SG3 |
| NHP6A | YPR052C | SOX5 | P35711 |
| SPS18 | YNL204C | AGFG1 | P52594 |
| RIX7 | YLL034C | FIGNL1 | Q6PIW4 |
| RIX7 | YLL034C | KATNAL1 | Q9BW62 |
| NHP6A | YPR052C | HMGB3 | O15347 |
| RIX7 | YLL034C | FIGN | Q5HY92 |
| NHP6A | YPR052C | SOX13 | Q9UN79 |
| PRP5 | YBR237W | DDX18 | Q9NVP1 |
| CYS4 | YGR155W | SDSL | Q96GA7 |
| PRP5 | YBR237W | DDX55 | Q8NHQ9 |
| HRP1 | YOL123W | ELAVL3 | Q14576 |
| ALT1 | YLR089C | CCBL2 | Q6YP21 |
| PRP5 | YBR237W | DDX10 | Q13206 |
| CYS4 | YGR155W | SRR | Q9GZT4 |
| AIR1 | YIL079C | CNBP | P62633 |
| RIX7 | YLL034C | ATAD2 | Q6PL18 |
| NHP6A | YPR052C | HMGB2 | P26583 |
| HSE1 | YHL002W | HGS | O14964 |
| ALT1 | YLR089C | ACCS | Q96QU6 |
| NHP6A | YPR052C | SOX3 | P41225 |
| NHP6A | YPR052C | SOX17 | Q9H6I2 |
| NHP6A | YPR052C | HMGB4 | Q8WW32 |
| ALT1 | YLR089C | ACCSL | Q4AC99 |
| NHP6A | YPR052C | HMGB1 | P09429 |
| PRP5 | YBR237W | DDX39B | Q13838 |
| PRP5 | YBR237W | DDX6 | P26196 |
| PRE10 | YOR362C | PSMB1 | P20618 |
| PRP5 | YBR237W | DDX39A | O00148 |
| NHP6A | YPR052C | SOX4 | Q06945 |
| PRP5 | YBR237W | DDX4 | Q9NQI0 |
| PRP5 | YBR237W | DDX49 | Q9Y6V7 |
| HRP1 | YOL123W | ELAVL2 | Q12926 |
| RIX7 | YLL034C | NSF | P46459 |

TABLE 1D-continued

Human Homologs of Yeast Genes Listed in Table 1B

| Yeast Gene Name | Yeast Systematic Name | Human Gene Name | Human Uniprot Acc. Number |
|---|---|---|---|
| RRI1 | YDL216C | PSMD14 | O00487 |
| YER152C | YER152C | GPT | P24298 |
| ALT1 | YLR089C | TAT | P17735 |
| AIR1 | YIL079C | ZCCHC13 | Q8WW36 |
| RPP0 | YLR340W | MRTO4 | Q9UKD2 |
| XRN1 | YGL173C | XRN2 | Q9H0D6 |
| NHP6A | YPR052C | TOX4 | O94842 |
| NHP6A | YPR052C | SOX11 | P35716 |
| PRP5 | YBR237W | DDX27 | Q96GQ7 |
| NHP6A | YPR052C | SOX7 | Q9BT81 |
| NHP6A | YPR052C | SOX1 | O00570 |
| PRP5 | YBR237W | DDX5 | P17844 |
| STE6 | YKL209C | ABCA12 | Q86UK0 |
| PRP5 | YBR237W | DDX52 | Q9Y2R4 |
| NHP6A | YPR052C | SRY | Q05066 |
| NGL3 | YML118W | CNOT6 | Q9ULM6 |
| PRP5 | YBR237W | DDX17 | Q92841 |
| AIR1 | YIL079C | ZCCHC9 | Q8N567 |
| STE6 | YKL209C | ABCA7 | Q8IZY2 |
| NHP6A | YPR052C | SOX21 | Q9Y651 |
| STE6 | YKL209C | ABCA5 | Q8WWZ7 |
| HRP1 | YOL123W | RBM15B | Q8NDT2 |
| RRI1 | YDL216C | STAMBPL1 | Q96FJ0 |
| HRP1 | YOL123W | PUF60 | Q9UHX1 |
| STE6 | YKL209C | ABCC6 | O95255 |
| STE6 | YKL209C | ABCC2 | Q92887 |
| PRP5 | YBR237W | DDX21 | Q9NR30 |
| PRP5 | YBR237W | DDX23 | Q9BUQ8 |
| STE6 | YKL209C | ABCA3 | Q99758 |
| STE6 | YKL209C | ABCC1 | P33527 |
| PRP5 | YBR237W | DDX59 | Q5T1V6 |
| PRP5 | YBR237W | DDX43 | Q9NXZ2 |
| DUS1 | YML080W | DUS2L | Q9NX74 |
| STE6 | YKL209C | ABCC3 | O15438 |
| NHP6A | YPR052C | SOX18 | P35713 |
| HRP1 | YOL123W | RBMXL1 | Q96E39 |
| APL6 | YGR261C | AP1B1 | Q10567 |
| NHP6A | YPR052C | SOX14 | O95416 |
| RVS161 | YCR009C | BIN1 | O00499 |
| RSM10 | YDR041W | RPS20 | P60866 |
| STE6 | YKL209C | ABCC10 | Q5T3U5 |
| NHP6A | YPR052C | SOX15 | O60248 |
| STE6 | YKL209C | ABCC9 | O60706 |
| HRP1 | YOL123W | RBMXL2 | O75526 |
| PRP5 | YBR237W | DDX53 | Q86TM3 |
| PRP5 | YBR237W | DDX41 | Q9UJV9 |
| APL6 | YGR261C | AP2B1 | P63010 |
| HRP1 | YOL123W | RBMX | P38159 |
| STE6 | YKL209C | ABCC12 | Q96J65 |
| NGL3 | YML118W | CCRN4L | Q9UK39 |
| MRP4 | YHL004W | RPSA | P08865 |
| DUS1 | YML080W | DUS4L | O95620 |
| STE6 | YKL209C | ABCC5 | O15440 |
| RIX7 | YLL034C | PEX1 | O43933 |
| STE6 | YKL209C | ABCC8 | Q09428 |
| HRP1 | YOL123W | RBM15 | Q96T37 |
| ADK2 | YER170W | AK1 | P00568 |
| STE6 | YKL209C | ABCC11 | Q96J66 |
| NHP6A | YPR052C | SOX2 | P48431 |
| RRI1 | YDL216C | MPND | Q8N594 |
| NHP6A | YPR052C | HMGXB4 | Q9UGU5 |
| STE6 | YKL209C | CFTR | P13569 |
| MUK1 | YPL070W | RABGEF1 | Q9UJ41 |
| STE6 | YKL209C | ABCC4 | O15439 |
| SOR1 | YJR159W | TP53I3 | Q53FA7 |
| VRP1 | YLR337C | WIPF1 | O43516 |
| NTG2 | YOL043C | MUTYH | Q9UIF7 |
| RVS161 | YCR009C | AMPH | P49418 |
| SOR1 | YJR159W | ZADH2 | Q8N4Q0 |
| CEX1 | YOR112W | SCYL2 | Q6P3W7 |
| APL6 | YGR261C | AP4B1 | Q9Y6B7 |
| RIX7 | YLL034C | PEX6 | Q13608 |
| ADK1 | YDR226W | AK7 | Q96M32 |
| STE6 | YKL209C | ABCB5 | Q2M3G0 |
| SOR1 | YJR159W | RTN4IP1 | Q8WWV3 |
| ADK2 | YER170W | CMPK1 | P30085 |
| YGR250C | YGR250C | ELAVL2 | Q12926 |
| MAK32 | YCR019W | ADK | P55263 |
| PTP2 | YOR208W | PTPN20A | Q4JDL3 |
| ADK1 | YDR226W | AK1 | P00568 |
| PTP2 | YOR208W | PTPN18 | Q99952 |
| SOR1 | YJR159W | VAT1L | Q9HCJ6 |
| RIX7 | YLL034C | VCP | P55072 |
| RRI1 | YDL216C | BRCC3 | P46736 |
| PTP2 | YOR208W | PTPN3 | P26045 |
| PTP2 | YOR208W | PTPN13 | Q12923 |
| CEX1 | YOR112W | SCYL3 | Q8IZE3 |
| PTP2 | YOR208W | PTPRA | P18433 |
| SOR1 | YJR159W | CRYZ | Q08257 |
| ADK1 | YDR226W | CMPK1 | P30085 |
| YGR250C | YGR250C | ELAVL4 | P26378 |
| MES1 | YGR264C | MARS2 | Q96GW9 |
| PTP2 | YOR208W | PTPN22 | Q9Y2R2 |
| PTP2 | YOR208W | PTPRE | P23469 |
| PRP5 | YBR237W | DDX42 | Q86XP3 |
| PTP2 | YOR208W | PTPN6 | P29350 |
| YER152C | YER152C | CCBL2 | Q6YP21 |
| PTP2 | YOR208W | PTPN21 | Q16825 |
| ADK2 | YER170W | AK5 | Q9Y6K8 |
| MAK32 | YCR019W | RBKS | Q9H477 |
| RIX7 | YLL034C | SPATA5L1 | Q9BVQ7 |
| PTP2 | YOR208W | PTPN14 | Q15678 |
| PTP2 | YOR208W | PTPN12 | Q05209 |
| SOR1 | YJR159W | MECR | Q9BV79 |
| LSC2 | YGR244C | ACLY | P53396 |
| NGL3 | YML118W | PDE12 | Q6L8Q7 |
| YNR064C | YNR064C | EPHX1 | P07099 |
| PRE10 | YOR362C | PSMA5 | P28066 |
| PRE10 | YOR362C | PSMA7 | O14818 |
| YNR064C | YNR064C | BPHL | Q86WA6 |
| YGR250C | YGR250C | CELF1 | Q92879 |
| NHP6A | YPR052C | HMG20A | Q9NP66 |
| YGR250C | YGR250C | CELF6 | Q96J87 |
| YER152C | YER152C | ACCS | Q96QU6 |
| PRE10 | YOR362C | PSMA2 | P25787 |
| PTP2 | YOR208W | PTPRM | P28827 |
| RIX7 | YLL034C | SPATA5 | Q8NB90 |
| SOR1 | YJR159W | ADH5 | P11766 |
| PTP2 | YOR208W | PTPRG | P23470 |
| SOR1 | YJR159W | ADH1C | P00326 |
| PTP2 | YOR208W | PTPRK | Q15262 |
| YGR250C | YGR250C | CELF2 | O95319 |
| PTP2 | YOR208W | PTPRJ | Q12913 |
| SOR1 | YJR159W | ADH1B | P00325 |
| SOR1 | YJR159W | ADH1A | P07327 |
| PTP2 | YOR208W | PTPRS | Q13332 |
| SOR1 | YJR159W | ADH6 | P28332 |
| PRE10 | YOR362C | PSMA8 | Q8TAA3 |
| PRE10 | YOR362C | PSMA4 | P25789 |
| YER152C | YER152C | ACCSL | Q4AC99 |
| PRE10 | YOR362C | PSMA6 | P60900 |
| ADK1 | YDR226W | AK5 | Q9Y6K8 |
| YNR064C | YNR064C | ABHD8 | Q96I13 |
| PTP2 | YOR208W | PTPRC | P08575 |
| PTP2 | YOR208W | PTPRD | P23468 |
| PTP2 | YOR208W | PTPRF | P10586 |
| SOR1 | YJR159W | ADH4 | P08319 |
| FLO8 | YER109C | SSBP2 | P81877 |
| NHP6A | YPR052C | SMARCE1 | Q969G3 |
| YER152C | YER152C | AADAT | Q8N5Z0 |
| SOR1 | YJR159W | ADH7 | P40394 |
| YNR064C | YNR064C | SERHL2 | Q9H4I8 |
| NHP6A | YPR052C | HMG20B | Q9P0W2 |
| RRI1 | YDL216C | COPS5 | Q92905 |
| PTP2 | YOR208W | PTPRZ1 | P23471 |
| HRP1 | YOL123W | HNRNPD | Q14103 |
| RSM26 | YJR101W | SOD2 | P04179 |
| ANB1 | YJR047C | EIF5A2 | Q9GZV4 |
| PRE10 | YOR362C | PSMA1 | P25786 |
| PDC6 | YGR087C | HACL1 | Q9UJ83 |

TABLE 1D-continued

Human Homologs of Yeast Genes Listed in Table 1B

| Yeast Gene Name | Yeast Systematic Name | Human Gene Name | Human Uniprot Acc. Number |
|---|---|---|---|
| RVS161 | YCR009C | BIN2 | Q9UBW5 |
| HRP1 | YOL123W | SF3B4 | Q15427 |
| PDC6 | YGR087C | ILVBL | A1L0T0 |
| HRP1 | YOL123W | TARDBP | Q13148 |
| YNR064C | YNR064C | MEST | Q5EB52 |
| HRP1 | YOL123W | HNRNPA1 | P09651 |
| ALT1 | YLR089C | GPT | P24298 |
| HRP1 | YOL123W | HNRNPA3 | P51991 |
| ADK2 | YER170W | AK2 | P54819 |
| ANB1 | YJR047C | EIF5A | P63241 |
| HSE1 | YHL002W | STAM | Q92783 |
| YNR064C | YNR064C | ABHD6 | Q9BV23 |
| HRP1 | YOL123W | HNRNPA0 | Q13151 |
| HRP1 | YOL123W | MSI2 | Q96DH6 |
| HRP1 | YOL123W | HNRNPA1L2 | Q32P51 |
| LSC2 | YGR244C | SUCLG2 | Q96I99 |
| HRP1 | YOL123W | HNRNPA2B1 | P22626 |
| HRP1 | YOL123W | MSI1 | O43347 |
| DIB1 | YPR082C | TXNL4A | P83876 |
| HRP1 | YOL123W | HNRNPAB | Q99729 |
| NHP6A | YPR052C | TOX | O94900 |
| APE2 | YKL157W | NPEPPS | P55786 |
| STE6 | YKL209C | ABCB1 | P08183 |
| SAH1 | YER043C | AHCY | P23526 |
| STE6 | YKL209C | ABCB4 | P21439 |
| ADE3 | YGR204W | MTHFD1L | Q6UB35 |
| APE2 | YKL157W | ERAP1 | Q9NZ08 |
| HRP1 | YOL123W | DAZAP1 | Q96EP5 |
| APE2 | YKL157W | ERAP2 | Q6P179 |
| APE2 | YKL157W | AQPEP | Q6Q4G3 |
| APL6 | YGR261C | AP3B2 | Q13367 |
| ADK2 | YER170W | AK8 | Q96MA6 |
| SOR1 | YJR159W | SORD | Q00796 |
| RIX7 | YLL034C | NVL | O15381 |
| SUR1 | YPL057C | A4GNT | Q9UNA3 |
| SUR1 | YPL057C | A4GALT | Q9NPC4 |
| YNR064C | YNR064C | EPHX4 | Q8IUS5 |
| SAH1 | YER043C | AHCYL1 | O43865 |
| YNR064C | YNR064C | EPHX3 | Q9H6B9 |
| NGL3 | YML118W | ANGEL2 | Q5VTE6 |
| HSE1 | YHL002W | STAM2 | O75886 |
| ADK1 | YDR226W | AK2 | P54819 |
| ADK1 | YDR226W | AK8 | Q96MA6 |
| APE2 | YKL157W | TRHDE | Q9UKU6 |
| ADK2 | YER170W | AK4 | P27144 |
| ADK2 | YER170W | AK3 | Q9UIJ7 |
| ADK1 | YDR226W | AKD1 | Q5TCS8 |
| RRD2 | YPL152W | PPP2R4 | Q15257 |
| RAD23 | YEL037C | RAD23A | P54725 |
| APE2 | YKL157W | ANPEP | P15144 |
| ADE3 | YGR204W | MTHFD1 | P11586 |
| ADK1 | YDR226W | AK4 | P27144 |
| FBP1 | YLR377C | FBP1 | P09467 |
| ADK2 | YER170W | AKD1 | Q5TCS8 |
| APE2 | YKL157W | LNPEP | Q9UIQ6 |
| ADK1 | YDR226W | AK3 | Q9UIJ7 |
| AIR1 | YIL079C | ZCCHC7 | Q8N3Z6 |
| ALT1 | YLR089C | GPT2 | Q8TD30 |
| APE2 | YKL157W | ENPEP | Q07075 |
| APL6 | YGR261C | AP3B1 | O00203 |
| AXL2 | YIL140W | DAG1 | Q14118 |
| CDD1 | YLR245C | CDA | P32320 |
| CEX1 | YOR112W | SCYL1 | Q96KG9 |
| COQ3 | YOL096C | COQ3 | Q9NZJ6 |
| COX8 | YLR395C | COX7C | P15954 |
| CYS4 | YGR155W | CBS | P35520 |
| DIB1 | YPR082C | TXNL4B | Q9NX01 |
| DUS1 | YML080W | DUS1L | Q6P1R4 |
| ECM2 | YBR065C | RBM22 | Q9NW64 |
| FBP1 | YLR377C | FBP2 | O00757 |
| HRP1 | YOL123W | HNRPDL | O14979 |
| LSC2 | YGR244C | SUCLA2 | Q9P2R7 |
| MES1 | YGR264C | MARS | P56192 |
| MRP4 | YHL004W | MRPS2 | Q9Y399 |
| MRPL24 | YMR193W | MRPL28 | Q13084 |
| NGL3 | YML118W | ANGEL1 | Q9UNK9 |
| NTG2 | YOL043C | NTHL1 | P78549 |
| OMA1 | YKR087C | OMA1 | Q96E52 |
| PCF11 | YDR228C | PCF11 | O94913 |
| PRE10 | YOR362C | PSMA3 | P25788 |
| PRP5 | YBR237W | DDX46 | Q7L014 |
| PTC7 | YHR076W | PPTC7 | Q8NI37 |
| RAD23 | YEL037C | RAD23B | P54727 |
| RPA43 | YOR340C | TWISTNB | Q3B726 |
| RPC53 | YDL150W | POLR3D | P05423 |
| RPP0 | YLR340W | RPLP0 | P05388 |
| RPS31 | YLR167W | RPS27A | P62979 |
| RPS6A | YPL090C | RPS6 | P62753 |
| RSM10 | YDR041W | MRPS10 | P82664 |
| RVS161 | YCR009C | BIN3 | Q9NQY0 |
| SAH1 | YER043C | AHCYL2 | Q96HN2 |
| SPS18 | YNL204C | ARFGAP1 | Q8N6T3 |
| STE14 | YDR410C | ICMT | O60725 |
| STE6 | YKL209C | ABCB11 | O95342 |
| TIP20 | YGL145W | RINT1 | Q6NUQ1 |
| TRS130 | YMR218C | TRAPPC10 | P48553 |
| XRN1 | YGL173C | XRN1 | Q8IZH2 |
| YJR008W | YJR008W | MEMO1 | Q9Y316 |
| YNR064C | YNR064C | EPHX2 | P34913 |
| FLO8 | YER109C | SSBP3 | Q9BWW4 |
| SPT7 | YBR081C | SUPT7L | O94864 |
| VRP1 | YLR337C | WIPF2 | Q8TF74 |

TABLE 2A

Genetic Modifiers of ApoE2-Mediated Toxicity

| ApoE2 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| VTH2 | 2.2 | 0.015 | SORL1 | 6653 | SORT1 | 6272 |
| RVS161 | 2.2 | 0.001 | BIN1 | 274 | BIN3 | 55909 |
| SNA3 | 2.1 | 0.000 | | | | |
| PFS1 | 2.0 | 0.006 | | | | |
| MBP1 | 1.8 | 0.003 | | | SDCCAG3 | 646891 |
| ECM7 | 1.8 | 0.014 | | | | |
| YFR032C-B | 1.8 | 0.012 | | | | |
| MRP4 | 1.7 | 0.001 | | | MRPS2 | 51116 |
| YHR131C | 1.7 | 0.006 | | | VPS72 | 6944 |

TABLE 2A-continued

Genetic Modifiers of ApoE2-Mediated Toxicity

| ApoE2 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| RAD30 | 1.7 | 0.024 | | | POLH | 5429 |
| KEL3 | 1.7 | 0.034 | | | KLHDC4 | 54758 |
| RPL14A | 1.7 | 0.030 | | | RPL14 | 9045 |
| UPF3 | 1.7 | 0.017 | | | UPF3B | 65109 |
| STE24 | 1.6 | 0.000 | | | ZMPSTE24 | 10269 |
| SED4 | 1.6 | 0.004 | | | FAM221B | |
| YFR018C | 1.5 | 0.004 | | | QPCT | 25797 |
| YER034W | 1.5 | 0.001 | | | SNPH | 9751 |
| YKL068W-A | 1.4 | 0.004 | | | | |
| HAP4 | 1.4 | 0.002 | | | TSKS | 60385 |
| HXT17 | 1.3 | 0.002 | | | SLC2A2 | 6514 |
| YHL026C | 1.2 | 0.004 | | | | |
| SKS1 | 0.7 | 0.002 | | | NEK1 | 4750 |
| YFL052W | 0.5 | 0.004 | | | | |
| NCL1 | 0.5 | 0.004 | | | | |
| XRN1 | 0.5 | 0.003 | | | XRN1 | 54464 |
| YOR394C-A | 0.5 | 0.003 | | | | |
| TPS2 | 0.5 | 0.004 | | | | |
| RSM26 | 0.5 | 0.003 | | | SOD2 | 6648 |
| NEO1 | 0.5 | 0.005 | | | ATP9B | 374868 |
| HRP1 | 0.4 | 0.001 | CELF1 | 10658 | MSI1 | 4440 |
| VPS53 | 0.3 | 0.001 | | | VPS53 | 55275 |
| VPS9 | 0.3 | 0.001 | RIN3 | 79890 | RABGEF1 | 27342 |
| ECM27 | 0.3 | 0.001 | SLC24A4 | 123041 | SLC24A6 | 80024 |
| YPT32 | 0.3 | 0.001 | | | RAB11B | 9230 |
| YNL050C | 0.3 | 0.001 | | | | |
| PBP4 | 0.3 | 0.001 | | | ZC3H4 | 23211 |
| YGR250c | 0.3 | 0.001 | CELF1 | 10658 | CSTF2 | 1478 |
| PIN3 | 0.3 | 0.001 | CASS4 | 57091 | GRB2 | 2885 |
| YKL100C | 0.3 | 0.001 | PSEN1 | 5663 | HM13 | 81502 |

*Effect size >10 indicates that gene is a suppressor of ApoE2-mediated toxicity when overexpressed. Effect size <1.0 indicates that gene is an enhancer of ApoE4-mediated toxicity when overexpressed.

TABLE 2B

Genetic Modifiers of ApoE3-Mediated Toxicity

| ApoE3 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| VTH2 | 2.9 | 0.008 | SORL1 | 6653 | SORT1 | 6272 |
| OSH2 | 2.4 | 0.025 | | | OSBP2 | 23762 |
| EXO70 | 2.3 | 0.001 | | | | |
| GPI17 | 2.3 | 0.002 | | | PIGS | 94005 |
| VRP1 | 2.2 | 0.002 | | | MUC1 | 4582 |
| SPO14 | 2.2 | 0.001 | PLD3 | 23646 | PLD2 | 5338 |
| PGS1 | 2.2 | 0.003 | PLD3 | 23646 | PGS1 | 9489 |
| YPT31 | 2.2 | 0.003 | | | | |
| YPT6 | 2.1 | 0.001 | | | | |
| SMP3 | 2.0 | 0.024 | | | PIGZ | 80235 |
| PER1 | 1.9 | 0.020 | | | PGAP3 | 93210 |
| RVS161 | 1.9 | 0.002 | BIN1 | 274 | BIN3 | 55909 |
| GPI8 | 1.9 | 0.004 | | | PIGK | 10026 |
| SLX1 | 1.8 | 0.016 | | | SLX1A | 548593 |
| PCD1 | 1.8 | 0.006 | | | NUDT7 | 283927 |
| MST1 | 1.7 | 0.006 | | | TARS2 | 80222 |
| OSH3 | 1.7 | 0.013 | FERMT2 | 10979 | OSBPL6 | 114880 |
| PCD1 | 1.7 | 0.007 | | | NUDT7 | 283927 |
| YER175W-A | 1.7 | 0.001 | | | | |
| MHR1 | 1.6 | 0.001 | | | | |
| RVS167 | 1.5 | 0.003 | BIN1 | 274 | ABI2 | 10152 |
| LDB16 | 1.4 | 0.000 | | | | |
| YOL057W | 1.4 | 0.000 | | | DPP3 | 10072 |
| RIM1 | 1.4 | 0.001 | MEF2C | 4208 | SSBP1 | 6742 |
| YKR011C | 1.3 | 0.000 | | | | |

TABLE 2B-continued

Genetic Modifiers of ApoE3-Mediated Toxicity

| ApoE3 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| ORC3 | 1.3 | 0.001 | | | ORC3 | 23595 |
| CDC42 | 1.3 | 0.000 | | | CDC42 | 643336 |
| UBC9 | 1.3 | 0.002 | | | UBE2I | 7329 |
| ALG1 | 1.3 | 0.002 | | | ALG1 | 56052 |
| YLR177W | 1.3 | 0.002 | | | | |
| YHR131C | 1.3 | 0.003 | | | VPS72 | 6944 |
| KEL3 | 1.3 | 0.001 | | | KLHDC4 | 54758 |
| STM1 | 1.3 | 0.002 | | | | |
| YNL193W | 1.3 | 0.002 | | | POLK | 51426 |
| GCD2 | 1.2 | 0.002 | | | EIF2B4 | 8890 |
| YER034W | 1.2 | 0.002 | | | SNPH | 9751 |
| ALG3 | 1.2 | 0.004 | | | ALG3 | 10195 |
| BUD21 | 1.2 | 0.004 | | | KANSL2 | 54934 |
| VID22 | 1.2 | 0.004 | | | | |
| MRP49 | 1.2 | 0.003 | | | | |
| TDA4 | 1.2 | 0.003 | | | TMEM56 | 148534 |
| YPT32 | 0.5 | 0.000 | | | RAB11B | 9230 |
| YLR455W | 0.5 | 0.000 | ZCWPW1 | 55063 | GLYR1 | 84656 |
| YKL100C | 0.5 | 0.000 | PSEN1 | 5663 | HM13 | 81502 |
| YGR250c | 0.5 | 0.000 | CELF1 | 10658 | CSTF2 | 1478 |
| VPS9 | 0.5 | 0.000 | RIN3 | 9890 | RABGEF1 | 27342 |
| VPS53 | 0.5 | 0.000 | | | VPS53 | 55275 |
| TPS2 | 0.0 | 0.000 | | | | |
| SED4 | 0.5 | 0.000 | | | FAM221B | 392307 |
| PIN3 | 0.5 | 0.000 | CASS4 | 57091 | GRB2 | 2885 |
| PBP4 | 0.4 | 0.000 | | | ZC3H4 | 23211 |
| LDB19 | 0.5 | 0.000 | | | ARRB1 | 408 |
| HRP1 | 0.0 | 0.000 | CELF1 | 10658 | MSI1 | 4440 |
| ECM27 | 0.5 | 0.000 | SLC24A4 | 123041 | SLC24A6 | 80024 |

*Effect size >1.0 indicates that gene is a suppressor of ApoE3-mediated toxicity when overexpressed. Effect size <1.0 indicates that gene is an enhancer of ApoE4-mediated toxicity when overexpressed.

TABLE 2C

Genetic Modifiers of ApoE4-Mediated Toxicity

| ApoE4 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| VTH2 | 3.0 | 0.011 | SORL1 | 6653 | SORT1 | 6272 |
| PRS2 | 2.7 | 0.003 | | | PRPS2 | 5634 |
| ERG11 | 2.5 | 0.019 | | | CYP51A1 | 1595 |
| AHA1 | 2.5 | 0.010 | | | AHSA1 | 10598 |
| DCP2 | 2.4 | 0.000 | | | DCP2 | 167227 |
| YML007C-A | 2.4 | 0.000 | | | | |
| STE14 | 2.3 | 0.005 | | | ICMT | 23463 |
| PER1 | 2.3 | 0.025 | | | PGAP3 | 93210 |
| BRE5 | 2.3 | 0.011 | | | ZNF804A | 91752 |
| YFR018C | 2.2 | 0.000 | | | QPCT | 25797 |
| MRPL10 | 2.2 | 0.001 | | | MRPL15 | 29088 |
| CGI121 | 2.2 | 0.001 | | | TPRKB | 51002 |
| YBR096W | 2.1 | 0.001 | | | THEM6 | |
| ILM1 | 2.1 | 0.001 | | | | |
| YLR413W | 2.1 | 0.000 | | | | |
| RRM3 | 2.1 | 0.000 | | | PIF1 | 80119 |
| YDL144C | 2.1 | 0.001 | | | | |
| URA4 | 2.1 | 0.000 | | | | |
| MAD1 | 2.1 | 0.000 | | | ANKRD26 | 22852 |
| YTA12 | 2.1 | 0.006 | | | AFG3L2 | 10939 |
| YBR139W | 2.0 | 0.000 | | | CTSA | 5476 |
| GUD1 | 2.0 | 0.001 | | | GDA | 9615 |
| EXO70 | 2.0 | 0.042 | | | | |
| MHR1 | 2.0 | 0.014 | | | | |
| MDH3 | 2.0 | 0.011 | | | MDH2 | 4191 |
| SPS4 | 2.0 | 0.000 | | | | |

TABLE 2C-continued

Genetic Modifiers of ApoE4-Mediated Toxicity

| ApoE4 MODIFIER GENE NAME | EFFECT SIZE* | P-value | HUMAN HOMOLOG THAT IS KNOWN AD RISK FACTOR | ENTREZ GENE ID FOR AD RISK FACTORS | HUMAN HOMOLOG | HUMAN HOMOLOG ENTREZ GENE ID |
|---|---|---|---|---|---|---|
| PRP3 | 2.0 | 0.000 | | | PRPF3 | 9129 |
| GYP5 | 1.9 | 0.002 | | | RABGAP1 | 23637 |
| HMS2 | 1.9 | 0.018 | | | HSF2 | 3298 |
| MAK32 | 1.9 | 0.001 | | | ADK | 132 |
| DCG1 | 1.9 | 0.001 | | | | |
| PCL2 | 1.9 | 0.000 | | | CCNYL2 | 414194 |
| YAP1802 | 1.9 | 0.038 | PICALM | 8301 | PICALM | 8301 |
| YFR032C-B | 1.9 | 0.008 | | | | |
| GPI8 | 1.9 | 0.063 | | | PIGK | 10026 |
| RPT4 | 1.9 | 0.001 | | | PSMC6 | 5706 |
| SEC62 | 1.8 | 0.001 | | | SEC62 | 7095 |
| RPL34A | 1.8 | 0.002 | | | RPL34 | 6164 |
| SMD2 | 1.8 | 0.001 | | | SNRPD2 | 119358 |
| YHR131C | 1.8 | 0.011 | | | VPS72 | 6944 |
| GNT1 | 1.8 | 0.002 | | | KIAA1383 | 54627 |
| YOR385W | 1.8 | 0.000 | | | | |
| RPL35A | 1.8 | 0.007 | | | RPL35 | 11224 |
| CYS4 | 1.8 | 0.000 | | | CBS | 875 |
| COQ3 | 1.8 | 0.000 | | | COQ3 | 51805 |
| YDL199C | 1.8 | 0.009 | | | SLC2A13 | 114134 |
| SLA1 | 1.8 | 0.094 | CD2AP | 23607 | EPS8L3 | 79574 |
| SRB5 | 1.7 | 0.005 | | | | |
| PUP2 | 1.8 | 0.000 | | | PSMA5 | 5686 |
| ATG20 | 1.8 | 0.000 | | | PXK | 54899 |
| SUR1 | 1.8 | 0.000 | | | A4GNT | 51146 |
| YLR149C | 1.8 | 0.001 | | | | |
| CDC73 | 1.7 | 0.000 | | | CDC73 | 79577 |
| RRI2 | 1.8 | 0.000 | | | | |
| PGI1 | 1.7 | 0.003 | | | GPI | 2821 |
| DUS1 | 1.7 | 0.001 | | | DUS1L | 64118 |
| MRP4 | 1.7 | 0.005 | | | MRPS2 | 51116 |
| PML1 | 1.7 | 0.001 | | | SNIP1 | 79753 |
| KRE11 | 1.7 | 0.000 | | | | |
| RPS26B | 1.7 | 0.004 | | | RPS26P11 | 441502 |
| IES6 | 1.7 | 0.021 | | | INO80C | 125476 |
| TRM112 | 1.7 | 0.018 | | | TRMTI12 | 391358 |
| MBP1 | 1.6 | 0.000 | | | SDCCAG3 | 646891 |
| YCL042W | 1.6 | 0.002 | | | | |
| RAD14 | 1.6 | 0.004 | | | XPA | 7507 |
| MGT1 | 1.6 | 0.000 | | | MGMT | 4255 |
| RPP0 | 1.6 | 0.002 | | | RPLP0 | 122589 |
| CWC24 | 1.6 | 0.000 | | | RNF113A | 7737 |
| OMA1 | 1.6 | 0.000 | | | OMA1 | 115209 |
| YNR064C | 1.6 | 0.001 | | | EPHX4 | 253152 |
| POR1 | 1.6 | 0.004 | | | VDAC3 | 7419 |
| FBP1 | 1.6 | 0.000 | | | FBP1 | 2203 |
| PTC7 | 1.5 | 0.000 | | | PPTC7 | 160760 |
| YDL012C | 1.5 | 0.000 | | | MAGEC1 | 9947 |
| PRM2 | 1.5 | 0.000 | | | | |
| MUK1 | 1.5 | 0.003 | RIN3 | 79890 | RIN3 | 79890 |
| RVS161 | 1.5 | 0.001 | BIN1 | 55909 | BIN3 | 55909 |
| ADK1 | 1.5 | 0.001 | | | AK2 | 204 |
| GLK1 | 1.5 | 0.000 | | | HKDC1 | 80201 |
| ATP11 | 1.4 | 0.000 | | | ATPAF1 | 64756 |
| FPS1 | 1.3 | 0.000 | | | AQP9 | 366 |
| SIC1 | 1.3 | 0.000 | | | SIPA1L3 | 23094 |
| TAD2 | 1.2 | 0.001 | | | ADAT2 | 134637 |
| RPL38 | 0.5 | 0.001 | | | RPL38 | 6169 |
| PPH21 | 0.5 | 0.001 | | | PPP2CB | 5516 |
| NAR1 | 0.5 | 0.000 | | | NARFL | 64428 |

*Effect size >1.0 indicates that gene is a suppressor of ApoE4-mediated toxicity when overexpressed. Effect size <1.0 indicates that gene is an enhancer of ApoE4-mediated toxicity when overexpressed.

TABLE 3

List of Revalidated Genetic Modifiers of ApoE4 toxicity (see Example 7)

| Gene Name | Name Description | Description |
|---|---|---|
| PGI1 | PhosphoGlucoIsomerase | Glycolytic enzyme phosphoglucose isomerase; catalyzes the interconversion of glucose-6-phosphate and fructose-6-phosphate; required for cell cycle progression and completion of the gluconeogenic events of sporulation |
| SLX1 | Synthetic Lethal of unknown (X) function | Endonuclease involved in DNA recombination and repair; subunit of a complex |
| PGS1 | Phosphatidyl Glycerolphosphate Synthase | Phosphatidylglycerolphosphate synthase; catalyzes the synthesis of phosphatidylglycerolphosphate from CDP-diacylglycerol and sn-glycerol 3-phosphate in the first committed and rate-limiting step of cardiolipin biosynthesis |
| LDB16 | Low Dye Binding | Protein of unknown function; null mutants have decreased net negative cell surface charge; GFP-fusion protein expression is induced in response to the DNA-damaging agent MMS; native protein is detected in purified mitochondria |
| GLK1 | GLucoKinase | Glucokinase; catalyzes the phosphorylation of glucose at C6 in the first irreversible step of glucose metabolism; one of three glucose phosphorylating enzymes; expression regulated by non-fermentable carbon sources; GLK1 has a paralog |
| RVS161 | Reduced Viability on Starvation | Amphiphysin-like lipid raft protein; interacts with Rvs167p and regulates polarization of the actin cytoskeleton |
| MAK32 | MAintenance of Killer | Protein necessary for stability of L-A dsRNA-containing particles |
| PER1 | Protein Processing in the ER | Protein of the endoplasmic reticulum; required for GPI-phospholipase A2 activity that remodels the GPI anchor as a prerequisite for association of GPI-anchored proteins with lipid rafts; functionally complemented by human ortholog PERLD1 |
| SED4 | Suppressor of Erd2 Deletion | Integral ER membrane protein that stimulates Sar1p GTPase activity; involved in COPII vesicle budding through disassociation of coat proteins from membranes onto liposomes; binds Sec16p; SED4 has a paralog |
| IES6 | Ino Eighty Subunit | Component of the INO80 chromatin remodeling complex; critical for INO80 function; involved in regulation of chromosome segregation and maintenance of normal centromeric chromatin structure; human ortholog INO80C is a member of the human INO80 complex; implicated in DNA repair based on genetic interactions with RAD52 epistasis genes |
| PRS2 | Phospho Ribosylpyrophosphate Synthetase | 5-phospho-ribosyl-1(alpha)-pyrophosphate synthetase |
| RPS26B | Ribosomal Protein of the Small subunit | Protein component of the small (40S) ribosomal subunit; homologous to mammalian ribosomal protein S26 |
| UBP3 | UBiquitin-specific Protease | Ubiquitin-specific protease involved in transport and osmotic response; interacts with Bre5p to co-regulate anterograde and retrograde transport between the ER and Golgi; involved in transcription elongation in response to osmostress through phosphorylation at Ser695 by Hog1p; inhibitor of gene silencing; cleaves ubiquitin fusions but not polyubiquitin; also has mRNA binding activity; protein abundance increases in response to DNA replication stress; role in ribophagy |
| MRP4 | Mitochondrial Ribosomal Protein | Mitochondrial ribosomal protein of the small subunit |
| RRM3 | rDNA Recombination Mutation | DNA helicase involved in rDNA replication and Ty1 transposition; binds to and suppresses DNA damage at G4 motifs in vivo; relieves replication fork pauses at telomeric regions; structurally and functionally related to Pif1p |
| OSH3 | OxySterol binding protein Homolog | Member of an oxysterol-binding protein family; this family has seven members in S. cerevisiae; family members have overlapping |
| PTC7 | Phosphatase type Two C | Type 2C serine/threonine protein phosphatase (PP2C); alternatively spliced to create two mRNA isoforms; protein from spliced form localizes to the mitochondria while the one from the unspliced form is localized to the nuclear envelope; activates coenzyme Q6 biosynthesis by dephosphorylation of demethoxy-Q6 hydroxylase Coq7p |
| PFS1 | Prospore Formation at Spindles | Sporulation protein required for prospore membrane formation; required for prospore membrane formation at selected spindle poles; ensures functionality of all four spindle pole bodies during meiosis II; not required for meiotic recombination or meiotic chromosome segregation |
| PRM2 | Pheromone-Regulated Membrane protein | Pheromone-regulated protein; predicted to have 4 transmembrane segments and a coiled coil domain; regulated by Ste12p; required for efficient nuclear fusion |
| UBP7 | UBiquitin-specific Protease | Ubiquitin-specific protease that cleaves ubiquitin-protein fusions; UBP7 has a paralog |
| DCG1 | Dal80p-Controlled Gene | Protein of unknown function; expression is sensitive to nitrogen catabolite repression and regulated by Dal80p; contains transmembrane domain |
| RPL14A | Ribosomal Protein of the Large subunit | Ribosomal 60S subunit protein L14A; N-terminally acetylated; homologous to mammalian ribosomal protein L14 |
| UFD4 | Ubiquitin Fusion Degradation protein | Ubiquitin-protein ligase (E3); interacts with Rpt4p and Rpt6p |
| HCS1 | dna HeliCaSe | Hexameric DNA polymerase alpha-associated DNA helicase A; involved in lagging strand DNA synthesis; contains single-stranded DNA stimulated ATPase and dATPase activities; replication protein A stimulates helicase and ATPase activities |
| YPF1 | Yeast Presenilin-like Family 1 | Intramembrane aspartyl protease of the perinuclear ER membrane; acts in a branch of ER-associated degradation (ERAD) that degrades functional proteins rather than misfolded proteins; regulates abundance of high-affinity plasma membrane transporters during the starvation response; has a presenilin fold; member of the GxGD family of intramembrane proteases; closest human homolog is signal peptide peptidase (SPP) |
| MST1 | Mitochondrial aminoacyl-tRNA Synthetase | threonine--tRNA ligase MST1 |
| OMA1 | Overlapping activity with M-AAA protease | Metalloendopeptidase of the mitochondrial inner membrane; important for adaptive responses to various homeostatic insults and preservation of normal mitochondrial function under damage-eliciting conditions; involved in turnover of membrane-embedded proteins; mediates degradation of |

TABLE 3-continued

List of Revalidated Genetic Modifiers of ApoE4 toxicity (see Example 7)

| Gene Name | Name Description | Description |
|---|---|---|
| | | Cox1p in coa2 mutant cells; member of a family of predicted membrane-bound metallopeptidases in prokaryotes and higher eukaryotes |
| RPL34A | Ribosomal Protein of the Large subunit | Ribosomal 60S subunit protein L34A; homologous to mammalian ribosomal protein L34 |
| APC11 | Anaphase Promoting Complex | Catalytic core subunit |
| OSH2 | OxySterol binding protein Homolog | Member of an oxysterol-binding protein family with seven members; in S. cerevisiae |
| PBP4 | Pbp1p Binding Protein | Pbp1p binding protein; interacts strongly with Pab1p-binding protein 1 (Pbp1p) in the yeast two-hybrid system; also interacts with Lsm12p in a copurification assay; relative distribution to the nucleus increases upon DNA replication stress |
| MBP1 | MluI-box Binding Protein | Transcription factor; involved in regulation of cell cycle progression from G1 to S phase |
| MDH3 | Malate DeHydrogenase | Peroxisomal malate dehydrogenase; catalyzes interconversion of malate and oxaloacetate; involved in the glyoxylate cycle |
| ATG20 | AuTophaGy related | Sorting nexin family member; required for the cytoplasm-to-vacuole targeting (Cvt) pathway and for endosomal sorting; has a Phox homology domain that binds phosphatidylinositol-3-phosphate; interacts with Snx4p; potential Cdc28p substrate |
| PCL2 | Pho85 CycLin | Cyclin |
| PPH21 | Protein PHosphatase | Catalytic subunit of protein phosphatase 2A (PP2A); functionally redundant with Pph22p; methylated at C terminus; forms alternate complexes with several regulatory subunits; involved in signal transduction and regulation of mitosis; forms nuclear foci upon DNA replication stress; PPH21 has a paralog |
| RPL35A | Ribosomal Protein of the Large subunit | Ribosomal 60S subunit protein L35A; homologous to mammalian ribosomal protein L35 and bacterial L29; RPL35A has a paralog |
| MGT1 | O-6-MethylGuanine-DNA methylTransferase | DNA repair methyltransferase (6-O-methylguanine-DNA methylase); involved in protection against DNA alkylation damage |
| GUD1 | GUanine Deaminase | Guanine deaminase; a catabolic enzyme of the guanine salvage pathway producing xanthine and ammonia from guanine; activity is low in exponentially-growing cultures but expression is increased in post-diauxic and stationary-phase cultures |
| TPS2 | Trehalose-6-phosphate PhoSphatase | Phosphatase subunit of the trehalose-6-P synthase/phosphatase complex; involved in synthesis of the storage carbohydrate trehalose; expression is induced by stress conditions and repressed by the Ras-cAMP pathway; protein abundance increases in response to DNA replication stress |
| AHA1 | Activator of Heat shock protein 90 ATPase | Co-chaperone that binds Hsp82p and activates its ATPase activity; plays a role in determining prion variants; similar to Hch1p; expression is regulated by stresses such as heat shock; protein abundance increases in response to DNA replication stress |
| ADK1 | ADenylate Kinase | Adenylate kinase |
| MHR1 | Mitochondrial Homologous Recombination | Protein involved in homologous recombination in mitochondria; required for recombination-dependent mtDNA partitioning; involved in stimulation of mitochondrial DNA replication in response to oxidative stress |
| GPI8 | Glycosyl PhosphatidylInositol anchor biosynthesis | ER membrane glycoprotein subunit of the GPI transamidase complex; adds glycosylphosphatidylinositol (GPI) anchors to newly synthesized proteins; human PIG-K protein is a functional homolog |
| RVS167 | Reduced Viability on Starvation | Actin-associated protein with roles in endocytosis and exocytosis; interacts with Rvs161p to regulate actin cytoskeleton |
| STE14 | STErile | Farnesyl cysteine-carboxyl methyltransferase; mediates the carboxyl methylation step during C-terminal CAAX motif processing of a-factor and RAS proteins in the endoplasmic reticulum |
| RAD30 | RADiation sensitive | DNA polymerase eta; involved in translesion synthesis during post-replication repair; catalyzes the synthesis of DNA opposite cyclobutane pyrimidine dimers and other lesions; involved in formation of post-replicative damage-induced genome-wide cohesion; may also have a role in protection against mitochondrial mutagenesis; mutations in human pol eta are responsible for XPV |
| PRP3 | Pre-mRNA Processing | Splicing factor; component of the U4/U6-U5 snRNP complex |
| MAD1 | Mitotic Arrest-Deficient | Coiled-coil protein involved in spindle-assembly checkpoint; required for inhibition of karyopherin/importin Pse1p (aka Kap121p) upon spindle assembly checkpoint arrest; phosphorylated by Mps1p upon checkpoint activation which leads to inhibition of anaphase promoting complex activity; forms a complex with Mad2p; gene dosage imbalance between MAD1 and MAD2 leads to chromosome instability |
| YPT32 | Yeast Protein Two | Rab family GTPase involved in the exocytic pathway; mediates intra-Golgi traffic or the budding of post-Golgi vesicles from the trans-Golgi; protein abundance increases in response to DNA replication stress; YPT32 has a paralog |
| UPF3 | UP Frameshift | Component of the nonsense-mediated mRNA decay (NMD) pathway; along with Nam7p and Nmd2p; involved in decay of mRNA containing nonsense codons; involved in telomere maintenance |
| SRB5 | Suppressor of RNA polymerase B | Subunit of the RNA polymerase II mediator complex; associates with core polymerase subunits to form the RNA polymerase II holoenzyme; essential for transcriptional regulation; required for proper termination of transcription for some genes; involved in telomere maintenance |
| CYS4 | CYStathionine beta-synthase | Cystathionine beta-synthase; catalyzes synthesis of cystathionine from serine and homocysteine |
| TRS65 | TRapp Subunit | Component of transport protein particle (TRAPP) complex II; TRAPPII is a multimeric guanine nucleotide-exchange factor for the GTPase Ypt1p |
| CRM1 | Chromosome Region Maintenance | Major karyopherin; involved in export of proteins |
| YAP1802 | Yeast Assembly Polypeptide | Protein of the AP180 family |

TABLE 3-continued

List of Revalidated Genetic Modifiers of ApoE4 toxicity (see Example 7)

| Gene Name | Name Description | Description |
|---|---|---|
| PUP2 | PUtative Proteasome subunit | Alpha 5 subunit of the 20S proteasome; involved in ubiquitin-dependent catabolism; human homolog is subunit zeta |
| VPS53 | Vacuolar Protein Sorting | Component of the GARP (Golgi-associated retrograde protein) complex; GARP is required for the recycling of proteins from endosomes to the late Golgi |
| SNA3 | Sensitivity to NA+ | Protein involved in efficient MVB sorting of proteins to the vacuole; may function as an RSP5 adapter protein for MVB cargos; integral membrane protein localized to vacuolar intralumenal vesicles |
| ECM27 | ExtraCellular Mutant | Putative protein of unknown function; may play a role in cell wall biosynthesis |
| STE24 | STErile | Highly conserved zinc metalloprotease; functions in two steps of a-factor maturation |
| ILM1 | Increased Loss of Mitochondrial DNA | Protein of unknown function; may be involved in mitochondrial DNA maintenance; required for slowed DNA synthesis-induced filamentous growth |
| HMS2 | High-copy Mep Suppressor | Protein with similarity to heat shock transcription factors; overexpression suppresses the pseudohyphal filamentation defect of a diploid mep1 mep2 homozygous null mutant; HMS2 has a paralog |
| PML1 | Pre-mRNA Leakage | Subunit of the RES complex; RES complex is required for nuclear retention of unspliced pre-mRNAs; acts in the same pathway as Pml39p and Mlp1p |
| PCD1 | Peroxisomal Coenzyme A Diphosphatase | 8-oxo-dGTP diphosphatase; prevents spontaneous mutagenesis via sanitization of oxidized purine nucleoside triphosphates; can also act as peroxisomal pyrophosphatase with specificity for coenzyme A and CoA derivatives |
| SMD2 | | Core Sm protein Sm D2; part of heteroheptameric complex (with Smb1p) |
| CWC24 | Complexed With Cef1p | General splicing factor; required for stable U2 snRNP binding to primary transcripts; essential for the first step of splicing; component of the pre-catalytic spliceosome complex containing Cef1p; similar to *S. pombe* Cwf24p |
| RPL38 | Ribosomal Protein of the Large subunit | Ribosomal 60S subunit protein L38; homologous to mammalian ribosomal protein L38 |
| RPP0 | Ribosomal Protein P0 | Conserved ribosomal protein P0 of the ribosomal stalk; involved in interaction between translational elongation factors and the ribosome; phosphorylated on serine 302; homologous to mammalian ribosomal protein LP0 and bacterial L10 |
| FBP1 | Fructose-1 | fructose 1 |
| CDC73 | Cell Division Cycle | Component of the Paf1p complex; binds to and modulates the activity of RNA polymerases I and II; required for expression of certain genes |
| URA4 | URAcil requiring | Dihydroorotase; catalyzes the third enzymatic step in the de novo biosynthesis of pyrimidines |
| ECM7 | ExtraCellular Mutant | Putative integral membrane protein with a role in calcium uptake; non-essential protein; mutant has cell wall defects and Ca+ uptake deficiencies; transcription is induced under conditions of zinc deficiency |
| CGI121 | | Component of the EKC/KEOPS complex; EKC/KEOPS complex is required for t6A tRNA modification and telomeric TG1-3 recombination; may have role in transcription; Cgi121p is dispensable for tRNA modification; other complex members are Bud32p |
| DUS1 | DihydroUridine Synthase | Dihydrouridine synthase; member of a widespread family of conserved proteins including Smm1p |
| VPS9 | Vacuolar Protein Sorting | Guanine nucleotide exchange factor (GEF); involved in vesicle-mediated vacuolar transport |
| YTA12 | Yeast Tat-binding Analog | Mitochondrial inner membrane m-AAA protease component; mediates degradation of misfolded or unassembled proteins; also required for correct assembly of mitochondrial enzyme complexes |
| RAD14 | RADiation sensitive | Protein that recognizes and binds damaged DNA during NER; subunit of Nucleotide Excision Repair Factor 1 (NEF1); contains zinc finger motif; homolog of human XPA protein; NER stands for nucleotide excision repair |
| POR1 | PORin | Mitochondrial porin (voltage-dependent anion channel); outer membrane protein required for maintenance of mitochondrial osmotic stability and mitochondrial membrane permeability; couples the glutathione pools of the intermembrane space (IMS) and the cytosol; interacts with Om45 and Om14 in the outer membrane; phosphorylated; protein abundance increases in response to DNA replication stress |
| NAR1 | Nuclear Architecture Related | Subunit of the cytosolic iron-sulfur (FeS) protein assembly machinery; required for maturation of cytosolic and nuclear FeS proteins and for normal resistance to oxidative stress; deficiency results in shortened lifespan and sensitivity to paraquat; homologous to human Narf |
| MRPL10 | Mitochondrial Ribosomal Protein | MRPL18 mitochondrial 54S ribosomal protein YmL10/YmL18 YmL18 YmL10 |
| TRM112 | TRna Methyltransferase | Protein involved in methylation of tRNA |
| BRE5 | BREfeldin A sensitivity | Ubiquitin protease cofactor; forms deubiquitination complex with Ubp3p that coregulates anterograde and retrograde transport between the endoplasmic reticulum and Golgi compartments; null is sensitive to brefeldin A |
| | | Epoxide hydrolase; member of the alpha/beta hydrolase fold family; may have a role in detoxification of epoxides |
| COQ3 | COenzyme Q | O-methyltransferase; catalyzes two different O-methylation steps in ubiquinone (Coenzyme Q) biosynthesis; component of a mitochondrial ubiquinone-synthesizing complex; phosphoprotein |
| RRI2 | | Subunit of the COP9 signalosome (CSN) complex; this complex cleaves the ubiquitin-like protein Nedd8 from SCF ubiquitin ligases; plays a role in the mating pheromone response |
| HRP1 | Heterogenous nuclear RibonucleoProtein | Subunit of cleavage factor I; cleavage factor I is a five-subunit complex required for the cleavage and polyadenylation of pre-mRNA 3' ends; RRM-containing heteronuclear RNA binding protein and hnRNPA/B family member that binds to poly (A) signal sequences; required for genome stability |
| RTS1 | Rox Three Suppressor | B-type regulatory subunit of protein phosphatase 2A (PP2A); Rts1p and Cdc55p are alternative regulatory subunits for PP2A catalytic subunits |
| SMP3 | | Alpha 1 |
| SPS4 | SPorulation Specific trancript | Protein whose expression is induced during sporulation; not required for sporulation; heterologous expression in *E. coli* induces the SOS response that senses DNA damage |

TABLE 3-continued

List of Revalidated Genetic Modifiers of ApoE4 toxicity (see Example 7)

| Gene Name | Name Description | Description |
|---|---|---|
| GNT1 | GlcNAc Transferase | N-acetylglucosaminyltransferase; capable of modification of N-linked glycans in the Golgi apparatus |
| LDB19 | Low Dye Binding | Alpha-arrestin involved in ubiquitin-dependent endocytosis; regulates endocytosis of plasma membrane proteins by recruiting the ubiquitin ligase Rsp5p to its targets; involved in the basal internalization and turnover of alpha-factor receptor Ste2p; recruits ubiquitin ligase Rsp5p to Ste2p via its 2 PPXY motifs; inhibited by Npr1p-mediated phosphorylation |
| SUR1 | SUppressor of Rvs161 and rvs167 mutations | Mannosylinositol phosphorylceramide (MIPC) synthase catalytic subunit; forms a complex with regulatory subunit Csg2p; function in sphingolipid biosynthesis is overlapping with that of Csh1p; SUR1 has a paralog |
| MUK1 | coMpUtationally-linked to Kap95 | Guanine nucleotide exchange factor (GEF); involved in vesicle-mediated vacuolar transport |
| SEC62 | SECretory | Essential subunit of Sec63 complex; with Sec61 complex |
| GYP5 | Gtpase-activating protein for Ypt Proteins | GTPase-activating protein (GAP) for yeast Rab family members; involved in ER to Golgi trafficking; exhibits GAP activity toward Ypt1p that is stimulated by Gyl1p |
| KEL3 | KELch | Cytoplasmic protein of unknown function |
| PIN3 | Psi+ INducibility | Negative regulator of actin nucleation-promoting factor activity; interacts with Las17p |

The nucleotide and protein sequences of the human genes listed in any one or more of Tables 1C, 1D, 2A, 2B, and 2C, and their encoded proteins, can be used to generate and/or identify compounds (including but not limited to nucleic acids, peptides, antibodies, and small molecules) that modulate expression of the genes or activity of encoded gene products. For example, as described further below, RNAi agents that inhibit expression of a gene can be designed based on the mRNA sequence. The proteins can be produced using recombinant DNA methods and used as immunogens or affinity reagents for production or selection of antibodies or aptamers or in screens of small molecule libraries to identify compounds that bind to or modulate activity of the protein. As noted above, one of ordinary skill in the art will appreciate that, due to the degeneracy of the genetic code, a given amino acid sequence may be encoded by any of a wide variety of nucleic acid sequences. Any such nucleic acid sequence may be used to encode a protein, e.g., for purposes of expressing the protein for any purpose.

Certain of the human genes that are homologs of yeast genes that are modifiers of ApoE-mediated toxicity may encode more than one isoform of a particular protein from the same genomic sequence, e.g., as a result of splice variation or use of alternative start codons. Certain embodiments of methods and compositions herein may be directed to or use particular isoform, e.g., any isoform having a Reference Sequence (RefSeq) in the NCBI RefSeq database or having an accession number in the UniProt database. In some embodiments, an isoform is normally expressed in the adult human brain (e.g., in one or more regions that is typically affected in individuals with AD, such as the hippocampus and/or cerebral cortex). In some embodiments, an isoform is the canonical isoform identified in the UniProt database. Certain of the human genes that are homologs of yeast genes that are modifiers of ApoE-mediated toxicity may have multiple different alleles. Certain embodiments of methods and compositions herein may be directed to or use any such allele. In some embodiments an allele is associated with an ApoE-mediated disease, e.g., Alzheimer's disease.

Counterparts of at least some of the yeast genes and encoded proteins identified as modifiers of ApoE-mediated toxicity are present in a variety of nonhuman multicellular organisms, e.g., worms, flies, mice, rats, and/or non-human primates. In some embodiments such genes or their encoded gene products may be used for a variety of purposes. For example, the genes can be overexpressed, inhibited, or disabled (e.g., by mutation or at least partial deletion), e.g., in cells of their organism of origin, and thereby used to modulate ApoE-mediated toxicity in such cells. In some embodiments the cells are used in screens for identifying compounds that modulate ApoE-mediated toxicity or for characterizing compounds identified in other systems. In some embodiments, non-human animals (e.g., mice, rats, Drosophila, C. elegans) in which the counterpart native to that animal species is overexpressed, inhibited, or disabled may be generated. In some embodiments such animals are used to screen for or characterize compounds that modulate ApoE-mediated toxicity.

The genes identified herein as modulators of ApoE-mediated toxicity are sometimes referred to in subsequent sections (e.g., regarding screening assays) as "target genes" and their encoded proteins are sometimes referred to as "target proteins". It will be understood that such terms refer to the yeast genes in any one or more of Tables 1A, 1B, 1C, 1D, 2A, 2B, 2C, and 3, and to their counterparts in other organisms, e.g., humans. Names of genes provided herein should be understood to encompass reference to the gene and its encoded gene product(s), e.g., protein(s) unless otherwise indicated or otherwise evident from the context. For example, where referring to modulating (e.g., inhibiting or increasing) expression of a gene, such reference should be understood to encompass modulating expression of the gene at the level of mRNA and/or protein (e.g., modulating the level of mRNA and/or modulating the level of protein). For example, overexpressing a gene encompasses overexpressing a protein encoded by the gene, wherein the protein may be encoded by a nucleic acid (e.g., an expression construct) that has been introduced into the cell or an ancestor of the cell. In some embodiments, expression or activity of a gene or gene product is increased by at least or about 25%, 50%, or 100%. In some embodiments, expression or activity of a gene or gene product is increased by a factor of at least or about 2, 3, 4, 5, 10, 20, 50, 100, or more. Inhibiting or disabling a gene encompasses inhibiting or disabling the gene in the genome of a cell or organism or inhibiting or disabling an expression product of the gene, e.g., a mRNA or protein encoded by the gene. Modulating activity of a gene encompasses modulating activity of a product, e.g., a protein, encoded by the gene. In some embodiments, expression or activity of a gene or gene product is reduced by at least or about 20%, 30%, 40%, 50%, 60%, 70%, 80%, 90%, 95%, 98%, 99%, or more. In some embodiments expression or activity is rendered undetectable.

It is expected that modulating expression of the yeast genes listed in any one or more of Tables 1A, 1B, 1C, 1D, 2A, 2B, 2C, and 3 or the human homologs listed in any one or more of Tables 1C, 1D, 2A, 2B, and 2C and/or modulating activity of proteins encoded by the genes will result in modulation of ApoE mediated toxicity, e.g., in ApoE expressing cells. For example, for those genes that were found to suppress toxicity when overexpressed in yeast, it is expected that, in general, enhancing expression of the genes or their human counterparts and/or enhancing activity of proteins encoded by the genes or their human counterparts will result in a suppression of ApoE-mediated toxicity, e.g., in ApoE-expressing cells. However, in some embodiments, inhibiting the expression or activity of certain of the yeast suppressors of ApoE-mediated toxicity or their human counterparts may suppress ApoE-mediated toxicity. For those genes that were found to suppress toxicity when overexpressed in yeast, it is expected that, in general, inhibiting expression of the genes and/or activity of proteins encoded by the genes will result in enhancement of ApoE-mediated toxicity, e.g., in ApoE-expressing cells. However, in some embodiments, enhancing the expression or activity of certain of the yeast suppressors of ApoE-mediated toxicity or their human counterparts may enhance ApoE-mediated toxicity For those genes that were found to enhance toxicity when overexpressed in yeast, it is expected that, in general, inhibiting expression of the genes or their human counterparts and/or inhibiting the activity of proteins encoded by the genes or their human counterparts will result in a suppression of ApoE-mediated toxicity, e.g., in ApoE-expressing cells. However, in some embodiments, inhibiting the expression or activity of certain of the yeast enhancers of ApoE-mediated toxicity or their human counterparts may suppress ApoE-mediated toxicity. For those genes that were found to enhance toxicity when overexpressed in yeast, it is expected, in some embodiments, that enhancing expression of the genes and/or enhancing the activity of proteins encoded by the genes will result in enhancement of ApoE-mediated toxicity, e.g., in ApoE-expressing cells. However, in some embodiments, enhancing the expression or activity of certain of the yeast enhancers of ApoE-mediated toxicity or their human counterparts may suppress ApoE-mediated toxicity.

In some embodiments the effect of enhancing or inhibiting the expression or activity of a yeast suppressor or enhancer of ApoE-associated toxicity, or a human homolog thereof, may be at least partly isoform specific, e.g., if the yeast suppressor suppresses toxicity of one or two of the three ApoE isoforms(s) but not the other(s), then modulating its expression or activity or that of a human homolog thereof may only significantly affect toxicity mediated by one or more of the particular isoforms whose toxicity the yeast suppressor suppresses. In some embodiments a suppressor suppresses only toxicity induced by ApoE2. In some embodiments a suppressor suppresses only toxicity induced by ApoE3 only. In some embodiments a suppressor suppresses only toxicity induced by ApoE4. In some embodiments, a suppressor suppresses toxicity induced by two or more isoforms, e.g., ApoE4 and at least one other isoform. In some embodiments an enhancer enhances only toxicity induced by ApoE2. In some embodiments an enhancer enhances only toxicity induced by ApoE3 only. In some embodiments an enhancer enhances only toxicity induced by ApoE4. In some embodiments, an enhancer enhances toxicity induced by two or more isoforms, e.g., ApoE4 and at least one other isoform. In some embodiments the effect of enhancing or inhibiting the expression or activity of a yeast suppressor or enhancer of ApoE-associated toxicity or a human homolog thereof may not be isoform-specific. In other words, modulating the expression or activity of a yeast suppressor or enhancer of ApoE-associated toxicity, or a human homolog, thereof would significantly affect toxicity mediated by any ApoE isoform. In some embodiments a suppressor or enhancer may be identified in a yeast strain expressing a first isoform and tested in a strain expressing a different isoform for ability to suppress or enhance toxicity induced by the different isoform. In some embodiments, a suppressor or enhancer that modulates, e.g., inhibits, toxicity induced by any one or more ApoE isoforms may be identified.

In some aspects, described herein are cells comprising a first expression construct comprising a first promoter operably linked to a first nucleic acid encoding a polypeptide comprising a human ApoE protein, wherein the cell: (a) further comprises a second expression construct comprising a second promoter operably linked to a second nucleic acid encoding a polypeptide encoded by a genetic suppressor or enhancer of ApoE-mediated toxicity listed in any one or more of Tables 1A, 1B, 2A, 2B, 2C, and 3 or a mammalian (e.g., human) homolog thereof or (b) has reduced or absent expression or activity of a protein encoded by a genetic suppressor or enhancer of ApoE-mediated toxicity listed in any one or more of Tables 1A, 1B, 2A, 2B, 2C, and 3 or a mammalian (e.g., human) homolog thereof. In some embodiments the first expression construct, the second expression construct, or both, are integrated into the genome of the cell. In some embodiments the polypeptide encoded by the second nucleic acid is a chimeric or fusion protein that comprises a protein encoded by a genetic suppressor or enhancer of ApoE-mediated toxicity and a heterologous polypeptide, e.g., at least a portion of a second protein such as a detection protein (e.g., a fluorescent protein, an enzyme, or an epitope tag). Thus the polypeptide encoded by the second nucleic acid may comprise or consist of a protein encoded by a genetic suppressor or enhancer of ApoE-mediated toxicity. In some embodiments the cells are yeast cells. In some embodiments the cells are vertebrate cells, e.g., mammalian cells, e.g., human cells. In some embodiments such cells, e.g., yeast cells or mammalian (e.g., human) cells, may be used in screens to identify compounds that modulate, e.g., inhibit, ApoE-mediated toxicity. In some embodiments the yeast gene has a human homolog that is a known genetic risk factor for an ApoE-mediated disease, e.g., AD. In some embodiments the yeast gene does not have a human homolog that is a known genetic risk factor for an ApoE-mediated disease, e.g., AD. As used herein, "known" in regard to a genetic risk factor for an ApoE-mediated disease means that the gene or one or more variants thereof has been identified as a genetic risk factor for an ApoE-mediated disease as of the filing date of the present application.

In some aspects, described herein are yeast cells that express human ApoE and that overexpress or have reduced or absent expression of a yeast gene that is a genetic modifier of ApoE-mediated toxicity (e.g., a yeast gene listed in any one or more of Tables 1A, 1B, 1C, 1D, 2A, 2B, 2C, and 3), wherein a human homolog of such yeast gene is a genetic risk factor for an ApoE-mediated disease, e.g., AD. In some embodiments, such yeast cells may serve as personalized models for identifying candidate agents (e.g., small molecules) that are of particular use for treating subjects with the disease who harbor the genetic risk factor. In some embodiments, screens are performed in such cells to identify such compounds. For example, in some embodiments, if the yeast gene is a suppressor of ApoE-mediated toxicity when overexpressed, then a yeast cell that expresses ApoE and has reduced or absent expression of the yeast gene may serve as a model for a subject who has a risk allele of the human homolog of the yeast gene. In some embodiments, if the yeast gene is an enhancer of ApoE-mediated toxicity when overexpressed, then a yeast cell that expresses ApoE and overexpresses the yeast gene may serve as a model for a subject who has a risk allele of the human homolog of the yeast gene.

In some embodiments, yeast expressing ApoE are used to identify biological pathways that are perturbed by ApoE and/or to identify phenotypes that correlate with ApoE-mediated toxicity. Genes and their encoded proteins that act in such biological pathways or processes may be useful targets for modulating, e.g., suppressing, ApoE-mediated toxicity. In some embodiments, genes (and their encoded proteins) that act in the same biological pathway or process as a yeast gene or human counterpart identified herein (e.g., in any one or more of Tables 1A, 1B, 1C, 1D, 2A, 2B, 2C, and 3) or that act as an endogenous inhibitor or activator of the expression or activity of such yeast gene or human counterpart may be useful targets for modulating, e.g., suppressing, ApoE-mediated toxicity. Compounds that modulate expression or activity of such genes may be identified using screening assays described herein. In some embodiments genes (and their encoded proteins) that act in the same biological pathway or process as a yeast gene or human counterpart of interest may be determined using knowledge bases such as Gene Ontology (The Gene Ontology Consortium. Gene ontology: tool for the unification of biology. Nat Genet; 25(1):25-9 (2000), KEGG (Kanehisa, M. and Goto, S.; KEGG: Kyoto Encyclopedia of Genes and Genomes. Nucleic Acids Res. 28, 27-30 (2000); Kanehisa, M., et al. Nucleic Acids Res. 42, D199D205 (2014), MetaCyc (Caspi et al., Nucleic Acids Research 42:D459-D471 2014), Reactome (Croft D, et al. *Nucleic Acids Res.* 42(Database issue):D472-7, (2014), STKE, and BioCarta.

For example, a number of the genes identified herein as modifiers of ApoE-mediated toxicity function in endocytosis. As described in Example 6, yeast that express ApoE display perturbed endocytosis, thus identifying endocytosis and genes involved in endocytosis pathway as targets for the identification of compounds that ameliorate ApoE-mediated toxicity. In some embodiments, the modulator of ApoE-mediated toxicity that is involved in endocytosis is RVS161, OSH2, RVS167, YAP1802, OSH3 or a mammalian (e.g., human) homolog thereof.

A number of genes identified herein as modifiers of ApoE-mediated toxicity function in vesicle transport. In some embodiments, the modulator of ApoE-mediated toxicity that is involved in vesicle transport is ATG20, UBP3, TRS65, BRE5, MUK1, GYPS, or a mammalian (e.g., human) homolog thereof.

A number of genes identified herein as modifiers of ApoE-mediated toxicity function in ubiquitination/deubiquitination. In some embodiments, the modulator of ApoE-mediated toxicity that is involved in ubiquitination/deubiquitination is APC11, UBP3, UBP7, CDC73, BRE5, RRI2, or a mammalian (e.g., human) homolog thereof.

A number of genes identified herein as modifiers of ApoE-mediated toxicity function in lipid metabolism. In some embodiments, the modulator of ApoE-mediated toxicity that is involved in lipid metabolism is PER1, MDH3, GPI8, SMP3, SUR1, or a mammalian (e.g., human) homolog thereof.

A number of genes identified herein as modulators of ApoE-mediated toxicity function in DNA repair. In some embodiments, the modulator of ApoE-mediated toxicity involved in DNA repair is MGT1, PCD1, CDC73, RAD14, or a mammalian (e.g., human) homolog thereof.

A number of genes identified herein as modulators of ApoE-mediated toxicity function in mitochondrion organization. In some embodiments, the modulator of ApoE-mediated toxicity involved in mitochondrion organization is ATG20, MHR1, MRP4, RRM3, ILM1, MST1, YTA12, POR1, MRPL10, or a mammalian (e.g., human) homolog thereof.

Screening Assays

Certain aspects of the present disclosure provide methods of screening for a candidate agent or a genetic factor that modulates, e.g., inhibits, ApoE-induced toxicity. In certain embodiments, screening methods described herein use yeast cells that are engineered to express an ApoE protein. In some embodiments, a method of screening for a compound for treating an ApoE-mediated disease comprises: (a) providing a yeast cell engineered to express a polypeptide comprising an ApoE protein; (b) contacting the yeast cell with a candidate compound; and (c) evaluating the yeast cell for viability, wherein an increase in viability of the yeast cell as compared to viability of the yeast cell in the absence of the candidate compound indicates that the candidate compound is a candidate therapeutic agent. Various types of candidate agents (also referred to as "candidate compounds", "test agents", or "test compounds") may be screened using methods described herein, including nucleic acids, polypeptides, small molecule compounds, and peptidomimetics. In some embodiments, candidate agents can be screened by contacting the yeast cell with the candidate agent. For example, yeast cells may be cultured in liquid medium containing a candidate agent. In some embodiments, genetic agents can be screened by contacting the yeast cell with a nucleic acid construct coding for a gene product. For example, one may screen cDNA libraries expressing a variety of gene products in order to identify genes that modulate ApoE-induced toxicity.

In some embodiments, e.g., for chemical screens, yeast strains harboring one or more mutations designed to affect membrane efflux pumps or increase permeability for drugs can be used. For example, yeast strains bearing mutations in the ERG6 gene, the PDR1 gene, the PDR3 gene, and/or the PDR5 gene are contemplated to be of use. For example, a yeast strain bearing mutations in one or more genes encoding a membrane efflux pump or transcription factor that directs expression of a gene encoding a membrane efflux pump (erg6, pdr1, pdr3, and/or pdr5) has been successfully used in many screens to identify growth regulators (Jensen-Pergakes K L, et al., 1998. Antimicrob Agents Chemother 42:1160-7). Yeast may be engineered to harbor mutations of any one or more genes encoding a membrane efflux pump or a transcription factor that regulates expression of a membrane efflux pump. In some aspects, described herein are yeast cells that are engineered to express an ApoE protein and that have a mutation in one or more genes encoding a membrane efflux pump or transcription factor that directs expression of a gene encoding a membrane efflux pump.

An attractive aspect of yeast is the possibility of performing high throughput screens that may identify small molecules, genes, peptides, and other compounds with the potential to ameliorate toxicity. A toxicity screen has the advantage of not only having the capacity to select for compounds that interact with ApoE, but also the capacity to select for compounds that may interact with upstream or downstream targets that are not themselves cytotoxic, including targets that may not yet be identified. Accordingly, irrespective of the exact mechanism of action, agents identified by the screening methods described herein are expected to provide therapeutic benefit in ApoE-mediated diseases, e.g., Alzheimer's disease.

Compounds to be screened or identified using any of the methods described herein can include various chemical classes, though typically small organic molecules having a molecular weight in the range of 50 to 2,500 daltons may be used. In some embodiments, the small molecule is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

In some embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, and polynucleotide analogs.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Compound libraries of interest include non-peptide combinatorial libraries, peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997).

In certain embodiments, candidate agents to be screened may be naturally occurring compounds or artificial compounds. In certain embodiments, candidate agents can be screened from large libraries of synthetic or natural compounds. One example is a library of FDA approved compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts, fermentation broths (e.g., soil, bacterial or fungal fermentation broths), are commercially available or can be readily prepared by methods well known in the art. In some embodiments a library may comprise, e.g., at least 100, at least 1,000, at least 10,000, at least 100,000, at least 250,000 compounds, at least 500,000 compounds or more, e.g., up to 1-2 million compounds, or more. Compounds may be arrayed in multiwell plates. They may be dissolved in a solvent (e.g., DMSO) or provided in dry form, e.g., as a powder or solid.

Identification of test compounds, e.g., through the use of libraries such as those herein, permits subsequent modification of the test compound "hit" or "lead" to optimize the capacity of the "hit" or "lead" to prevent or suppress ApoE-mediated toxicity and/or to prevent or suppress amyloid beta-mediated toxicity. Such optimization is an aspect of the present disclosure. For example, analogs of compounds identified as hits in a screen can be obtained, e.g., synthesized. In some embodiments, multiple analogs of a hit are tested, e.g., to identify those that have one or more altered properties (e.g., physico-chemical, pharmacokinetic and/or pharmacodynamic properties) e.g., one or more improved properties, relative to the hit. An improved property may be, for example, increased potency, increased binding affinity for a target protein, reduced off-target effects, lower affinity for a non-target molecule, reduced toxicity, increased half-life, increased bioavailability (e.g., increased oral bioavailability), increased stability (in vitro and/or in vivo), increased solubility (e.g., increased aqueous solubility), increased ability to cross the blood-brain barrier (e.g., where such passage is useful for treatment of a neurodegenerative disease), increased or decreased plasma protein binding (either of which may be desirable in certain embodiments), etc. Optimization can be accomplished through empirical modification of the hit structure (e.g., synthesizing compounds with related structures and testing them in cell-free or cell-based assays or in non-human animals), using established principles of medicinal chemistry, using computational approaches, or a combination thereof. In some embodiments, structures of hit compounds are examined to identify a pharmacophore, which can be used to design additional compounds.

In some embodiments the effect of a compound on ApoE-associated toxicity may be at least partly isoform specific, e.g., the compound modulates, e.g., inhibits, toxicity of one or two of the three ApoE isoforms(s) but not the other(s). In some embodiments a compound inhibits only toxicity induced by ApoE2. In some embodiments a compound inhibits only toxicity induced by ApoE3. In some embodiments a compound inhibits only toxicity induced by ApoE4. In some embodiments a compound inhibits toxicity induced by two or more isoforms, e.g., ApoE4 and at least one other isoform. In some embodiments the effect of a compound on ApoE-associated toxicity may not be isoform-specific. In other words, the compound significantly affects, e.g., inhibits, toxicity mediated by any ApoE isoform. In some embodiments a compound may be identified as a modulator, e.g., an inhibitor, of ApoE-mediated toxicity in a yeast strain expressing a first isoform and tested in a strain expressing a different isoform for ability to inhibit or enhance toxicity induced by the different isoform. In some embodiments, compounds that modulate, e.g., inhibit, toxicity induced by any one or more ApoE isoforms may be identified.

As detailed in Example 6, expression of ApoE in yeast cells resulted in a defect in endocytosis. In addition to this biological finding, several toxicity suppressors identified in a genetic screen encode proteins that function in endocytosis. Thus, two distinct approaches identify defects in endocytosis as a cellular consequence of ApoE-mediated toxicity. An exemplary assay for measuring endocytosis in yeast cells is described in Example 6. In this assay, the endocytosis of wild-type proteins (such as the methionine transporter MUP1) that are normally endocytosed (e.g., under appropriate conditions) is monitored. As detailed herein, expression of ApoE inhibits endocytosis of MUP1. Screening methods can be performed (using, e.g., candidate agents described herein) to identify compounds that modulate (increase or decrease) endocytosis in cells expressing ApoE. Compounds that increase endocytosis are expected to be candidate therapeutic agents for reducing ApoE-mediated toxicity and treating ApoE-mediated diseases. Additional assays that can be used (in the screening methods described herein) for measuring endocytosis are known in the art.

Compounds tested or identified as described herein can be synthesized by any chemical or biological method. The compounds tested or identified as described herein may be pure or may be in a composition that contains one or more additional component(s). Compounds can be prepared in an assay-, physiologic-, or pharmaceutically-acceptable diluent or carrier (see below).

Certain embodiments of the present disclosure relate to genetic screens. For example, genomic libraries, open reading frame libraries, and disruption libraries can be screened to find extragenic suppressors or enhancers of ApoE-induced toxicity. The particular gene that is overexpressed or disrupted can be determined. In some embodiments individual transformants with reduced or enhanced ability to grow are isolated, and the particular gene that is overexpressed or disrupted in the transformant is determined.

In some embodiments, a pooled screen may be performed, e.g., as described in the Examples. In certain embodiments a pooled screen comprises co-culturing yeast cells that have been transformed with a pool of vectors each comprising an individual open reading frame under control of a promoter. After the cells have been cultured for a suitable period of time under conditions in which ApoE is expressed at an appropriate level (i.e., a level that would be sufficient to detectably induce toxicity in the absence of a suppressor of ApoE-mediated toxicity), DNA is harvested, and high throughput sequencing performed to identify those ORFs that are overrepresented or underrepresented in the culture as compared to their representation in a control culture in which ApoE expression was not induced. In certain embodiments a pooled screen comprises co-culturing yeast cells that harbor disruptions of individual ORFs. The disruptions may comprise insertions of distinct DNA segments that serve as molecular barcodes, allowing the identification of the ORF that was disrupted.

Screens (e.g., for compounds and/or for suppressors or enhancers) can be carried out under a variety of different conditions. If desired, compounds can be screened under a variety of growth conditions and in a variety of genetic backgrounds. For example, a variety of different culture media can be used. Culture media can contain different carbon sources, e.g., different sugars such as glucose, glycerol, galactose, raffinose, etc. In some embodiments, multiple screens are performed using two, three, or more different culture conditions (e.g., culture media containing different carbon sources), and compounds or genes identified as "hits" under at least two different culture conditions are identified.

Certain embodiments provide methods that comprise testing a candidate agent (e.g., a small molecule) that has been identified in the yeast system in one or more other model systems. Such model systems include, but are not limited to, cell-based models, e.g., mammalian cells, and in vivo animal models such as worms, flies, and non-human mammalian models. Non-mammalian cells or organisms can be genetically engineered to express a polypeptide comprising human ApoE. Non-human mammalian cells or organisms can be genetically engineered to express a polypeptide comprising any human ApoE isoform or to overexpress a polypeptide comprising the endogenous ApoE counterpart native to that organism. In some embodiments the polypeptide comprises the human ApoE signal sequence (SEQ ID NO: 5) fused to mature human ApoE2 (SEQ ID NO: 1), mature human ApoE3 (SEQ ID NO: 2), or mature human ApoE4 (SEQ ID NO: 3). In some embodiments the polypeptide comprises the human insulin preprotein signal sequence (SEQ ID NO: 11) fused to mature human ApoE2 (SEQ ID NO: 1), mature human ApoE3 (SEQ ID NO: 2), or mature human ApoE4 (SEQ ID NO: 3). In some embodiments a signal sequence from a protein native to the non-human organism may be used. For example, a signal sequence from a non-human mammal such as a mouse or rat may be used. In some embodiments the signal sequence from a non-human mammal is the ApoE or insulin secretion signal sequence native to that organism. Mouse ApoE gene has NCBI Gene ID 11816. Rat ApoE gene has NCBI Gene ID 25728.

Human cells may be of any APOE genotype. In some embodiments they may be engineered to overexpress any human ApoE isoform and/or to include any ApoE mutation. The cells may comprise neural progenitor cells, neurons, glial progenitor cells, glial cells, or a combination thereof. In some embodiments the cells may be derived from a subject suffering from an ApoE-mediated disease, e.g., AD. In some embodiments the human cells may be derived by reprogramming from pluripotent stem cells (e.g., ES cells or iPS cells)

or by transdifferentiation. Methods of deriving or engineering human cells described further below may be used to derive or engineer the cells.

Certain embodiments provide methods that comprise testing genes and proteins that are identified as genetic modifiers of ApoE-mediated toxicity in yeast, e.g., genes and proteins identified herein (and/or counterparts thereof) in other model systems. For example, worm, fly, rodent (e.g., mouse or rat) counterparts of yeast genes identified as genetic modifiers of ApoE-induced toxicity can be overexpressed or inhibited or disabled in worms, flies, rodent(s), respectively, or in cells derived from organism of such types (e.g., primary cells or cell lines, e.g., immortalized cell lines) or a human gene that is a counterpart of a can be expressed in a non-human cell or in a non-human animal. In some aspects, the invention provides such non-human animals and cells. In some embodiments, the cells are isolated cells. In some embodiments, the cells are primary cells isolated from an animal. In some embodiments, a cell line is used. The cells may be genetically engineered to express human ApoE of any isoform.

In some embodiments, human cells may be genetically engineered to express or overexpress a human homolog of a yeast gene that is a genetic modifier of ApoE-mediated toxicity or to have reduced expression or lack expression of the human homolog. The human cells may have any APOE genotype in various embodiments. They may be homozygous or heterozygous for any APOE allele.

It will be understood that the terms "genetically engineered cell" and "genetically modified cell" includes those cells that are subjected to a procedure that results in a genetic modification as well as their descendants, which inherit the modification. Likewise a "genetically engineered organism" and "genetically modified organism" includes those organisms that are subjected to a procedure that results in a genetic modification as well as their descendants, which inherit the modification.

In some aspects, described herein are methods (also referred to herein as "target gene screening assays") for identifying compounds that modulate (i.e., increase or decrease) expression or activity of selected target genes or their protein products. Such compounds include, e.g., polypeptides, peptides, antibodies, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that bind to the target proteins, or have a stimulatory or inhibitory effect on, for example, expression of a target gene or activity of a target protein. Any of the test compounds and/or compound libraries described above may be used in the target gene screening assays. Compounds thus identified can be used to modulate the expression or activity of target genes or target proteins in a therapeutic protocol and/or in further screening methods.

In some embodiments, target gene screening assays of the invention involve assaying the effect of a test compound on expression or activity of a target nucleic acid or target protein in a test sample (i.e., a sample containing the target nucleic acid or target protein). Expression or activity in the presence of the test compound can be compared to expression or activity in a control sample (i.e., a sample containing the target protein that is incubated under the same conditions, but without the test compound). A change in the expression or activity of the target nucleic acid or target protein in the test sample compared to the control indicates that the test compound modulates expression or activity of the target nucleic acid or target protein and is a candidate agent. Compounds can be tested for their ability to modulate one or more activities mediated by a target protein described herein. For example, compounds that modulate expression of a gene or activity of a protein listed in any one or more of Tables 1A, 1B, 1C, 1D, 2A, 2B, 2C, and 3 can be tested for their ability to modulate toxicity in cells expressing ApoE. Methods of assaying a compound for such activities are known in the art. In some cases, a compound is tested for its ability to directly affect target gene expression or binding to a target protein (e.g., by decreasing the amount of target RNA in a cell or decreasing the amount of target protein in a cell) and/or tested for its ability to modulate a metabolic effect or phenotype associated with the target protein.

In some embodiments, assays are provided for screening candidate or test molecules that are substrates of a target protein or a biologically active portion thereof in a cell. In some embodiments, the assays are for screening candidate or test compounds that bind to a target protein or modulate the activity of a target protein or a biologically active portion thereof. Such compounds include those that disrupt the interaction between a target protein and its ligand or receptor. In some embodiments, the assays comprise screening to identify such compounds.

In some embodiments, a cell-based assay is employed in which a cell that expresses a target protein or biologically active portion thereof is contacted with a test compound. The ability of the test compound to modulate expression or activity of the target protein is then determined. The cell may, for example, be a yeast cell or a cell of mammalian origin, e.g., a rat, mouse, or human cell.

The ability of the test compound to bind to a target protein or modulate target protein binding to a compound, e.g., a target protein substrate, can also be evaluated. This can be accomplished, for example, by coupling the compound, e.g., the substrate, with a radioisotope or enzymatic label such that binding of the compound, e.g., the substrate, to the target protein can be determined by detecting the labeled compound, e.g., substrate, in a complex. Alternatively, the target protein can be coupled with a radioisotope or enzymatic label to monitor the ability of a test compound to modulate target protein binding to a target protein substrate in a complex. For example, compounds (e.g., target protein substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In some embodiments, the ability of a compound to interact with a target protein in a cell or at the cell surface may be evaluated without labeling any of the interactants. For example, an alteration in intracellular concentration of various ions, metabolites, pH, or other parameters may be detected using suitable indicators (e.g., ion-sensitive or pH-sensitive proteins or small molecules).

In some embodiments, a cell-free assay is provided in which a target protein or biologically active portion thereof is contacted with a test compound and the ability of the test compound to bind to the target protein or biologically active portion thereof is evaluated. In general, biologically active portions of target proteins to be used in assays described herein include fragments that participate in interactions with other molecules, e.g., fragments with high surface probability scores. In some embodiments, a cell-free assay involves preparing a reaction mixture of the target protein and the test compound under conditions and for a time sufficient to allow the two components to interact and bind, thus forming a complex that can be removed and/or detected. The interaction between two molecules can also be detected using fluorescence energy transfer (FET) (see, for example, Lakowicz et al., U.S. Pat. No. 5,631,169; Stavrianopoulos et al, U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule may use the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

In another embodiment, the ability of a target protein to bind to a target molecule can be determined using real-time Biomolecular Interaction Analysis (BIA) (e.g., Sjolander et al., Anal. Chem., 63:2338-2345, 1991, and Szabo et al., Curr. Opin. Struct. Biol., 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR), resulting in a detectable signal which can be used as an indication of real-time reactions between biological molecules.

In various of these assays, the target protein or the test substance is anchored onto a solid phase. The target protein/test compound complexes anchored on the solid phase can be detected at the end of the reaction. Generally, the target protein is anchored onto a solid surface, and the test compound (which is not anchored) can be labeled, either directly or indirectly, with detectable labels discussed herein. It may be desirable to immobilize either the target protein, an anti-target protein antibody, or its target molecule to facilitate separation of complexed from uncomplexed forms of one or both of the proteins, as well as to accommodate automation of the assay. Binding of a test compound to a target protein, or interaction of a target protein with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase/target protein fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein. The mixture is then incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target protein binding or activity determined using standard techniques. Other techniques for immobilizing a target protein on matrices include using conjugation of biotin and streptavidin. Biotinylated target protein can be prepared from biotin-NHS (N-hydroxy-succinimide) using techniques known in the art and immobilized in the wells of streptavidin-coated 96 well plates. To conduct the assay, the non-immobilized component is added to the coated surface containing the anchored component. After the reaction is complete, unreacted components are removed (e.g., by washing) under conditions such that any complexes formed will remain immobilized on the solid surface. The complexes anchored on the solid surface can be detected in a number of ways. Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with target protein, but which do not interfere with binding of the target protein to its target molecule. Such antibodies can be derivatized to the wells of the plate, and unbound target protein trapped in the wells by antibody conjugation. Methods for detecting such complexes, in addition to those described above for the GST-immobilized complexes, include immunodetection of complexes using antibodies reactive with the target protein or target molecule, as well as enzyme-linked assays which rely on detecting an enzymatic activity associated with the target protein.

Alternatively, cell-free assays can be conducted in a liquid phase. In such an assay, the reaction products are separated from unreacted components, by any of a number of standard techniques, including but not limited to: differential centrifugation (see, for example, Rivas and Minton, Trends Biochem. Sci., 18:284-7, 1993); chromatography (gel filtration chromatography, ion-exchange chromatography); electrophoresis (e.g., Ausubel et al., eds. Current Protocols in Molecular Biology 1999, J. Wiley: New York.); and immunoprecipitation (see, for example, Ausubel et al., eds., 1999, Current Protocols in Molecular Biology, J. Wiley: New York). Such resins and chromatographic techniques are known to one skilled in the art (e.g., Heegaard, J. Mol. Recognit, 11: 141-148, 1998; Hage et al., J. Chromatogr. B. Biomed. Sci. Appl., 699:499-525, 1997). Further, fluorescence energy transfer may also be conveniently utilized, as described herein, to detect binding without further purification of the complex from solution.

The assay can include contacting the target protein or a biologically active portion thereof with a known compound that binds to the target protein to form an assay mixture, contacting the assay mixture with a test compound, and determining the ability of the test compound to interact with the target protein, wherein determining the ability of the test compound to interact with the target protein includes determining the ability of the test compound to preferentially bind to the target protein or biologically active portion thereof, or to modulate the activity of a target molecule, as compared to the known compound.

A target protein can, in vivo, interact with one or more cellular or extracellular macromolecules, such as proteins. For the purposes of this discussion, such cellular and extracellular macromolecules are referred to herein as "binding partners." Compounds that disrupt such interactions are useful for regulating the activity of the target protein. Such compounds can include, but are not limited, to molecules such as antibodies, peptides, and small molecules. In some embodiments, target proteins for use in identifying agents that disrupt interactions are the target proteins identified herein. In some embodiments, the invention provides methods for determining the ability of the test compound to modulate the activity of a target protein through modulation of the activity of a downstream effector of a target protein or another protein that functions in the same biological pathway or process as a target protein. For example, the activity of the effector molecule on an appropriate target can be determined, or the binding of the effector to an appropriate target can be determined, as described herein. To identify compounds that interfere with the interaction between the target protein and its binding partner(s), a reaction mixture containing the target protein and the binding partner is prepared, under conditions and for a time sufficient, to allow the two products to form a complex. To test an inhibitory agent, the reaction mixture is provided in the presence (test sample) and absence (control sample) of the test compound. The test compound can be initially included in the reaction mixture, or can be added at a time subsequent to the addition of the target gene and its cellular or extracellular binding partner. Control reaction mixtures are incubated without the test compound or with a control compound. The formation of complexes between the target protein and the cellular or extracellular binding partner is then detected. The formation of a complex in the control reaction, and less formation of complex in the reaction mixture containing the test compound, indicates that the compound interferes with the interaction of the target protein and the interactive binding partner. Such compounds are candidate compounds for inhibiting the expression or activity or a target protein. Additionally, complex formation within reaction mixtures containing the test compound and normal target protein can also be compared to complex formation within reaction mixtures containing the test compound and mutant target gene product. This comparison can be important in those cases wherein it is desirable to identify compounds that disrupt interactions of mutant but not normal target protein.

Binding assays can be carried out in a liquid phase or in heterogeneous formats. In one type of heterogeneous assay system, either the target protein or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface. To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

In another embodiment, modulators of target expression (RNA or protein) are identified. For example, a cell or cell-free mixture is contacted with a test compound and the expression of target mRNA or protein evaluated relative to the level of expression of target mRNA or protein in the absence of the test compound. When expression of target mRNA or protein is greater in the presence of the test compound than in its absence, the test compound is identified as a stimulator (candidate compound) of target mRNA or protein expression. Alternatively, when expression of target mRNA or protein is less (statistically significantly less) in the presence of the test compound than in its absence, the test compound is identified as an inhibitor of target mRNA or protein expression. The level of target mRNA or protein expression can be determined by methods described herein and methods known in the art such as Northern blot, microarray hybridization, reverse transcription (RT-PCR), or RNA sequencing (RNA-Seq) for detecting target mRNA, or Western blot or immunoassays (e.g., ELISA assays, fluorescently labeled antibodies, SPR) for detecting target protein, respectively.

In another aspect, the methods described herein pertain to a combination of two or more of the assays described herein. For example, a modulating agent can be identified using a cell-based or a cell-free assay, and the ability of the agent to modulate the activity of a target protein can be confirmed in vivo, e.g., in an animal. The animal may, for example, be a normal animal or an animal model for an ApoE-mediated disease, e.g., Alzheimer's disease.

Aspects of the invention further pertain to agents identified by the screening assays described herein. In some embodiments an agent (compound) identified as described herein (e.g., a target protein modulating agent, an siRNA, a target protein-specific antibody, or a target protein-binding partner) is tested in an appropriate animal model to determine the efficacy, toxicity, side effects, or mechanism of action, of treatment with such an agent. Furthermore, agents identified by the above-described screening assays can be used for treatments as described herein. Compounds that modulate target protein expression or activity (target protein modulators) can be tested for their ability to affect biological or biochemical effects associated with the target protein, e.g., with decreased expression or activity of target protein using methods known in the art and methods described herein. For example, the ability of a compound to modulate ApoE-mediated toxicity can be tested using an in vitro or in vivo model for Alzheimer's disease.

Binding Partners of Human ApoE Proteins

Disclosed herein are methods of identifying a binding partner of a human ApoE protein. Any of the preceding yeast cells or mammalian (e.g., human) cells, or any yeast cell or mammalian (e.g., human) cell described herein may be used in a method of identifying a binding partner of a human ApoE protein. A binding partner of a human ApoE protein may be an endogenous polypeptide. As used herein, an "endogenous protein" is a protein that originates from within an organism, tissue, or cell. Typically an endogenous protein is a naturally occurring protein, for instance, as encoded by a wild-type genome of the organism. In other embodiments, a binding partner of a human ApoE protein may be an endogenous lipid. As used herein, an "endogenous lipid" is a lipid that originates from within an organism, tissue, or cell. Typically, an endogenous lipid is a naturally occurring lipid. In some embodiments, a binding partner of a human ApoE protein may be considered a target protein as described herein. In some embodiments, a binding partner of human ApoE protein may be a candidate therapeutic target.

Disclosed herein is a method of identifying a binding partner of a human ApoE protein, the method comprising: providing a cell described herein; expressing the nucleic acid encoding a polypeptide comprising a human ApoE protein; and identifying an endogenous polypeptide or an endogenous lipid that binds the polypeptide, thereby identifying a human ApoE protein binding partner.

Also disclosed herein is a method of identifying a binding partner of a human ApoE protein, the method comprising: providing a yeast cell comprising an expression construct comprising a promoter operably linked to a nucleic acid encoding a polypeptide comprising a human ApoE protein; culturing the yeast cell under conditions that allow for expression of the nucleic acid; and identifying an endogenous yeast polypeptide that binds the polypeptide, thereby identifying a human ApoE protein binding partner.

Also disclosed herein is a method of identifying a binding partner of a human ApoE protein, the method comprising: expressing a nucleic acid encoding a polypeptide comprising a human ApoE protein in a yeast cell under conditions that allow for expression of the nucleic acid; and identifying an endogenous lipid or an endogenous polypeptide that binds the polypeptide, wherein said identifying comprises (i) isolating a human ApoE protein complex, and (ii) identifying an endogenous lipid or an endogenous polypeptide present in the human ApoE protein complex by mass spectrometry, thereby identifying the endogenous lipid or the endogenous polypeptide as a binding partner of the human ApoE protein.

The human ApoE protein may be selected from ApoE2, ApoE3, and ApoE4. In some embodiments, the human ApoE protein is ApoE2. In some embodiments, the human ApoE protein is ApoE3. In some embodiments, the human ApoE protein is ApoE4. Any of the human ApoE proteins or variants thereof described herein or known in the art may be used in a method of identifying a binding partner of a human ApoE protein.

In some embodiments, the polypeptide comprising a human ApoE binding protein includes a detectable marker. In some embodiments, the detectable marker is a fluorescent protein or an epitope tag. In some embodiments, the detectable marker is a fluorescent protein. Any of the fluorescent proteins described herein and/or known in the art may be used in the methods of the invention. In other embodiments, the detectable marker is an epitope tag. In some embodiments, the epitope tag is selected from the group consisting of tandem affinity purification tag, glutathione-S-transferase tag, V5 tag, polyhistidine tag, maltose binding protein tag, chitin binding protein tag, calmodulin tag, E-tag, SPB tag, Strep-tag, VSV-tag, Fc, haemagglutinin tag, myc-tag, and FLAG-tag. However, other suitable epitope tags are known in the art and may be used in the methods of the invention.

In some embodiments, methods of identifying a binding partner of a human ApoE protein may involve lysing the cells to produce an extract. Any suitable method of cell lysis may be used in the methods of the invention. A skilled artisan recognizes that different cells have different suitable methods for cell lysis. Lysis of yeast cells may involve, for example, mechanical lysis (e.g., bead beating or grinding frozen yeast cells with a mortar and pestle), liquid homogenization (e.g., French press), sonication, enzymatic digestion (e.g., by zymolyase or lyticase, or alkaline (e.g., NaOH) lysis, and the like. Lysis of mammalian cells may involve, for example, detergent-based cell lysis, mechanical lysis (e.g., Waring blender), liquid homogenization (e.g., French press, dounce homogenizer), sonication, freeze-thaw, and the like.

In some embodiments, the method involves isolating the human ApoE protein from the extract to form a human ApoE complex. Any suitable method of isolating a protein may be used in the methods of the invention. In some embodiments, isolating the human ApoE protein comprises co-immunoprecipitation, co-purification, affinity chromatography, size-exclusion chromatography, or ion exchange chromatography. In some embodiments, a detectable marker is used in isolating the human ApoE protein from the extract. In other embodiments, an antibody that specifically binds to the human ApoE protein is used in isolating the human ApoE protein, for example, by immunoprecipitation or affinity chromatography.

In some embodiments, the method involves identifying an endogenous polypeptide present in the human ApoE protein complex. Any suitable method for identifying an endogenous polypeptide may be used in the methods of the invention, for example, Western blot, mass spectrometry, Edman degradation, and the like. In some embodiments, identifying an endogenous polypeptide present in the ApoE protein complex includes mass spectrometry or Edman degradation. Any suitable method of mass spectrometry (MS) may be used to identify an endogenous polypeptide, for example, matrix-assisted laser desorption/ionization (MALDI) mass spectrometry (e.g., MALDI-TOF mass spectrometry) and liquid chromatography (LC)-MS, e.g., LC/MS/MS.

In some embodiments, the method further comprises identifying an endogenous lipid present in the human ApoE protein complex. In some embodiments, identifying an endogenous lipid comprises mass spectrometry. In other embodiments, identifying an endogenous lipid comprises metabolic labeling and thin layer chromatography. Any suitable method of mass spectrometry may be used to identify an endogenous lipid, including electrospray ionization mass spectrometry (ESI-MS), MALDI-MS, atmospheric pressure chemical ionization (APCI) mass spectrometry, and gas chromatography-mass spectrometry (GC-MS).

Binding partners of human ApoE proteins identified by the methods of the invention may be candidate therapeutic target for treatment of an ApoE-associated disease. In some embodiments, the ApoE-associated disease is an ApoE4-associated neurodegenerative disease. In some embodiments, the ApoE4-associated disease is Alzheimer's disease, vascular cognitive impairment, cerebral amyloid angiopathy, traumatic brain injury, or multiple sclerosis. In some embodiments, the method may further include identifying a biological process or biological pathway that is involved in ApoE-mediated toxicity based on the identity of a binding partner identified by the steps of the method.

Modulators of Target Gene or Protein Expression or Activity

Methods of modulating target gene or protein expression or activity can be accomplished using a variety of compounds. Compounds that may be useful for inhibiting or enhancing target protein expression or activity include polynucleotides, polypeptides, small non-nucleic acid organic molecules, small inorganic molecules, antibodies or fragments thereof, antisense oligonucleotides, siRNAs, and ribozymes. Exemplary methods of identifying and/or producing such compounds are described herein.

Nucleic Acids

Molecules, e.g., nucleic acids, that are targeted to a target RNA are useful for certain of the methods described herein, e.g., inhibition of target protein expression, e.g., for treating an ApoE-mediated disease such as Alzheimer's disease. Examples of such nucleic acids include double-stranded RNA such as short interfering RNAs (siRNAs) or short hairpin RNAs (shRNAs) that inhibit gene expression by RNA interference (RNAi). Nucleic acid molecules or constructs that are useful as described herein include siRNA molecules that comprise, e.g., 15-30 nucleotides in each strand, e.g., 15, 16, 17, 18, 19, 20, 21, 22, 23, 24, 25, 26, 27, 28, 29, or 30 nucleotides in each strand (e.g., 19-21 nucleotides), wherein one of the strands is substantially complementary, e.g., at least 80% (or more, e.g., 85%, 90%, 95%, or 100%) complementary, e.g., having 3, 2, 1, or 0 mismatched (i.e., non-complementary) nucleotide(s), to a target region in a target mRNA, and the other strand is substantially complementary to the first strand. In some embodiments, the siRNA comprises a double-stranded portion at least 15 nucleotides in length, e.g., between 15-30 nucleotides in length. In some embodiments, the siRNA comprises a 3' overhang on one or both strands. In some embodiments, the 3' overhang is between 1 and 5 nucleotides, e.g., 1, 2, 3, 4, or 5 nucleotides in length, wherein the lengths can be the same or different on the two strands. As known in the art, shRNAs comprise a similar double-stranded portion but the strands are connected by a loop structure.

dsRNA molecules (e.g., siRNA) can be produced using methods known in the art. For example, they can be chemically synthesized, can transcribed be in vitro or in vivo from a DNA template. The dsRNA molecules can be designed using methods known in the art. A variety of different computer programs are available to assist in siRNA design. See, e.g., Muhonen P & Holthofer H (2010) Methods Mol Biol. 2010; 623:93-107 for review and links to websites of numerous siRNA design tools. The sequence of an siRNA can be selected to reduce the likelihood of "off-target" effects. For example, a sequence unique in the genome (e.g., unique in the human genome) can be selected as a target sequence for siRNA design. Negative control siRNAs ("scrambled") can be used, if desired, to confirm the effect of an siRNA on a target gene expression and/or to confirm the effect of the siRNA on amyloid beta mediated toxicity. Such siRNAs generally have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. Controls can also be designed by introducing an appropriate number of base mismatches into the selected siRNA sequence.

The nucleic acid compositions that are useful for certain of the methods described herein include both siRNA and crosslinked siRNA derivatives. Crosslinking can be used to alter the pharmacokinetics of the composition, for example, to increase half-life in the body. Thus, the invention includes siRNA derivatives that include siRNA having two substantially complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some cases, the siRNA or siRNA derivative has, e.g., at its 3' terminus, a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA or siRNA derivatives in this way can improve cellular uptake or enhance cellular targeting activities of the resulting siRNA or siRNA derivative as compared to the corresponding unmodified siRNA or siRNA derivative, are useful for tracing the siRNA or siRNA derivative in the cell, or improve the stability of the siRNA derivative compared to the corresponding siRNA.

microRNA (miRNAs) are endogenous noncoding RNAs of approximately 22 nucleotides in length that can regulate gene expression at the post transcriptional or translational level. A large number of animal genes are regulated by miRNAs, sometimes in a cell or tissue-specific or developmental stage-specific manner. miRNAs are excised from an approximately 70 nucleotide precursor RNA stem-loop, which in turn is derived from a longer RNA precursor. By substituting the stem sequences of an miRNA precursor with sequence substantially complementary to the target mRNA, a vector construct that expresses the novel miRNA can be used to produce siRNAs to initiate RNAi against specific mRNA targets in mammalian cells. In other embodiments, a naturally occurring endogenous miRNA that inhibits expression of a target gene is identified or an artificial miRNA is designed. Such miRNA can then be overexpressed or delivered to cells or subjects (in order to inhibit the target gene) or its effects can be inhibited (e.g., using synthetic oligonucleotides termed "antagomirs" that are antisense to the miRNA) in order to upregulate expression of the target gene.

Antisense nucleic acids are useful for inhibiting expression of a target protein in certain embodiments of the invention. Antisense nucleic acid molecules are single-stranded molecules whose nucleotide sequence is substantially complementary to all or part of an RNA, e.g., a mRNA encoding a target protein. An antisense nucleic acid molecule can be antisense to all or part of a non-coding region or coding region of the coding strand of a nucleotide sequence encoding a target protein. As known in the art, non-coding regions ("5' and 3' untranslated regions") are the 5' and 3' sequences that flank the coding region and are not translated into amino acids. Based upon the nucleotide sequences disclosed herein, one of skill in the art can select and synthesize any of a number of appropriate antisense molecules to target a gene identified herein. For example, a series of oligonucleotides of 15-30 nucleotides spanning the length of a nucleic acid (e.g., a target nucleic acid) can be prepared, followed by testing for inhibition of expression of the gene. An antisense oligonucleotide can be, for example, about 5, 10, 15, 20, 25, 30, 35, 40, 45, or 50 nucleotides or more in length. An antisense nucleic acid described herein can be constructed using chemical synthesis and/or enzymatic ligation reactions using procedures known in the art.

In some cases, a pool of siRNAs or miRNAs or antisense molecules is used to modulate the expression of a target gene. The pool is composed of at least 2, 3, 4, 5, 8, or 10 different sequences targeted to the target gene.

Aptamers are nucleic acid molecules having a structure that permits them to specifically bind to protein ligands and offer a means by which target protein activity can be specifically decreased (see, e.g., Osbome, et al., Curr. Opin. Chem. Biol., 1: 5-9, 1997; and Patel, Curr. Opin. Chem. Biol., 1:32-46, 1997; Mayer G. (2009) Angew Chem Int Ed Engl. 48(15):2672-89). Aptamers can be identified using a technique termed systematic evolution of ligands by exponential enrichment (SELEX, reviewed in Stoltenburg R, et al. Biomol Eng. (2007) 24(4):381-403). The invention provides for identification of aptamers that specifically bind to and inhibit a target protein identified herein.

Nucleic acids (e.g., siRNAs, aptamers) can comprise standard nucleotides (A, G, C, T, U), non-standard nucleotides (which may or may not be naturally occurring nucleotides) or variously modified nucleotides designed, e.g., to increase the biological stability of the molecules or to increase the physical stability of the duplex formed between complementary nucleic acids. Nucleic acids can comprise nucleotides that comprise modified bases, modified backbones (e.g., modified sugars, and/or modified inter-nucleotide linkages (as compared with the bases, sugars, and phosphodiester backbone found in DNA and RNA). In some embodiments, the nucleic acid modification is selected to stabilize the nucleic acid (e.g., to reduce its sensitivity to nuclease(s) or otherwise prolong its half-life in the body. Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl) uracil, S-carboxymethylaminomethyl-Z-thioiiridirie, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Modified sugars include, e.g., 2'-O alkyl derivatives. Modified inter-nucleotide linkages include, e.g., use of phosphorothioate derivatives, peptide nucleic acid, morpholino- and locked nucleic acid, as well as glycol nucleic acid and threose nucleic acid structures. See, e.g., Deleavey, G, et al., Current Protocols in Nucleic Acid Chemistry 16.3.1-16.3.22, 2009, for discussion of exemplary nucleic acid modifications of use in various embodiments of the invention, e.g., siRNA. Modification(s) may be present in one or both strands and may be located throughout the strand(s) or at particular positions in various embodiments. Multiple different modifications can be used in combination.

Exemplary routes of administration for nucleic acids (e.g., siRNAs, miRNAs, aptamers, or antisense nucleic acids) include direct administration, e.g., by injection, at a tissue site. For example, they may be administered directly to the brain. Alternatively, nucleic acid molecules, optionally modified to target selected cells or tissues, can be administered systemically. For example, for systemic administration, molecules can be modified such that they specifically bind to receptors or antigens expressed on a selected cell surface, e.g., by linking the nucleic acid molecules to peptides, small molecules, or antibodies that bind to cell surface receptors or antigens.

Nucleic acids, e.g., siRNAs, can be delivered into cells by a variety of means, e.g., cationic liposome transfection and electroporation. Sequences that are modified to improve their stability or cell uptake can be used. Such stabilized molecules are particularly useful for in vivo methods such as for administration to a subject to decrease target protein expression. Compounds, e.g., nucleic acids, e.g., siRNA, can be conjugated to a variety of moieties that target them to cells or tissues, e.g., the brain. For example, vitamin E (alpha tocopherol) can be conjugated to siRNAs, and the conjugated siRNAs optionally delivered with HDL. In some embodiments, a compound is conjugated to a moiety that binds to a receptor expressed by neurons. Expression can be achieved by delivering a vector (e.g., a viral vector) that causes the cell to express the siRNA molecule (or other nucleic acid) to a cell, e.g., a neuron. The vector can comprise a recombinant nucleic acid in which a sequence encoding a short hairpin RNA or miRNA precursor or sequence encoding an antisense RNA is operably linked to a promoter (e.g., a Pol II or Pol III promoter) that directs expression in a cell type of interest.

Viral-mediated delivery mechanisms include, e.g., recombinant adenoviruses, retroviruses, e.g., lentiviruses, and vectors comprising at least part of a genome derived from such virus(es) are also of use to express shRNA and/or miRNA precursors in cells, e.g., for research or therapeutic purposes.

Nanoparticles and liposomes can also be used to deliver nucleic acids, e.g., oligonucleotides, e.g., siRNAs, into cells or organisms (e.g., non-human animals or humans). Likewise, in some embodiments, viral gene delivery, direct injection, nanoparticle particle-mediated injection, or liposome injection may be used to express or introduce siRNA into cells or non-human animals or humans.

In some embodiments, siRNAs or other compounds that inhibit target protein expression or activity are effective for ameliorating undesirable effects of ApoE when target RNA levels are reduced by at least 25%, 50%, 75%, 90%, or 95%. In some cases, it is desired that target RNA levels be reduced by not more than 10%, 25%, 50%, or 75%. Methods of determining the level of target gene expression (or reduction therein), are known in the art. For example, the level of target RNA can be determined, e.g., using Northern blot, microarray, RT-PCR, or RNA-SEQ on a sample from cell(s) (e.g., of a cell line) or a subject. Levels of target protein can also be measured using, e.g., Western blot, immunoassay method(s), etc. Such methods can be used, e.g., to assess the effect of a small molecule, peptide, antibody, nucleic acid, or other compound, on the target mRNA or protein.

Polypeptides

Isolated target proteins, fragments thereof, and variants thereof are provided herein. These polypeptides can be used, e.g., as immunogens to raise antibodies, in screening methods, or in methods of treating subjects, e.g., by administration of the target proteins. An "isolated" or "purified" polypeptide or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of polypeptides in which the polypeptide of interest is separated from cellular components of the cells from which it is isolated or recombinantly produced. Thus, a polypeptide that is substantially free of cellular material includes preparations of polypeptides having less than about 30%, 20%, 10%, or 5% (by dry weight) of heterologous protein (also referred to herein as "contaminating protein"). In general, when the polypeptide or biologically active portion thereof is recombinantly produced, it is also substantially free of culture medium, i.e., culture medium represents less than about 20%, 10%, or 5% of the volume of the protein preparation. In general, when the polypeptide is produced by chemical synthesis, it is substantially free of chemical precursors or other chemicals, i.e., it is separated from chemical precursors or other chemicals that are involved in the synthesis of the polypeptide. Accordingly such preparations of the polypeptide have less than about 30%, 20%, 10%, or 5% (by dry weight) of chemical precursors or compounds other than the polypeptide of interest. Expression of target proteins can be assayed to determine the amount of expression. Methods for assaying protein expression are known in the art and include Western blot, immunoprecipitation, mass spectrometry, and radioimmunoassay. The amount of a target protein as a percentage of total protein or total dry weight in a preparation can be determined using standard methods.

As used herein, a "biologically active portion" of a target protein comprises a portion of a target protein that retains at least one biological function of a full length protein. The biologically active portion may have an activity that differs in magnitude from that of the full length protein. For example, the biologically active portion may have between 20% and 100% of the activity of the full length portion. In some embodiments, the biologically active portion may have increased activity relative to the full length portion (e.g., if the biologically active portion lacks an inhibitory domain present in the full length portion). In some embodiments, the biologically active portion may retain the ability to participate in an interaction with a second molecule, e.g., a different protein. Biologically active portions of a target protein include polypeptides that include fewer amino acids than a full-length target protein, and exhibit at least one activity of a target protein. In some embodiments, a biologically active portion includes a domain or motif with at least one activity of the target protein. In some embodiments, the activity is ability to suppress or enhance amyloid beta mediated toxicity. In some embodiments, the activity is an enzymatic activity.

A biologically active portion of a target protein can be a polypeptide that is, for example, 10, 25, 50, 75, 100, 150, 200, 250, 300, 350, 400, 450, 500, or more amino acids in length. It may be, for example, between 10% and 99.9% as long as the parent polypeptide. Biologically active portions of a target protein can be used as targets for developing agents that modulate a target protein mediated activity, e.g., compounds that inhibit target protein activity. In some embodiments, the target protein has a sequence identical to a sequence disclosed herein (e.g., an amino acid sequence found under an Accession Number, gene name, or gene identifier listed in any one or more of Tables 1A, 1B, 1C, 1D, 2A, 2B, 2C, and 3 or encoded by a nucleic acid or gene found under an Accession Number, gene name, or gene identifier listed in any one or more of Tables 1A, 1B, 1C, 1D, 2A, 2B, 2C, and 3). Other useful polypeptides are substantially identical (e.g., at least about 45%, 55%, 65%, 75%, 85%, 95%, 96%, 97%, 98%, or 99% identical) to any such sequence and (a) retain at least one functional activity of the target protein yet differs in amino acid sequence due to natural allelic variation or mutagenesis, or (b) exhibit an altered functional activity (e.g., as a dominant negative) where desired. Provided herein are variants that have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the polypeptide. An antagonist of a polypeptide can inhibit one or more of the activities of the naturally occurring form of the polypeptide by, for example, competitively binding to a downstream or upstream member of a cellular signaling cascade that includes the polypeptide. Thus, specific biological effects can be elicited by treatment with a variant of limited function. Treatment of a subject with a variant having a subset of the biological activities of the naturally occurring form of the polypeptide can have fewer side effects in a subject relative to treatment with the naturally occurring form of the polypeptide. In some embodiments, the variant target protein is a dominant negative form of the target protein. Dominant negatives can be used, e.g., in methods in which inhibition of target protein action is desired. The comparison of sequences and determination of percent identity between two sequences is accomplished using a mathematical algorithm. In some embodiments, percent identity between two amino acid sequences is determined using the Needleman and Wunsch, J. Mol. Biol., 48:444-453, 1970) algorithm, which has been incorporated into the GAP program in the GCG software package, using either a Blosum 62 matrix or a PAM250 matrix, and a gap weight of 16 and a length weight of 1. The percent identity between two nucleotide sequences can be determined using the GAP program in the GCG software package using a NWSgapdna.CMP matrix, a gap weight of 40, and a length weight of 1.

In general, percent identity between amino acid sequences referred to herein can be determined using the BLAST 2.0 program, which is available to the public on the Internet at ncbi.nhn.nih.gov/BLAST. In some embodiments, sequence comparison is performed using an ungapped alignment and using the default parameters (Blosum 62 matrix, gap existence cost of 11, per residue gap cost of 1, and a lambda ratio of 0.85). In some embodiments, default parameters are used. The mathematical algorithm used in BLAST programs is described in Altschul et al., Nucleic Acids Research 25:3389-3402, 1997. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a target protein is generally replaced with another amino acid residue from the same side chain family. Alternatively, mutations can be introduced randomly along all or part of a target protein coding sequence, such as by saturation mutagenesis, and the resultant mutants can be screened for target protein biological activity to identify mutants that retain activity. The encoded protein can be expressed recombinantly and the activity of the protein can be determined.

Also provided herein are chimeric or fusion proteins that comprise at least a portion of a target protein (e.g., a biologically active portion) and at least a portion (e.g., a biologically active portion) of a second protein such as a detection protein (e.g., a fluorescent protein, an enzyme, or an epitope tag).

Nucleic acids that encode a target protein (e.g., a human target protein) or fragment or variant thereof or a chimeric or fusion protein comprising a target protein are provided, wherein such nucleic acid(s) are operably linked to a promoter, e.g., in an expression vector. Such nucleic acids are of use, e.g., to express the protein for therapeutic or research purposes, e.g., in order to produce the protein in vivo (e.g., in a human subject for therapeutic purposes or in an animal model) or in vitro (e.g., to produce the protein for therapeutic, research, or other purposes). In some embodiments cells, e.g., yeast cells, that express a polypeptide comprising ApoE and that express or overexpress a polypeptide comprising a target protein or have reduced or absent expression of a target protein are of use as cellular models, e.g., for identifying compounds or genetic modifiers that modulate ApoE-mediated toxicity. In some embodiments isolated mammalian cells that overexpress the protein or have decreased expression of the protein are useful as cellular models. The promoter may be appropriately selected to direct expression of the protein in cells of interest, e.g., bacteria, yeast or other fungi, plant, invertebrate (e.g., insect, worm, fly), vertebrate (e.g., mammalian, e.g., mouse, rat, or human, or avian). In some embodiments the promoter is regulatable, e.g., inducible. In some embodiments the promoter is tissue- or cell-type specific, e.g., for neurons, glial cells, or precursors thereof. One of ordinary skill in the art will be aware of suitable promoters and expression vectors and methods of introducing nucleic acids into cells. For example, regulatable promoters suitable for use in mammalian cells include those regulatable by small molecules such as tetracycline-responsive promoters, hormone-responsive promoters, etc. Constitutive promoters commonly used in mammalian systems include viral promoters such as the simian virus 40 early promoter (SV40) and the cytomegalovirus immediate-early promoter (CMV), promoters of mammalian origin such as the human ubiquitin C promoter (UBC), human elongation factor 1α promoter (EF1A), human phosphoglycerate kinase 1 promoter (PGK), and human β-Actin promoter, and hybrid promoters such as the CAG promoter. In some embodiments a promoter from a homologous mouse or other non-human mammalian or avian gene may be used instead of one from a human gene in certain embodiments. Regulatable promoters useful in mammalian cells include the tetracycline response element (TRE) promoter (inducible using tetracyline or its derivatives such as doxycycline), with which transcription can be induced or repressed depending on what tet transactivator is used (tetracycline transactivator (tTA) to turn expression off in the presence of tetracycline or a derivative thereof (Tet-Off) or reverse tetracycline-controlled transactivator (rtTA) to turn expression on in the presence of tetracycline or a derivative thereof (Tet-On). It will be understood that intronic sequences and/or polyadenylation signals can also be included in an expression construct, e.g., to increase the efficiency of expression. Methods of introducing nucleic acids into cells or administering nucleic acids to subjects described herein, or others known in the art, be used to deliver any nucleic acid of interest to cells or non-human animals. For example, such methods may be used to deliver nucleic acids encoding ApoE to cells or non-human animals, e.g., for purposes of creating cellular or non-human animal models of ApoE-mediated toxicity.

Antibodies

In some aspects, the invention provides antibodies that bind to a target protein identified herein, e.g., a target protein listed in any one or more of Tables 1A, 1B, 1C, 1D, 2A, 2B, 2C, and 3 or otherwise of use in one or more of the methods described herein. "Antibodies" as used herein can be polyclonal, monoclonal, humanized, anti-idiotypic, chimeric or single chain antibodies, and Fab, F(ab')2 and Fab expression library fragments, scFV molecules, and epitope-binding fragments thereof, in various embodiments of the invention. A target protein, or a fragment thereof, can be used as an immunogen to generate antibodies using standard techniques for polyclonal and monoclonal antibody preparation. The full-length polypeptide or protein can be used or, alternatively, antigenic peptide fragments can be used as immunogens. The antigenic peptide of a protein typically comprises at least 8 (e.g., at least 10, 15, 20, or 30) amino acid residues of the amino acid sequence of a target protein, and encompasses an epitope of a target protein such that an antibody raised against the peptide forms a specific immune complex with the polypeptide.

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a target protein as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, Nature, 256: 495-497, 1975, the human B cell hybridoma technique (Kozbor et al., Immunol. Today, 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known. Hybridoma cells producing a monoclonal antibody can be detected by screening the hybridoma culture supernatants for antibodies that bind the polypeptide of interest, e.g., using a standard ELISA assay. As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available. Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art. Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a target protein. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (Int. Rev. Immunol., 13:65-93, 1995). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and 5,545,806. Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., Biotechnology, 12:899-903, 1994). Methods of producing monoclonal antibodies, e.g., human monoclonal antibodies, also include display techniques such as phage display.

An antibody directed against a target protein can be used to detect the polypeptide (e.g., in a cellular lysate or cell supernatant) to evaluate its abundance and pattern of expression. The antibodies can also be used diagnostically to monitor protein levels in tissue as part of a clinical testing procedure, e.g., for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. Antibodies can also be used to modulate the activity of a target protein, e.g., for research or therapeutic purposes. Antibodies often inhibit their target but, depending on the epitope to which they bind, could activate their target, or antibodies that bind to an endogenous inhibitor of the target can enhance the activity of the target.

In some embodiments, a target protein has one or more particular biochemical activities and/or biological functions, and a compound that modulates such function(s) is identified. For example, the target protein may be an enzyme that catalyzes a biochemical reaction or may be a regulator (e.g., an activator or inhibitor) of an enzyme. Enzymes may be classified broadly as oxidoreductases, transferases, hydrolases, lyases, isomerase, or ligases. (See, e.g., Enzyme Nomenclature: Recommendations of the Nomenclature Committee of the International Union of Biochemistry and Molecular Biology on the Nomenclature and Classification of Enzymes by the Reactions they Catalyse). Exemplary enzymes include, e.g., kinases, phosphatases, and GTPases. Exemplary enzyme regulators include, e.g., guanine nucleotide exchange factors.

Compounds can be tested for their ability to modulate one or more enzymatic activities or enzyme regulatory activities mediated by a target protein described herein. One of skill in the art will be aware of suitable assays to identify modulators of such enzymes. For example, kits for performing a wide variety of enzyme assays, e.g., assays for kinase, phosphatase, ATPase, GTPase, and ubiquitinating activity, among others, are commercially available. In some embodiments, a suitable assay involves (i) incubating the target protein, a suitable substrate, and a test compound under appropriate conditions; and (ii) detecting production of one or more products of the reaction, wherein an increased amount of reaction product(s) as compared with the amount of reaction product(s) that would be expected in the absence of the test compound indicates that the test compound enhances activity of the enzyme, and a decreased amount of reaction product(s) as compared with the amount of reaction product(s) that would be expected in the absence of the test compound indicates that the test compound inhibits activity of the enzyme. Detecting can be qualitative or quantitative in various embodiments. "Appropriate conditions" refer to conditions under which the target protein would (in the absence of the test compound), effectively catalyze the reaction, so that reaction product(s) would appear in a detectable amount in a reasonable time frame for detection (e.g., seconds, minutes, hours). Appropriate conditions may include, e.g., an appropriate temperature, pH, salt concentration, presence of one or more organic or inorganic co-factors and/or energy source(s), etc. It will be understood that many enzymes can often tolerate a range of different conditions, e.g., a range of values for temperature, pH, salt concentration, etc. In some embodiments, an enzyme is a multisubunit protein, in which case the assay components can include at least the catalytic subunit(s) and, optionally, one or more additional subunits of the enzyme, e.g., those subunit(s) that form a complex with the catalytic subunit in nature. Optionally, at least one of the substrates is labeled (e.g., with a radiolabel, colorimetric, fluorescent, luminescent, or enzymatic label, etc., to facilitate detection of the reaction or reaction product(s) or a colorimetric, fluorescent, luminescent signal is generated upon occurrence of the reaction. In some embodiments, the enzymatic reaction converts a non-fluorescent moiety into a fluorescent moiety, which can then be detected. In some embodiments, a substrate contains a fluorophore and a dark quencher, wherein the dark quencher absorbs energy from the fluorophore and dissipates the energy as heat. Upon cleavage of the substrate, the dark quencher becomes separated from the fluorophore, so that the energy from the flurophore is no longer absorbed and can be detected, thereby providing a means to detect the reaction.

Functional assays can also be used to identify modulators of expression or activity of a gene or protein identified herein or that modulate a biological pathway or process in which a gene or protein identified herein is involved. For example, high content screens can involve use of automated imaging, cell sorting, etc., to analyze localization of a protein or alterations in a process in which a gene or protein identified herein is involved.

In some embodiments, computationally based drug design and/or virtual screening may be used to identify a modulator of a protein identified herein. Computationally based drug design and/or virtual screening may be based on 2- or 3-dimensional structure(s) of a protein identified herein. In certain embodiments structures of compounds may be screened for ability to bind to a region (e.g., a "pocket") of the protein that is accessible to the compound. The region may be a known or potential active site or any region of the protein accessible to the compound, e.g., a concave region on the surface or a cleft. A variety of docking and pharmacophore-based algorithms are known in the art, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007. Numerous small molecule structures are available and can be used for virtual screening. A collection of compound structures may sometimes be referred to as a "virtual library". For example, ZINC is a publicly available database containing structures of millions of commercially available compounds that can be used for virtual screening (Shoichet, J. Chem. Inf. Model., 45(1):177-82, 2005). A database containing about 250,000 small molecule structures is available on the National Cancer Institute (U.S.) website. In some embodiments multiple small molecules may be screened, e.g., up to 50,000; 100,000; 250,000; 500,000, or up to 1 million, 2 million, 5 million, 10 million, or more. Compounds can be scored and, optionally, ranked by their potential to bind to a target. Compounds identified in virtual screens can be tested in cell-free or cell-based assays or in animal models to confirm their ability to bind to and/or modulate, e.g., inhibit, activity of the target protein and/or to assess their effect on ApoE-mediated toxicity.

Identification of test compounds that modulate a target protein permits subsequent modification of the test compound "hit" or "lead" to optimize the capacity of the "hit" or "lead" to, e.g., prevent or suppress ApoE-mediated toxicity and/or to prevent or suppress amyloid beta-mediated toxicity. Such optimization is an aspect of the present disclosure and may be performed as described above for test compounds identified using ApoE-expressing yeast cells.

Computational approaches can be used to predict one or more physico-chemical, pharmacokinetic and/or pharmacodynamic properties of compounds identified in any of the physical or virtual screens described herein. For example, absorption, distribution, metabolism, and excretion (ADME) parameters can be predicted. Such information can be used, e.g., to select hits for further testing or modification. For example, small molecules having characteristics typical of "drug-like" molecules can be selected and/or small molecules having one or more undesired characteristics can be avoided.

In some embodiments, a human protein identified herein as a homolog of a yeast suppressor or enhancer of ApoE-mediated toxicity is introduced into non-human cells, e.g., yeast cells. In some embodiments, such cells are used for performing a screen to identify compounds that modulate activity of the human protein. For example, compounds that counteract or augment the effect of a suppressor or enhancer of ApoE-mediated toxicity may be identified. In some embodiments, the gene encoding the counterpart homologous protein in said non-human cells may be disabled or deleted. For example, in some embodiments, a yeast gene identified herein as a suppressor or enhancer of ApoE-mediated toxicity is deleted in a yeast cell, and the counterpart human gene is expressed in the cell. For example, the counterpart human gene can be integrated into the yeast genome, optionally under control of an inducible promoter. In some embodiments, the cells express a toxicity-inducing amount of ApoE.

In some embodiments, screens and/or further characterization of compounds is/are carried out using vertebrate cells or tissues, e.g., mammalian (e.g., mouse, rat, or human) cells or tissues or non-human animals. In some embodiments, the cells may be any of the vertebrate cells described herein. In some embodiments, the vertebrate cells, e.g., mammalian cells, comprise nervous system cells, e.g., neurons or glial cells. In some embodiments the cells are from a region of the brain such as the forebrain, midbrain, cortex, hippocampus, or striatum. In some embodiments, the neurons comprise cortical neurons. In some embodiments, the neurons comprise hippocampal neurons. In some embodiments, the neurons comprise pyramidal neurons. In some embodiments the neurons comprise cholinergic neurons. In some embodiments the neurons comprise glutamatergic neurons. In some embodiments the glial cells comprise oligodendrocytes, astrocytes, or both. In some embodiments a mixed culture comprising neurons and glial cells is used. In some embodiments, the tissues comprise brain tissue, e.g., brain slices, e.g., hippocampal brain slices from non-human animals. In some embodiments the cells may display at least one phenotype associated with ApoE-mediated toxicity. In some embodiments the cells may display at least one phenotype associated with ApoE. In some embodiments the cells comprise a heterologous gene that encodes a polypeptide comprising ApoE and/or a heterologous gene that encodes a mammalian homolog of a yeast protein encoded by a yeast gene that is a genetic modifier of ApoE-mediated toxicity.

Biomarkers and Predictive Methods; Kits

In some aspects, described herein are methods of identifying biomarkers for ApoE-mediated diseases, e.g., AD. In some embodiments, a method comprises identifying a polymorphism or mutation in the sequence of a human gene that is a homolog of a yeast gene identified in any one or more of Tables 1A, 1B, 1C, 1D, 2A, 2B, 2C, and 3, e.g., a human gene identified in any one or more of Tables 1C, 1D, 2A, 2B, and 2C or an alteration in the expression of a human gene identified herein or the activity of its encoded protein; and (b) determining whether the polymorphism, mutation, or alteration is correlated with development of an ApoE-mediated disease, e.g., AD. In some embodiments, a binding partner of a human ApoE protein identified by the methods of the invention may be a biomarker for an ApoE-mediated disease. Such methods may, for example, utilize available genotyping, clinical and pathological data from studies, e.g., epidemiological studies, of aging, cognition, and AD or another ApoE-mediated disease. Collections of data and samples and methods (e.g., statistical methods) known in the art can be used to identify and/or confirm correlations. In some embodiments, a genome-wide association study is performed. In some embodiments, a case-control study is performed. In some embodiments, one or more SNPs or other nucleotide variations available in the dbSNP database in a gene identified herein is evaluated for association with an ApoE-mediated disease.

Once a correlation is confirmed, it may be used, e.g., in the identification of subjects who may benefit from therapy using a compound identified as described herein or a therapy known in the art to be of use for treating an ApoE-associated disease such as AD. For example, such subjects may benefit from early treatment (prior to development of symptoms) and/or may benefit from treatment with a compound that modulates expression or activity of a gene product (e.g., a protein) encoded by the gene, or in some embodiments, with the gene product itself.

In some aspects, described herein are methods for identifying subjects who are at increased risk of developing an ApoE-associated disease, e.g., AD. Certain of the methods comprise determining whether a human subject exhibits altered sequence, expression, or activity of a human homolog of a yeast gene identified in any one or more of Tables 1A, 1B, 2A, 2B, 2C, and 3 (e.g., a human homolog identified in any one or more of Tables 2A, 2B, and 2C) and/or of a protein encoded by a gene identified herein, as compared with a reference sequence, wherein altered sequence, expression, or activity of the gene or protein encoded by the gene indicates that the subject is at increased risk of developing or having an ApoE-associated disease, e.g., AD. In some embodiments the gene may be any gene that has not been previously identified as a risk factor for an ApoE-associated disease, or for a particular ApoE-mediated disease, e.g., AD.

In some embodiments, the gene is selected from human genes listed in any one or more of Tables 1C, 1D, 2A, 2B, and 2C. In some embodiments, at least two of the genes (or their encoded proteins) are assessed. In some embodiments, increased expression in a subject of a human gene that is a homolog of a yeast gene identified as an enhancer of ApoE-mediated toxicity and/or increased activity of a protein encoded by such a human gene indicates that the subject is at increased likelihood of developing or having an ApoE-associated disease, e.g., AD. In some embodiments, decreased expression in a subject of a human gene that is a homolog of a yeast gene identified as a suppressor of ApoE-mediated toxicity and/or decreased activity of a protein encoded by such a gene indicates that the subject is at increased likelihood of developing or having an ApoE-associated disease, e.g., AD. A reference sequence or reference level may, e.g., be a sequence or level of expression or activity typically found in control subjects. For example, a reference level may be an average level among control subjects or a range around that level (e.g., a range within which at least 80%, 90%, or 95% of control subjects fall. In some embodiments, control subjects are individuals who are not suffering from an ApoE-associated disease and do not have signs or symptoms associated with cognitive impairment or other characteristics that might indicate a significant likelihood of developing an ApoE-associated disease. Control subjects may be matched for a variety of characteristics such as age, gender, general health status (e.g., absence of cardiovascular disease), etc. Historical controls can be used. In some embodiments, the methods can be used to monitor progression of the disease and/or response to therapy. In some embodiments, a result, e.g., a difference in level of expression or activity as compared with a reference level, is statistically significant. For example, a result can have a P value of less than 0.05 or less than 0.01 in various embodiments.

An alteration in gene expression can be caused, e.g., by a mutation or polymorphism in a coding region or non-coding region (e.g., a regulatory region) of a gene or an alteration (increase or decrease) in copy number or an epigenetic change (e.g., altered DNA methylation or altered histone modification (e.g., altered acetylation or methylation). A mutation can be, e.g., an insertion, deletion, or substitution. A polymorphism may be a single nucleotide polymorphism. An alteration in activity of a protein may be caused by a mutation in a coding region of the gene, wherein the mutation alters the sequence of the encoded protein. The invention encompasses analyzing a sample comprising DNA, mRNA, or protein obtained from a subject (e.g., from lymphocytes), to assess the sequence (e.g., to determine the identity of one or more nucleotides or amino acids), expression level, and/or activity of a gene identified herein or its encoded protein and, optionally, comparing said sequence, expression, and/or activity level with a reference sequence or reference level of expression or activity. Methods known in the art including, but not limited to, methods mentioned herein, can be used to assess gene sequence, expression level, and/or activity of a protein. For example, genotyping can be performed using DNA microarrays (e.g., available from Affymetrix, Illumina, Agilent), real-time PCR, and/or sequencing (e.g., high throughput sequencing, such as Illumina/Solexa technology or the SOLiD™ system). Epigenetic changes can be detected, e.g., using bisulfite sequencing, ChIP-on-chip and/or ChIP-Seq. Alterations in protein level or modification can be detected, e.g., using immunoassays or mass spectrometry. In some embodiments, an alteration in activity of a protein may be caused by an alteration in post-translational modification of the protein, e.g., an alteration in phosphorylation, glycosylation, lipidation, alkylation, ubiquitination, sumoylation, etc. Thus some embodiments comprise detecting one or more such modification or alteration.

In some embodiments, a subject who exhibits decreased expression of a gene and/or decreased expression of a protein identified herein (e.g., a human homolog of a yeast gene that is a suppressor of ApoE-mediated toxicity) is treated or selected as a candidate for treatment with a compound that increases expression or activity of the protein. In some embodiments, a subject who exhibits increased expression of a gene and/or increased expression of a protein identified herein (e.g., a human homolog of a yeast gene that is an enhancer of ApoE-mediated toxicity) is treated or selected as a candidate for treatment with a compound that decreases expression or activity of the protein.

Further provided are kits containing reagent(s) useful for detecting sequence, expression, or activity of a gene identified herein and/or of a protein encoded by a gene identified herein and/or for detecting alteration in any of the foregoing. Such reagents can comprise, e.g., nucleic acid probes or primers for detecting gene sequence or expression or alteration therein (optionally attached to a support such as a chip or beads), antibodies for detecting protein level, size, modification, or alteration therein. The kits can comprise control or reference samples, instructions for performing the assay and/or for interpreting results, etc. In some embodiments, a kit is adapted specifically for identifying subjects at risk of or suffering from an ApoE-mediated disease and/or for assessing a selected set of genes and/or proteins identified as potentially harboring mutation(s), polymorphism(s), or epigenetic changes that are risk factors for an ApoE-mediated disease. For example, if the kit provides for assessment of multiple genes or proteins, the proportion of genes or proteins implicated or confirmed as risk factors for an ApoE-mediated disease is greater than would be expected by chance. In some embodiments, at least 10%, 20%, 30%, 40%, 50%, 60%, 70%, 80%, 90% or 100% of the genes or proteins to be assessed are implicated or confirmed as risk factors for an ApoE-mediated disease. In some embodiments, the kit components are enclosed in one or more containers that are labeled or packaged with information or instructions that indicate, e.g., that the kit is useful for identifying or assessing subjects at risk of or suffering from an ApoE-mediated disease.

Detection of an alteration in sequence, expression, or activity of a human gene or protein identified herein may be used together with additional information to assess the likelihood that a subject will develop or has an ApoE-associated disease, e.g., AD. Such information may be genetic information (e.g., presence of particular allele(s) or isoforms associated with increased risk), imaging information, biochemical information (e.g., measurement of amyloid beta or tau levels in CSF), neuropsychological information, and/or clinical information.

Mammalian Model Systems

In some aspects, described herein are mammalian cells and non-human mammals in which expression or activity of a mammalian gene that is a homolog of a yeast gene that modulates ApoE-mediated toxicity is modulated, e.g., the gene or a gene product encoded by the gene is overexpressed or inhibited or disabled. In some embodiments the mammalian gene is a human gene. The human gene may be a homolog of any of the yeast genes listed in any one or more of Tables 1A, 1B, 1C, 1D, 2A, 2B, 2C, and 3. For example, the human gene may be any of the human genes listed in any one or more of Tables 1C, 1D, 2A, 2B, and 2C. In particular embodiments, the human gene may be a homolog of any of the yeast genes listed in Table 3. In some embodiments the human gene is a known AD risk factor. In some embodiments the human gene is not a known AD risk factor. In some embodiments the mammalian gene is a non-human mammalian gene that is a homolog of any of the yeast genes listed in any one or more of Tables 1A, 1B, 1C, 1D, 2A, 2B, 2C, and 3.

In some embodiments the mammalian gene is a homolog of a yeast gene that is a suppressor of ApoE2-mediated toxicity listed in any one or more of Tables 1A, 1B, or 2A. In some embodiments the mammalian gene is a homolog of a yeast gene that is an enhancer of ApoE2-mediated toxicity listed in any one or more of Tables 1A, 1B, and 2A. In some embodiments the mammalian gene is a homolog of a yeast gene that is a suppressor of ApoE3-mediated toxicity listed in any one or more of Tables 1A, 1B, and 2B. In some embodiments the mammalian gene is a homolog of a yeast gene that is an enhancer of ApoE3-mediated toxicity listed in any one or more of Tables 1A, 1B, and 2B. In some embodiments the mammalian gene, is a homolog of a yeast gene that is a suppressor of ApoE4-mediated toxicity listed in any one or more of Tables 1A, 1B, and 2C. In some embodiments the mammalian gene is a homolog of a yeast gene that is an enhancer of ApoE4-mediated toxicity listed in any one or more of Tables 1A, 1B, and 2C. In some embodiments the mammalian gene is a homolog of a yeast gene listed in Table 3. The human or non-human mammalian cells or animals may have any APOE genotype in various embodiments. They may be homozygous or heterozygous for any APOE allele. In some embodiments the mammalian gene, e.g., human gene, is a homolog of a yeast gene that is a suppressor or enhancer of ApoE2-mediated toxicity and the mammalian cell, e.g., human cell, expresses ApoE2. In some embodiments the mammalian gene, e.g., human gene, is a homolog of a yeast gene that is a suppressor or enhancer of ApoE3-mediated toxicity and the mammalian cell, e.g., human cell, expresses ApoE3. In some embodiments the mammalian gene, e.g., human gene, is a homolog of a yeast gene that is a suppressor or enhancer of ApoE2-mediated toxicity and the mammalian cell, e.g., human cell, expresses ApoE4.

In some embodiments, overexpressing a gene in a cell or organism comprises expressing a protein encoded by the gene in the cell or organism, wherein the protein is encoded by a nucleic acid (e.g., an expression construct) that has been introduced into the cell or organism or into an ancestor of the cell or organism. In some embodiments, inhibiting or disabling a gene comprises inhibiting or disabling the gene in the genome of a cell or organism or inhibiting or disabling an expression product of the gene, e.g., a mRNA or protein encoded by the gene, in the cell or organism.

In some embodiments the mammalian cells are neural progenitor cells, neurons, glial progenitor cells or glial cells. In some embodiments the neurons are cortical neurons or hippocampal neurons. In some embodiments the neurons are glutamatergic neurons. In some embodiments the neurons are cholinergic neurons. In some embodiments the glial cells are astrocytes. In some embodiments the glial cells are oligodendrocytes. In some embodiments a composition, e.g., a cell culture, comprising two or more such cell types is provided, wherein the cells comprise neurons and glial cells.

In some embodiments the mammalian cells are pluripotent stem cells, e.g., induced pluripotent stem (iPS) cells or embryonic stem (ES) cells. In some embodiments the mammalian cells are neurons or glial cells derived in vitro by differentiation from pluripotent stem cells (iPS or ES cells), neural progenitor cells, or glial progenitor cells. In some embodiments the mammalian cells are neurons or glial cells derived by transdifferentiation from non-pluripotent somatic cells of a different cell type, e.g., a cell of non-neural, non-glial lineage. In some embodiments the mammalian cells are isolated cells, e.g., isolated human cells. In some embodiments the mammalian cells are non-human mammalian cells, e.g., rodent cells (e.g., mouse cells or rat cells) or non-human primate (e.g., monkey) cells, that express a human ApoE protein. In some embodiments a human gene identified as a homolog of a yeast gene that modulates ApoE-mediated toxicity is expressed in a transgenic non-human animal, e.g., a mouse, that expresses human ApoE in at least some of its cells.

In some embodiments a human gene that is a homolog of a yeast gene that modulates ApoE-mediated toxicity is expressed in non-human mammalian cells that express human ApoE. In some embodiments a non-human mammalian homolog of a yeast gene that modulates ApoE-mediated toxicity is expressed in non-human mammalian cells that express human ApoE. For example, a mouse homolog of a yeast gene that modulates ApoE-mediated toxicity may be expressed in mouse cells that express human ApoE. In some embodiments the cells express both endogenous ApoE and human ApoE. In some embodiments an endogenous ApoE gene of a non-human mammalian cell, e.g., a mouse cell, encodes, or is genetically modified to encode, arginine at the positions corresponding to residues 112, 158, or both, of human ApoE. In some embodiments a transgenic non-human animal expresses both endogenous ApoE and human ApoE in at least some of its cells, e.g., at least some of its neurons and/or glial cells. In some embodiments either or both alleles of an endogenous ApoE gene of a non-human mammal, e.g., a mouse, contains, or is genetically modified to contain, arginine at the positions corresponding to residues 112, 158, or both, of human ApoE.

In some embodiments a genetic modification is engineered in a pluripotent stem cell, neural stem cell, neural or glial progenitor cell, or other dividing cell, so that the modification is inherited by descendants of the cell. In some embodiments mature neurons and/or glial cells harboring the modification are derived from the cell. Methods of use for creating genetic modifications in mammalian cells are known in the art, and any such method may be applied to create genetically modified mammalian cells. In some embodiments the genetic modification comprises a heritable modification to the genome, e.g., insertion of exogenous DNA into the genome, deletion or substitution of one or more nucleotides of native DNA, or a combination thereof. In some embodiments an expression construct comprising a promoter operably linked to a sequence encoding a protein that is encoded by a human homolog of a yeast suppressor or enhancer of ApoE-mediated toxicity is introduced into a mammalian cell. The expression construct may be delivered to the cell in a vector (e.g., a viral vector or plasmid). In some embodiments an expression construct comprising a promoter (e.g., a Pol II or Pol III promoter) operably linked to a nucleic acid sequence encoding a shRNA, siRNA, antisense, or microRNA precursor molecule is introduced into a cell, wherein the shRNA, siRNA, antisense, or microRNA inhibits expression of a human homolog of a yeast suppressor or enhancer of ApoE-mediated toxicity by RNA interference (RNAi). In some embodiments expression of the mRNA or protein targeted by the shRNA, siRNA, antisense, or microRNA molecule may be decreased by at least 10%, 25%, 50%, 70%, 80%, 90%, or more.

In some embodiments exogenous nucleic acid, e.g., exogenous DNA, encoding a protein encoded by a human gene (or a counterpart thereof found in another mammalian species) listed in any one or more of Tables 1C, 1D, 2A, 2B, and 2C is introduced into a mammalian cell, e.g., a human cell. For example, an expression construct comprising a nucleic acid that encodes a protein encoded by a human gene (or a counterpart thereof found in another mammalian species) listed in any one or more of Tables 1C, 1D, 2A, 2B, and 2C, operably linked to a promoter, may be introduced into a mammalian cell, e.g., a human cell. In some embodiments a gene listed in any one or more of Tables 1C, 1D, 2A, 2B, and 2C is rendered dysfunctional in a mammalian cell, e.g., a human cell, e.g., by deleting or altering a portion of the promoter, other regulatory sequence, or coding sequence. In some embodiments a human gene (or a counterpart thereof found in another mammalian species) identified in any one or more of Tables 1C, 1D, 2A, 2B, and 2C is rendered conditional in a mammalian cell, e.g., a human cell, e.g., by placing it under control of a regulatable promoter. In some embodiments a gene is rendered conditional by placing at least a portion of the gen between recognition sites for a recombinase. DNA located between such sites can be removed by introducing or inducing expression of the recombinase in the cell. Such systems may be used, for example, to produce deletions, which may reduce expression of a gene or result in a gene product with altered (e.g., reduced) function or may bring a coding sequence under control of a promoter and thereby induce expression, etc. Suitable systems are known in the art. For example, the Cre/Lox recombinase system may be used. A gene may be modified by the insertion of two loxP sites that allow the excision of the flanked (foxed) gene segment through Cre-mediated recombination. In some embodiments, expression of Cre may be under control of a regulatable promoter or Cre activity may be regulated by a small molecule. For example, Cre may be fused to a steroid hormone ligand binding domain so that its activity is regulated by receptor ligands. Cre-ER(T) or Cre-ER(T2) recombinases may be used, which comprise a fusion protein between a mutated ligand binding domain of the human estrogen receptor (ER) and the Cre recombinase, the activity of which can be induced by, e.g., 4-hydroxy-tamoxifen. Other methods of generating inducible genetic alterations, e.g., knockouts, known in the art may be used. For example, different recombinases (e.g., Dre or the Flp/Frt system) may be used, and/or other means of rendering recombinase activity regulatable may be used.

In some embodiments, integration of exogenous DNA into the genome of a mammalian cell, e.g., a human cell, occurs at a "safe harbor" locus. A "safe harbor" locus is an intragenic or extragenic region of the mammalian genome, e.g., the human genome, that is able to accommodate the predictable expression of newly integrated DNA without adverse effects on the host cell. In some embodiments the safe harbour locus is the AAVSV1 (the natural integration site for the wild-type AAV on chromosome 19), ROSA26, or CCR5 locus. The locations of these loci are well known in the art. The AAVS1 site is in chromosome 19 (position 19q13.42) and integration in the AAVS1 locus may disrupt the gene phosphatase 1 regulatory subunit 12C (PPP1R12C). The human ROSA26 locus is in chromosome 3 (position 3p25.3). The human CCR5 gene is located on chromosome 3 (position 3p21.31).

In some embodiments, a mammalian cell may be genetically modified using a nuclease that is targeted to one or more selected DNA sequences, e.g., in order to insert, replace, or remove DNA at a defined location of interest in the genome. Genetic engineering in which DNA is inserted, replaced, or removed from a genome, e.g., at a defined location of interest, using targetable nucleases, may be referred to as "genome editing". In some embodiments genome editing may be used, e.g., to engineer an alteration in a human gene identified in any one or more of Tables 1C, 1D, 2A, 2B, and 2C and/or to generate a particular APOE allele in a mammalian cell. In some embodiments two or more cells or cell lines that are isogenic except for a particular genetic variation of interest. For example, cells or cell lines that are isogenic except with respect to their APOE genotype may be generated. Nucleic acids that are targeted to a particular location in the genome may be used to induce precise cleavage at selected sites in endogenous genomic loci. A nucleic acid (e.g., a plasmid or linear DNA) comprising a sequence to be inserted into the genome at the location of cleavage is also introduced into a cell containing the nuclease. In some embodiments two or more cleavages are produced, and a nucleic acid of interest is inserted between the cleavage locations, optionally at least in part replacing an endogenous gene by a version that incorporates a mutation, genetic variation, or genetic correction. In some embodiments the nucleic acid comprises regions of homology to the regions flanking the cleavage site, so that homology-directed repair is stimulated. In some embodiments a nucleic acid comprising a sequence that is homologous to either side of the target site and contains a desired alteration as compared to a sequence present in the cell's genome is introduced in addition to the polypeptide, e.g., resulting in homology directed repair. Thus, a sequence in a cell's genome can be altered and, in certain embodiments, can be converted into a sequence present in a donor nucleic acid. It will be understood that terms such as "insert", "replace", etc., represent insertion of a nucleic acid sequence or replacement of one nucleotide sequence by another, (i.e., insertion or replacement of a sequence in the informational sense), and do not necessarily require physical or chemical incorporation of an introduced nucleic acid into the genome, e.g., repair may entail producing a copy of at least a portion of the donor sequence. Examples of suitable nucleases include zinc-finger nucleases (ZFNs), TALENs, engineered meganuclease homing endonucleases, and RNA directed nucleases such as CRISPR (clustered regularly interspaced short palindromic repeats)-associated (Cas) nucleases, e.g., derived from type II bacterial CRISPR/Cas systems (e.g., Cas9). Methods of designing, generating and using ZFNs and/or TALENs are described in, e.g., WO2011097036; Urnov, F D, et al., Nature Reviews Genetics (2010), 11: 636-646; Miller J C, et al., Nat Biotechnol. (2011) 29(2): 143-8; Cermak, T., et al. Nucleic Acids Research (2011) 39 (12): e82, Sanjana, N. E. et al. Nat Protoc 7, 171-192 (2012) and references in any of the foregoing. Use of ZFNs to perform genetic engineering of human pluripotent cells is described in US Pat. Pub. No. 20110027235 and/or in US Pat. Pub. No. 20120192301, which also describes use of TALENs. ZFN, TALEN, and CRISPR/Cas-based methods for genome engineering are reviewed in Gaj, T., et al., Trends Biotechnol. 2013; 31(7):397-405. Use of CRISPR/ Cas systems in genome engineering is described in, e.g., Cong L, et al. Multiplex genome engineering using CRISPR/Cas systems. Science. 2013; Wang, H. et al. One-step generation of mice carrying mutations in multiple genes by CRISPR/Cas-mediated genome engineering. Cell 153, 910-918 (2013); Ran, F. A. et al. Cell 154, 1380-1389 (2013), and US Pat. Pub. No. 20140170753.

Methods of generating transgenic non-human animals, e.g., mice and rats, are known in the art, and any such method may be applied to generate transgenic non-human animals. As used herein, the term "transgenic animal" refers to an animal that has a modification to the sequence of the genomic DNA of at least some of its cells, wherein the modification was generated by the hand of man. It will be understood that the term includes the original transgenic animal as well as its descendants that have inherited the modification. The modification may comprise, e.g., insertion of non-native DNA, deletion of native DNA, substitution of one or more nucleotides, or a combination thereof. Transgenic animals include those that are modified to express a nucleic acid that is not native to the animal as well as "knock-out" animals in which an endogenous gene is at least partly deleted or otherwise rendered nonfunctional and "knock-in" animals in which a selected endogenous gene is modified in a targeted manner. Transgenic animals that are modified to express a nucleic acid that is not native to the animal include those in which an exogenous DNA is inserted randomly into the genome, those in which exogenous DNA is inserted at a defined location such as a safe harbor locus, and those in which an endogenous gene of interest is altered. It will be understood that intronic sequences and/or polyadenylation signals can also be included in a transgene, e.g., to increase the efficiency of expression of the transgene. A transgenic founder animal may be identified based upon the presence of the transgene in its genome and/or expression of a mRNA or protein encoded by the transgene in tissues or cells of the animals. A transgenic founder animal can then be used to breed additional animals carrying the transgene. Transgenic animals carrying a particular transgene can be bred to other transgenic animals carrying other transgenes to generate animals with multiple genetic modifications.

Methods of use for generating or isolating mammalian, e.g., human, pluripotent cells (e.g., iPS cells, ES cells), neural progenitor cells, neurons, glial progenitor cells, and glial cells are known in the art, and any such method may be used to generate or isolate iPS cells, ES cells, neural progenitor cells, glial progenitor cells, neurons, and/or glial cells. A pluripotent cell is an undifferentiated cell that is capable of giving rise to cells of the three germ layers: endoderm, mesoderm, and ectoderm, and typically has the ability to self-renew for a prolonged or indefinite period. In general, pluripotent cells are positive for at least one master pluripotency transcription factor such as OCT4 (also known as POU5F1), SOX2, and/or NANOG, e.g., all three of these factors. In some embodiments a pluripotent stem cell is an embryonic stem cell (ES cell). ES cells are pluripotent stem cells derived from an early stage embryo, e.g., a blastocyst, or from a blastomere isolated from an early stage embryo. As used herein the term "early stage embryo" encompasses pre-implantation embryos from the first cell division up to and including the blastocyst stage e.g., 4-cell embryos, 8-cell embryos, morulas, or blastocysts. An ES cell is typically derived in vitro from an early stage embryo that has been created using in vitro fertilization or from a blastomere isolated from such an embryo. Any of a variety of methods known in the art may be used to derive, identify, and/or characterize an ES cell. See, e.g., Turksen, K. (ed.) Human Embryonic Stem Cell Protocols, Methods in Molecular Biology, Vol. 331 Humana Press, Inc. Totowa, N H, 2006, Turksen, K. (ed.), *Human Embryonic Stem Cell Handbook*, Methods in Molecular Biology, Vol. 873 Humana Press (a brand of Springer), 2012 (e.g., Ch. 1-6 in particular for methods of deriving human ES cells). See also U.S. Pat. Nos. 5,843,780; 6,200,806; 7,029,913; U.S. Pat. Pub. No. 20090186407; PCT/US2011/000850 (WO/2011/142832).

In some embodiments a pluripotent cell is an induced pluripotent stem cell. As used herein, an induced pluripotent stem (iPS) cell is a cell that is derived from a somatic cell by reprogramming the cell to a pluripotent state. iPS cells possess certain key features of ES cells including cell morphology, colony morphology, long-term self-renewal, expression of pluripotency-associated markers, similar genome-wide expression profile, ability to form teratomas in immunocompromised mice, and ability to give rise to cells of multiple cell lineages in vitro under appropriate conditions. It will be understood that the term "iPS cell" includes the original derived pluripotent cell and its descendants that retain pluripotent stem cell properties. "Reprogramming", as used herein, refers to altering the differentiation state or identity of a cell (e.g., its cell type) or a process by which this occurs. In general, reprogramming a first cell generates a second cell with a differentiation state or identity distinct from that which would result from a differentiation program that the first cell or a corresponding cell would normally follow in vivo and results in cells of one or more types distinct from those that the first cell or a corresponding cell would give rise to in vivo. A "corresponding cell" is a cell of the same type or having sufficiently similar features that a person of ordinary skill in the art would reasonably consider it to be of the same or substantially the same cell type. Cell type may refer to a category of cell such as "neuron" or "glial cell" or a subtype within a broader category. A subtype may be defined on the basis of characteristic features, characteristic cellular markers (e.g., neurotransmitters produced by the cell or that stimulate the cell) characteristic location where cells of that subtype may be found in the body, functional properties, etc.

In some embodiments reprogramming generates a pluripotent cell from a somatic cell. In some embodiments a somatic cell is a mature, differentiated cell. In some embodiments reprogramming alters a cell to one of a cell lineage different to that which a corresponding cell would develop into or give rise to in vivo under normal conditions. In some embodiments reprogramming generates somatic cells of a second cell lineage or second cell type from somatic cells of a first cell lineage or first cell type that is different to the second cell lineage or first cell type. In some embodiments this transformation may occur without generating a detectable pluripotent cell as an intermediate, in which case it may be referred to as "transdifferentiation." Reprogramming a cell to a particular cell type, cell lineage, or cell state may occur over the course of one or more cell cycles. For example, it may take multiple rounds of cell division to generate a pluripotent stem cell from a somatic cell or to generate a differentiated cell of a first cell type from a differentiated cell of a different cell type.

In general, reprogramming may be performed by a method comprising contacting at least one somatic cell with one or more reprogramming agents under suitable conditions and for a suitable time for the cell to be reprogrammed. In some embodiments reprogramming is performed by a method comprising introducing a reprogramming factor or a nucleic acid encoding a reprogramming factor into a cell or inducing expression in a cell of a reprogramming factor encoded by an exogenous nucleic acid. The term "reprogramming factor" encompasses proteins that are capable of causing or contributing to reprogramming a cell. Many useful reprogramming factors are transcription factors that are naturally expressed by or present in mammalian cells of the type or state to be generated. These proteins may normally contribute to inducing or maintaining cell identity or state by affecting gene expression. The term "reprogramming agent" encompasses reprogramming factors and also agents that are capable of (i) substituting for a reprogramming factor in a method of reprogramming, (ii) inhibiting expression of an endogenous RNA or protein that may otherwise inhibit reprogramming, and/or (iii) detectably increasing reprogramming efficiency or speed as compared with the efficiency or speed that would be achieved in the absence of the reprogramming agent. In some embodiments a reprogramming agent may stimulate a signaling pathway that leads to expression or activation of an endogenous reprogramming factor, inhibit a signaling pathway that leads to expression or activation of an endogenous inhibitor of reprogramming, or activate or inhibit an enzyme that modifies chromatin structure, such as a DNA or hi stone acetylase, deacetylase, methylase, or demethylase. In some embodiments reprogramming comprises performing one or more manipulations on cells such as introducing nucleic acid(s), e.g., vector(s), that encode particular proteins or RNAs into cells and/or culturing them in medium containing particular compounds, which may enter the cells or act on cell surface receptors to induce reprogramming and/or increase its efficiency or speed. The particular manipulations and/or protocol used may be selected as appropriate depending, e.g., on the desired cell type or state, the type or state of the cells to be reprogrammed, etc. In general, reprogramming is performed in vitro. In some aspects reprogramming does not include nuclear or cytoplasmic transfer or cell fusion, e.g., with oocytes, embryos, germ cells, or pluripotent cells.

Reprogramming methods often comprise exposing a plurality of cells to a reprogramming agent or combination thereof in culture and identifying or selecting one or more cells or cell colonies having features of a desired cell type or state. The one or more cells or at least a portion of the cell colony may be isolated and expanded in culture and may be propagated as a distinct cell line under conditions appropriate to maintain its new cell identity or state. In some embodiments such conditions are typical culture conditions for a cell of that type. In some embodiments continued exposure to at least one, some, or all of the exogenous reprogramming agents is not necessary in order to maintain the identity or state of the reprogrammed cells, e.g., the identity or state of the reprogrammed cells is stable in the absence of such agents.

Somatic cells may be reprogrammed to iPS cells by a variety of methods. In some embodiments iPS cells are generated by a method comprising introducing one or more reprogramming factors or nucleic acids encoding such factor (s) into a somatic cell and/or inducing expression in the cell of one or more exogenous nucleic acid(s) encoding such factors. In some embodiments the reprogramming factors include at least one, two, or all of OCT4, SOX2, and KLF4 (OSK factors), and, optionally, c-MYC (OSKM factors). Other reprogramming factors, such as NANOG and LIN28 are also of use. For example, the combination of OCT4, SOX2, NANOG, and LIN28 (OSNL factors) can induce pluripotency. Many variations or alternative combinations are possible. For example, different KLF and/or MYC family members may be used instead of or in addition to KLF4 and/or c-MYC. For example, KLF2 or KLF5 can substitute for KLF4; N-MYC or L-Myc for c-MYC. Those of ordinary skill in the art will be aware of various reprogramming agents that can substitute for one or more of the OKSM or OSNL factors. In some embodiments 1, 2, 3, 4, 5, or more reprogramming factors are used. In some embodiments the reprogramming factors include at least OCT4.

In some embodiments an appropriate set of reprogramming factors introduced or expressed for a sufficient time at an appropriate level under suitable culture conditions causes activation of the endogenous pluripotency genes OCT4, SOX2, and NANOG, which may result in a self-sustaining pluripotent state in some of the cells. In some embodiments exogenous DNA (e.g., DNA encoding reprogramming factors) introduced into cells is naturally silenced and/or at least in part removed or lost after induction of pluripotency, e.g., after a self-sustaining pluripotent state is reached, or after a pluripotent cell, induced neural stem cell or induced neural progenitor cell has been differentiated to a desired cell type. Inserted DNA may comprise target sites for a recombinase so that removal of the region between these sites may be performed by recombinase-mediated excision. Such excision may leave only a short residual sequence comprising portions of the recombinase target site. Episomal plasmids used to reprogram cells may thereafter be lost. iPS cells and/or induced nervous system cells free of introduced genetic material or essentially free of exogenous genetic material (e.g., containing only a residual recombinase target site or portions thereof) can be produced by such methods.

In some embodiments, one or more reprogramming factors are introduced into cells by introducing one or more nucleic acid sequences encoding the factor(s). In some embodiments, the one or more nucleic acid sequences comprise DNA. In some embodiments, the one or more nucleic acid sequences comprise RNA. In some embodiments, the one or more nucleic acid sequences comprise a nucleic acid construct. In some embodiments, the one or more nucleic acid sequences comprise a vector for delivery of the reprogramming factors into a target cell (e.g., a mammalian somatic cell, e.g., a human fibroblast, keratinocyte, or blood cell). For example, iPS cells can be generated by introducing genes encoding a suitable set of reprogramming factors into somatic cells by infection with retroviruses, e.g., lentiviruses. Any suitable vector may be used. Examples of suitable vectors are described by Stadtfeld and Hochedlinger (Genes Dev. 24:2239-2263, 2010, incorporated herein by reference). Other suitable vectors are apparent to those skilled in the art. In some embodiments two, three, four, or more factors are encoded in a nucleic acid single cassette. For example, reprogramming factors may be delivered in a single virus using 2A "self-cleaving" peptides, which support efficient polycistronic expression from a single promoter. Biologically active variants of reprogramming factors or other reprogramming agents may be used in certain embodiments. A variety of techniques can be employed in the generation of iPS cells instead of or in addition to inserting genes encoding one or more of the factors into the genome. Such methods may involve use of small molecules, transient transfection, infection using non-integrating viruses (e.g., adenovirus, Sendai virus) or plasmids (e.g., comprising elements of the Epstein-Barr virus such as the EBNA1 gene and the OriP DNA) able to replicate extrachromosomally as a circular episome, protein transduction, introduction of translatable mRNA encoding one or more reprogramming factors, and/or RNA interference to inhibit expression of selected genes (e.g., p53-p21 pathway genes). Molecules that act on signaling pathways involved in ES cell self-renewal and pluripotency, such as TGFβ and/or MEK pathways, may be used. Non-limiting examples of reprogramming agents that may be used in place of a reprogramming factor and/or in combination with one or more reprogramming factors to enhance reprogramming include kinase inhibitors, e.g., Aurora A kinase inhibitors (Li Z, Rana T M Nat Commun. 2012; 3:1085), TGF-beta pathway inhibitors such as TGF-β/Activin/Nodal receptor inhibitors (e.g., A-83-01), MEK inhibitors (e.g., PD0325901), GSK3β inhibitors (e.g., CHIR99021), ROCK inhibitors (e.g., HA-100), compounds that activate Oct-4 such as Oct4 activating compound 1 and structural analogs thereof (Li, T, et al, Proc Natl Acad Sci USA. 2012; 109(51):20853-8), retinoic acid receptor agonists, among others, may be used in certain embodiments. Histone deacetylase (HDAC) inhibitors (e.g., valproic acid, suberoylanilide hydroxamic acid, sodium butyrate, trichostatin A), histone methyltransferase inhibitors (e.g., BIX-01294), and other modulators of endogenous chromatin modifying enzymes can improve reprogramming efficiency. These compounds may act by reducing the epigenetic barriers to reprogramming. In some embodiments reprogramming agents include one or more microRNAs or microRNA precursors that enhance reprogramming, such as ESC specific cell cycle (ESCC)-regulating miRNAs or siRNA or antisense molecules that inhibit target genes of such miRNA. In some embodiments inhibiting expression of certain microRNAs (e.g., let-7) enhances reprogramming. In some embodiments reprogramming agents include inhibitors of such miRNA, such as antagomirs or antisense molecules. In some embodiments inhibiting expression of one or more genes, e.g., p53, DOT1, 4E-BP (e.g., using siRNA, shRNA, or antisense) enhances reprogramming.

In some embodiments reprogramming may be performed at least in part by introducing mRNA into a cell wherein the introduced mRNA encodes at least one reprogramming factor. The mRNA may be in vitro transcribed mRNA. Non-limiting examples of producing in vitro transcribed mRNA are described by Warren et al. (Cell Stem Cell 7(5):618-30, 2010, Mandal P K, Rossi D J. Nat Protoc. 2013 8(3):568-82, and/or PCT/US2011/032679 (WO/2011/130624) the teachings of each of which are incorporated herein by reference). The protocols described may be adapted to produce one or more mRNAs of interest herein. In some embodiments, mRNA, e.g., in vitro transcribed mRNA, comprises one or more modifications (e.g., modified ribonucleotides) that increase stability or translatability of said mRNA. In some embodiments the modification comprises substitution of 5-methylcytidine (5mC) for cytidine, substitution of pseudouridine (psi) for uridine, or both. In some embodiments at least 50%, 60%, 70%, 80%, 90%, 95%, or all of the cytidines, uridines, or both, are substituted by 5mC or psi, respectively. In some embodiments the mRNA is subjected to phosphatase treatment. In some embodiments the modification attenuates interferon signaling. In some embodiments media is supplemented with an inhibitor of interferon signaling. In some embodiments the inhibitor binds to an interferon. In some embodiments the inhibitor comprises a decoy receptor, such as B18R protein, a vaccinia virus decoy receptor for type I interferons.

In some embodiments, mRNA, e.g., in vitro transcribed mRNA comprises a 5' cap. The cap may be wild-type or modified. Examples of suitable caps and methods of synthesizing mRNA containing such caps are apparent to those skilled in the art. In some embodiments, mRNA, e.g., in vitro transcribed mRNA, comprises an open reading frame flanked by a 5' untranslated region and a 3' untranslated region that enhance translation of said open reading frame, e.g., a 5' untranslated region that comprises a strong Kozak translation initiation signal, and/or a 3' untranslated region comprises an alpha-globin 3' untranslated region. In some embodiments, mRNA, e.g., in vitro transcribed mRNA, comprises a polyA tail. Methods of adding a polyA tail to mRNA are known in the art, e.g., enzymatic addition via polyA polymerase or ligation with a suitable ligase. In some embodiments, mRNA is introduced into a somatic cell in an amount and for a period of time sufficient to maintain expression of a reprogramming factor or other reprogramming agent encoded by said mRNA until cellular reprogramming of said somatic cell occurs. The sufficient period of time may vary depending, e.g., on the type of somatic cell and the reprogramming factors employed. One of ordinary skill in the art can readily determine the appropriate period of time by routine experimentation. In some embodiments, mRNA is introduced into somatic cells at various intervals during the course of reprogramming.

Further discussion and description of reprogramming, certain reprogramming methods, methods of characterizing reprogrammed cells, and/or methods of generating differentiated cells from iPS cells that may be used in certain embodiments may be found in, e.g., US Pat. Pub. Nos. 20110076678; 20110088107; 20100310525; Lyssiotis, C A, et al, Proc Natl Acad Sci USA., 106(22):8912-7, 2009; Carey B W, Proc Natl Acad Sci USA; 106(1): 157-62, 2009, Hockemeyer D, et al., Cell Stem Cell. 2008; 3(3):346-53; and/or Lakshmipathy, U. and Vemuri, M C (eds.), Pluripotent Stem Cells—Methods and Protocols, Methods in Molecular Biology, Vol. 997 (2013) Humana Press (a brand of Springer), and references cited in any of the foregoing. A non-exhaustive, non-limiting discussion of various reprogramming methods is found in Theunissen T W and Jaenisch R., Cell Stem Cell. (2014), 14(6):720-34.

The present disclosure contemplates any suitable method for introducing nucleic acids, e.g., DNA or RNA, into cells, e.g., to carry out reprogramming and/or genetic modification. In some embodiments, a nucleic acid is introduced into a somatic cell via electroporation. In some embodiments, a nucleic acid is introduced into a somatic cell via transfection. A suitable transfection reagent may be used, of which many are known in the art. In some embodiments, a nucleic acid may be complexed with a vehicle, e.g., a cationic vehicle, e.g., a cationic liposome or a nanoparticle. In some embodiments the vehicle facilitates uptake of nucleic acids via endocytosis and/or facilitates release of the nucleic acid from an endosome. In some embodiments the nucleic acid may be incorporated into or carried by a vector.

In general, human iPS cells may be generated from somatic cells of any type. In some embodiments human iPS cells are generated from fibroblasts, keratinocytes, adipose tissue cells, mesenchymal stem cells (which may be obtained from adipose tissue), peripheral blood mononuclear cells (PMNCs), or epithelial cells recovered from urine. These cell types may be particularly convenient for deriving human iPS cells as they may be readily obtained from living human subjects noninvasively or with minimal or low invasiveness. In some embodiments human iPS cells are derived from purified human $CD34^+$ cells, which may be isolated from peripheral blood.

In some embodiments reprogrammed cells may be induced to differentiate to yield cells of one or more different cell lineages or cell types. For example, pluripotent cells generated through reprogramming may be allowed or induced to differentiate into multipotent progenitor cells, e.g., neural progenitor cells, which may be allowed or induced to further differentiate to give rise to mature, differentiated cells of various types. Differentiation to one or more desired cell lineages or cell types may be induced by subjecting a cell to an appropriate set of one or more manipulations or placing the cell under conditions that are permissive for differentiation. It will be understood that differentiation may occur over the course of one or multiple cell cycles. The particular manipulations and/or protocol to be used to cause differentiation may be selected as appropriate depending, e.g., on the desired cell type(s) and/or the starting cell type.

In some embodiments neural stem cells are derived from pluripotent human cells. The term "neural stem cell" refers to a nervous system cell that exhibits features characteristic of neural stem cells, such as multipotency, self-renewal, neurosphere forming ability, and expression of cellular markers characteristic of neural stem cells. Neural stem cells are multipotent and have the capacity to give rise to mature neurons, astrocytes, and oligodendrocytes. In some embodiments neural progenitor cells are derived in vitro from pluripotent human cells. The term "neural progenitor cell" refers to a nervous system cell that is more differentiated or specified towards a particular cell fate than a neural stem cell, is less differentiated than a mature neuron, and is capable of giving rise to cells with characteristics of mature neurons. In some embodiments an induced neural progenitor cell is capable of giving rise both to neurons and glial cells (e.g., astrocytes and/or oligodendrocytes). It will be understood that the process of giving rise to mature neurons and glial cells may entail one or more cell division cycles involving increasing differentiation.

Neural stem cells and neural progenitor cells may be differentiated in culture to give rise to mature neurons and, in some embodiments, glial cells. In some embodiments mature neurons are post-mitotic. Methods for inducing such differentiation are known in the art. In general, such methods comprise culturing neural stem cells or neural progenitor cells in suitable culture medium for an appropriate time to generate the desired cell type(s). The culture medium may comprise one or more agents that promotes neural differentiation and/or may lack one or more agents that may inhibit neural differentiation or promote differentiation along a non-neural cell lineage pathway. Methods for generating neurons in culture from human pluripotent stem cells (PSCs) such as iPS or ES cells, neural stem cells, and neural progenitor cells are known in the art. The particular methods, culture media, may be selected as appropriate to generate cells of desired cell types or subtypes. In some embodiments a cell culture comprising both neurons and glial cells may be generated. For example, in some embodiments neural cells may be generated from iPS cells as described in U.S. Pat. Pub. No. 20100021437 and/or in Chung, C., et al., Science. (2013); 342(6161):983-7.

Methods are available for generating glial progenitor cells from pluripotent human cells. Glial progenitor cells can be differentiated to oligodendrocytic and astrocytic cells. Both astrocytes and oligodendrocytes are efficiently derived from human iPSC-derived human oligodendrocyte precursor cells (OPCs) (Wang., S., et al. Cell Stem Cell 12, 252-264).

In some embodiments, mammalian, e.g., human, nervous system cells may be generated by transdifferentiation, e.g., in vitro. In some embodiments neural stem cells, neural progenitor cells, or neurons are generated by transdifferentiation from somatic cells, e.g., fibroblasts or keratinocytes. Methods for generating such cells by transdifferentiation are known in the art (see, e.g., Ring, K L, et al., (2012) Cell Stem Cell 11, 100-109 and/or Pang, Z P, et al., (2012), Nature, 476: 220-224).

In some embodiments, neural or glial cells of a particular type are generated, isolated, and/or used in a method described herein. One of ordinary skill in the art will be aware of characteristics and cellular markers indicative of cells that are typically found in and/or are fated to develop into neurons and/or glial cells located in the brain or a particular region or subregion of the brain, such as the forebrain, midbrain, cortex, hippocampus, striatum, or a particular nucleus of the brain, e.g., a region, subregion, or nucleus that is frequently affected in a neurodegenerative disease. One of ordinary skill in the art will be aware of appropriate markers for identifying nervous system cells of interest. Suitable markers may be, for example, transcription factors, enzymes involved in the synthesis of neurotransmitters or uptake of molecules that serve as neurotransmitter precursors, receptors for neurotransmitters, intermediate filament proteins, ion channel subunits, cell adhesion molecules, etc. One of ordinary skill in the art will be aware of suitable regulatory elements, e.g., promoters, that may be used to express a nucleic acid or protein of interest, e.g., a human homolog of a yeast gene that is a genetic modifier of ApoE-mediated toxicity, in tissues or cells of interest. For example, regulatory elements, e.g., promoters, of the genes that encode afore-mentioned markers may be used. In some embodiments the neuron-specific promoter synapsin may be used.

In some embodiments the cells may overexpress Aβ. In some embodiments the cells may express a mutant form of Aβ, e.g., a mutant form associated with AD.

Mammalian cells and/or non-human transgenic animals in which a mammalian homolog of a yeast gene that modulates ApoE-mediated toxicity is overexpressed or inhibited or disabled may be used for a variety of purposes. For example, such cells and/or animals may be used as model systems for testing candidate agents that have been identified in the yeast system described herein or in other systems or may be used for identifying candidate agents de novo. In some embodiments mammalian cells, e.g., human cells, that harbor a mammalian homolog of a yeast gene that is a genetic risk factor for an ApoE-mediated disease, e.g., AD, may serve as personalized models for identifying candidate agents of particular use for treating subjects with the disease who harbor the genetic risk factor. In some embodiments such cells harbor human ApoE, e.g., human ApoE4, or an ApoE that mimics a particular ApoE isoform. For example, an ApoE that mimics the human ApoE4 has arginine at the positions corresponding to residues 112 and 158 of human ApoE. In some embodiments the cells may have any APOE genotype.

Any of the preceding mammalian model systems may be used in a method of identifying a binding partner for a human ApoE protein as described herein.

Pharmaceutical Compositions and Methods of Treatment

A compound that is found to prevent or suppress ApoE-mediated toxicity in a cell can be formulated as a pharmaceutical composition, e.g., for administration to a subject to treat an ApoE-associated disease, e.g., an ApoE-associated neurodegenerative disease such as Alzheimer's disease.

A pharmaceutical composition typically includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The compound can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In some embodiments, a compound that prevents or suppresses ApoE-mediated toxicity in a cell can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The preferred form can depend on the intended mode of administration and therapeutic application. In some embodiments, compositions comprising one or more agents described herein are in the form of injectable or infusible solutions. Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating a compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of a compound plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the compound can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A compound identified as one that prevents or suppresses ApoE-induced toxicity in a cell can be modified, e.g., with a moiety that improves its stabilization and/or retention in circulation, e.g., in blood, serum, or other tissues, e.g., by at least 1.5, 2, 5, 10, or 50 fold. The modified compound can be evaluated to assess whether it can reach treatment sites of interest such as can occur in a cell in a subject with a neurodegenerative disease such as Alzheimer's disease (e.g., by using a labeled form of the compound).

For example, the compound can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, a compound can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (PLURONICS®); polymethacrylates; carbomers; and branched or unbranched polysaccharides.

When the compound is used in combination with a second agent (e.g., any additional therapies for Alzheimer's disease or other ApoE-associated diseases, the two agents can be formulated separately or together. For example, the respective pharmaceutical compositions can be mixed, e.g., just prior to administration, and administered together or can be administered separately, e.g., at the same or different times. Separately administered compounds may be administered by the same route or different routes depending, e.g., on the particular agents. In some embodiments, first and second compounds are administered one or more times within 1, 2, 3, 4, 5, 6, 7 days of each other or within 2, 3, 4, or 6 weeks of each other.

Compounds described herein and those identified as described herein can be used to treat a subject (e.g., a human subject) that is at risk for or has a disorder associated with ApoE-mediated toxicity, amyloid beta-mediated toxicity, and/or the formation, deposition, accumulation, or persistence of amyloid beta aggregates, e.g., amyloid beta oligomers and/or dimers. In certain embodiments, the disorder is Alzheimer's disease. Methods of identifying an individual at risk for or having such disorders are known in the art. For example, AD can be diagnosed based on, e.g., patient history (e.g., memory loss) clinical observations, the presence of characteristic neurological and neuropsychological features, and the absence of detecting other conditions that might be responsible for the foregoing. Imaging techniques such as computed tomography (CT), magnetic resonance imaging (MM), single photon emission computed tomography (SPECT), or positron emission tomography (PET) can be of use. Diagnosis can be confirmed by post-mortem examination of brain material. Exemplary criteria for diagnosis of AD are found in the Diagnostic and Statistical Manual of Mental Disorders (DSM)-IV (text revision, 2000) or DSM-V and the National Institute of Neurological and Communicative Disorders and Stroke (NINCDS)-Alzheimer's Disease and Related Disorders Association (ADRDA) criteria (McKhann G, et al. (1984) Neurology 34 (7): 939-44), e.g., as updated (Dubois B, et al. (2007) Lancet Neurol 6 (8): 734-46). Analysis of cerebrospinal fluid (CSF) for various biomarkers, e.g., amyloid beta or tau proteins (e.g., total tau protein and phosphorylated tau) and/or imaging (e.g., PET imaging) with labeled compounds that bind to amyloid beta deposits (e.g., 11C-labeled Pittsburgh Compound-B (11C-PIB) or 18F-AV-45 (flobetapir F18) can be used to predict the onset of AD, e.g., to identify individuals who have a significant likelihood of progressing to AD in the future (e.g., within the next two years). Such imaging methods may also be of use in the instant invention to assess the in vivo effect of compounds identified herein and/or identified using an inventive screening assay. In some embodiments, a subject has a mutation in a gene encoding amyloid precursor protein (APP), presenilin 1, or presenilin 2. In some embodiments, the mutation increases the production of Aβ42 or alters the ratio of Aβ42 to Aβ40.

In some embodiments the subject's genotype with respect to the APOE gene is known. In some embodiments the subject has at least one copy of the ε4 allele of the APOE gene. The common ApoE isoforms are determined by C/T polymorphisms at the codons encoding the amino acids at positions 112 and 158 of the ApoE polypeptide. Of the six possible genotypes three are homozygous (ε2/ε2, ε3/ε3, ε4/ε4), and three heterozygous (ε2/ε3, ε2/ε4, ε3/ε4). In some embodiments the subject is heterozygous for the ε4 allele (the subject's genotype is ε2/ε4 or ε3/ε4). In some embodiments the subject is homozygous for the ε4 allele. In some embodiments the subject is heterozygous for the ε3 allele (the subject's genotype is ε2/ε3 or ε3/ε4). In some embodiments the subject is homozygous for the ε3 allele. In some embodiments the subject is heterozygous for the ε2 allele (the subject's genotype is ε2/ε3 or ε2/ε4). In some embodiments the subject is homozygous for the ε2 allele. The genotype at the APOE locus can be determined using any of a variety of methods useful for genetic testing known in the art, such as sequencing (e.g., after amplification by PCR), hybridization of allele-specific probes followed by detection, hybridization of allele-specific primers followed by real-time PCR (Calero O, et al., (2009) J Neurosci Methods. 183(2):238-40), SNaPshot™ mini-sequencing (Ben-Avi L, et al., J Alzheimers Dis. 2004 October; 6(5):497-501), and multiplex tetra-primer amplification refractory mutation system (T-ARMS) PCR, TaqMan assays (Koch W, et al., (2002) Clin Chem Lab Med. 40(11):1123-31), FRET-based methods (Rihn, B H (2009) Clin Exp Med; 9(1):61-5.), PCR followed by restriction fragment length polymorphism assessment (Zivelin A, et al., (1997) Clin Chem. 43:1657-9).

As used herein, the term "treatment" is defined as the application or administration of a therapeutic compound to a patient, or application or administration of a therapeutic compound to a subject (e.g., a human subject, who may be referred to as a "patient") who has a disease (or other medically recognized disorder or syndrome), a symptom of disease or a predisposition toward a disease (e.g., one or more risk factors (e.g., genetic risk factors) associated with the disease), with the purpose to cure, heal, alleviate, relieve, alter, remedy, ameliorate, improve, or affect (in a manner beneficial to the subject) the disease, the symptoms of disease or the predisposition toward disease. In some embodiments, treatment is prophylactic, i.e., it is administered to a subject who has not developed the disease (and who may or may not have a predisposition to develop the disease) with an intent to delay, prevent, or reduce the likelihood that the subject will develop the disease or reduce the severity should the subject develop the disease. Compounds may also or alternately be administered to a subject for purposes of testing, research, or diagnosis and/or may be contacted with an isolated tissue, cells, or cell line from a patient, e.g., for purposes of testing, research, diagnosis, or with an intent to subsequently administer the isolated tissue, cells, or cell line to the subject for treatment.

In some aspects, described herein are methods for preventing in a subject (e.g., a human), an ApoE-mediated disease by administering to the subject a target protein or a compound that modulates target protein expression or at least one target protein activity. In certain embodiments, the target protein may be a binding partner of a human ApoE protein, for example, as identified by the methods of the invention. Subjects at risk for a disease that is caused or contributed to by aberrant or unwanted target protein expression or activity can be identified by, for example, any or a combination of diagnostic or prognostic assays as described herein. Administration of a prophylactic compound can occur prior to the manifestation of symptoms characteristic of the disease, such that the disease or disorder is prevented or, alternatively, delayed in its progression. Methods known in the art can be used to determine the efficacy of the treatment. The appropriate compound used for treating the subject can be determined based on screening assays described herein. Some cases of AD (or other ApoE-mediated disease) may be caused, at least in part, by an abnormal level of a target gene product, or by the presence of a target protein exhibiting abnormal activity. In some aspects of the invention, altering the level and/or activity of such gene product(s) will bring about the amelioration of disorder symptoms. For example, an abnormally high level of a target gene product or an abnormally high level of activity of a target protein can be reduced and/or an abnormally low level of a target gene product or an abnormally low level of activity of a target protein can be increased. Accordingly, the modulation in the level and/or activity of such gene products will bring about the amelioration of disorder symptoms. Thus in some embodiments, treatment of an ApoE-mediated or amyloid beta mediated disorder can be accomplished by techniques that inhibit the expression or activity of selected target gene products (e.g., enhancers of ApoE-mediated toxicity). In some embodiments, treatment of an ApoE-mediated or amyloid beta mediated disorder can be accomplished by techniques that enhance the expression or activity of selected target gene products (e.g., suppressors of ApoE-mediated toxicity). For example, compounds, e.g., an agent identified using one or more of the assays described above, that exhibits negative modulatory activity (e.g., that inhibits gene expression or protein activity), can be used as described herein to prevent and/or ameliorate symptoms of an ApoE-mediated or amyloid beta mediated disorder. Such molecules can include, but are not limited to, peptides, small organic or inorganic molecules, antibodies, siRNA, miRNA, antisense, aptamer, ribozyme, or triple helix molecules. In some embodiments, the compound enhances one or more target protein activities. Examples of such compounds can include, but are not limited to, active target protein (or biologically active fragment or variant thereof), nucleic acid molecules encoding the target protein or encoding a biologically active fragment or variant thereof, antagomirs that inhibit miRNA that would otherwise inhibit expression of the gene, peptides, small organic or inorganic molecules, and antibodies.

Compounds that inhibit ApoE-mediated toxicity and/or that modulate (inhibit or enhance) target gene expression, synthesis and/or activity can be administered to a patient at therapeutically effective doses to prevent, treat, or ameliorate an ApoE-mediated or amyloid beta mediated disorder. A therapeutically effective dose can be an amount of the compound sufficient to result in amelioration of a one or more symptom(s) or sign(s) of the disorder and/or reduction in rate at which one or more symptom(s) or sign(s) of the disorder increases in severity (e.g., as compared with the rate that would be expected in the absence of therapy). Criteria for assessing efficacy in AD are known in the art. Toxicity and therapeutic efficacy of such compounds can be determined by standard pharmacological procedures. In some embodiments, one or more endpoints or sets of endpoints described in Vellas, B., et al., Lancet Neurology (2008) 7(5): 436-450 may be used. In some embodiments, one or more endpoints or sets of endpoints described in Aisen, P S, et al., 2011; 76(3):280-6 are used for evaluating efficacy in early (predementia) AD. It will be understood that an effective dose is typically administered multiple times, e.g., once or more times daily, weekly, monthly, etc., depending on various factors such as, e.g., its half-life. In exemplary embodiments, a therapeutically effective amount ranges from about 0.001 to 100 mg/kg body weight, e.g., about 0.01 to 25 mg/kg body weight, about 0.1 to 20 mg/kg body weight, about 1 to 10 mg/kg body weight. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an agent, e.g., a small molecule, protein, polypeptide, nucleic acid, or antibody can include a single treatment or can include a series of treatments.

In some aspects, described herein are methods of treating an individual afflicted with a disease or disorder characterized by aberrant or unwanted expression or activity of a target protein or nucleic acid molecule. In some embodiments, the methods involve administering a compound (e.g., a compound identified by a screening assay described herein), or combination of compounds that modulate (e.g., up regulates or down regulates) target protein expression or activity. Stimulation of target protein activity may be desirable in situations in which target protein is abnormally downregulated and/or in which increased target protein activity is likely to have a beneficial effect. Inhibition of target protein activity may be desirable in situations in which target protein is abnormally upregulated and/or in which decreased target protein activity is likely to have a beneficial effect. In certain embodiments, one or more compounds (e.g., compounds that modulate expression or activity of different genes or proteins) can be administered, together (simultaneously) or at different times (sequentially). In certain embodiments, the target protein may be a binding partner of a human ApoE protein, for example, as identified by the methods of the invention.

The following are examples of the practice of the invention. They are not to be construed as limiting the scope of the invention in any way.

EXAMPLES

Example 1

Yeast Model of ApoE Toxicity

A number of yeast strains that enable galactose-inducible expression of human ApoE were generated. The expression construct used in these studies encodes a fusion polypeptide containing the yeast Kar2p signal sequence at the amino terminus, followed by a human ApoE protein, followed by a EGFP protein at the carboxy terminus. A signal sequence was included in the fusion polypeptide to cause the transport of the human ApoE protein to the endoplasmic reticulum within the cell, whereby it enters the secretory pathway. Constructs were generated encoding the human ApoE2, ApoE3, or ApoE4 isoform under control of the GAL1 promoter.

The following sequences were inserted into the pAG304 Gal ccDB EGFP vector (Alberti, S., et al., (2007) Yeast. 24(10):913-9) using the Gateway Cloning Technology LR reaction. In these sequences, the underlined italicized capital letters encode the yeast Kar2 signal sequence MFFNRL-SAGKLLVPLSVVLYALFVVILPLQNSFHSSNVLVRG (SEQ ID NO: 4), the remainder of the capitalized sequence is the human APOE ε2, ε3, or ε4 nucleotide sequence encoding the corresponding human ApoE isoform, and the italicized lower case letters (tgccc) are part of the ATTB2 recombination sequence used for Gateway cloning). Bold underlined letters within sequences encoding ApoE isoforms encode amino acids at position 112 and 158 in the ApoE portion of the proteins.

ApoE2
(SEQ ID NO: 8)
<u>*ATGTTTTTCAACAGACTAAGCGCTGGCAAGCTGCTGGTACCACTCTCCGT*</u>

<u>*GGTCCTGTACGCCCTTTTCGTGGTAATATTACCTTTACAGAATTCTTTCC*</u>

<u>*ACTCCTCCAATGTTTTAGTTAGAGGT*</u>AAGGTGGAGCAAGCGGTGGAGACA

GAGCCGGAGCCCGAGCTGCGCCAGCAGACCGAGTGGCAGAGCGGCCAGCG

CTGGGAACTGGCACTGGGTCGCTTTTGGGATTACCTGCGCTGGGTGCAGA

CACTGTCTGAGCAGGTGCAGGAGGAGCTGCTCAGCTCCCAGGTCACCCAG

GAACTGAGGGCGCTGATGGACGAGACCATGAAGGAGTTGAAGGCCTACAA

ATCGGAACTGGAGGAACAACTGACCCCGGTGGCGGAGGAGACGCGGGCAC

GGCTGTCCAAGGAGCTGCAGGCGGCGCAGGCCCGGCTGGGCGCGGACATG

GAGGACGTGTGCGGCCGCCTGGTGCAGTACCGCGGCGAGGTGCAGGCCAT

GCTCGGCCAGAGCACCGAGGAGCTGCGGGTGCGCCTCGCCTCCCACCTGC

GCAAGCTGCGTAAGCGGCTCCTCCGCGATGCCGATGACCTGCAGAAGTGC

CTGGCAGTGTACCAGGCCGGGGCCCGCGAGGGCGCCGAGCGCGGCCTCAG

CGCCATCCGCGAGCGCCTGGGGCCCCTGGTGGAACAGGGCCGCGTGCGGG

CCGCCACTGTGGGCTCCCTGGCCGGCCAGCCGCTACAGGAGCGGGCCCAG

GCCTGGGGCGAGCGGCTGCGCGCGCGGATGGAGGAGATGGGCAGCCGGAC

CCGCGACCGCCTGGACGAGGTGAAGGAGCAGGTGGCGGAGGTGCGCGCCA

AGCTGGAGGAGCAGGCCCAGCAGATACGCCTGCAGGCCGAGGCCTTCCAG

GCCCGCCTCAAGAGCTGGTTCGAGCCCCTGGTGGAAGACATGCAGCGCCA

GTGGGCCGGGCTGGTGGAGAAGGTGCAGGCTGCCGTGGGCACCAGCGCCG

CCCCTGTGCCCAGCGACAATCAC*tgccc*

ApoE3
(SEQ ID NO: 9)
<u>*ATGTTTTTCAACAGACTAAGCGCTGGCAAGCTGCTGGTACCACTCTCCGT*</u>

<u>*GGTCCTGTACGCCCTTTTCGTGGTAATATTACCTTTACAGAATTCTTTCC*</u>

-continued

ACTCCTCCAATGTTTTAGTTAGAGGTAAGGTGGAGCAAGCGGTGGAGACA

GAGCCGGAGCCCGAGCTGCGCCAGCAGACCGAGTGGCAGAGCGGCCAGCG

CTGGGAACTGGCACTGGGTCGCTTTTGGGATTACCTGCGCTGGGTGCAGA

CACTGTCTGAGCAGGTGCAGGAGGAGCTGCTCAGCTCCCAGGTCACCCAG

GAACTGAGGGCGCTGATGGACGAGACCATGAAGGAGTTGAAGGCCTACAA

ATCGGAACTGGAGGAACAACTGACCCCGGTGGCGGAGGAGACGCGGGCAC

GGCTGTCCAAGGAGCTGCAGGCGGCGCAGGCCCGGCTGGGCGCGGACATG

GAGGACGTGCGCGGCCGCCTGGTGCAGTACCGCGGCGAGGTGCAGGCCAT

GCTCGGCCAGAGCACCGAGGAGCTGCGGGTGCGCCTCGCCTCCCACCTGC

GCAAGCTGCGTAAGCGGCTCCTCCGCGATGCCGATGACCTGCAGAAGTGC

CTGGCAGTGTACCAGGCCGGGGCCCGCGAGGGCGCCGAGCGCGGCCTCAG

CGCCATCCGCGAGCGCCTGGGGCCCCTGGTGGAACAGGGCCGCGTGCGGG

CCGCCACTGTGGGCTCCCTGGCCGGCCAGCCGCTACAGGAGCGGGCCCAG

GCCTGGGGCGAGCGGCTGCGCGCGCGGATGGAGGAGATGGGCAGCCGGAC

CCGCGACCGCCTGGACGAGGTGAAGGAGCAGGTGGCGGAGGTGCGCGCCA

AGCTGGAGGAGCAGGCCCAGCAGATACGCCTGCAGGCCGAGGCCTTCCAG

GCCCGCCTCAAGAGCTGGTTCGAGCCCCTGGTGGAAGACATGCAGCGCCA

GTGGGCCGGGCTGGTGGAGAAGGTGCAGGCTGCCGTGGGCACCAGCGCCG

CCCCTGTGCCCAGCGACAATCACtgccc

ApoE4

(SEQ ID NO: 10)
ATGTTTTTCAACAGACTAAGCGCTGGCAAGCTGCTGGTACCACTCTCCGT

GGTCCTGTACGCCCTTTTCGTGGTAATATTACCTTTACAGAATTCTTTCC

ACTCCTCCAATGTTTTAGTTAGAGGTAAGGTGGAGCAAGCGGTGGAGACA

GAGCCGGAGCCCGAGCTGCGCCAGCAGACCGAGTGGCAGAGCGGCCAGCG

CTGGGAACTGGCACTGGGTCGCTTTTGGGATTACCTGCGCTGGGTGCAGA

CACTGTCTGAGCAGGTGCAGGAGGAGCTGCTCAGCTCCCAGGTCACCCAG

GAACTGAGGGCGCTGATGGACGAGACCATGAAGGAGTTGAAGGCCTACAA

ATCGGAACTGGAGGAACAACTGACCCCGGTGGCGGAGGAGACGCGGGCAC

GGCTGTCCAAGGAGCTGCAGGCGGCGCAGGCCCGGCTGGGCGCGGACATG

GAGGACGTGCGCGGCCGCCTGGTGCAGTACCGCGGCGAGGTGCAGGCCAT

GCTCGGCCAGAGCACCGAGGAGCTGCGGGTGCGCCTCGCCTCCCACCTGC

GCAAGCTGCGTAAGCGGCTCCTCCGCGATGCCGATGACCTGCAGAAGCGC

CTGGCAGTGTACCAGGCCGGGGCCCGCGAGGGCGCCGAGCGCGGCCTCAG

CGCCATCCGCGAGCGCCTGGGGCCCCTGGTGGAACAGGGCCGCGTGCGGG

CCGCCACTGTGGGCTCCCTGGCCGGCCAGCCGCTACAGGAGCGGGCCCAG

GCCTGGGGCGAGCGGCTGCGCGCGCGGATGGAGGAGATGGGCAGCCGGAC

CCGCGACCGCCTGGACGAGGTGAAGGAGCAGGTGGCGGAGGTGCGCGCCA

AGCTGGAGGAGCAGGCCCAGCAGATACGCCTGCAGGCCGAGGCCTTCCAG

GCCCGCCTCAAGAGCTGGTTCGAGCCCCTGGTGGAAGACATGCAGCGCCA

GTGGGCCGGGCTGGTGGAGAAGGTGCAGGCTGCCGTGGGCACCAGCGCCG

CCCCTGTGCCCAGCGACAATCACtgccc

Figure 2A:
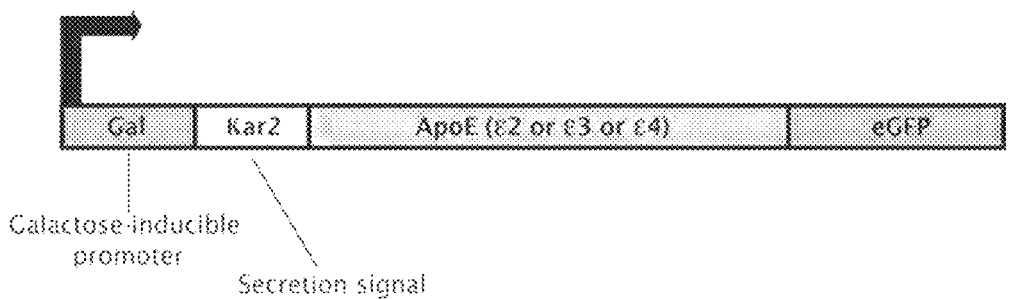
FIGS. 2A-C. Yeast show ApoE isoform-specific toxic phenotypes.
Figure 2B:
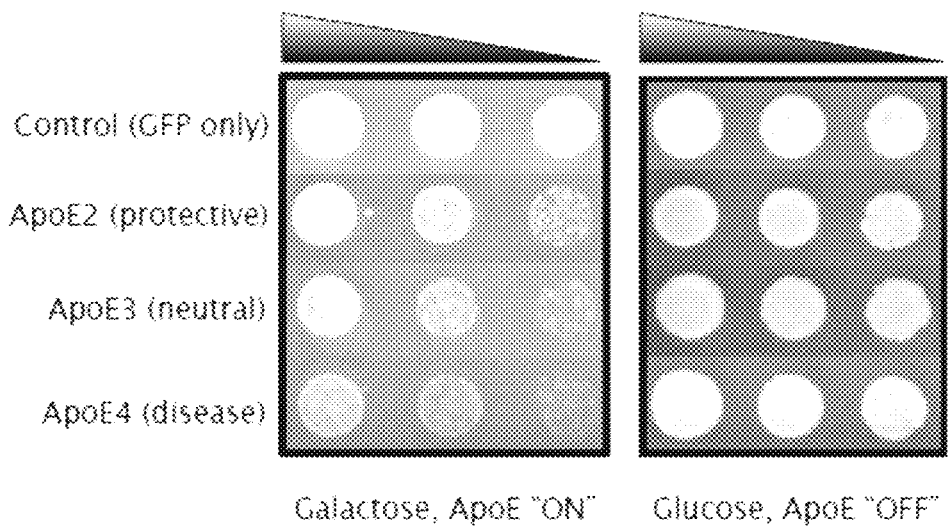

The ApoE fusion polypeptides were expressed in yeast, and the effect on yeast cell viability was assessed as follows: Yeast cells were transformed with either an empty vector or a galactose-inducible expression plasmid encoding one of the ApoE fusion polypeptides. Serial dilutions of transformants were spotted on plates containing glucose or galactose medium, and growth was assessed. Expression of the ApoE proteins (i.e., in transformants grown on galactose plates) was found to be toxic to yeast cells (FIG. 2(B); within each photograph, the control vector is on the top and the experimental expression vectors (encoding ApoE2, ApoE3, or ApoE4 fusion polypeptides) are in the lower three rows as indicated. All three isoforms induced toxicity but to different degrees. The degree of toxicity induced by each allele correlated with the degree of AD risk conferred by that allele in humans—the E4 isoform has the greatest toxicity in yeast and confers the greatest AD risk in humans; the E3 isoform displays a moderate amount of toxicity in yeast and is associated with an intermediate AD risk in humans; and the E2 isoform displays the least amount of toxicity in yeast and confers the lowest AD risk in humans.

Figure 2C:
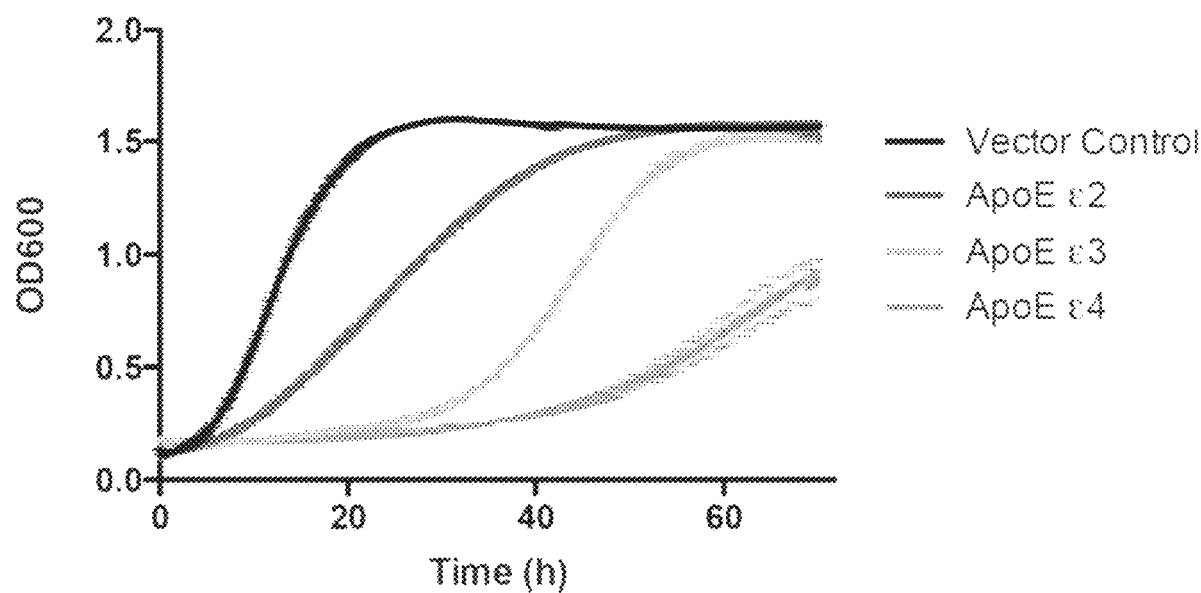

A similar pattern was observed when transformants were cultured in liquid medium containing galactose and growth assessed by monitoring OD600 over time (FIG. 2C). For each of the growth curves, the strain was grown overnight at 30 deg C., shaking, in tryptophan dropout media containing 2% raffinose to saturation. The cultures were then diluted down to an optical density (OD at 600 nm) of 0.1 and left to grow for 7-8 h until the OD(600 nm) was ~0.4-0.8. The cells were then diluted again to an OD of 0.1 in tryptophan dropout media with 2% galactose to induce production of ApoE. The growth was measured by tracking the OD as a function of time every 15 min for up to 72 h.

The transformants harbored 4 copies of the ApoE2 construct, 3-4 copies of the ApoE3 construct, or 3-4 copies of the ApoE4 construct, as assessed by qPCR, thus demonstrating that the different levels of toxicity were not due to differences in copy number of the constructs.

The level of ApoE protein in the respective transformants was determined by Western blot and compared relative to the level of PGK1 as follows: For Western blots, the cells were harvested 24 h post induction and the cell numbers were normalized by OD. Using a TCA precipitation protocol, the cells were lysed and proteins harvested. They were run on a 4-12% Bis-Tris SDS-PAGE gel at 150V for ~1 h. The gel was transferred onto a nitrocellulose 0.2 um pore size membrane using the Invitrogen Iblot apparatus. The blot was then blocked overnight in 5% non-fat milk and probed with the anti-GFP antibody (1:1000 dilution; Roche Diagnostics Cat. No. 11814460001) in 5% milk, washed with PBS 1% Tween20 and reprobed using secondary antibody anti-mouse HRP (SIGMA, 1:10000). The blot was developed using the SuperSignal Femto substrate imaged using a BioRad gel-doc device. The loading control was performed using an anti-Rabbit PGK1 antibody (1:1000) and an anti-Rabbit HRP secondary antibody (1:10000).

Figure 3A:
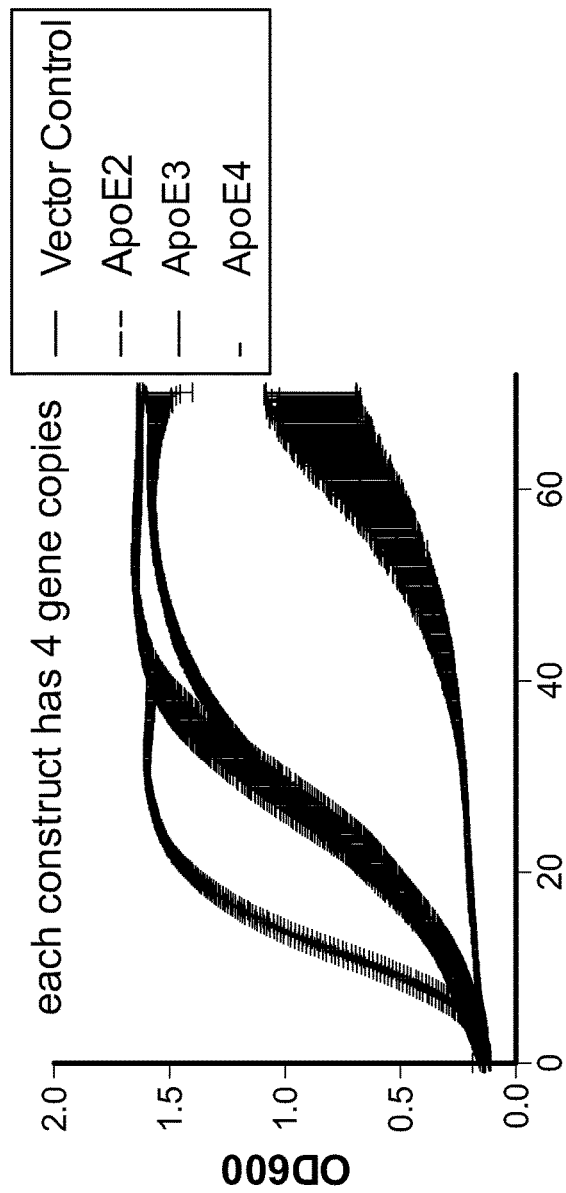
FIGS. 3A-3B. ApoE isoforms display different levels of toxicity in yeast.
Figure 3B:
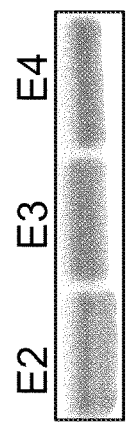
Figure 3B:

Cells having four gene copies of Kar2ss-ApoE2-EGFP, Kar2ss-ApoE3-EGFP, or Kar2ss-ApoE4-EGFP (see FIG. 2A) were cultured in liquid medium containing galactose and growth assessed by monitoring OD600 over time as described above (FIG. 3A). FIG. 3B shows the results of Western blots using an anti-GFP primary antibody to assess the protein levels of the ApoE isoforms expressed in these strains, as compared to a loading control (PGK1).

Figure 4:
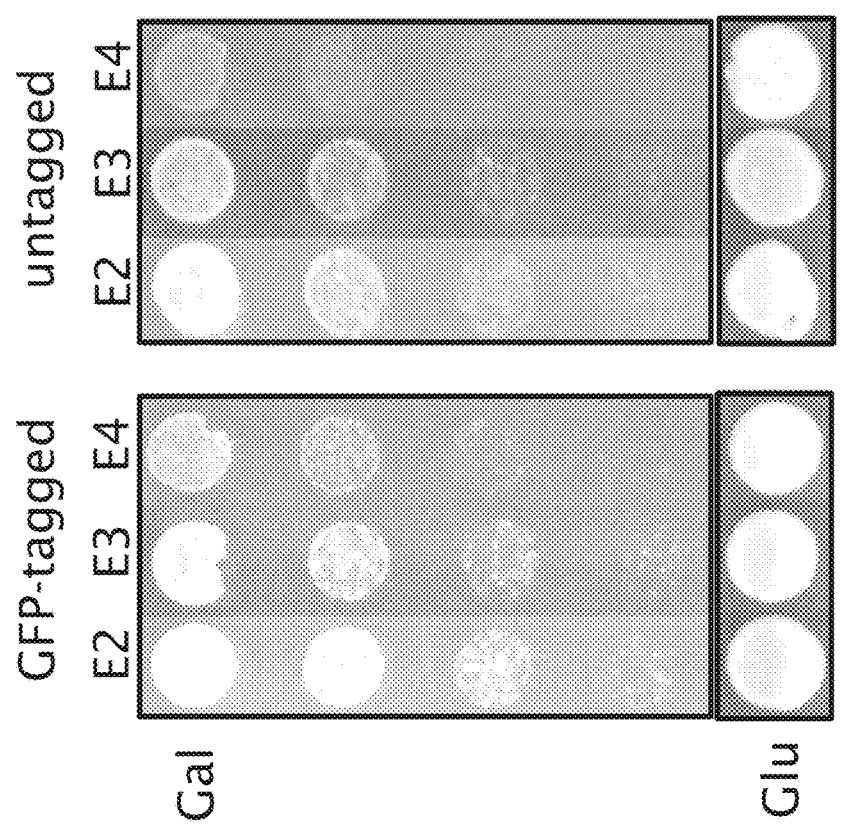
FIG. 4. Tagging ApoE constructs with GFP does not affect their toxicity. Left panel: Photographs of yeast cells transformed with either a galactose-inducible expression plasmid encoding a Kar2ss-ApoE2-eGFP fusion polypeptide (left column), a galactose-inducible expression plasmid encoding a Kar2ss-ApoE3-eGFP fusion polypeptide (middle column), or a galactose-inducible expression plasmid encoding a yeast Kar2ss-ApoE4-eGFP fusion polypeptide (right column). The yeast cells were spotted on galactose (upper portions, left and right panels) or glucose (lower portions, left and right panels) and growth was assessed. Right panel: Photographs of yeast cells transformed with a galactose-inducible expression plasmid encoding a Kar2ss-ApoE2 fusion polypeptide (left column), a galactose-inducible expression plasmid encoding a yeast Kar2ss-ApoE3 fusion polypeptide (middle column), or a galactose-inducible expression plasmid encoding a Kar2ss-ApoE4 fusion polypeptide (right column). The yeast cells were spotted on galactose (upper portions, left and right panels) or glucose (lower portions, left and right panels) and growth was assessed. The transformants grew equally well on the glucose plates. ApoE expression inhibited cell growth in an allele-dependent manner regardless of whether the protein was fused to eGFP. These experiments were performed with ApoE constructs that are in 2 micron expression plasmids.
Figure 6B:
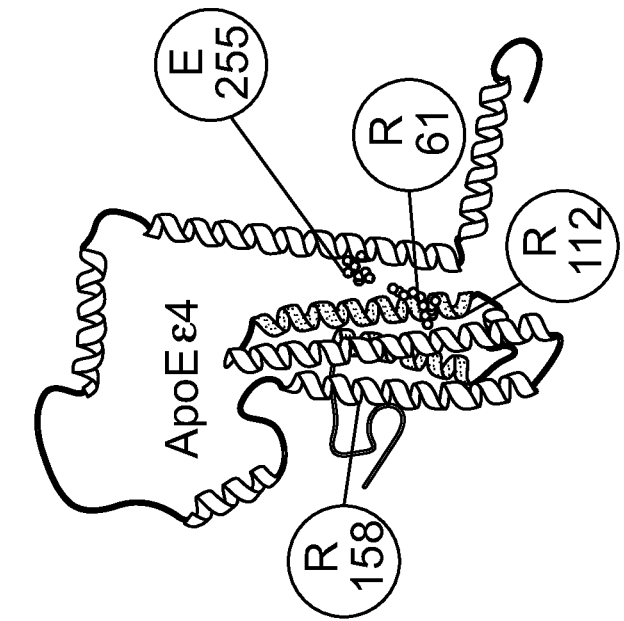
FIGS. 6A-6D.
Figure 6A:
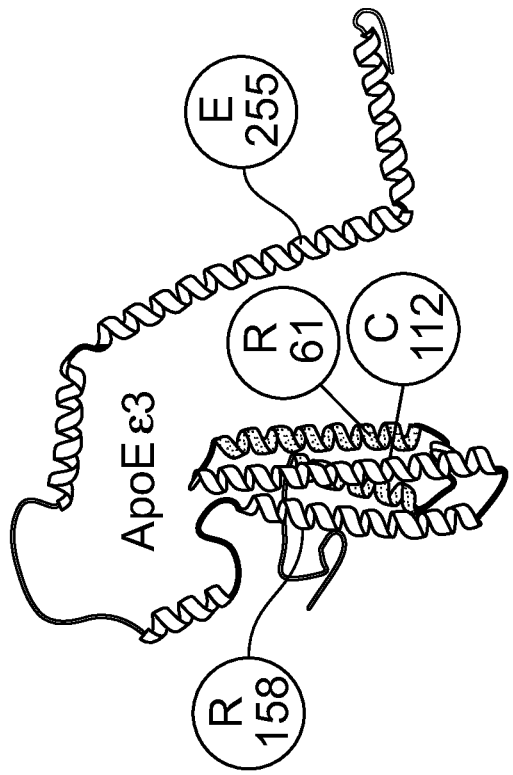
Figure 6C:
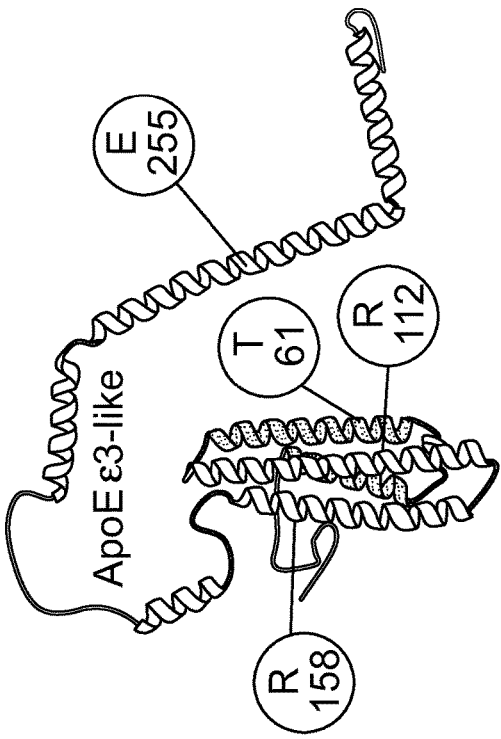
Figure 6C:
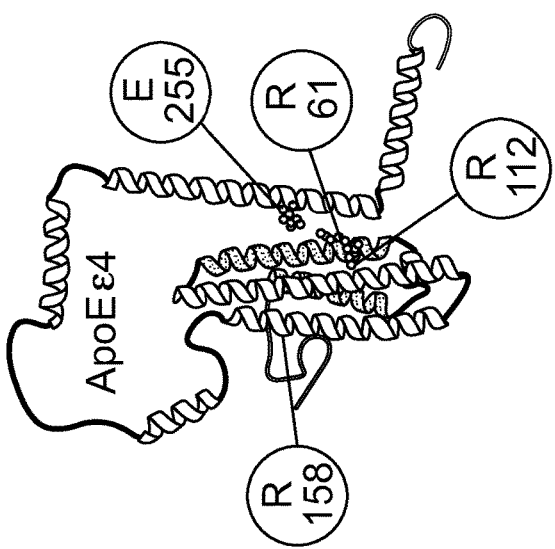
Figure 6D:
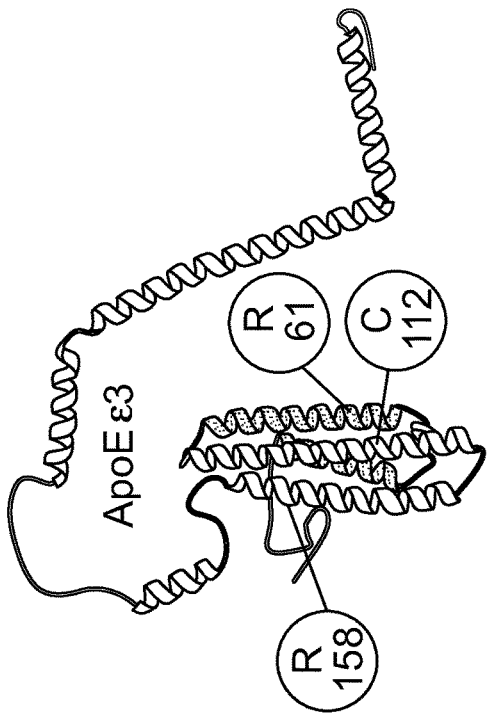

To confirm that the results described above were due to the ApoE portion of the polypeptide and not to EGFP, constructs similar to those described above, but lacking the EGFP portion of the fusion polypeptide, were generated and transformed into yeast. These experiments were performed with ApoE constructs in 2 micron expression plasmids. Serial dilutions of transformants were spotted on plates containing glucose or galactose medium, and growth was assessed as described above. The results were similar to those described above, confirming that the presence of EGFP does not affect the phenotypes observed (FIG. 4).

Example 2

Generation of ApoE-Expressing Strains with Intermediate or High Levels of Toxicity Additional yeast strains harboring varying numbers of copies of the expression constructs encoding ApoE2, ApoE3, or ApoE4 fusion polypeptides were generated. Strains displaying either an intermediate level of toxicity (termed "intox" strains) or a high level of toxicity (termed "hitox" strains) were isolated for each isoform. Growth of the various strains in liquid medium containing galactose was assessed by monitoring OD600 over time as described above (FIG. 5A). The levels of expression of the respective ApoE protein in each strain were determined by Western blot relative to PGK expression as described above (FIG. 5B).

The number of copies of the relevant coding sequence in the various intox and hitox strains determined using qPCR. Results are presented in Table 4.

TABLE 4

Copy number of ApoE-encoding construct in intox and hitox strains

| Strain | Copies |
| --- | --- |
| ApoE2 intox | 4 |
| ApoE3 intox | 3-4 |
| ApoE4 intox | 2 |
| ApoE2 hitox | ~13 (integrated at 2 sites) |
| ApoE3 hitox | 7 |
| ApoE4 hitox | 3-4 |

Example 3

R61T Mutation Restores ApoE3-Like Phenotype

Figure 7:
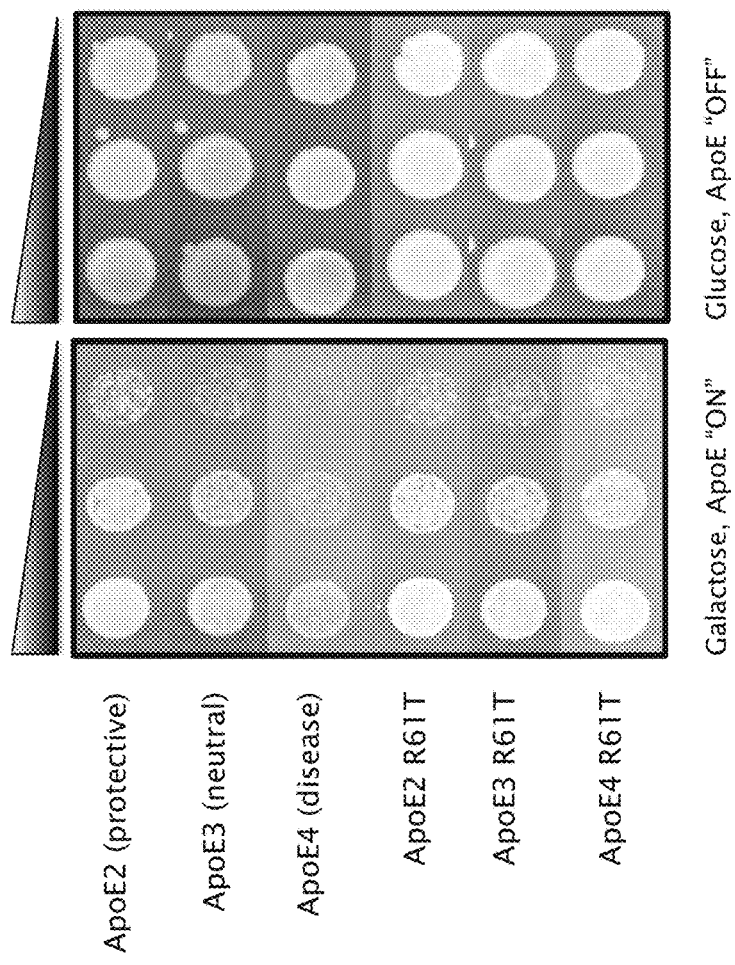
FIG. 7. The R61T mutation restores an ApoE3-like phenotype when introduced into ApoE4. Photographs of yeast cells transformed with galactose-inducible expression plasmids encoding a Kar2ss-ApoE2-eGFP fusion polypeptide (top row), a Kar2ss-ApoE3-eGFP fusion polypeptide (second row), Kar2ss-ApoE4-eGFP fusion polypeptide (third row), Kar2ss-ApoE2 (R61T)-eGFP fusion polypeptide (fourth row), a Kar2ss-ApoE3(R61T)-eGFP fusion polypeptide (fifth row), Kar2ss-ApoE4(R61T)-eGFP fusion polypeptide (bottom row), as indicated. The yeast cells were spotted on galactose (left photograph) or glucose (right photograph) at increasing dilutions (lower yeast cell concentrations) from left to right and growth was assessed. The experimental and control transformants grew equally well in the absence of ApoE expression (Glucose, ApoE "OFF"). Expression of ApoE isoforms with R at position 61 profoundly inhibited cell growth (Galactose, ApoE "ON", upper 3 rows), with ApoE4 showing the greatest effect. Reduced toxicity of ApoE4 R61T relative to the toxicity of ApoE4 is clearly evident (compare third row (ApoE4 (disease) and bottom row (ApoE4 R61T). The relative growth level is indicated above the photographs. These experiments were performed with ApoE constructs that are in a 2 micron expression plasmid.
Figure 8:
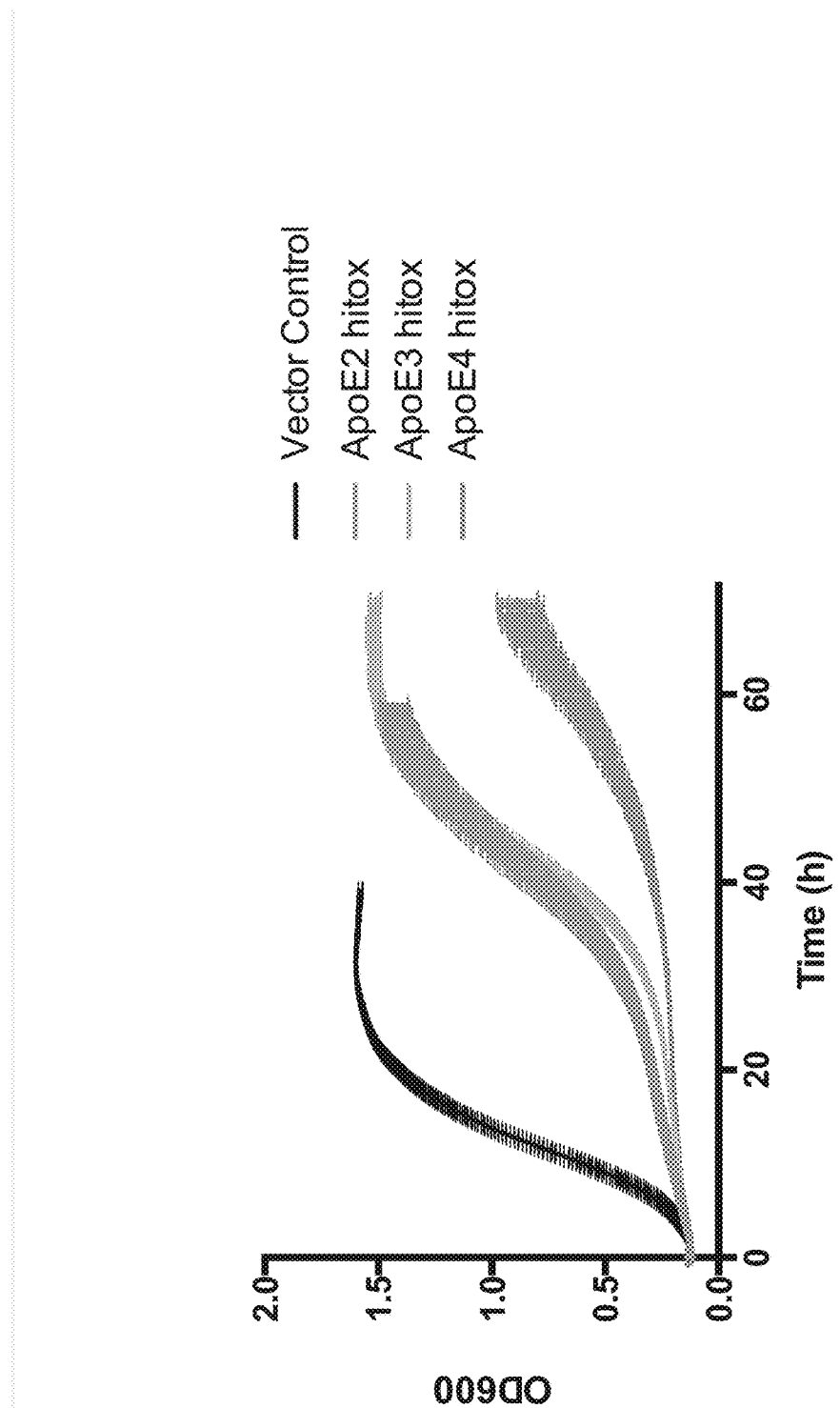
FIG. 8. Growth curves in galactose-containing liquid medium of the ApoE-expressing strains ("ApoE hitox" strains) that were used in screens to identify genetic suppressors of ApoE-induced toxicity.
Figure 9A:
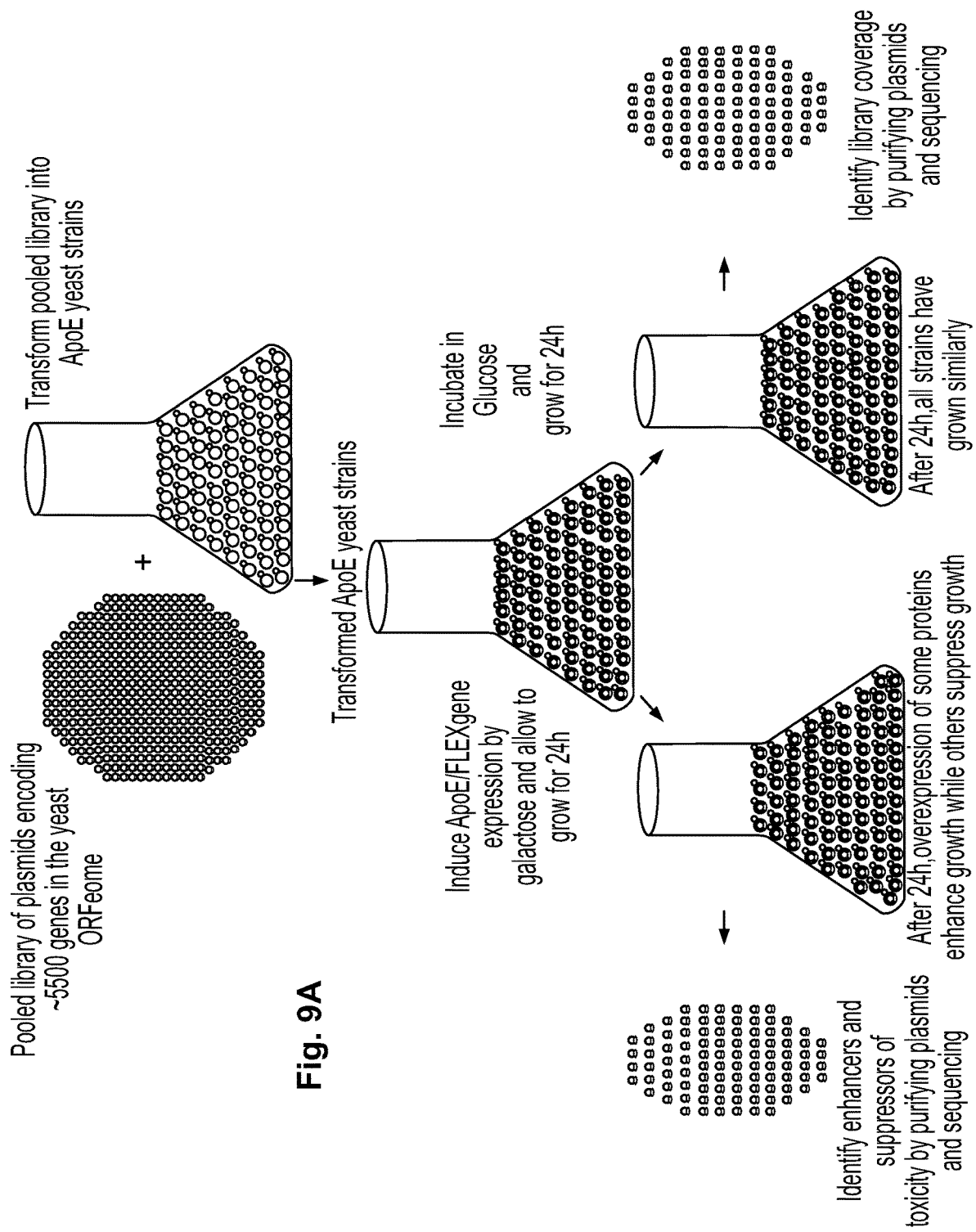
FIGS. 9A-9C.
Figure 9B:
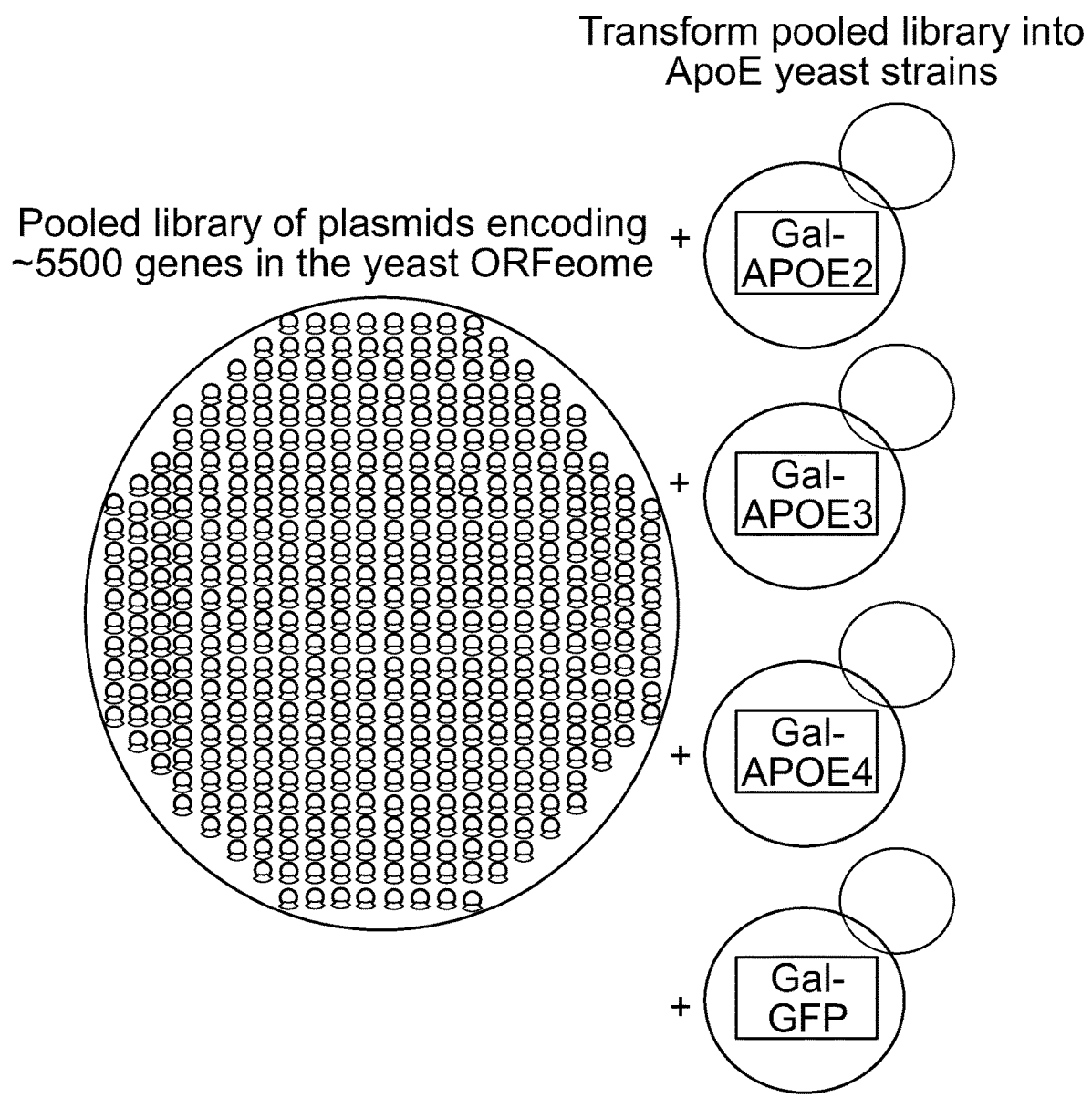
Figure 9C:
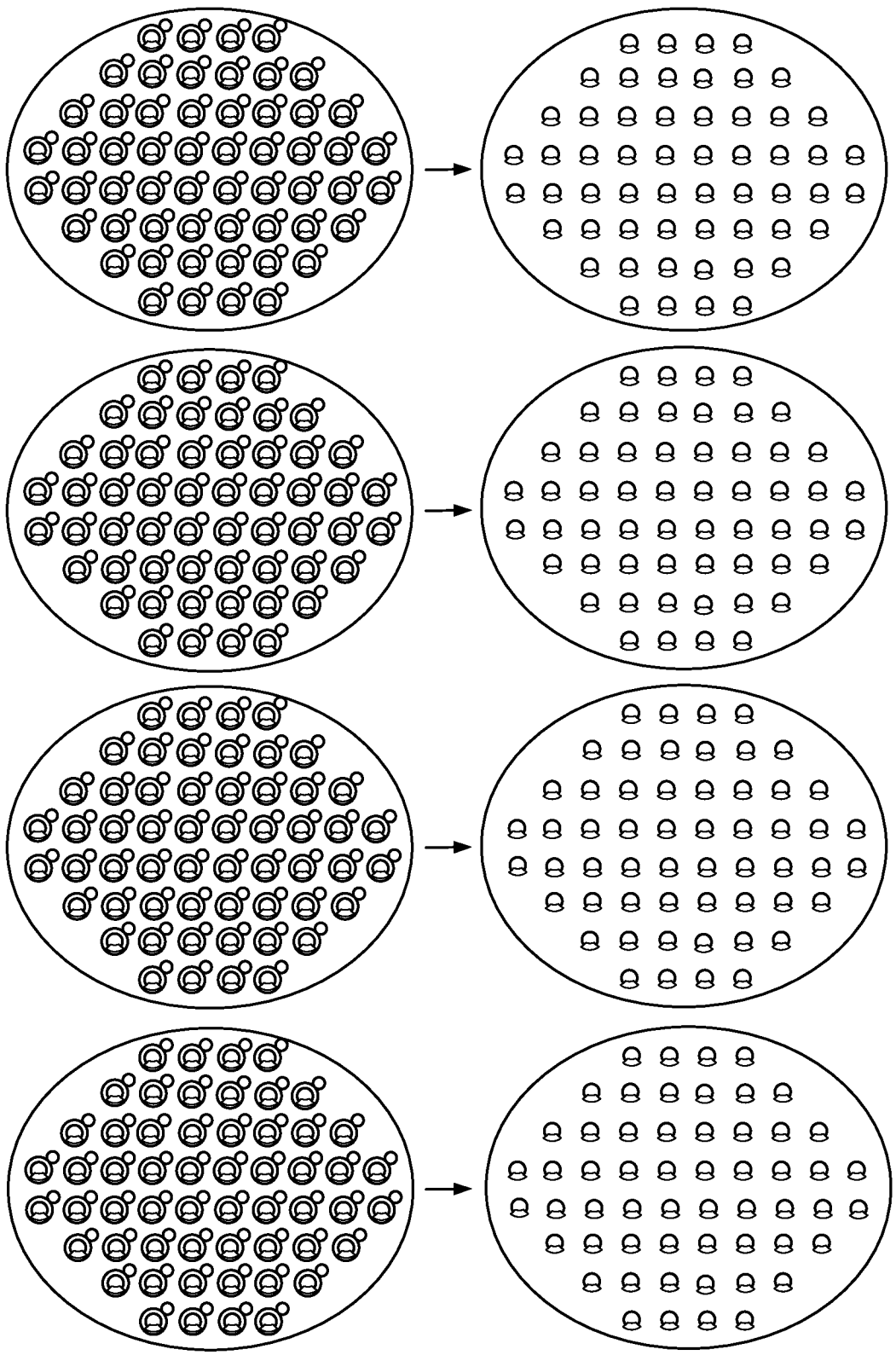

Yeast expression constructs were generated encoding Kar2ss-ApoE-eGFP fusion proteins harboring an R61T mutation, with expression under the control of the GAL1 promoter in 2 micron expression plasmids. As described above, the R61T mutation makes the structure of ApoE4 like that of ApoE3. The Kar2ss-ApoE-eGFP sequences of the expression constructs were identical to those described above except for the presence of the R61T mutation. The constructs encoding ApoE fusion polypeptides harboring the R61T mutation were introduced into yeast in a 2 micron expression plasmid, and the effect on yeast cell viability of each protein was assessed by spotting serial dilutions of the transformants on galactose-containing medium to induce expression of the fusion polypeptide (FIG. 7). The ApoE4 R61T fusion polypeptide displayed reduced toxicity compared to the ApoE4 wild type fusion polypeptide, closely resembling that displayed by the ApoE3 fusion polypeptide. These results further confirm that the mechanism underlying the toxicity induced by ApoE in the yeast model system is directly relevant to the mechanism by which ApoE exerts its effect in humans.

Example 4

Screen for Genetic Modifiers of ApoE Toxicity

A screen was performed to identify genetic modifiers of ApoE toxicity. The screen was performed in a pooled format. Each of the hitox strains described above (ApoE2 hitox, ApoE3 hitox, and ApoE4 hitox) as well as the eGFP-expressing control strain was transformed with a pooled library of ~5700 plasmids in the FLEXGENE library (Hu, Y., et al. (2007) Genome Res. 17: 536-43), each with a GAL-inducible ORF in the yeast genome. The clones obtained from each strain (each harboring roughly a single plasmid) were harvested, pooled, and grown under induction with galactose (so that the toxic protein ApoE or control GFP was expressed along with the ORF of interest). Simultaneously another aliquot of the strains was grown in glucose-containing medium to get a sense of library coverage. The plasmids were extracted, and the ORFs were amplified using PCR. The DNA was sonicated, and the genes were sequenced. Hits were thresholded based on their effect size (comparing both ApoE vs GFP control and glucose vs galactose).

Many of the hits were retested by individually transforming the individual plasmids from the FLEXGENE library (unpooled) into yeast strains expressing ApoE2, ApoE3, or ApoE4 and tracking their growth in galactose medium (i.e., under conditions in which expression of both ApoE and the ORF in the plasmid was induced). Hits that enhanced or suppressed growth in each strain relative to the empty vector were identified. The ApoE2 strain used for this validation contained between ~11-15 copies of the expression construct encoding ApoE2. The ApoE3 strain used for validation contained 7 copies of the expression construct encoding ApoE3. The ApoE4 strain used for validation contained 4 copies of the expression construct encoding ApoE4.

Table 1A lists those hits that were validated as suppressors or enhancers of ApoE toxicity in the validation strain expressing the same ApoE isoform as the strain used in the screen from which the hit was initially identified. A number of these hits also modulated ApoE toxicity in either or both of the validation strains expressing the other isoforms. Table 1B lists those hits that were validated as modulating ApoE toxicity in a validation strain (or in two validation strains) expressing a different ApoE isoform from that expressed by the strain used in the screen from which the hit was initially identified. Tables 2A, 2B, and 2C list hits from the same screens that were identified as suppressors or enhancers of at least one ApoE isoform, using more stringent cut-off criteria. The effects of each yeast gene on growth of each strain are indicated in each table (columns showing Effect Size). The numbers represent the relative growth of the strain expressing the indicated yeast gene, as compared to a control strain (same strain but transformed with a vector lacking an inserted yeast gene). Thus, numbers greater than 1.0 indicate that the gene suppressed ApoE-mediated toxicity when overexpressed. Numbers less than 1.0 indicate that the gene enhanced ApoE-mediated toxicity when overexpressed. Suppressors of toxicity are indicated with the letter "S" and enhancers of toxicity are indicated with the letter "E" in Tables 1A and 1B. Genes for which the value is less than or equal 0.5 or greater than or equal to 1.5 had a particularly large effect.

Tables 2A, 2B, and 2C list human homologs of certain of the yeast suppressors and enhancers of ApoE-induced toxicity. Human homologs that are known genetic risk factors for Alzheimer's disease are listed in a separate column. The human homologs were identified using sequence and structure based homology search tools. Additional criteria based on the length of the similar sequences as well as literature data were taken into account in addition to the sequence and structure based criteria in identification of certain of the homologs that are AD risk factors.

Example 5

Testing Compounds for Ability to Modulate ApoE-Mediated Toxicity

Figure 10:
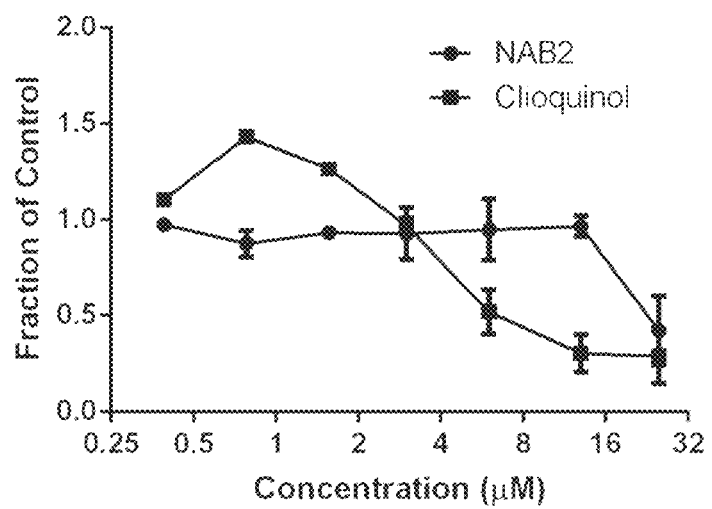
FIG. 10. Growth curve of ApoE-expressing yeast strain in the presence of clioquinol or NAB2.

ApoE4-expressing yeast cells harboring the construct encoding Kar2ss-ApoE4-eGFP were used in a screening assay to assess the utility of the recombinant cells in screening for candidate therapeutic compounds. An ApoE4 hitox strain harboring 3-4 copies of the ApoE4 construct and with the drug-pump transcription factors PDR1 and PDR 3 deleted was used in this experiment. Cells were grown in raffinose; cells were diluted into galactose medium (to initiate expression of the expression construct). Test compounds were added to the cultures at various concentrations ranging from 0.25 µM to 32.0 µM; cells were grown for 24 hours after addition of the compounds, and the optical densities were then read at A600. The test compounds were clioquinol, a known candidate compound for the treatment of Alzheimer's disease, and NAB2, a small molecule that selectively protects diverse cell types, including yeast and mammalian neurons, from α-synuclein toxicity (Tardiff, D L, et al., Science (2013); 342(6161):979-83). It is known from other experiments that clioquinol itself becomes toxic to yeast at high concentrations. The results (FIG. 10) demonstrated that clioquinol at concentrations below about 1.5 µM was able to reduce ApoE4-mediated toxicity in the yeast model system, whereas NAB2 was not able to do so. These results confirm that yeast can be used as a model system for ApoE-induced cellular toxicity and that candidate therapeutic compounds can be identified that alleviate this toxicity.

Example 6

Yeast Cells Expressing ApoE Display Defects in Endocytosis

S. cerevisiae MUP1 is a high affinity methionine permease that, under normal conditions, is expressed at the plasma membrane and undergoes endocytosis in the presence of methionine. MUP1 localization can be used as a marker of endocytosis. An endocytosis assay based on MUP1 localization was performed to assess the effect of ApoE on endocytosis in yeast.

Each of the ApoE hitox strains described above (ApoE2 hitox, ApoE3 hitox, and ApoE4 hitox) as well as the eGFP-expressing control strain was transformed with a MUP1 reporter construct (an expression construct containing the promoter of the S. cerevisiae methionine permease MUP1 driving expression of a fusion protein containing MUP1 fused to the fluorescent protein mKate2. In addition, yeast strains harboring expression constructs encoding additional human neurodegenerative disease-associated proteins alpha-synuclein (α-syn intox, α-syn hitox strains) or Aβ (Kar2ss-Aβ strain described in Treusch, S., et al., Science. (2011), 334:1241-5) were transformed with the MUP1 reporter construct. (FIG. 11(A).

Cells of each strain were cultured for 6 hours in medium containing galactose (to induce expression of the human neurodegenerative disease proteins) and either containing standard levels of methionine or lacking methionine. Cells were then examined by fluorescence microscopy. The yeast strains expressing human neurodegenerative disease-associated proteins exhibited severely perturbed endocytosis (especially the ApoE and α-syn strains) as compared to the GFP only control (FIG. 11(B), upper panel).

Figure 11E:
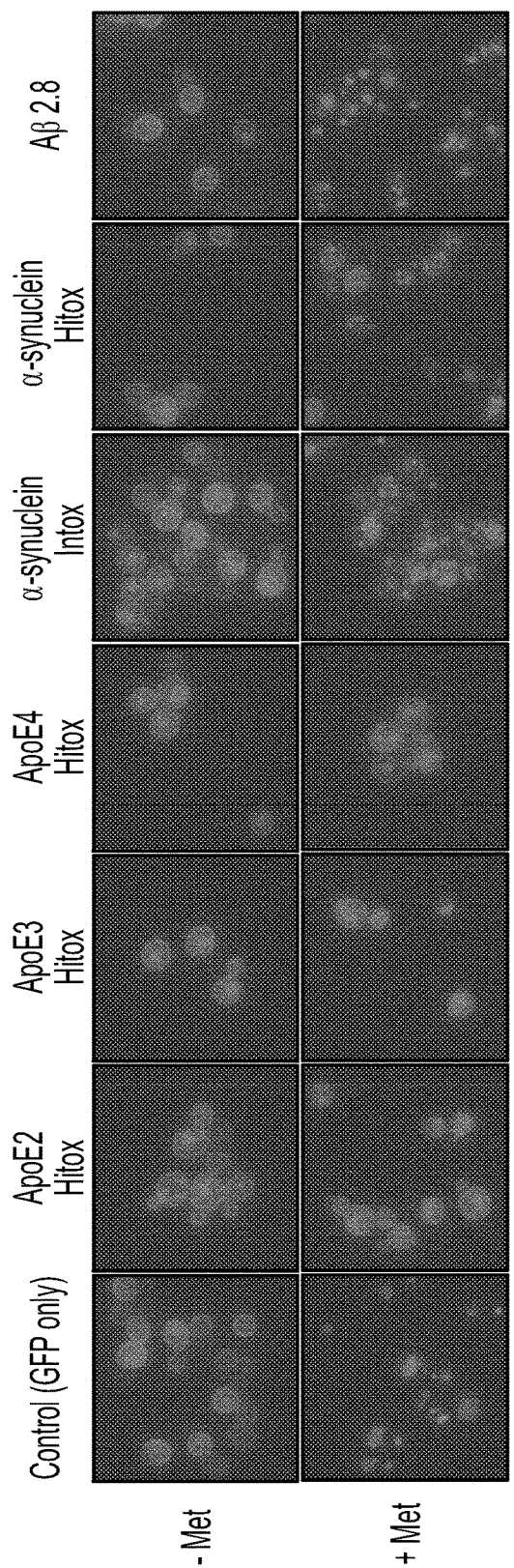
Figure 11F:
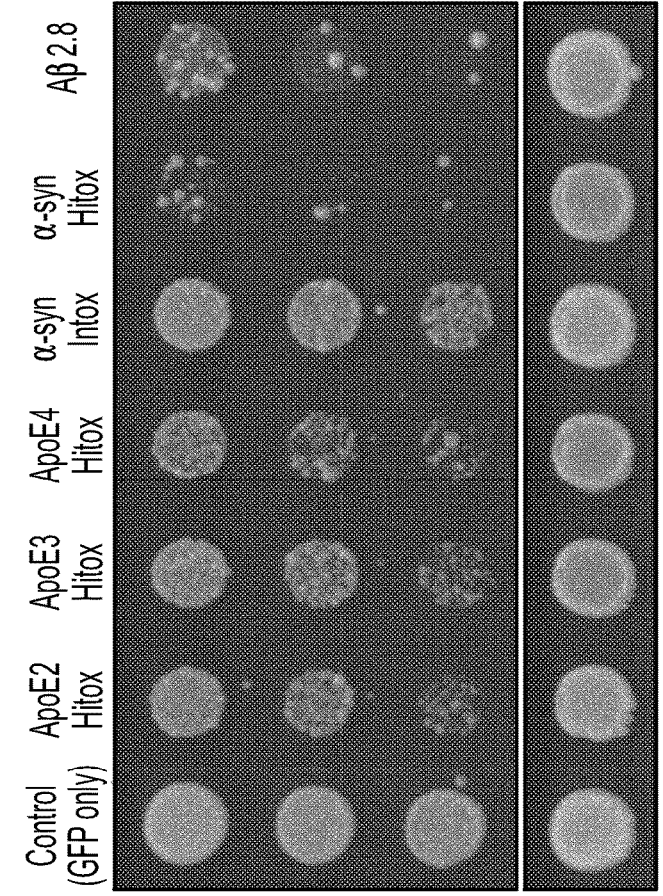

ApoE4, Aβ, and α-synuclein caused distinct phenotypes in disruption of endosomal trafficking of MUP1 (FIG. 11(C). ApoE4 "hitox", AO screening strain 2.8 (ADE2+) and alpha-synuclein "intox" strains were induced to express the ApoE4, Aβ, or α-synuclein construct as described above for 8 h prior to obtaining the images shown in FIG. 11(C). Without wishing to be bound by theory, the nature of the endosomal trafficking defects caused by these proteins could be distinct.

Example 7

Revalidation of Top Hits from Genetic Modifier Screen of ApoE Toxicity

Figure 12:
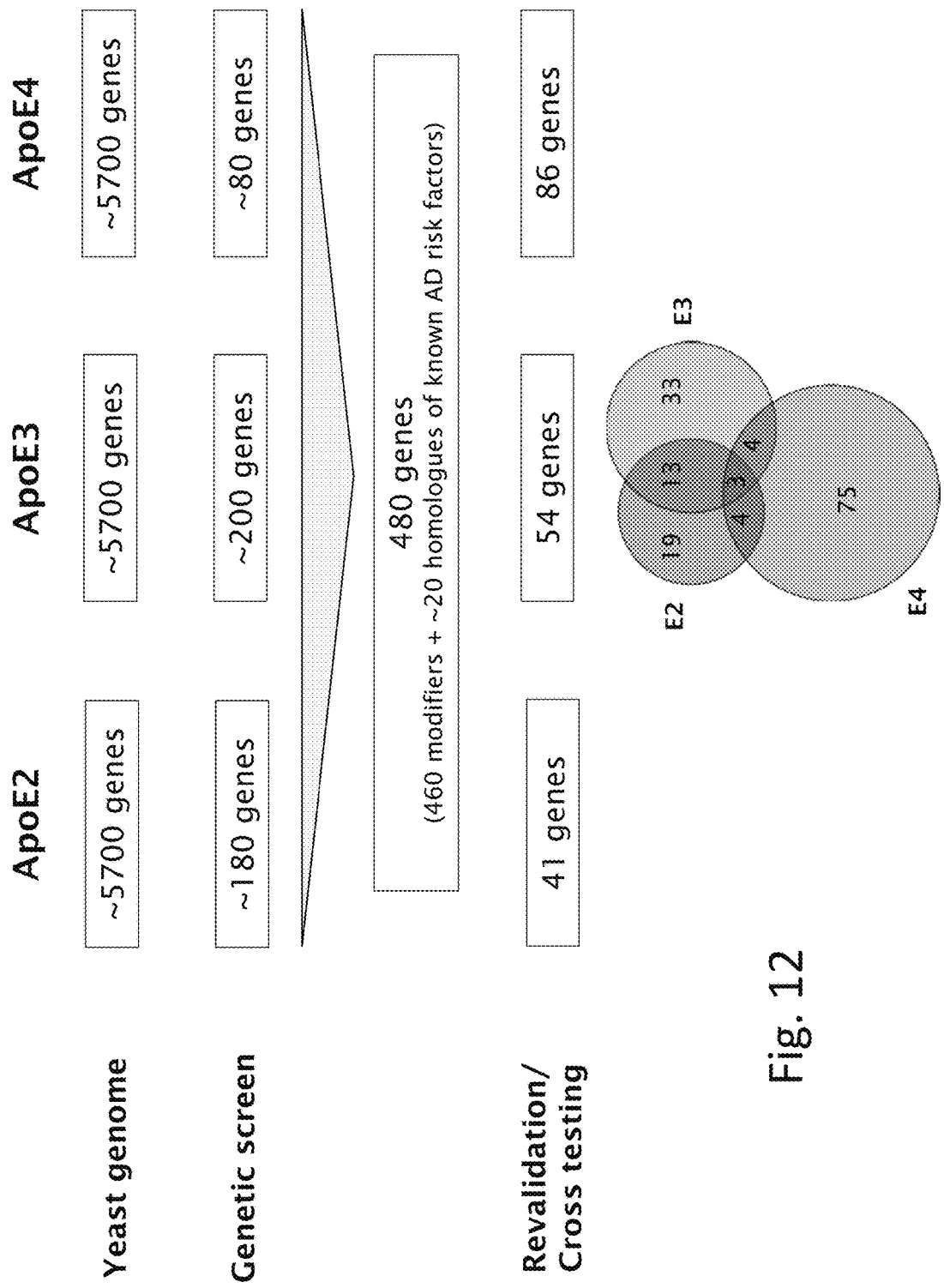
FIG. 12. Summary of results from ApoE genetic modifier screens. 480 genes were selected for revalidation analysis. The Venn diagram (bottom) shows overlap of revalidated hits for the indicated ApoE isoform.

A revalidation of approximately 500 of the top hits from the genetic modifier screen for ApoE toxicity described in Example 4 was performed (FIG. 12). These hits were selected using a 3 sigma fold change in enrichment/depletion cutoff. These hits were revalidated using growth assays in 384-well plate format using the FLEXGENE library centromeric plasmids described above. They were also cross-validated in the alpha-synuclein and amyloid-beta expressing yeast models.

Table 3 shows a summary of the revalidated hits for enhancers and suppressors of ApoE4-mediated toxicity. FIG. 12 includes a Venn diagram summarizing the number of hits that were revalidated for each ApoE isoform, as well as the overlap in rescue observed in cross testing experiments. Without wishing to be bound by theory, the lack of overlap between revalidated hits in the ApoE4 screen could be due to the difference in toxicity.

Hits that were confirmed by the revalidation analysis suggested ApoE-mediated perturbations in several biological pathways, including vesicle transport (e.g., ATG20, UBP3, TRS65, BRE5, MUK1, and GYPS), endocytosis (e.g., RVS161, OSH2, RVS167, YAP1802, and OSH3), ubiquitination/deubiquitination (e.g., APC11, UBP3, UBP7, CDC73, BRE5, and RRI2), lipid metabolism (e.g., PER1, MDH3, GPI8, SMP3, and SUR1), DNA repair (e.g., MGT1, PCD1, CDC73, and RAD14), and mitochondrion organization (e.g., ATG20, MHR1, MRP4, RRM3, ILM1, MST1, YTA12, POR1, and MRPL10).

Example 8

Chemical Screening for Compounds that Modulate ApoE-Mediated Toxicity

To identify compounds that suppress toxicity associated with expression of proteins associated with neurodegenerative disease, the Molecular Libraries Probe Production Centers Network (MLPCN) library (NIH-NCATS program) was screened at 7 doses for compounds that rescue yeast models of alpha-synuclein (a "hitox" strain with copies of alpha-synuclein integrated at TRP and URA loci with the PDR1 and PDR3 transcription factors deleted) and TDP-43 (the TDP-43 model as described in Tardiff et al. *J. Biol. Chem.* 287:4107-4120, 2012) toxicity. The assays were performed in 1536 well plates using BACTITER-GLO™ luminescence as a proxy for growth. From these two screens, 164 compounds that exhibited rescuing activity against the alpha-synuclein model, the TDP-43 model, or both, were selected and obtained for further analysis.

These compounds were rescreened against the alpha-synuclein and the TDP-43 yeast models to verify their activity in 384 well plates with optical density at 600 nm to measure growth. These compounds were also cross-screened against other yeast model systems including yeast cells expressing ApoE4, yeast cells expressing amyloid-beta (1-42), and yeast cells expressing FUS-protein. The ApoE4 cells were a hitox strain as described in Example 5 with deletions for the genes encoding the transcription factors PDR1 and PDR3. The amyloid-beta (1-42) cells were as described in Kent et al. *Proc. Natl. Acad. Sci. USA* 11:4013-4018, 2014. These cross-screens were performed using strains with deletions of two transcription factors PDR1 and PDR3 to minimize drug efflux from the cells. For the purpose of this exemplary analysis, compounds that increased the growth of cells 1.15-fold that of untreated cells were considered "rescuing" compounds.

From these screens, 49% (80) of compounds rescued the alpha-synuclein yeast model, 21% (35) of compounds tested rescued the TDP-43 yeast model, 57% (94) rescued the ApoE4 yeast model, 18% (29) rescued a FUS-protein yeast model (as described in Ju et al. PLoS Biology 9(4):e1001052 but with the genes encoding PDR1 and PDR3 deleted), and 33% (54) rescued the amyloid-beta yeast model.

3 compounds rescued all 5 yeast models tested. 19 compounds rescued both the FUS-protein model and the ApoE4 yeast model. 18 compounds rescued both the TDP-43 yeast model and the ApoE4 yeast model. 43 compounds rescued both the amyloid-beta yeast model and the ApoE4 yeast model. The same 43 compounds also rescued both the alpha-synuclein yeast model and the ApoE4 yeast model. 26 compounds distinctly rescued the ApoE4 yeast model and no other model tested.

The foregoing results further demonstrate that the yeast model system for ApoE-induced cellular toxicity described herein is a robust screening platform for identification of candidate therapeutic compounds that alleviate ApoE-mediated toxicity, which may also be candidate therapeutic compounds for treatment of ApoE-associated diseases including Alzheimer's disease.

Example 9

Yeast Cells Expressing ApoE Display Defects in Ste3 Endocytosis

The effect of ApoE on endocytosis in yeast was further analyzed using a Ste3-mKate2 assay. Ste3 is a yeast G-protein coupled receptor (GPCR) that natively undergoes endocytosis from the cell surface to the vacuole. When clathrin-mediated endocytosis is disrupted, Ste3 trafficking can be disrupted as well.

Figure 13:
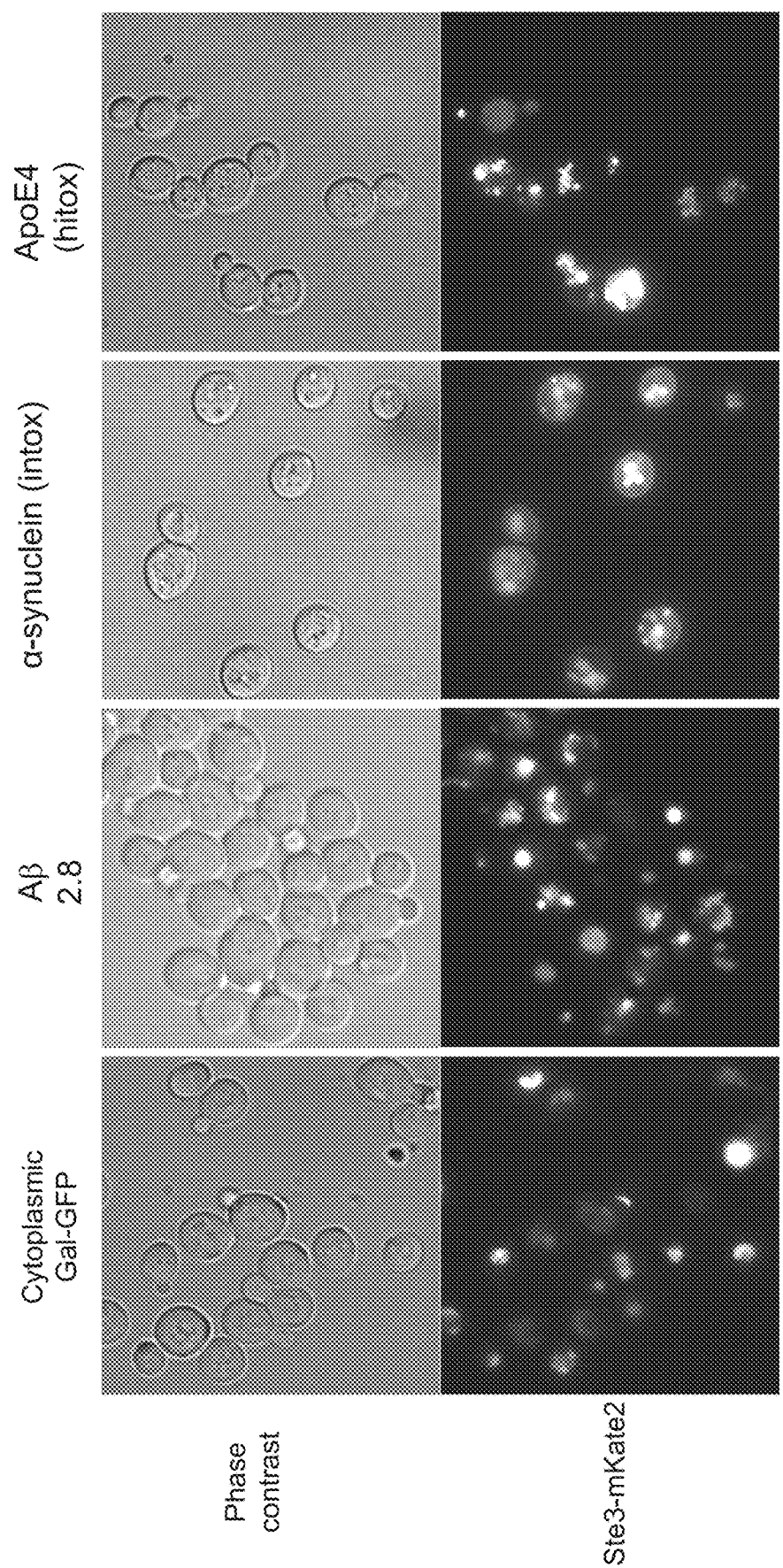
FIG. 13. ApoE4 expression disrupts endocytosis of Ste3. Yeast cells harboring the indicated neurodegenerative protein expression constructs were transformed with the pAG423-Ste3-mKate2 plasmid and induced to express Ste3-mKate2 and the neurodegenerative protein by addition of galactose to the culture medium for 6-8 hrs. The top row shows representative images of the cells using phase contrast microscopy. The bottom row shows representative fluorescent micrographs for mKate2 fluorescence. Ste3 endocytosis to the vacuole is disrupted by expression of ApoE4, as well as by expression of Aβ and α-synuclein.

The trafficking of Ste3 was observed using fluorescence microscopy by overexpressing a fluorescently-tagged (mKate2) version of Ste3 from a pAG423 galactose-inducible plasmid. The ApoE4 hitox strain described above was transformed with the pAG423-Ste3-mKate2 plasmid. In addition, yeast strains as described in Example 4 harboring expression constructs encoding human neurodegenerative disease-associated proteins alpha-synuclein ($\alpha$-syn intox) or A$\beta$ (Kar2ss-A$\beta$ strain described in Treusch, S., et al., *Science*. (2011), 334:1241-5) were also transformed with the pAG423-Ste3-mKate2 plasmid. A strain transformed with a Gal-GFP plasmid served as a negative control. After 6-8 hours of induction with galactose, the production of ApoE4 resulted in a severe disruption in Ste3 endocytosis to the vacuole. (FIG. 13). Expression of alpha-synuclein and A$\beta$ also resulted in disruption of Ste3 endocytosis (FIG. 13).

Example 10

Identification of Candidate Therapeutic Target ApoE Binding Partners

Identification of ApoE binding partners may reveal interactions and interactor proteins that serve as potential therapeutic targets. Cells expressing ApoE proteins are analyzed by isolation or purification of the ApoE protein followed by identification of binding partners that co-purify with the ApoE protein.

For example, yeast strains harboring expression constructs encoding N- or C-terminally TAP (tandem-affinity purification tag) or GFP-tagged ApoE isoforms are generated. The TAP tag includes two IgG binding domains of *S. aureus* protein A and a calmodulin binding peptide (CBP) separated by a TEV protease cleavage site (see, e.g., Puig et al. *Methods* 24:218-229, 2001). For example, yeast strains are generated harboring integrative expression constructs encoding either Kar2ss-ApoE2-TAP, Kar2ss-ApoE3-TAP, or Kar2ss-ApoE4-TAP under control of the galactose-inducible GAL1-10 promoter using methods described herein. The yeast strains harbor different copy numbers of the expression constructs in order to express the different ApoE isoforms at equivalent levels across the strains. Another approach to ensure that the cells express ApoE isoforms at equivalent levels is titration of an inducible promoter such as a galactose-inducible promoter. Control strains lacking tagged ApoE are also generated. Western blots performed with an anti-TAP tag antibody (e.g., anti-TAP tag antibody [22F12-1E3], Abcam) are used to confirm that the strains express equivalent levels of the different ApoE isoforms. Cells having intermediate levels of toxicity (e.g., intox strains) are compatible with identification of binding partners. In some examples, the length of induction may be varied (e.g., shortened) to balance between sufficient protein expression and toxicity.

The yeast strains expressing the TAP-tagged ApoE isoforms or control cells are grown in parallel, for example, in 2 liter cultures to early log phase, and production of the ApoE isoform fusion protein is induced by addition of galactose to the growth media. The induction time may be varied in order to produce sufficient ApoE protein without causing excessive toxicity. The cultures are centrifuged in order to pellet the cells for lysis.

Next, the yeast cells are lysed in parallel to prepare extracts, for example, as described by Puig et al., supra. Briefly, the pellet is washed once with water and pelleted again into a 50 ml polypropylene tube. The pellet is frozen with liquid nitrogen. To prepare a lysate, one packed cell volume of Buffer A (10 mM HEPES ph 7.0, 10 mM Kcl, 1.5 mM MgCl2, 0.5 mM dithiothreitol (DTT), and protease inhibitors) is added to the pellet, which is thawed and kept at 4° C. Cells are lysed by passing them three times through a French press (Sim-Aminco) at a pressure of 8.27 MPa. KCL is adjusted to 0.2 M by addition of 2 M KCl. The lysate is typically centrifuged to remove debris to obtain an extract. Other methods of yeast lysis may also be employed, for example, bead beating, alkaline lysis, enzymatic lysis (e.g., with zymolyase), or grinding frozen yeast with a liquid-nitrogen chilled mortar and pestle.

Tandem affinity purification is performed to isolate (or enrich for) ApoE-containing protein complexes, for example, as described by Puig et al., supra. Briefly, IgG SEPHAROSE™ beads are added to a column, washed with IPP150 buffer (10 mM Tris HCl, pH 8.0, 150 mM NaCl, 0.1% Nonidet P-40), and the extract is added to the beads and incubated at 4° C. Elution is performed by gravity flow, and the beads are washed three times with IPP150 buffer and once with TEV cleavage buffer (IPP150 adjusted to 0.1 mM EDTA and 1 mM DTT). Cleavage is performed in the same column by adding TEV cleavage buffer and TEV protease (Gibco). The beads are rotated for 2 h at 16° C., and the eluate is recovered by gravity flow. Next, the eluate is added to a column containing calmodulin beads (Stratagene), and washed with 10 mL of IPP150 calmodulin binding buffer (10 mM Tris-HCl, ph 8, 10 mM beta-mercaptoethanol, 150 mM NaCL, 1 mM magnesium acetate, 1 mM imidazole, 2 mM $CaCl_2$, and 0.1% NP-40). Next, the beads are washed once with IPP150 calmodulin binding buffer, and bound proteins are eluted from the column.

Next, the identity of the binding partners of the different ApoE isoforms is determined by mass spectrometry (MS), for example, as described by Gavin et al. *Nature* 415:141-147, 2002. The eluate from the TAP purification is concentrated, separated by SDS-page, and stained with Coomassie blue or Silver stain. Bands may be cut, digested with trypsin, and subjected to MALDI-TOF MS. ApoE binding partners may be identified by automated peptide mass fingerprinting, and compared to a sequence database of yeast proteins (for example, the *Saccharomyces* Genome Database (SGD), yeastgenome.org). Alternatively, ApoE binding partners may be identified by automated LC/MS/MS in conjunction with database searches. The proteins that interact with ApoE2, ApoE3, and ApoE4 may be compared in order to determine binding partners that interact with more than one isoform as well as binding partners that interact with a specific isoform.

An optional parallel screen using a different affinity tag (e.g., GFP) is conducted to confirm that binding partners identified by the foregoing approach bind specifically to ApoE. For example, intox ApoE-GFP yeast strains described herein may be used or adapted for this analysis. A similar approach is used, except that an anti-GFP antibody is used to immunoprecipitate ApoE-containing protein complexes prior to mass spectrometry.

Human homologs of the ApoE binding partners are identified as described herein, for example, using Homologene, BioMart—Ensembl, BLAST searching, structural homology, and/or based on homologous function. Subsequent studies may include use of high-throughput random-mutagenesis approaches, e.g., variomics libraries (see, e.g., Huang et al. *Cell Rep.* 3(2):577-585, 2013) in order to probe the regions of the binding partner proteins that mediate their interaction with ApoE.

Identifying ApoE binding partners, for instance, using the exemplary, non-limiting approaches set forth in this Example, will identify candidate therapeutic targets for treatment of ApoE-associated diseases.

Example 11

Analysis of Lipids Associated with ApoE Proteins

An analysis of lipids associated with ApoE proteins is performed. ApoE isoforms are isolated from cells, for example, yeast cells (e.g., by affinity purification or immunoprecipitation), and the associated lipids are identified by mass spectrometry.

For example, yeast strains harboring expression constructs encoding N- or C-terminally TAP (tandem-affinity purification tag) or GFP-tagged ApoE isoforms are generated, for example, as described in Example 10. ApoE isoforms are expressed in yeast and purified, for example, as described in Example 10. Alternatively, untagged ApoE isoforms may be expressed in yeast as described herein, and immunoprecipitated using an appropriate anti-ApoE antibody.

The lipids associated with the purified ApoE isoforms are identified by mass spectrometry. Any suitable approach is used to identify ApoE protein-associated lipids. For example, liquid chromatography MS (LC/MS), multidimensional mass spectrometry-based shotgun lipidomics (MDMS-SL), MALDI-based mass spectrometry, gas chromatography-MS (GCOMS), and/or electrospray ionization mass spectrometry (ESI-MS) are performed to identify lipids associated with ApoE2, ApoE3, and/or ApoE4.

The lipids associated with each ApoE isoform are compared to identify lipids that interact with more than one isoform as well as lipids that specifically interact with particular ApoE isoforms. The identified lipids may indicate candidate therapeutic targets for treatment of ApoE-associated diseases.

Example 12

Lipidomic and Metabolomic Analysis of Cells Expressing ApoE Proteins

Cells expressing ApoE proteins are analyzed using lipidomic and metabolomic analysis to identify biological pathways perturbed by ApoE expression, as well as candidate therapeutic targets for treatment of neurodegenerative diseases including ApoE-associated diseases.

For example, yeast cells expressing ApoE isoforms (for instance, intox and/or hitox ApoE2, ApoE3, and ApoE4 strains described in Example 2) are subjected to global lipidomic analysis to determine the effect of expression of ApoE on cellular lipid content. Lipid composition is measured by any suitable approach. For example, shotgun lipidomics may be performed using approaches similar to those described by Guan et al. *Methods in Enzymology* 470:369-391, 2010; Tarasov et al. *Mol. BioSyst.* 10:1364-1376, 2014; or da Silveira dos Santos et al. *Mol. Biol. Cell.* 25(20)3234-3246, 2014.

Yeast strains harboring expression constructs encoding different ApoE isoforms are induced to express ApoE for an appropriate amount of time. In some instances, samples are taken at different time points to determine the effect of ApoE isoform expression on lipid composition over time. ApoE-expressing yeast are harvested and lysed, for example, by bead beating, followed by lipid extraction (e.g., using an extraction solvent of chloroform/methanol or an extraction solvent of ethanol, water, diethyl ether, pyridine, and 4.2 N ammonium hydroxide [15:15:5:1:0.018, vol/vol]). The organic phase is collected and subjected to vacuum evaporation. The lipids are then analyzed by mass spectrometry. Any suitable method of mass spectrometry is used, for example, ESI-MS, MALDI-MS, atmospheric pressure chemical ionization (APCI) mass spectrometry, and gas chromatography-mass spectrometry (GC-MS). Glycerophospholipids and sphingolipids may be analyzed and quantified, for example, by ESI-MS or high-resolution mass spectrometry. Sterols may be analyzed and quantified using, for example, GC-MS. The effect of each ApoE isoform on global lipid composition is determined to identify biological pathways that are perturbed by ApoE protein expression. Changes in lipid composition may also indicate candidate therapeutic targets for treatment of neurodegenerative diseases including ApoE-associated diseases.

In another example, yeast cells expressing ApoE isoforms (for instance, intox and/or hitox ApoE2, ApoE3, and ApoE4 strains described in Example 2) are subjected to global metabolomic analysis to determine the effect of expression of ApoE on metabolites. Yeast strains harboring expression constructs encoding different ApoE isoforms are induced to express ApoE for an appropriate amount of time. In some instances, samples are taken at different time points to determine the effect of ApoE isoform expression on metabolite composition over time. Metabolite composition is measured by any suitable approach. Both extracellular metabolites and intracellular metabolites may be assayed.

LC-MS is performed to determine the concentrations of metabolites in the samples derived from yeast cells expressing different ApoE isoforms. LC-MS is performed as described in Zhou et al. *Mol. Biosyst.* 8(2):470-481, 2012; Theodoridis et al. *Anal Chim Acta.* 711:7-16, 2012; or Gika et al. J. Pharm. Biomed Anal. 87:12-25, 2014. Changes in metabolite composition may identify biological pathways that are perturbed by ApoE protein expression. Changes in metabolite concentration may also indicate candidate therapeutic targets for treatment of neurodegenerative diseases including ApoE-associated diseases.

Various Embodiments

It is to be understood that, while the invention has been described in conjunction with the detailed description thereof, the foregoing description is intended to illustrate and not limit the scope of the invention. It is also to be understood that claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all embodiments in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise and such embodiments do not constitute added matter or extend beyond the content of the application as filed. Where elements are presented as lists, it is to be understood that each subgroup of the elements is also disclosed, and any one or more element(s) can be removed from the group, and such subgroup or resulting list is explicitly disclosed herein and does not constitute added matter or extend beyond the content of the application as filed. It should it be understood that, in general, where the invention, or aspects of the invention, is/are referred to as comprising particular elements, features, etc., certain embodiments of the invention or aspects of the invention consist, or consist essentially of, such elements, features, etc. It should also be understood that any embodiment of the invention can be explicitly excluded from the claims.

Where the claims or description relate to a product (e.g., a composition of matter), it should be understood that methods of making or using the product according to any of the methods disclosed herein, and methods of using the product for any one or more of the purposes disclosed herein, are encompassed by the present disclosure, where applicable, unless otherwise indicated or unless it would be evident to one of ordinary skill in the art that a contradiction or inconsistency would arise. Where the claims or description relate to a method, it should be understood that product (s), e.g., compositions of matter, device(s), or system(s), useful for performing one or more steps of the method are encompassed by the present disclosure, where applicable, unless otherwise indicated or unless it would be evident to one of ordinary skill in the art that a contradiction or inconsistency would arise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided.

Section headings used herein are not to be construed as limiting in any way. It is expressly contemplated that subject matter presented under any section heading may be applicable to any aspect or embodiment described herein. Embodiments or aspects herein may be directed to any agent, composition, article, kit, and/or method described herein. It is contemplated that any one or more embodiments or aspects can be freely combined with any one or more other embodiments or aspects whenever appropriate.

Other aspects, advantages, and modifications of the invention are within the scope of the claims set forth below.

What is claimed is:

1. A *Saccharomyces* yeast cell comprising an expression construct comprising an inducible promoter operably linked to a nucleic acid encoding a polypeptide comprising a signal sequence and a human ApoE4 protein, wherein the expression construct is present in at least two copies in the cell, and wherein the polypeptide comprises the amino acid sequence encoded by the nucleic acid sequence of SEQ ID NO: 10.

2. The *Saccharomyces* yeast cell of claim 1, wherein expression of the nucleic acid and production of the polypeptide comprising a signal sequence and a human ApoE4 protein renders the cell non-viable.

3. The *Saccharomyces* yeast cell of claim 1, wherein the expression construct comprising an inducible promoter operably linked to a nucleic acid encoding a polypeptide comprising a signal sequence and a human ApoE4 protein (i) is integrated in the genome of the yeast cell and/or (ii) is an integrative plasmid.

4. The *Saccharomyces* yeast cell of claim 1, wherein the yeast cell comprises a disruption of at least one gene that encodes a protein involved in drug efflux or cell permeability.

5. The *Saccharomyces* yeast cell of claim 1, wherein the inducible promoter is an inducible promoter selected from GAL1-10, GAL1, GALL, and GALS.

6. The *Saccharomyces* yeast cell of claim 1, wherein the expression construct comprising an inducible promoter operably linked to a nucleic acid encoding a polypeptide comprising a signal sequence and a human ApoE4 protein is present in three or four copies in the cell.

7. The *Saccharomyces* yeast cell of claim 1, wherein the yeast is *Saccharomyces cerevisiae, Saccharomyces uvae*, or *Saccharomyces kluyveri*.

8. The *Saccharomyces* yeast cell of claim 1, further comprising an expression construct comprising a promoter operably linked to a nucleic acid encoding a polypeptide comprising a signal sequence and human amyloid beta protein.

9. The *Saccharomyces* yeast cell of claim 8, wherein the human amyloid beta protein is selected from the group consisting of wild type amyloid beta 1-38, wild type amyloid beta 1-39, wild type amyloid beta 1-40, wild type amyloid beta 1-41, wild type amyloid beta 1-42, and wild type amyloid beta 1-43.

10. The *Saccharomyces* yeast cell of claim 8, wherein the expression construct comprising a promoter operably linked to a nucleic acid encoding a polypeptide comprising a signal sequence and human amyloid beta protein (i) is an integrative plasmid; (ii) is integrated in the genome of the yeast cell; (iii) comprises an inducible promoter; (iv) is present in at least one copy in the cell; (v) comprises a yeast signal sequence; or (vi) any combination of (i) (v).

11. The yeast cell of claim 10, wherein the inducible promoter is an inducible promoter selected from GAL1-10, GAL1, GALL, and GALS.

12. The yeast cell of claim 10, wherein the yeast signal sequence comprises a yeast Kar2 signal sequence.

* * * * *

SEQUENCE LISTING

<160> NUMBER OF SEQ ID NOS: 13

<210> SEQ ID NO 1
<211> LENGTH: 299
<212> TYPE: PRT
<213> ORGANISM: Homo sapiens

<400> SEQUENCE: 1

```
Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
             20                  25                  30

Phe Trp Asp Tyr Leu Arg Trp Val Gln Thr Leu Ser Glu Gln Val Gln
         35                  40                  45

Glu Glu Leu Leu Ser Ser Gln Val Thr Gln Glu Leu Arg Ala Leu Met
     50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Cys Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
        210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
        290                 295
```

<210> SEQ ID NO 2
<211> LENGTH: 299
<212> TYPE: PRT
<213> ORGANISM: Homo sapiens

<400> SEQUENCE: 2

```
Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
```

```
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
 50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
                100                 105                 110

Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
        130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
        210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
        290                 295

<210> SEQ ID NO 3
<211> LENGTH: 299
<212> TYPE: PRT
<213> ORGANISM: Homo sapiens

<400> SEQUENCE: 3

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
 50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95
```

```
Leu Gln Ala Ala Gln Ala Arg Leu Gly Ala Asp Met Glu Asp Val Arg
            100                 105                 110

Gly Arg Leu Val Gln Tyr Arg Gly Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 4
<211> LENGTH: 42
<212> TYPE: PRT
<213> ORGANISM: Saccharomyces sp.

<400> SEQUENCE: 4

Met Phe Phe Asn Arg Leu Ser Ala Gly Lys Leu Leu Val Pro Leu Ser
1               5                   10                  15

Val Val Leu Tyr Ala Leu Phe Val Ile Leu Pro Leu Gln Asn Ser
                20                  25                  30

Phe His Ser Ser Asn Val Leu Val Arg Gly
            35                  40

<210> SEQ ID NO 5
<211> LENGTH: 18
<212> TYPE: PRT
<213> ORGANISM: Homo sapiens

<400> SEQUENCE: 5

Met Lys Val Leu Trp Ala Ala Leu Leu Val Thr Phe Leu Ala Gly Cys
1               5                   10                  15

Gln Ala

<210> SEQ ID NO 6
<211> LENGTH: 43
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15
```

| Leu | Val | Phe | Phe | Ala | Glu | Asp | Val | Gly | Ser | Asn | Lys | Gly | Ala | Ile | Ile |
|---|---|---|---|---|---|---|---|---|---|---|---|---|---|---|---|
|  |  | 20 |  |  |  | 25 |  |  |  | 30 |  |  |  |  |  |

| Gly | Leu | Met | Val | Gly | Gly | Val | Ile | Ala | Thr |
|---|---|---|---|---|---|---|---|---|---|
|  |  | 35 |  |  |  | 40 |  |  |  |

<210> SEQ ID NO 7

<400> SEQUENCE: 7

000

<210> SEQ ID NO 8
<211> LENGTH: 1028
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atgttttca acagactaag cgctggcaag ctgctggtac cactctccgt ggtcctgtac      60
gccctttcg tggtaatatt acctttacag aattctttcc actcctccaa tgttttagtt     120
agaggtaagg tggagcaagc ggtggagaca gagccggagc ccgagctgcg ccagcagacc    180
gagtggcaga gcggccagcg ctgggaactg gcactgggtc gcttttggga ttacctgcgc    240
tgggtgcaga cactgtctga gcaggtgcag gaggagctgc tcagctccca ggtcacccag    300
gaactgaggg cgctgatgga cgagaccatg aaggagttga aggcctacaa atcggaactg    360
gaggaacaac tgaccccggt ggcggaggag acgcgggcac ggctgtccaa ggagctgcag    420
gcggcgcagg cccggctggg cgcggacatg gaggacgtgt gcggccgcct ggtgcagtac    480
cgcggcgagg tgcaggccat gctcggccag agcaccgagg agctgcgggt gcgcctcgcc    540
tcccacctgc gcaagctgcg taagcggctc ctccgcgatg ccgatgacct gcagaagtgc    600
ctggcagtgt accaggccgg ggcccgcgag ggcgccgagc gcggcctcag cgccatccgc    660
gagcgcctgg ggcccctggt ggaacagggc cgcgtgcggg ccgccactgt gggctccctg    720
gccggccagc cgctacagga gcgggcccag gcctggggcg agcggctgcg cgcgcggatg    780
gaggagatgg gcagccggac ccgcgaccgc ctggacgagg tgaaggagca ggtggcggag    840
gtgcgcgcca gctggagga gcaggcccag cagatacgcc tgcaggccga ggccttccag    900
gcccgcctca gagctggtt cgagcccctg gtgaagaca tgcagcgcca gtgggccggg    960
ctggtggaga aggtgcaggc tgccgtgggc accagcgccg ccctgtgcc cagcgacaat   1020
cactgccc                                                           1028
```

<210> SEQ ID NO 9
<211> LENGTH: 1028
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atgttttca acagactaag cgctggcaag ctgctggtac cactctccgt ggtcctgtac      60
gccctttcg tggtaatatt acctttacag aattctttcc actcctccaa tgttttagtt     120
agaggtaagg tggagcaagc ggtggagaca gagccggagc ccgagctgcg ccagcagacc    180
gagtggcaga gcggccagcg ctgggaactg gcactgggtc gcttttggga ttacctgcgc    240
```

```
tgggtgcaga cactgtctga gcaggtgcag gaggagctgc tcagctccca ggtcacccag    300
gaactgaggg cgctgatgga cgagaccatg aaggagttga aggcctacaa atcggaactg    360
gaggaacaac tgaccccggt ggcggaggag acgcgggcac ggctgtccaa ggagctgcag    420
gcggcgcagg cccggctggg cgcggacatg gaggacgtgc gcggccgcct ggtgcagtac    480
cgcggcgagg tgcaggccat gctcggccag agcaccgagg agctgcgggt gcgcctcgcc    540
tcccacctgc gcaagctgcg taagcggctc ctccgcgatg ccgatgacct gcagaagtgc    600
ctggcagtgt accaggccgg ggcccgcgag ggcgccgagc gcggcctcag cgccatccgc    660
gagcgcctgg ggcccctggt ggaacagggc gcgtgcgggc cgccactgt gggctccctg     720 gccggccagc cgctacagga gcgggcccag gcctggggcg agcggctgcg cgcgcggatg    780
gaggagatgg gcagccggac ccgcgaccgc ctggacgagg tgaaggagca ggtggcggag    840
gtgcgcgcca agctggagga gcaggcccag cagatacgcc tgcaggccga ggccttccag    900
gcccgcctca agagctggtt cgagcccctg gtggaagaca tgcagcgcca gtgggccggg    960
ctggtggaga aggtgcaggc tgccgtgggc accagcgccg cccctgtgcc cagcgacaat   1020
cactgccc                                                             1028
```

<210> SEQ ID NO 10
<211> LENGTH: 1028
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgttttca acagactaag cgctggcaag ctgctggtac cactctccgt ggtcctgtac     60 gccctttcg tggtaatatt acctttacag aattctttcc actcctccaa tgttttagtt    120
agaggtaagg tggagcaagc ggtggagaca gagccggagc ccgagctgcg ccagcagacc    180
gagtggcaga gcggccagcg ctggaactg gcactgggtc gcttttggga ttacctgcgc    240
tgggtgcaga cactgtctga gcaggtgcag gaggagctgc tcagctccca ggtcacccag    300
gaactgaggg cgctgatgga cgagaccatg aaggagttga aggcctacaa atcggaactg    360
gaggaacaac tgaccccggt ggcggaggag acgcgggcac ggctgtccaa ggagctgcag    420
gcggcgcagg cccggctggg cgcggacatg gaggacgtgc gcggccgcct ggtgcagtac    480
cgcggcgagg tgcaggccat gctcggccag agcaccgagg agctgcgggt gcgcctcgcc    540
tcccacctgc gcaagctgcg taagcggctc ctccgcgatg ccgatgacct gcagaagcgc    600
ctggcagtgt accaggccgg ggcccgcgag ggcgccgagc gcggcctcag cgccatccgc    660
gagcgcctgg ggcccctggt ggaacagggc gcgtgcgggc cgccactgt gggctccctg     720 gccggccagc cgctacagga gcgggcccag gcctggggcg agcggctgcg cgcgcggatg    780
gaggagatgg gcagccggac ccgcgaccgc ctggacgagg tgaaggagca ggtggcggag    840
gtgcgcgcca agctggagga gcaggcccag cagatacgcc tgcaggccga ggccttccag    900
gcccgcctca agagctggtt cgagcccctg gtggaagaca tgcagcgcca gtgggccggg    960
ctggtggaga aggtgcaggc tgccgtgggc accagcgccg cccctgtgcc cagcgacaat   1020
cactgccc                                                             1028
```

<210> SEQ ID NO 11
<211> LENGTH: 24

```
<212> TYPE: PRT
<213> ORGANISM: Homo sapiens

<400> SEQUENCE: 11

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 4
<212> TYPE: PRT
<213> ORGANISM: Saccharomyces sp.

<400> SEQUENCE: 13

Asp Glu Ala Asp
1
```